US011845770B2

(12) United States Patent
Stoltz et al.

(10) Patent No.: US 11,845,770 B2
(45) Date of Patent: *Dec. 19, 2023

(54) ASCAROSIDE DERIVATIVES AND METHODS OF USE

(71) Applicants: California Institute of Technology, Pasadena, CA (US); Holoclara, Inc., Pasadena, CA (US)

(72) Inventors: Brian M. Stoltz, San Marino, CA (US); Corey M. Reeves, San Mateo, CA (US); Eduardo J. Martinez, Bryn Mawr, PA (US); Simon Bailey, San Diego, CA (US)

(73) Assignees: California Institute of Technology, Pasadena, CA (US); Holoclara, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/971,194

(22) Filed: Oct. 21, 2022

(65) Prior Publication Data

US 2023/0135574 A1 May 4, 2023

Related U.S. Application Data

(63) Continuation of application No. 17/611,812, filed as application No. PCT/US2020/033205 on May 15, 2020.

(60) Provisional application No. 62/849,387, filed on May 17, 2019.

(51) Int. Cl.
| | |
|---|---|
| *C07H 15/18* | (2006.01) |
| *A61P 29/00* | (2006.01) |
| *C07H 15/04* | (2006.01) |
| *C07H 15/10* | (2006.01) |
| *C07H 15/26* | (2006.01) |

(52) U.S. Cl.
CPC .............. *C07H 15/18* (2013.01); *A61P 29/00* (2018.01); *C07H 15/04* (2013.01); *C07H 15/10* (2013.01); *C07H 15/26* (2013.01)

(58) Field of Classification Search
None
See application file for complete search history.

(56) References Cited

U.S. PATENT DOCUMENTS

| | | | |
|---|---|---|---|
| 5,945,445 A | 8/1999 | Barringer et al. |
| 6,444,686 B1 | 9/2002 | Ko et al. |
| 8,318,146 B1 | 11/2012 | Teal et al. |
| 9,445,596 B2 | 9/2016 | Schroeder et al. |
| 9,487,551 B2 | 11/2016 | Choe et al. |
| 9,534,008 B2 | 1/2017 | Choe et al. |
| 9,868,754 B2 | 1/2018 | Choe et al. |
| 10,136,595 B2 | 11/2018 | Klessig et al. |
| 10,183,963 B2 | 1/2019 | Choe et al. |
| 10,479,813 B2 | 11/2019 | Choe et al. |
| 11,019,776 B2 | 6/2021 | Klessig et al. |
| 11,077,151 B2 | 8/2021 | Choe et al. |
| 11,464,810 B2 | 10/2022 | Choe et al. |
| 11,673,908 B2 | 6/2023 | Choe et al. |
| 2005/0075389 A1 | 4/2005 | Paik et al. |
| 2008/0188646 A1 | 8/2008 | Jung et al. |
| 2009/0264392 A1 | 10/2009 | Warndahl et al. |
| 2010/0048497 A1 | 2/2010 | Andersch et al. |
| 2010/0056469 A1 | 3/2010 | Langewald et al. |
| 2014/0303102 A1 | 10/2014 | Choe et al. |
| 2014/0303360 A1 | 10/2014 | Schroeder et al. |
| 2014/0364386 A1 | 12/2014 | Choe et al. |
| 2014/0364586 A1 | 12/2014 | Watts et al. |
| 2015/0018291 A1 | 1/2015 | Choe et al. |
| 2016/0271188 A1 | 9/2016 | Berry et al. |
| 2017/0136049 A1 | 5/2017 | Newburg et al. |
| 2018/0162893 A1 | 6/2018 | Choe et al. |
| 2020/0262856 A1 | 8/2020 | Choe et al. |
| 2022/0016182 A1 | 1/2022 | Choe et al. |
| 2022/0235086 A1 | 7/2022 | Stoltz et al. |
| 2022/0409650 A1 | 12/2022 | Choe et al. |
| 2023/0024046 A1 | 1/2023 | Choe et al. |
| 2023/0026686 A1 | 1/2023 | Choe et al. |

FOREIGN PATENT DOCUMENTS

| | | |
|---|---|---|
| DE | 10163602 A1 | 7/2003 |
| JP | 2006506420 A | 2/2006 |
| JP | 2007500186 A | 1/2007 |
| KR | 10-2009-0088496 | 8/2009 |
| KR | 20100117665 A | 11/2010 |
| WO | WO-96/19920 A1 | 7/1996 |
| WO | WO-2004/043944 A1 | 5/2004 |
| WO | WO-2005/075491 A1 | 8/2005 |
| WO | WO-2005/089068 A2 | 9/2005 |

(Continued)

OTHER PUBLICATIONS

Rautio, Nature Reviews, vol. 7, Mar. 2008, pp. 255-270. (Year: 2008).*
U.S. Appl. No. 14/237,774, Granted.
U.S. Appl. No. 14/237,774, Abandoned.
U.S. Appl. No. 14/237,786, Granted.
U.S. Appl. No. 15/395,459, Abandoned.
U.S. Appl. No. 14/237,795, Granted.
U.S. Appl. No. 15/833,474, Granted.
U.S. Appl. No. 16/251,750, Granted.
U.S. Appl. No. 16/685,375, Abandoned.
U.S. Appl. No. 17/878,650, Pending.
U.S. Appl. No. 14/237,800, Granted.
U.S. Appl. No. 15/343,775, Abandoned.

(Continued)

*Primary Examiner* — Layla D Berry
(74) *Attorney, Agent, or Firm* — Foley Hoag LLP; Janine S. Ladislaw; Lawrence P. Tardibono

(57) ABSTRACT

The present invention relates to methods of treating immune disorders and/or inflammation using certain modulator compounds. For example, the present invention provides methods of treating immune and/or inflammatory disorders by administering a composition comprising a compound having the structure of Formula (I).

21 Claims, 30 Drawing Sheets

(56) References Cited

FOREIGN PATENT DOCUMENTS

| WO | WO-2005/110040 A2 | 11/2005 |
| --- | --- | --- |
| WO | WO-2009/102736 A1 | 8/2009 |
| WO | WO-2011/155687 A1 | 12/2011 |
| WO | WO-2012/033266 A1 | 3/2012 |
| WO | WO-2013/022985 A2 | 2/2013 |
| WO | WO-2013/022996 A2 | 2/2013 |
| WO | WO-2013/022997 A2 | 2/2013 |
| WO | WO-2013/023000 A2 | 2/2013 |
| WO | WO-2013/039872 A1 | 3/2013 |
| WO | WO-2014/145380 A2 | 9/2014 |
| WO | WO-2014/151648 A1 | 9/2014 |
| WO | WO-2018/039591 A1 | 3/2018 |
| WO | WO-2018/039593 A1 | 3/2018 |
| WO | WO-2020/236621 A1 | 11/2020 |
| WO | WO-2020/247480 A1 | 12/2020 |

OTHER PUBLICATIONS

U.S. Appl. No. 16/327,659, Granted.
U.S. Appl. No. 17/390,096, Pending.
U.S. Appl. No. 16/327,670, Granted.
U.S. Appl. No. 17/941,589, Pending.
U.S. Appl. No. 17/611,812, Pending.
U.S. Appl. No. 17/616,506, Pending.
Ben-Yakir, D. et al., "Evaluation of entomopathogenic nematodes for biocontrol of the European Corn Borer, Ostrinia nubilalis, on sweet corn in Israel," Phytoparasitica, 26(2):101-8 (1998).
Bose et al., "Complex small-molecule architectures regulate phenotypic plasticity in a nematode," Angew Chem Int Ed, 51:12438-43 (2012).
Butcher et al., "An Indole-Containing Dauer Pheromone Component with Unusual Dauer Inhibitory Activity at Higher Concentrations," Organic Letters 11 (14):3100-3103 (2009).
Butcher et al., "Biosynthesis of the Caenorhabditis elegans dauer pheromone," PNAS, 106(6):1875-1879 (2009).
Butcher, R. A. "Small-molecule pheromonese that control dauer development in Caenorhadbiditus elegans," J. Nat. Chem. Ciol. 3(7): 420-422 (2007).
Cheng et al., "Insertational mutagenesis of a fungal biocontrol agent led to discovery of a rare cellobiose lipid with antifungal activity," Appl Environ Microb, 69(5):2595-602 (2003).
Choe et al., "Ascaroside Signaling is Widely Conserved Among Nematodes," Curr Biol., 22(9):772-780 (2012).
Choe, "Pheromones in Free-Living and Parasitic Nematodes," Thesis for California Institute of Technology, (Jun. 17, 2011) (Made publically available Dec. 2, 2013).
Chuman et al., "Identification and Characterization of Nematode Pheromones," National High Magnetic Field Laboratory (2009).
European C. elegans Neurobiology Meeting; Oct. 9, 2010. (http://ww.worms.gr/ewnm2010/files/abstracts.pdf).
European Extended Search Report for EP Patent Application: 12822518.2 dated Jan. 30, 2015.
European Extended Search Report for EP Patent Application: 12822698.2 dated Mar. 4, 2015.
European Search Report for EP Patent Application No. 12822518.2 dated Feb. 17, 2017.
Extended European Search Report for EP Application No. 17844508.6 dated Feb. 20, 2020.
Extended European Search Report for EP Application No. EP 17844507 dated Feb. 20, 2020.
Extended European Search Report for EP Application No. EP 19169996 dated Jul. 26, 2019.
Gallo et al., "Effects of a Caenorhabditis elegans dauer pheromone ascaroside on physiology and signal transduction pathways," J. Chem. Ecol., 35(2):272-279 (2009).
International Preliminary Report on Patentability for International Application No. PCT/US2017/048672 dated Feb. 26, 2019.
International Preliminary Report on Patentability for International Application No. PCT/US2020/033205 dated Dec. 2, 2021.
International Preliminary Report on Patentability for International Application No. PCT/US2020/035900 dated Dec. 16, 2021.
International Search Report and Written Opinion for International Application No. PCT/US2017/048665 dated Dec. 20, 2017.
International Search Report and Written Opinion for International Application No. PCT/US2017/048672 dated Dec. 18, 2017.
International Search Report and Written Opinion for International Application No. PCT/US2020/033205 dated Aug. 27, 2020.
International Search Report and Written Opinion for International Application No. PCT/US2020/035900 dated Oct. 6, 2020.
International Search Report dated Jul. 25, 2013 from PCT/US2012/050016.
International Search Report dated May 2, 2013 from PCT/US2012/050032.
Jeong et al., "Chemical structure and biological activity of the Caenorhabditis elegans dauer-inducing pheromone," Nature, 433(7025):541-545 (2005).
Kaplan et al., "Ascaroside Expression in Caenorhabditis elegans Is Strongly Dependent on Diet and Developmental Stage," PLOSOne, 6(3):e17804 (2011).
Lacey, L.A. et al., "Insect pathogens as biological control agents: Do they have a future?" Biol Control, 21:230-48 (2001).
Lucendo et al., "Emerging Therapeutic Strategies for Eosinophilic Esophagitis," Current Treatment Options in Gastroenterology, 12: 1-17 (2014).
Manosalva et al., "Conserved nematode signalling molecules elicit plant defenses and pathogen resistance," Nature Communications, 6:7795 (2015).
Martin et al., "Improved Synthesis of an Ascaroside Pheromone Controlling Dauer Larva Development in Caenorhabditis Elegans," Synthesis, 20:3488 (2009).
Noguez et al., "A novel ascaroside controls the parasitic life cycle of the entomopathogenic nematode Heterorhabditis bacteriophora," ACS Chem Biol., 7(6): 1-11 (2013).
Noh et al., "Quantitative determination of daumone in rat plasma by liquid chromatography—mass spectrometry," J. Pharm. Biomed. Anal., 56(1):114-117 (2011).
Non-Final Office Action for European Patent Application No. 12822698.2, dated Jan. 20, 2017.
Pungaliya et al., "A shortcut to identifying small molecule signals that regulate behavior and development in Caenorgabditis elegans," PNAS, 106(19): 7708-7713 (2009).
Riga, E. et al., " In vitro effect of marigold seed exudates on plant parasitic nematodes," Phytoprotection, 86:31-5 (2004).
Srinivasan et al., "A blend of small molecules regulates both mating and development in Caenorhabditis elegans," Nat Lett, 454:1115-9 (2008)/.
Von Reuss et al., "Comparative Metabolomics Reveals Biogenesis of Ascarosides, a Modular Library of Small-Molecule Signals in C. elegans," Journal of the American Chemical Society, 134(3):1817-1824 (2012).
Wisnewski et al., "Characterization of novel fucosyl- and tyvelosyl-containing glycoconjugates from Trichinella spiralis muscle stage larvae," Molecular and Biochemical Parasitology, 61(1):25-36 (1993).
Written Opinion for International Application No. PCT/US2012/050016 dated Apr. 24, 2013.
Written Opinion for International Application No. PCT/US2012/050031 dated Feb. 13, 2013.
Written Opinion for International Application No. PCT/US2012/050032 dated Feb. 26, 2013.
Written Opinion for International Application No. PCT/US2012/050037 dated Feb. 7, 2013.
Extended European Search Report for EP Application No. 20808981.3 dated Feb. 8, 2023.
Jung et al., "Total synthesis and anticancer activity of highly potent novel glycolipid derivatives" European Journal of Medicinal Chemistry, 44: 3120-3129 (2009).

* cited by examiner

FIG. 4

| Compound | Cell Conc. (×10⁶ cells/mL) | Mouse | | | | | Rat | | | | | | Human | | | | |
|---|---|---|---|---|---|---|---|---|---|---|---|---|---|---|---|---|---|
| | | $R^2$ | k | T½ (min) | CLint (hep) (µL/min/10⁶) | CLint (liver) (mL/min/kg) | $R^2$ | k | T½ (min) | CLint (hep) (µL/min/10⁶) | CLint (liver) (mL/min/kg) | | $R^2$ | k | T½ (min) | CLint (hep) (µL/min/10⁶) | CLint (liver) (mL/min/kg) |
| ascr#7 | 0.5 | 0.8027 | -0.0005 | >216.8 | <6.4 | <75.9 | 0.0732 | -0.0007 | >216.8 | <6.4 | <29.9 | | 0.0794 | 0.0002 | >216.8 | <6.4 | <17.8 |
| Compound 1 | | NA | NA | NA | NA | NA | 0.9647 | 0.0301 | 23.1 | 60.1 | 281.4 | | 0.9773 | 0.0065 | 106.0 | 13.1 | 36.4 |
| 7-Ethoxycoumarin | | 0.9422 | 0.0995 | 7.0 | 199.1 | 2365.2 | 0.9129 | 0.0302 | 22.9 | 60.4 | 282.7 | | 0.9496 | 0.0305 | 22.7 | 61.0 | 169.7 |
| 7-Hydroxycoumarin | | 0.9994 | 0.0815 | 8.5 | 162.9 | 1935.5 | 0.9974 | 0.0600 | 11.5 | 120.0 | 561.7 | | 0.9942 | 0.0426 | 16.3 | 85.2 | 236.9 |

FIG. 5A

| Result Summary of Plasma Stability Assay | | | |
|---|---|---|---|
| Compound | Time Point (min) | % Remaining | |
| | | Rat | Human |
| Compound 1 | 0 | 100.0 | 100.0 |
| | 10 | 83.4 | 106.2 |
| | 30 | 60.7 | 89.0 |
| | 60 | 40.5 | 89.7 |
| | 120 | 19.2 | 86.5 |
| ascr#7 | 0 | 100.0 | 100.0 |
| | 10 | 99.7 | 89.5 |
| | 30 | 101.1 | 88.9 |
| | 60 | 105.2 | 91.6 |
| | 120 | 99.8 | 89.8 |
| Propantheline bromide | 0 | / | 100.0 |
| | 10 | / | 65.1 |
| | 30 | / | 26.8 |
| | 60 | / | 7.0 |
| | 120 | / | 0.7 |
| Enalapril maleate salt | 0 | 100.0 | / |
| | 10 | 52.3 | / |
| | 30 | 12.1 | / |
| | 60 | 1.0 | / |
| | 120 | 0.0 | / |

FIG. 5B

| Result Summary of Plasma Stability Assay |||
|---|---|---|
| Compound | Time Point (min) | % Remaining |
| | | Mouse |
| ascr#7 | 0 | 100.0 |
| | 10 | 112.4 |
| | 30 | 117.3 |
| | 60 | 113.5 |
| | 120 | 103.4 |
| Propantheline bromide | 0 | 100.0 |
| | 10 | 81.0 |
| | 30 | 56.5 |
| | 60 | 31.5 |
| | 120 | 6.9 |

FIG. 6

| Serial Number | Compound | Mean $P_{app}$ ($10^{-6}$ cm/s) | | Efflux Ratio | Mean Recovery % | | Rank |
| --- | --- | --- | --- | --- | --- | --- | --- |
| | | A to B | B to A | | A to B | B to A | $P_{app}$ |
| PC1 | Nadolol (Low permeability marker) | 0.06 | ND | - | 92.96 | ND | Low |
| PC2 | Metoprolol (High permeability marker) | 13.74 | ND | - | 94.03 | ND | High |
| PC3 | Digoxin (P-gp substrate) | 0.01 | 9.12 | 717.51 | 90.70 | 92.63 | Low |
| CPD1 | ascr#7 | <0.10 | 0.23 | >2.29 | <91.62 | 98.65 | Low |
| CPD2 | Compound 1 | 12.15 | 16.97 | 1.40 | 83.18 | 88.75 | High |

| Result Summary of Test Compounds in Plasma Using Equilibrium Dialysis |||||||
|---|---|---|---|---|---|---|
| Compound | Test Concentration(μM) | Species / Matrix | % Unbound (n = 3) | SD | % Bound | % Recovery (n = 3) | SD |
| ascr#7 | 2 | Human Plasma | 86.8 | 10.4 | 13.2 | 95.9 | 3.6 |
| | | SD Rat Plasma | 94.6 | 3.2 | 5.4 | 98.6 | 3.7 |
| Compound 1 | | Human Plasma | 32.9 | 2.5 | 67.1 | 101.7 | 1.9 |
| | | SD Rat Plasma | NA | NC | NA | 25.6 | 0.4 |
| Warfarin | | Human Plasma | 1.0 | 0.2 | 99.0 | 86.5 | 4.8 |
| | | SD Rat Plasma | 0.7 | NC | 99.3 | 91.3 | NC |

| Compound | 1A2 | | 2C9 | | 2C19 | | 2D6 | | 3A4 | |
|---|---|---|---|---|---|---|---|---|---|---|
| | %Inhibition | *IC$_{50}$ (μM) | %Inhibition | *IC$_{50}$ (μM) | %Inhibition | *IC$_{50}$ (μM) | %Inhibition | *IC$_{50}$ (μM) | %Inhibition | *IC$_{50}$ (μM) |
| ascr#7 | 2.3 | >100 | 0.0 | >100 | 4.0 | >100 | 4.6 | >100 | 0.0 | >100 |
| Compound 1 | 10.9 | 82.1 | 4.3 | >100 | 16.2 | 51.6 | 10.1 | 89.3 | 1.0 | >100 |

Positive Controls at 3 μM on P450 inhibition

| CYP Isozyme | Standard Inhibitor | **IC$_{50}$ (μM) | IC$_{50}$ Acceptance Range (μM) | Pass/Fail |
|---|---|---|---|---|
| 1A2 | α-Naphthoflavone | 0.315 | 0.125-0.448 | Pass |
| 2C9 | Sulfaphenazole | 0.547 | 0.333-0.750 | Pass |
| 2C19 | N-3-benzylnirvanol | 0.218 | 0.0928-0.333 | Pass |
| 2D6 | Quinidine | 0.125 | 0.0928-0.226 | Pass |
| 3A4 | Ketoconazole | 0.0346 | 0.0303-0.0928 | Pass |

ASCAROSIDE DERIVATIVES AND METHODS OF USE

CROSS-REFERENCE TO RELATED APPLICATIONS

This application is a continuation of U.S. application Ser. No. 17/611,812, which is a 371(c) national stage of PCT/US2020/033205, filed on May 15, 2020, which claims the benefit of U.S. Provisional Application 62/849,387, filed May 17, 2019, each of which is incorporated by reference herein in its entirety.

COMMON OWNERSHIP UNDER JOINT RESEARCH AGREEMENT 35 U.S.C. 102(c)

The subject matter disclosed in this application was developed, and the claimed invention was made by, or on behalf of, one or more parties to a joint Research Agreement that was in effect on or before the effective filing date of the claimed invention. The parties to the Joint Research Agreement are as follows: California Institute of Technology and Holoclara, Inc.

BACKGROUND

Many nematode species are known to parasitize humans; this relationship is thought to have existed for thousands of years.

There is an inverse relationship between areas endemic with parasitic nematodes and areas with a high incidence of autoimmune disease. This observation spurred the hypothesis that parasitic nematodes or nematode derived secretions may protect against autoimmune disease, and it has been corroborated by numerous human clinical trials and animal model studies, where administration of parasitic nematodes has alleviated disease symptoms.

Some nematode-based approaches for treating autoimmune and inflammatory diseases have been identified. However, there exists a need for treatments that are improved as compared to factors and/or isolates of parasitic nematodes.

SUMMARY

In one aspect, provided herein is a compound having the structure of Formula (I):

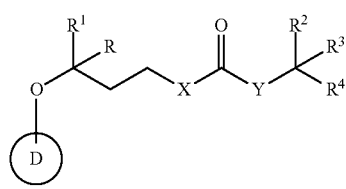

Formula (I)

wherein
Ring D is selected from

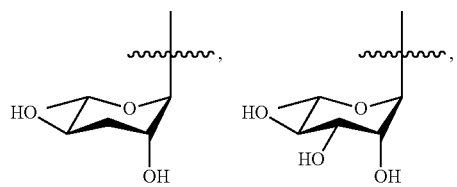

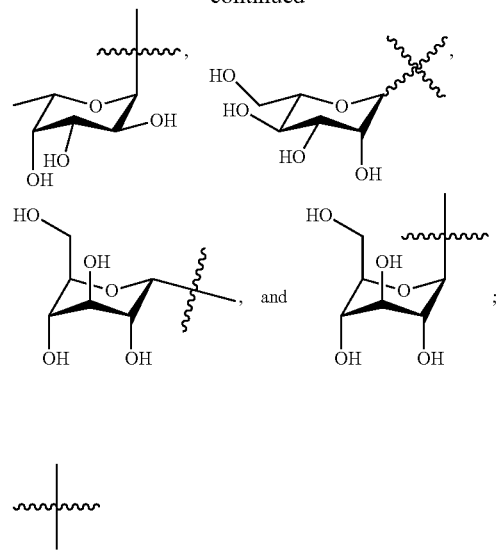

represents the point of attachment of Ring D to the oxygen atom;

X is $-C(R^5)_2-C(R^5)_2-$ or E or Z $-CH=CH-$;

Y is O or $NR^6$;

R is H or $CH_3$, $R^1$ is H or $CH_3$;

or, R and $R^1$, taken together with the carbon atom to which they are bonded, form a 3- or 4-membered carbocyclic ring;

$R^2$ is H or $CH_3$;

$R^3$ is H or $CH_3$;

$R^4$ is $CH_3$, $CH_2CH_3$, a straight- or branched-chain $C_3$-$C_6$ alkyl, a $C_5$-$C_7$ cycloalkyl, a 6-membered aryl or heteroaryl, an aryl-substituted $C_1$-$C_6$ alkyl, or a heterocyclyl-substituted $C_1$-$C_6$ alkyl;

$R^5$, independently for each occurrence, is H or OH, or two instances of $R^5$, taken together with the carbon atom or carbon atoms to which they are bonded, form a 3-membered carbocyclic ring; and $R^6$ is H or $C_1$-$C_6$ alkyl, or, when Y is $NR^6$, $R^4$ and $NR^6$, taken together with the carbon atom to which they are bonded, form a 5- or 6-membered heterocyclic ring.

In another aspect, provided herein are pharmaceutical formulations comprising a pharmaceutically acceptable carrier; and the compound having the structure of Formula (I):

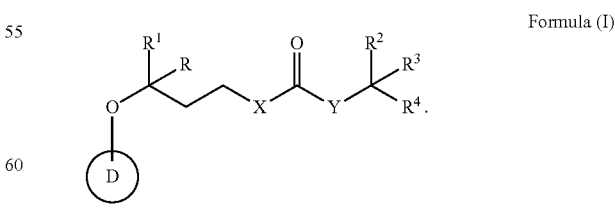

Formula (I)

In another aspect, provided herein are methods of treating a disease or condition in a subject in need thereof comprising administering to the subject an effective amount of the compound having the structure of Formula (I),

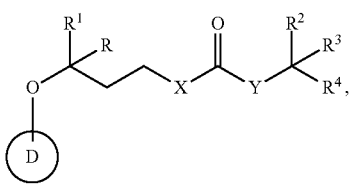

Formula (I)

wherein the disease or condition is an inflammatory disorder, an autoimmune disorder, or both.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

Example embodiments are illustrated in referenced figures. It is intended that the embodiments and figures disclosed herein are to be considered illustrative rather than restrictive.

FIG. 4 shows the half-life of ascr #7 in mouse, rat, and human hepatocytes, and the half-life of compound 1 in rat hepatocytes and human hepatocytes.

FIG. 5A shows the clearance of ascr #7 in rat plasma and human plasma, and the clearance of compound 1 in rat plasma and in human plasma.

FIG. 5B shows the clearance of ascr #7 in mouse plasma.

FIG. 6 shows the bidirectional permeability of ascr #7 in CaCo-2 cells, and the bidirectional permeability of compound 1 in CaCo-2 cells.

FIG. 7 shows the degree of plasma protein binding of ascr #7 and compound 1.

FIG. 8 shows the inhibition of cytochrome P450 isoforms of ascr #7 and the compound of 1 in a CYP Inhibition assay.

DETAILED DESCRIPTION

Overview

Figure 1A:
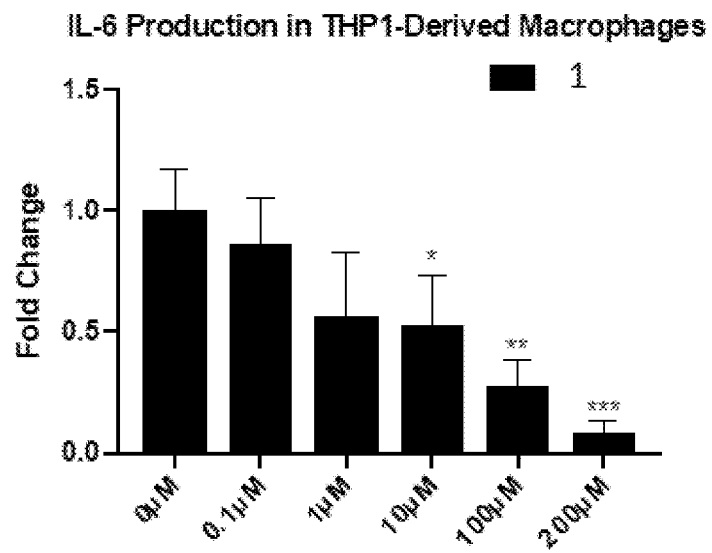
FIG. 1A shows that compound 1 diminishes the amount of IL-6 released by THP-1 derived macrophages 72 h post stimulation in an in vitro assay.

The present invention is based, at least in part, on the discovery that ascarosides, a family of small-molecule nematode pheromones, modulate the immune response and have a therapeutic effect on various autoimmune and inflammatory disorders. One of the ascaroside derivatives, the compound of Formula (I) or (II), markedly inhibits the hallmark pathologies in mouse models of asthma, inflammatory bowel disease, and type 1 diabetes, and significantly reduces both IL-6 and IL-1β secretion. These findings suggest that this compound has a therapeutic effect in diseases where elevated levels of IL-6 and/or IL-1β contribute to the diseases' pathogeneses.

In some aspects, the invention provides a method of treating an inflammatory disorder, an autoimmune disorder, or both in a subject. The method comprises administering to the subject an effective amount of the compound having the structure of Formula (I) or (II).

In some embodiments, the subject has an elevated level of IL-6, IL-1β, and/or TNFα (also referred to herein as TNF-α). In certain embodiments, IL-6, IL-1β, and/or TNFα contribute to one or more symptoms of the disease. In embodiments such as these, the method may comprise assessing the level of IL-6, IL-1β, and/or TNFα in an affected tissue of the subject and, if the level exceeds 200% of a normal level for the affected tissue, administering the compound of Formula (I) or (II).

Accordingly, the present invention relates, in part, to methods of treating an inflammatory disorder, an autoimmune disorder, or both in a subject. In some embodiments, the present invention relates to treating an IL-6, IL-1β, and/or TNFα-mediated disease in a subject by administering to the subject a compound of Formula (I). In other aspects, the present invention relates to methods of reducing IL-6 and/or IL-1β production from a cell by contacting the cell, or affiliated cells, with a compound of Formula (I) or (II).

Definitions

Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "compounds of the invention," and equivalent expressions, are meant to embrace the compounds, as well as any stereoisomeric form, or a mixture of any such forms of that compound in any ratio, unless otherwise specified. Inclusion complexes are described in Remington, The Science and Practice of Pharmacy, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. For the sake of clarity, particular instances when the context so permits are sometimes indicated in the text, but these instances are purely illustrative and it is not intended to exclude other instances when the context so permits.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

In some embodiments, a compound of Formula (I) or (II) is enantioenriched at the side chain methyl group stereogenic center. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R)-enantiomer, then the ee of the compound is (98−2)/(98+2), or 96%. In certain embodiments, the compound of Formula (I) has about 5% ee or greater, 10% ee or greater, 15% ee or greater, 20% ee or greater, 25% ee or greater, 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In some embodiments, the compound of Formula (I) or (II) is enantioenriched. In some embodiments, the compound of Formula (I) or (II) is enantiopure e.g., has the structure of compound 1 or 10. In embodiments where the starting material has more than one stereocenter, reactions of the disclosure may enrich the stereocenter bearing a methyl group relative to the enrichment at this center, if any, of the starting material, and substantially independently of the stereochemical disposition/enrichment (de) of any other stereocenters of the molecule.

For example, a compound of Formula (I) or (II) described herein may have 5% de or greater, 10% de or greater, 15% de or greater, 20% de or greater, 25% de or greater, 30% de or greater, 40% de or greater, 50% de or greater, 60% de or greater, 70% de or greater, 80% de or greater, 90% de or greater, 95% de or greater, or even 98% de or greater at the stereocenter of the compound of Formula (I) bearing a methyl group.

As used herein, the term "ascr #7" refers to the compound,

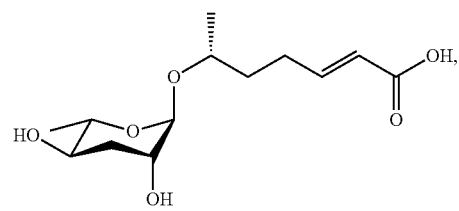

which is also referred to herein as NDM-X, or a pharmaceutically acceptable salt thereof.

Compounds

In one aspect, provided herein is a compound having the structure of Formula (I):

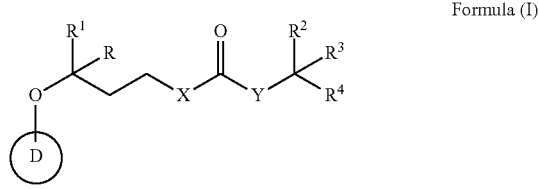

Formula (I)

wherein
Ring D is selected from

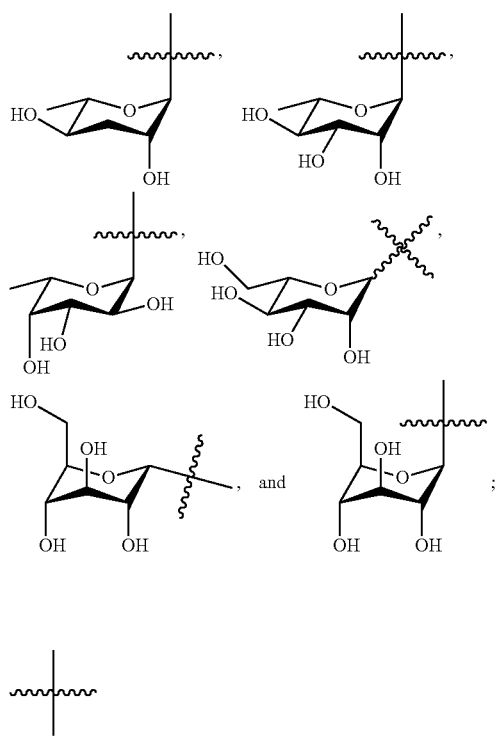

represents the point of attachment of Ring D to the oxygen atom;

X is —C($R^5$)$_2$—C($R^5$)$_2$— or E or Z—CH=CH—;
Y is O or N$R^6$;
R is H or CH$_3$,
$R^1$ is H or CH$_3$;
  or, R and $R^1$, taken together with the carbon atom to which they are bonded, form a 3- or 4-membered carbocyclic ring;
$R^2$ is H or CH$_3$;
$R^3$ is H or CH$_3$;
$R^4$ is CH$_3$, CH$_2$CH$_3$, a straight- or branched-chain C$_3$-C$_6$ alkyl, a C$_5$-C$_7$ cycloalkyl, a 6-membered aryl or heteroaryl, an aryl-substituted C$_1$-C$_6$ alkyl, or a heterocyclyl-substituted C$_1$-C$_6$ alkyl;
$R^5$, independently for each occurrence, is H or OH,
  or two instances of $R^5$, taken together with the carbon atom or carbon atoms to which they are bonded, form a 3-membered carbocyclic ring; and $R^6$ is H or C$_1$-C$_6$ alkyl,
  or, when Y is N$R^6$, $R^4$ and N$R^6$, taken together with the carbon atom to which they are bonded, form a 5- or 6-membered heterocyclic ring.

In some embodiments, the compound of Formula (I) is selected from

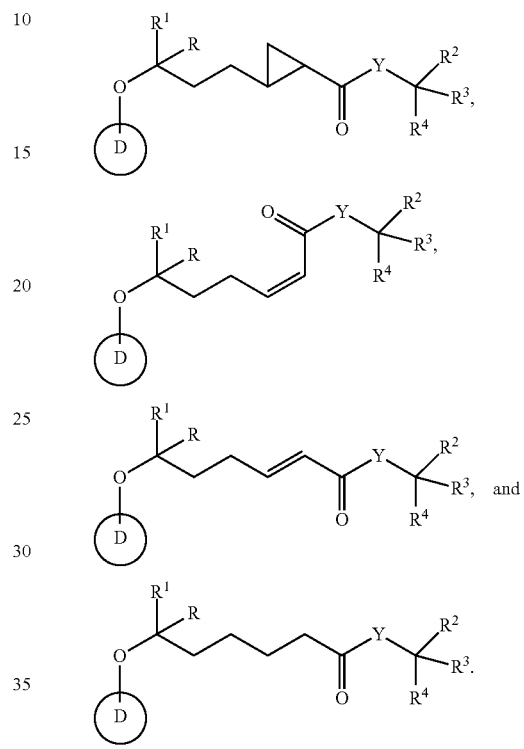

In some embodiments, X is —C($R^5$)$_2$—C($R^5$)$_2$—. In some embodiments, X is E or Z—CH=CH—. In some embodiments, X is —C(H)$_2$—C(H)$_2$—. In some embodiments, X is —C(H)(OH)—C(H)$_2$—.

In some embodiments, X—C($R^5$)$_2$—C($R^5$)$_2$, two instances of $R^5$, taken together with the carbon atom or carbon atoms to which they are bonded, form a 3-membered carbocyclic ring. In some embodiments, X is

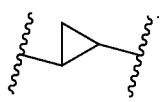 [SMILES: *C1CC1*]

In some embodiments, X is

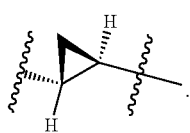 [SMILES: *[C@@H]1C[C@H]1*]

In some embodiments, X is

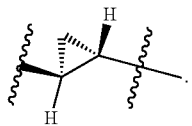 [SMILES: *[C@H]1C[C@@H]1*]

In some embodiments, X is

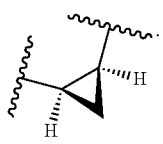

In some embodiments, X is

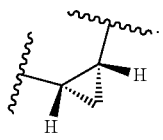 [SMILES: *[C@@H]1C[C@@H]1*]

In some embodiments, Y is $NR^6$. In some embodiments, Y is $NR^6$, wherein $R^6$ is H. In some embodiments, Y is $NR^6$, wherein $R^6$ is $C_1$-$C_6$ alkyl. In some embodiments, Y is $NR^6$, wherein $R^6$ is $CH_3$. In some embodiments, Y is $NR^6$, wherein $R^6$ is $CH_2CH_3$. In some embodiments, Y is $NR^6$, wherein $R^4$ and $NR^6$, taken together with the carbon atom to which they are bonded, form a 5- or 6-membered heterocyclic ring. In some embodiments, Y is O.

In some embodiments, R and $R^1$ are each $CH_3$. In some embodiments, R and $R^1$ are each $CH_3$. In some embodiments, R is $CH_3$; and $R^1$ is H. In some embodiments, R and $R^1$, taken together with the carbon atom to which they are bonded, form a cyclopropyl. In some embodiments, R and $R^1$, taken together with the carbon atom to which they are bonded, form a cyclobutyl.

In some embodiments, $R^2$ is H; $R^3$ is H or $CH_3$; and $R^4$ is $CH_3$, $CH_2CH_3$, a straight- or branched-chain $C_3$-$C_6$ alkyl, a $C_5$-$C_7$ cycloalkyl, a 6-membered aryl or heteroaryl, an aryl-substituted $C_1$-$C_6$ alkyl, or a heterocyclyl-substituted $C_1$-$C_6$ alkyl, or, when Y is $NR^6$, $R^4$ and $NR^6$, taken together with the carbon atom to which they are bonded, form a 5- or 6-membered heterocyclic ring. In some embodiments, $R^2$, $R^3$ and $R^4$ are each $CH_3$. In some embodiments, $R^2$ is H; $R^3$ is $CH_3$; and $R^4$ is $CH_3$. In some embodiments, $R^2$ is H; $R^3$ is H; and $R^4$ is $CH_2CH_3$. In some embodiments, $R^2$ is H; $R^3$ is H; and $R^4$ is $CH(CH_2CH_3)_2$. In some embodiments, $R^2$ is H; $R^3$ is H; and $R^4$ is $CH(CH_2CH_3)_2$. In some embodiments, $R^2$ is H; $R^3$ is H; and $R^4$ is cyclohexyl. In some embodiments, $R^2$ is H; $R^3$ is H; and $R^4$ is phenyl. In some embodiments, $R^2$ is H; $R^3$ is H; and $R^4$ is pyridinyl.

In some embodiments, the compound of Formula (I) is selected from

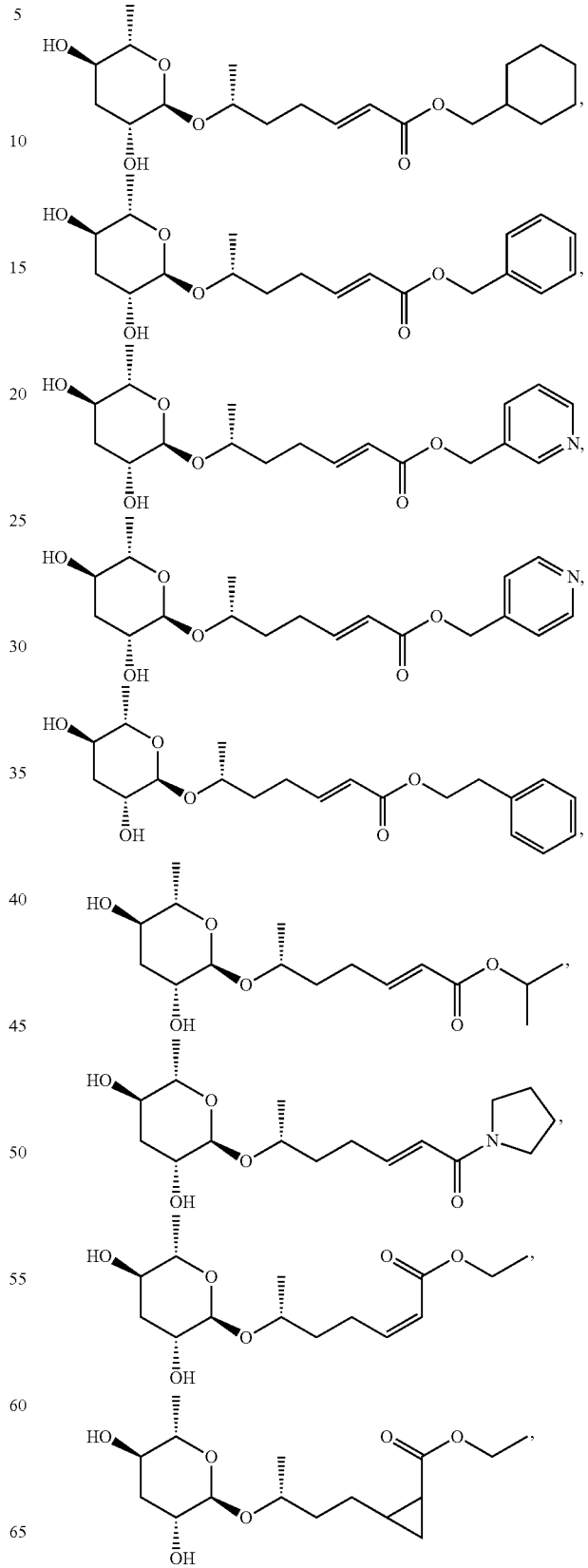

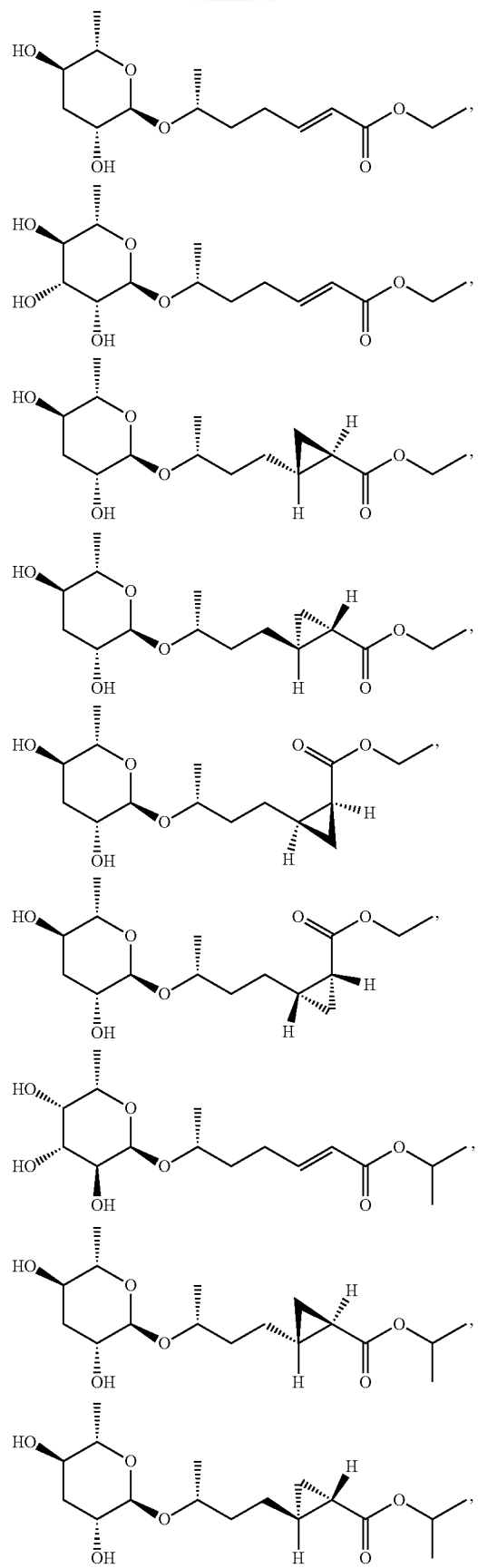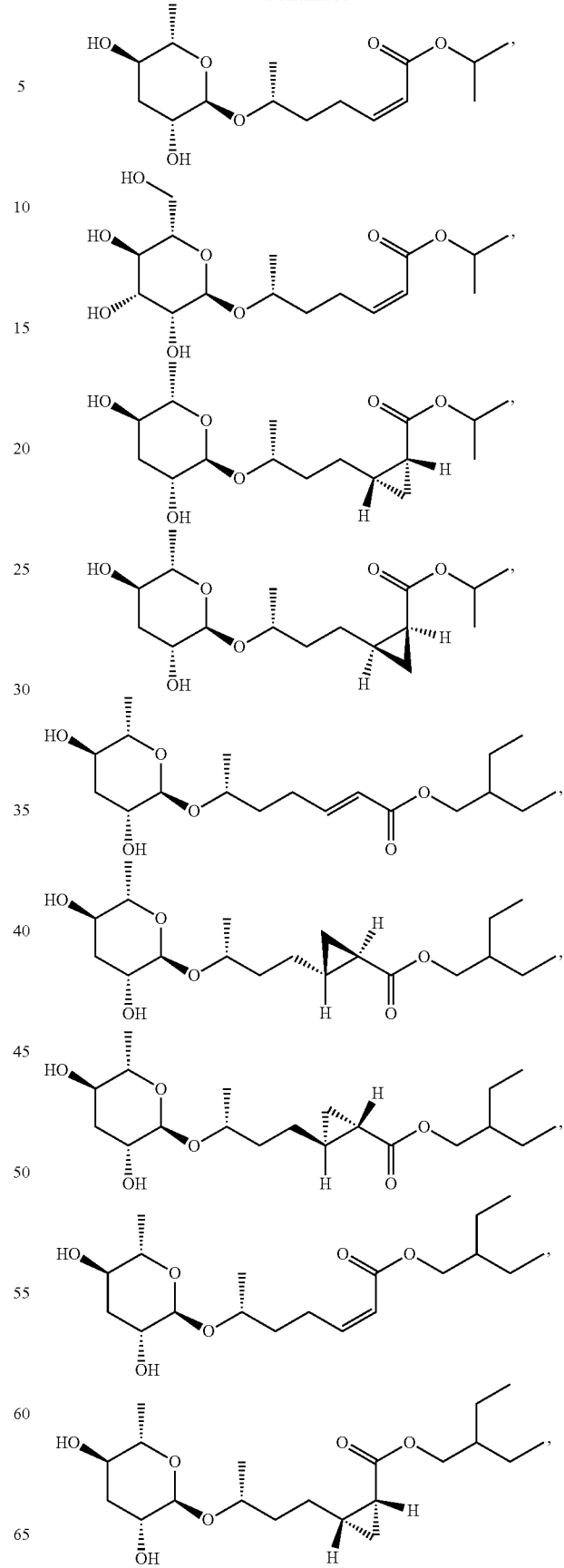

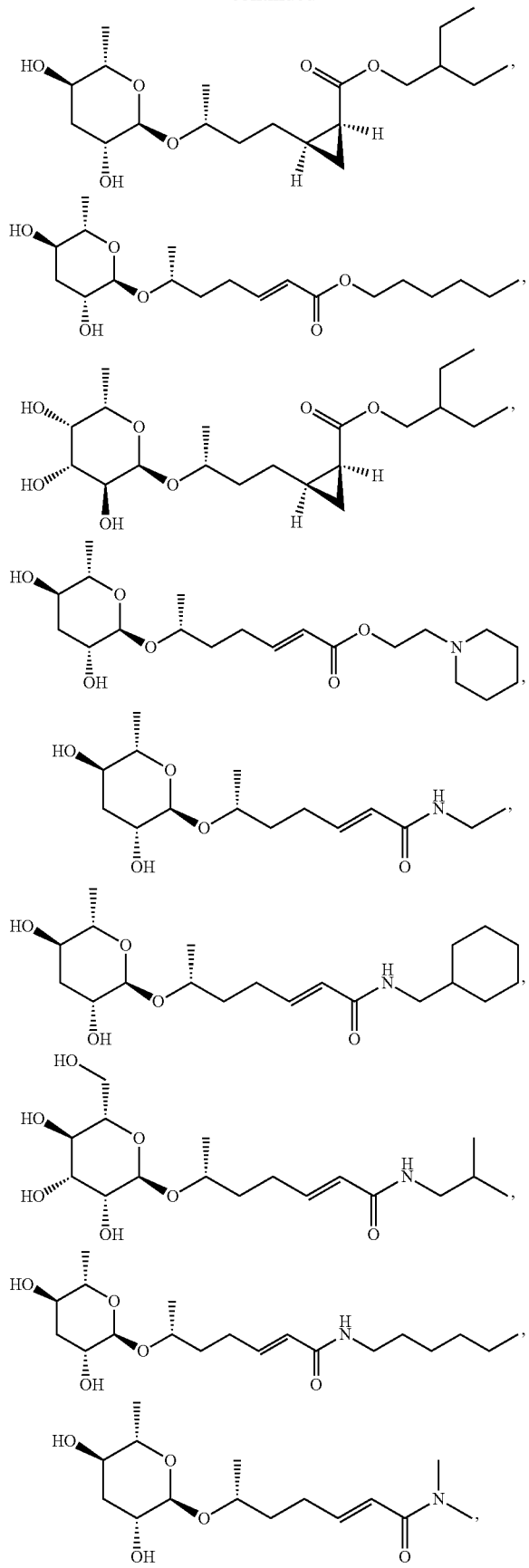
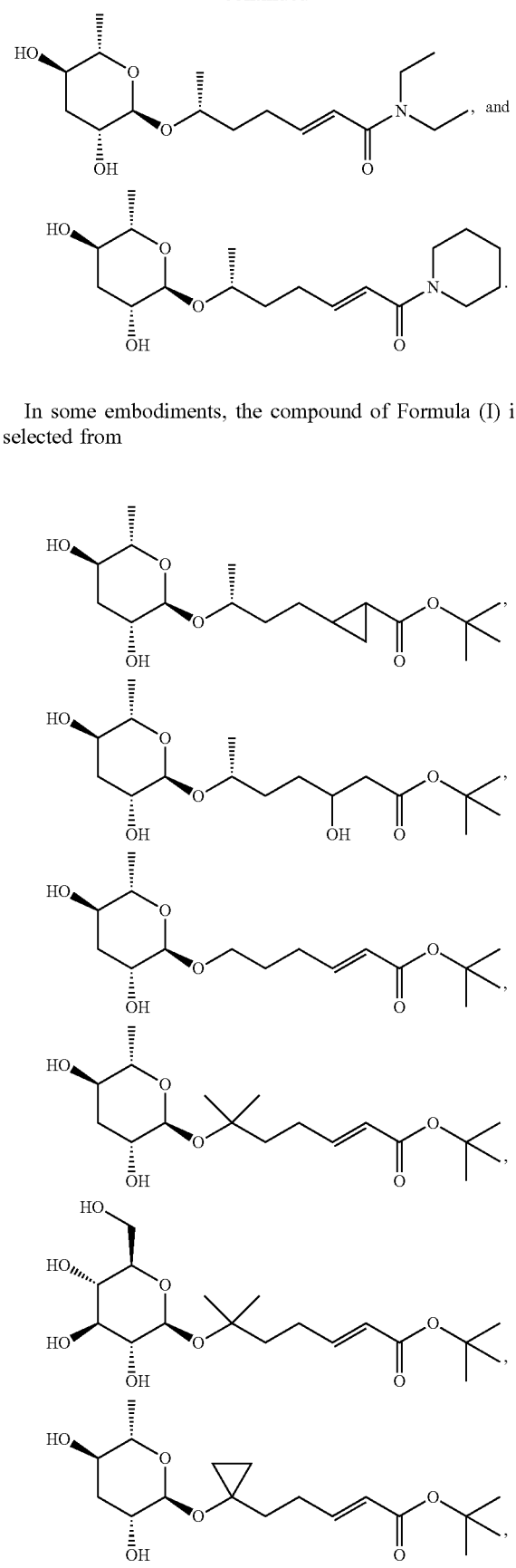
In some embodiments, the compound of Formula (I) is selected from -continued

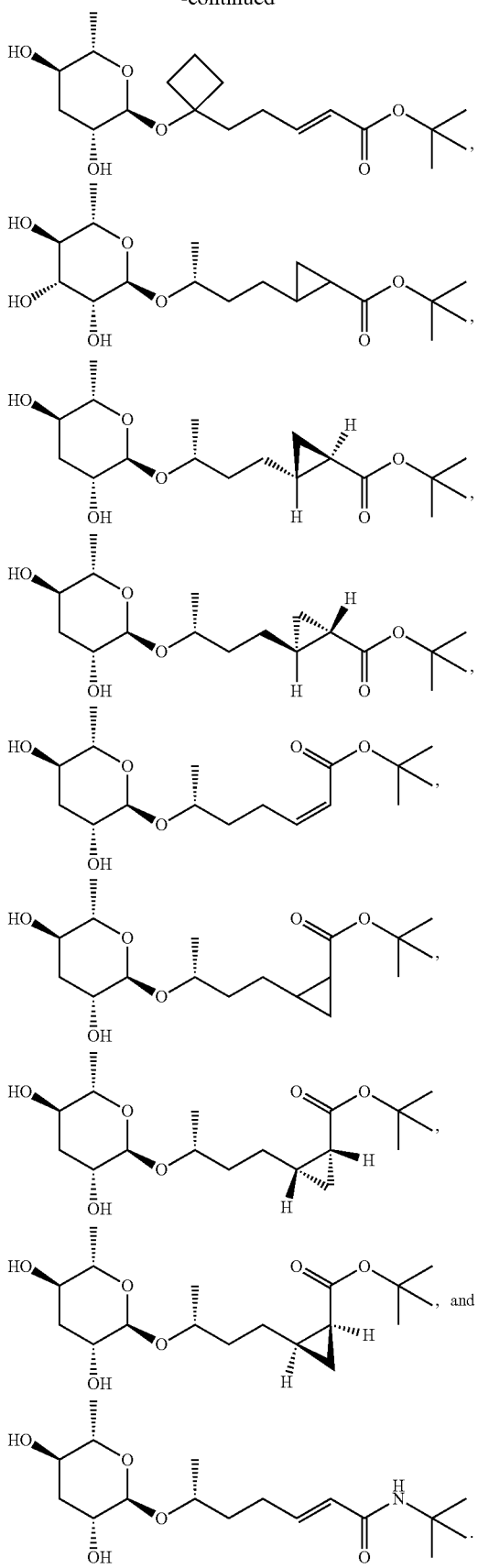

In one aspect, provided herein is a compound of Formula (II) with the following structural formula:

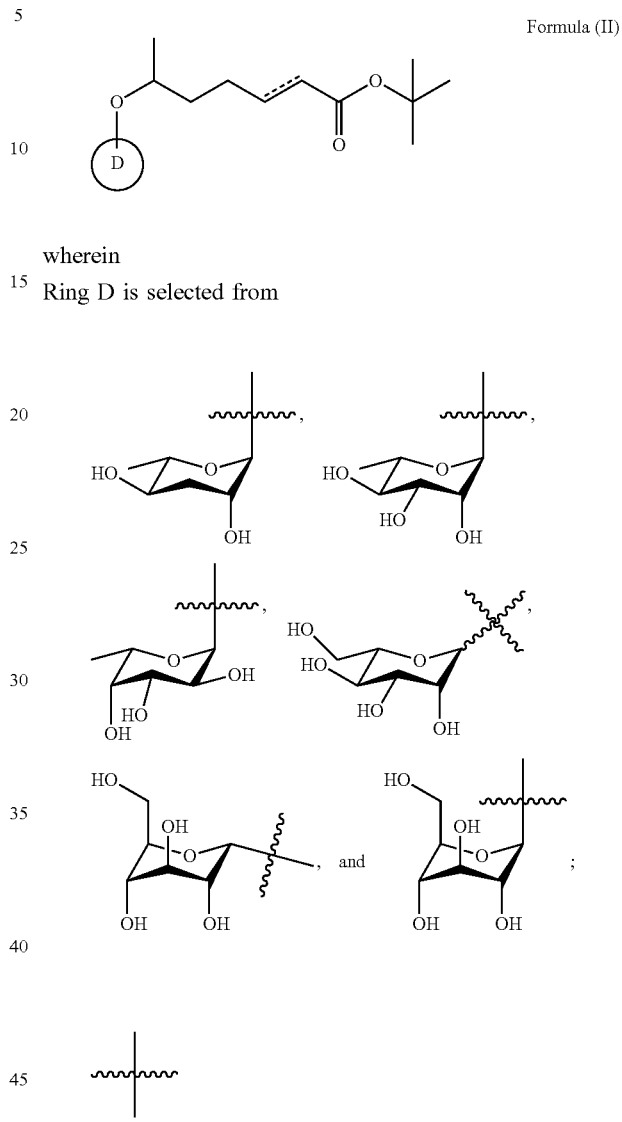

Formula (II)

wherein
Ring D is selected from represents the point of attachment of Ring D to the oxygen atom; and ⫽ is a double bond or a single bond.

In some embodiments, the compound of Formula (II) is the compound with the following structural formula:

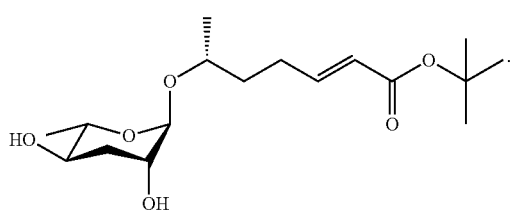

In some embodiments, the compound of Formula (II) is the compound with the following structural formula:

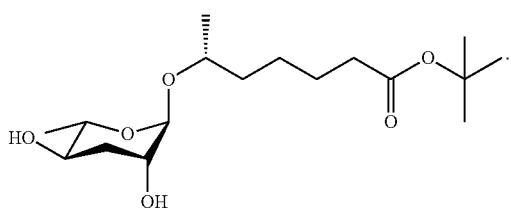
In some embodiments, the compound of Formula (II) is selected from
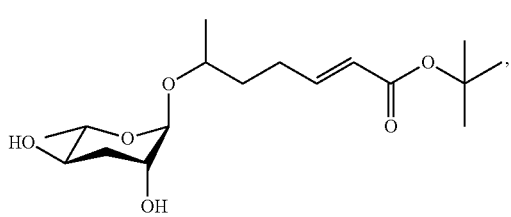
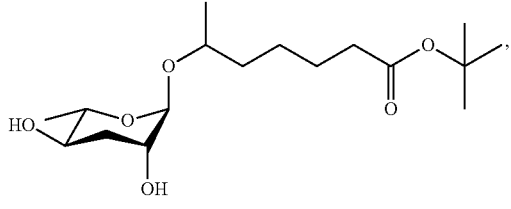
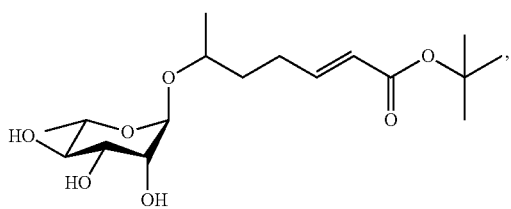
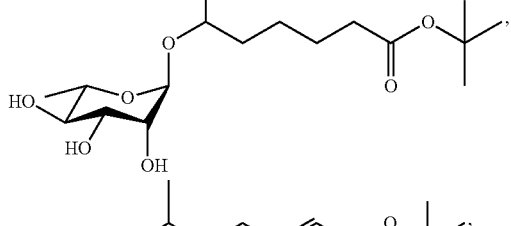
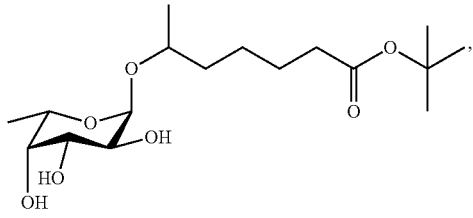
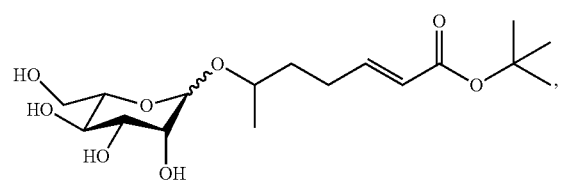
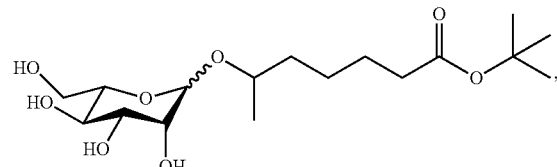
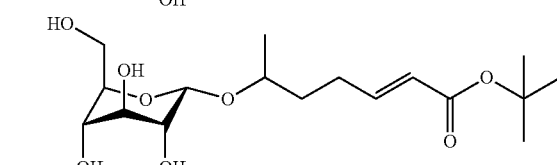
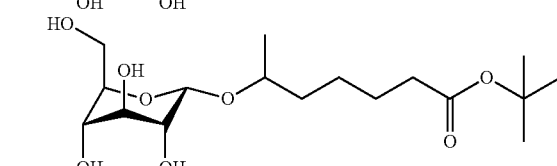
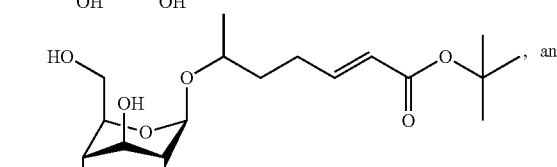
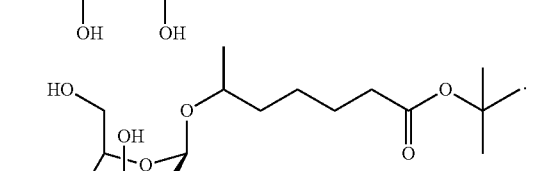
, and
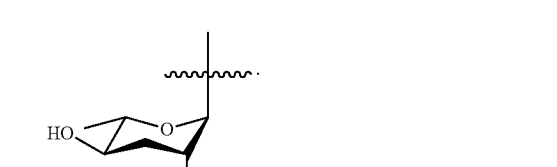
In certain embodiments, Ring D is
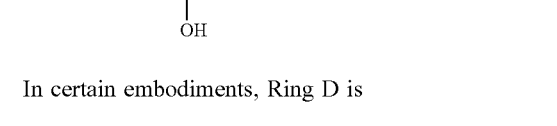
In certain embodiments, Ring D is
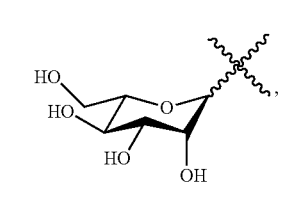

where

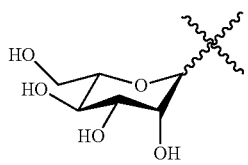

represents a mixture of

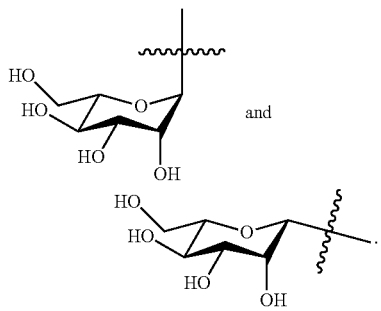

In certain embodiments, Ring D is

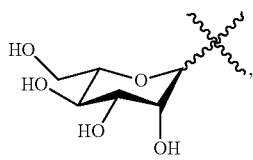

where

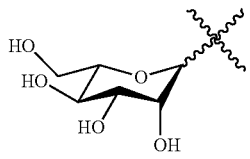

represents

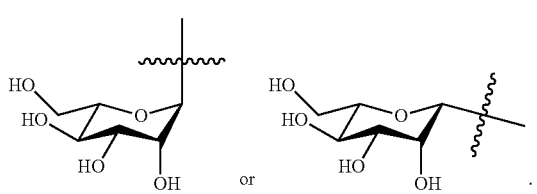

In some embodiments, ⫽ is a double bond.

In some embodiments, the stereochemistry at the methyl-substituted carbon is R.

In some embodiments, ⫽ is a double bond; and the stereochemistry at the methyl-substituted carbon is R.

Methods

In another aspect, provided herein are methods of reducing the proliferation or activation of macrophages, T cells, B cells, neutrophils, eosinophils, basophils, or lymphocytes, or a combination thereof, in a subject in need thereof comprising administering to the subject a therapeutically effective amount of the compound of having the structure of Formula (I)

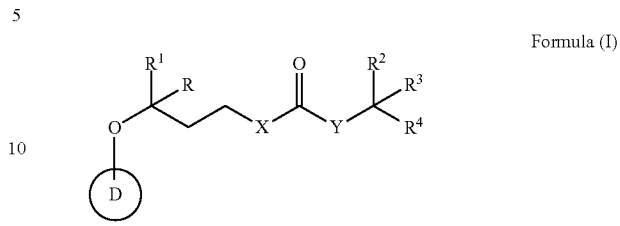

Formula (I)

wherein
Ring D is selected from

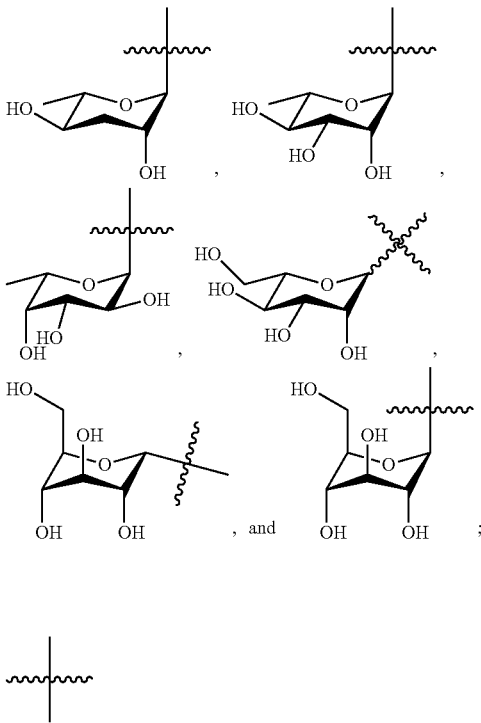

represents the point of attachment of Ring D to the oxygen atom;

X is —C($R^5$)$_2$—C($R^5$)$_2$— or E or Z —CH=CH—;

Y is O or N$R^6$;

R is H or CH$_3$, $R^1$ is H or CH$_3$;

or, R and $R^1$, taken together with the carbon atom to which they are bonded, form a 3- or 4-membered carbocyclic ring;

$R^2$ is H or CH$_3$;

$R^3$ is H or CH$_3$;

$R^4$ is CH$_3$, CH$_2$CH$_3$, a straight- or branched-chain C$_3$-C$_6$ alkyl, a C$_5$-C$_7$ cycloalkyl, a 6-membered aryl or heteroaryl, an aryl-substituted C$_1$-C$_6$ alkyl, or a heterocyclyl-substituted C$_1$-C$_6$ alkyl;

$R^5$, independently for each occurrence, is H or OH, or two instances of $R^5$, taken together with the carbon atom or carbon atoms to which they are bonded, form a 3-membered carbocyclic ring; and $R^6$ is H or $C_1$-$C_6$ alkyl,
or, when Y is $NR^6$, $R^4$ and $NR^6$, taken together with the carbon atom to which they are bonded, form a 5- or 6-membered heterocyclic ring;
thereby reducing the proliferation or activation of macrophages, T cells, B cells, neutrophils, eosinophils, basophils, lymphocytes, or a combination thereof in a subject.

In some embodiments of the methods disclosed herein, the compound of Formula (I) is selected from

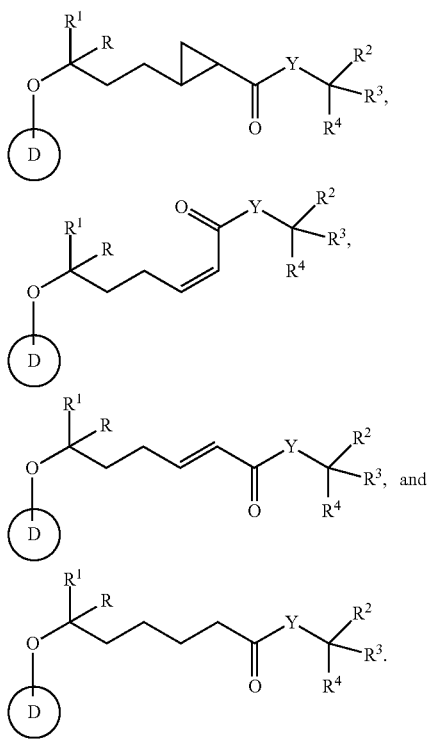

In some embodiments of the methods disclosed herein, X is —$C(R^5)_2$—$C(R^5)_2$—. In some embodiments, X is E or Z—CH=CH—. In some embodiments, X is —$C(H)_2$—$C(H)_2$—.

In some embodiments, X is —C(H)(OH)—$C(H)_2$—.

In some embodiments, X—$C(R^5)_2$—$C(R^5)_2$, two instances of $R^5$, taken together with the carbon atom or carbon atoms to which they are bonded, form a 3-membered carbocyclic ring. In some embodiments, X is

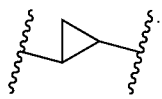 [SMILES: *C1CC1*]

In some embodiments, X is

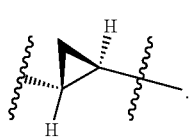 [SMILES: *[C@@H]1C[C@H]1*]

In some embodiments, X is

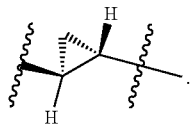 [SMILES: *[C@H]1C[C@@H]1*]

In some embodiments, X is

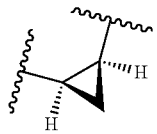

In some embodiments, X is

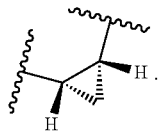 [SMILES: *[C@@H]1C[C@@H]1*]

In some embodiments of the methods disclosed herein, Y is $NR^6$. In some embodiments, Y is $NR^6$, wherein $R^6$ is H. In some embodiments, Y is $NR^6$, wherein $R^6$ is $C_1$-$C_6$ alkyl. In some embodiments, Y is $NR^6$, wherein $R^6$ is $CH_3$. In some embodiments, Y is $NR^6$, wherein $R^6$ is $CH_2CH_3$. In some embodiments, Y is $NR^6$, wherein $R^4$ and $NR^6$, taken together with the carbon atom to which they are bonded, form a 5- or 6-membered heterocyclic ring. In some embodiments, Y is O.

In some embodiments of the methods disclosed herein, R and $R^1$ are each $CH_3$. In some embodiments, R and $R^1$ are each $CH_3$. In some embodiments, R is $CH_3$; and $R^1$ is H. In some embodiments, R and $R^1$, taken together with the carbon atom to which they are bonded, form a cyclopropyl. In some embodiments, R and $R^1$, taken together with the carbon atom to which they are bonded, form a cyclobutyl.

In some embodiments of the methods disclosed herein, $R^2$ is H; $R^3$ is H or $CH_3$; and $R^4$ is $CH_3$, $CH_2CH_3$, a straight- or branched-chain $C_3$-$C_6$ alkyl, a $C_5$-$C_7$ cycloalkyl, a 6-membered aryl or heteroaryl, an aryl-substituted $C_1$-$C_6$ alkyl, or a heterocyclyl-substituted $C_1$-$C_6$ alkyl, or, when Y is $NR^6$, $R^4$ and $NR^6$, taken together with the carbon atom to which they are bonded, form a 5- or 6-membered heterocyclic ring. In some embodiments, $R^2$, $R^3$ and $R^4$ are each $CH_3$. In some embodiments, $R^2$ is H; $R^3$ is $CH_3$; and $R^4$ is $CH_3$. In some embodiments, $R^2$ is H; $R^3$ is H; and $R^4$ is $CH_2CH_3$. In some embodiments, $R^2$ is H; $R^3$ is H; and $R^4$ is $CH(CH_2CH_3)_2$. In some embodiments, $R^2$ is H; $R^3$ is H; and $R^4$ is $CH(CH_2CH_3)_2$. In some embodiments, $R^2$ is H; $R^3$ is H; and $R^4$ is cyclohexyl. In some embodiments, $R^2$ is H; $R^3$ is H; and $R^4$ is phenyl. In some embodiments, $R^2$ is H; $R^3$ is H; and $R^4$ is pyridinyl.

In another aspect, provided herein are methods of reducing the proliferation or activation of macrophages, T cells, B cells, neutrophils, eosinophils, basophils, or lymphocytes, or a combination thereof, in a subject in need thereof comprising administering to the subject a therapeutically effective amount of the compound of having the structure of Formula (II)

Formula (II)

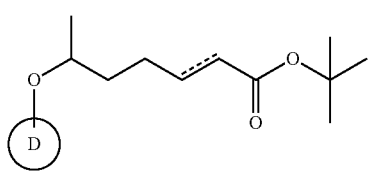

wherein
Ring D is selected from

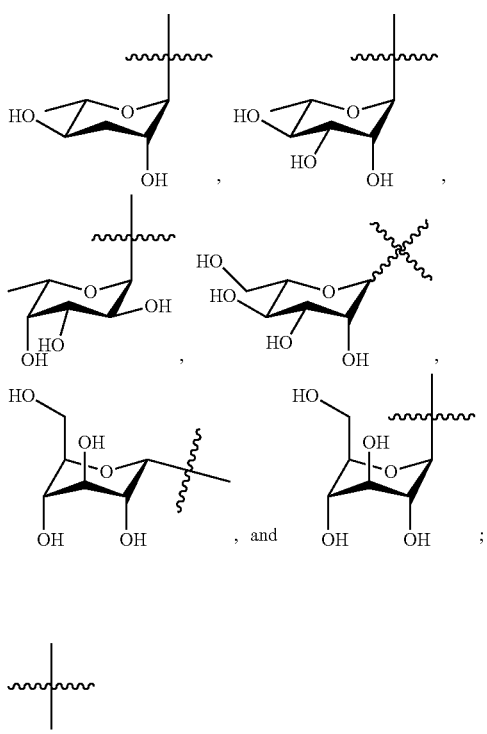

represents the point of attachment of Ring D to the oxygen atom; and

⫽ is a double bond or a single bond;

thereby reducing the proliferation or activation of macrophages, T cells, B cells, neutrophils, eosinophils, basophils, lymphocytes, or a combination thereof in a subject.

In some embodiments of the methods disclosed herein, the compound of Formula (II) is the compound having the structure:

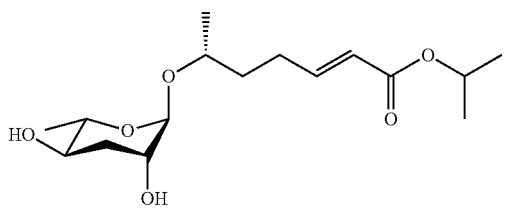

In some embodiments of the methods disclosed herein, the compound of Formula (II) is the compound having the structure:

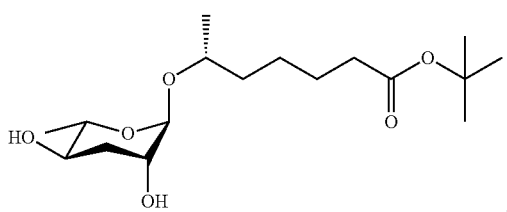

In some embodiments of the methods disclosed herein, the compound of Formula (II) is a compound selected from

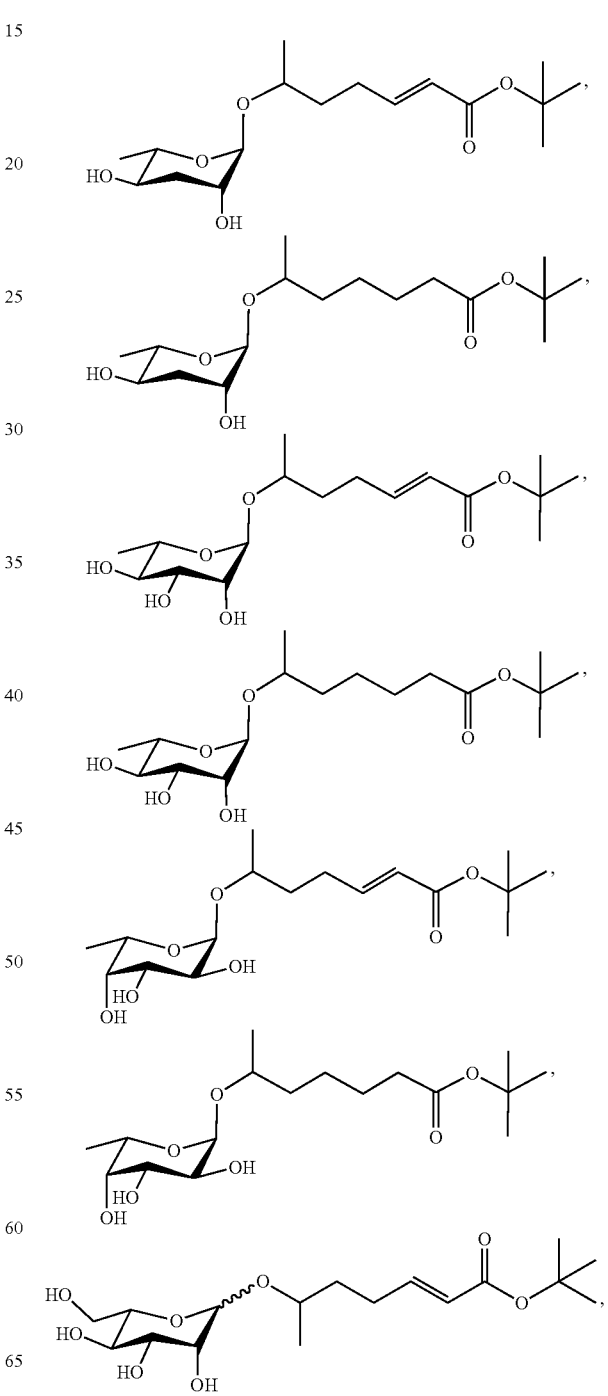

-continued

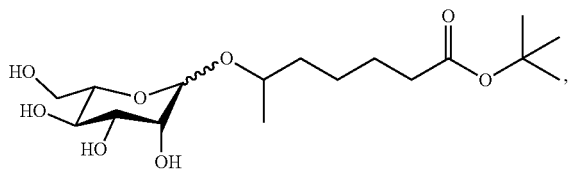

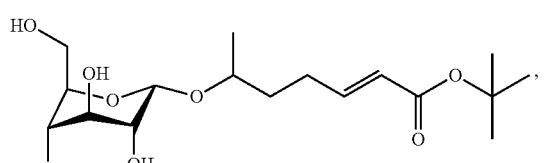

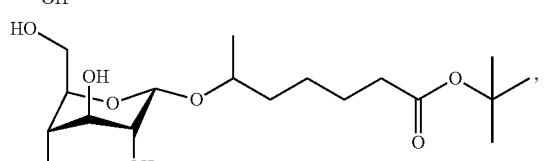

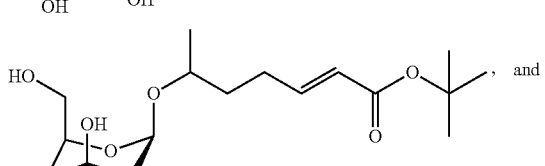

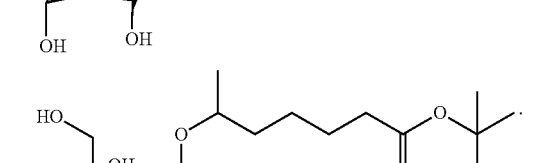

In another aspect, provided herein are methods of treating a disease or condition in a subject in need thereof comprising administering to the subject an effective amount of the compound having the structure of Formula (I), Formula (I)

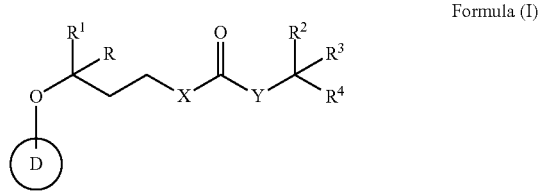

wherein
Ring D is selected from

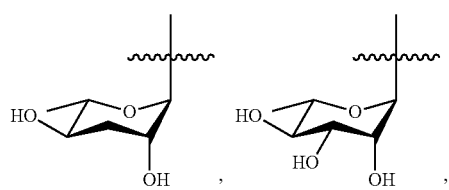

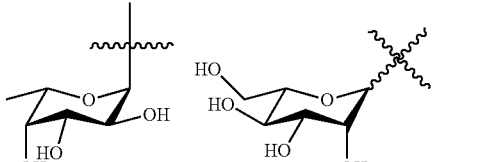

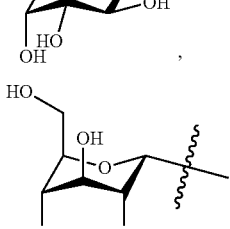

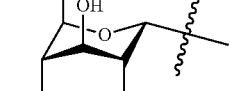

X is —C($R^5$)$_2$—C($R^5$)$_2$— or E or Z—CH=CH—;
Y is O or $NR^6$;
R is H or $CH_3$,
$R^1$ is H or $CH_3$;
  or, R and $R^1$, taken together with the carbon atom to which they are bonded, form a 3- or 4-membered carbocyclic ring;
$R^2$ is H or $CH_3$;
$R^3$ is H or $CH_3$;
$R^4$ is $CH_3$, $CH_2CH_3$, a straight- or branched-chain $C_3$-$C_6$ alkyl, a $C_5$-$C_7$ cycloalkyl, a 6-membered aryl or heteroaryl, an aryl-substituted $C_1$-$C_6$ alkyl, or a heterocyclyl-substituted $C_1$-$C_6$ alkyl;
$R^5$, independently for each occurrence, is H or OH,
  or two instances of $R^5$, taken together with the carbon atom or carbon atoms to which they are bonded, form a 3-membered carbocyclic ring; and
$R^6$ is H or $C_1$-$C_6$ alkyl,
  or, when Y is $NR^1$, $R^4$ and $NR^6$, taken together with the carbon atom to which they are bonded, form a 5- or 6-membered heterocyclic ring; and
the disease or condition is an inflammatory disorder, an autoimmune disorder, or both.

In some embodiments of the methods disclosed herein, the compound of Formula (I) is selected from

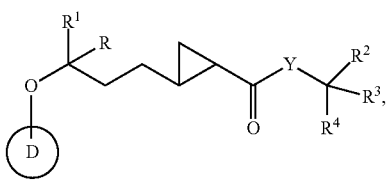

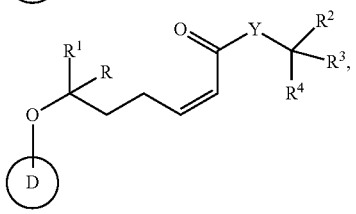

-continued

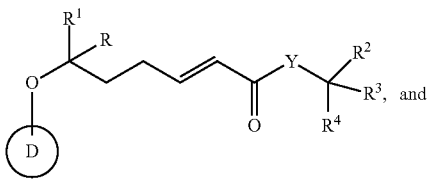

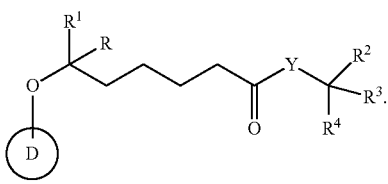

In some embodiments of the methods disclosed herein, X is —C(R⁵)₂—C(R⁵)₂—. In some embodiments, X is E or Z—CH═CH—. In some embodiments, X is —C(H)₂—C(H)₂—. In some embodiments, X is —C(H)(OH)—C(H)₂—.

In some embodiments, X—C(R⁵)₂—C(R⁵)₂, two instances of R⁵, taken together with the carbon atom or carbon atoms to which they are bonded, form a 3-membered carbocyclic ring. In some embodiments, X is

In some embodiments, X is

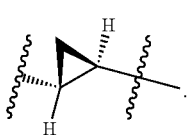 [SMILES: *[C@@H]1C[C@H]1*]

In some embodiments, X is

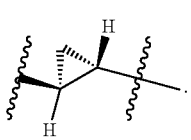 [SMILES: *[C@H]1C[C@@H]1*]

In some embodiments, X is

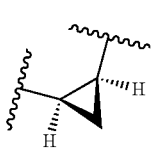

In some embodiments, X is

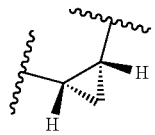

In some embodiments of the methods disclosed herein, Y is NR⁶. In some embodiments, Y is NR⁶, wherein R⁶ is H. In some embodiments, Y is NR⁶, wherein R⁶ is C₁-C₆ alkyl. In some embodiments, Y is NR⁶, wherein R⁶ is CH₃. In some embodiments, Y is NR⁶, wherein R⁶ is CH₂CH₃. In some embodiments, Y is NR⁶, wherein R⁴ and NR⁶, taken together with the carbon atom to which they are bonded, form a 5- or 6-membered heterocyclic ring. In some embodiments, Y is O.

In some embodiments of the methods disclosed herein, R and R¹ are each CH₃. In some embodiments, R and R¹ are each CH₃. In some embodiments, R is CH₃; and R¹ is H. In some embodiments, R and R¹, taken together with the carbon atom to which they are bonded, form a cyclopropyl. In some embodiments, R and R¹, taken together with the carbon atom to which they are bonded, form a cyclobutyl.

In some embodiments of the methods disclosed herein, R² is H; R³ is H or CH₃; and R⁴ is CH₃, CH₂CH₃, a straight- or branched-chain C₃-C₆ alkyl, a C₅-C₇ cycloalkyl, a 6-membered aryl or heteroaryl, an aryl-substituted C₁-C₆ alkyl, or a heterocyclyl-substituted C₁-C₆ alkyl, or, when Y is NR⁶, R⁴ and NR⁶, taken together with the carbon atom to which they are bonded, form a 5- or 6-membered heterocyclic ring. In some embodiments, R², R³ and R⁴ are each CH₃. In some embodiments, R² is H; R³ is CH₃; and R⁴ is CH₃. In some embodiments, R² is H; R³ is H; and R⁴ is CH₂CH₃. In some embodiments, R² is H; R³ is H; and R⁴ is CH(CH₂CH₃)₂. In some embodiments, R² is H; R³ is H; and R⁴ is CH(CH₂CH₃)₂. In some embodiments, R² is H; R³ is H; and R⁴ is cyclohexyl. In some embodiments, R² is H; R³ is H; and R⁴ is phenyl. In some embodiments, R² is H; R³ is H; and R⁴ is pyridinyl.

In another aspect, provided herein are methods of treating a disease or condition in a subject in need thereof comprising administering to the subject an effective amount of the compound having the structure of Formula (II)

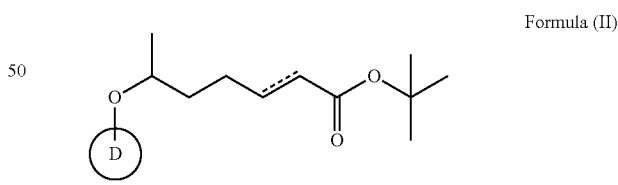

Formula (II)

wherein
Ring D is selected from

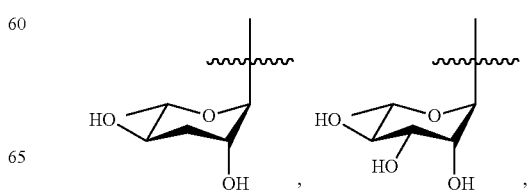

-continued

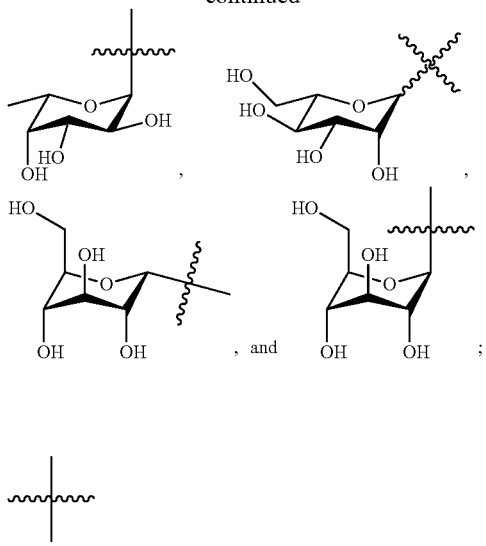

, and represents the point of attachment of Ring D to the oxygen atom; and

⫽ is a double bond or a single bond; and the disease or condition is an inflammatory disorder, an autoimmune disorder, or both.

In certain embodiments, the disorder is an IL-6, IL-1β and TNFα-mediated disease. The IL-6-IL-1β and/or TNFα-mediated diseases that can be treated with a composition comprising the compound having the structure of Formula (I) include but are not limited to the diseases discussed herein.

In some embodiments, the inflammatory disorder, the autoimmune disorder, or both is selected from Acne vulgaris,
Agammaglobulinemia,
Allergic rhinitis,
Amyloidosis,
Anaphylaxis,
Ankylosing spondylitis,
Anti-GBM/Anti-TBM nephritis (anti-glomerular basement membrane antibody disease),
Antiphospholipid syndrome,
Autism,
Autoimmune hepatitis,
Autoimmune inner ear disease,
Atopic dermatitis,
Asthma,
Castleman disease,
Celiac disease,
Chagas disease,
Chronic nonbacterial osteomyelitis,
chronic prostatitis,
Chronic recurrent multifocal osteomyelitis,
Cogan's syndrome,
Cold agglutinin disease,
CREST syndrome,
Crohn's disease,
Dermatomyositis,
Devic's disease (neuromyelitis optica),
Discoid lupus,
Endometriosis,
Eosinophilic asthma,
Eosinophilic cardiomyopathy,
Eosinophilic colitis,
Eosinophilic cystitis,
Eosinophilic disorder,
Eosinophilic enteritis,
Eosinophilic esophagitis (EoE),
Eosinophilic fasciitis,
Eosinophilic gastritis,
Eosinophilic gastroenteritis,
Eosinophilic granulomatosis with polyangiitis,
Eosinophilic pneumonia,
Evan's syndrome,
Fibromyalgia,
Food allergy,
Giant cell arteritis,
Giant cell myocarditis,
Glomerulonephritis,
Goodpasture's syndrome (anti-GBM),
Granulomatosis with polyangiitis (Wegener's),
Graves' disease,
Guillain-Barre syndrome,
Hashimoto's thyroiditis,
Hemolytic anemia (some types),
Hemophagocytic lymphohistiocytosis,
Henoch-Schonlein purpura,
Hypereosinophilic syndrome,
Hypersensitivities,
Hypogammaglobulinemia,
Hypoproliferative anemia,
IgA Nephropathy,
Inclusion body myositis,
Interstitial cystitis,
Inflammatory Bowel Disease,
Juvenile arthritis,
Juvenile/Type 1 Diabetes,
Juvenile myositis,
Kawasaki syndrome,
Lichen planus,
Lichen sclerosus,
Mastocytosis,
Meniere's disease,
Multiple sclerosis,
Myasthenia gravis,
Myopathy (some types),
Microscopic polyangiitis,
Optic neuritis,
paroxysmal nocturnal hemoglobinuria,
Pemphigus,
Perennial allergy,
Pernicious anemia,
pelvic inflammatory disease,
Polyarteritis nodosa,
Polymyalgia rheumatica,
Polymyositis,
Primary biliary cirrhosis,
Primary sclerosing cholangitis,
Psoriasis,
Psoriatic arthritis,
Reactive arthritis,
Reperfusion Injury,
Rheumatic fever,
Rheumatoid arthritis,
Sarcoidosis,
Scleroderma,
Seasonal allergy,
Selective IgA Deficiency,
sickle cell disease,
Sjogren's syndrome, Still disease,
systemic Lupus erythematosus (SLE),
Systemic juvenile idiopathic arthritis,
Systemic sclerosis,
Takayasu arthritis,
Temporal arteritis/Giant cell arteritis,
Transplant rejection,
Transverse myelitis,
Ulcerative colitis,
Uveitis,
Vasculitis,
Vitiligo,
Viral myocarditis, and
Wegener's granulomatosis (Granulomatosis with Polyangiitis (GPA)).

In certain embodiments, the composition is administered orally. In other embodiments, the composition is administered by direct injection, topically, and/or intravenously.

In some embodiments, the subject is selected from primates, humans, equines, horses, cattle, cows, swine, sheep, rodents, rats, pets, dogs, and guinea pigs. In certain preferred embodiments, the subject is a human. In other embodiments, the subject is a rodent. In yet other embodiments, the subject is selected from primates, equines, horses, cattle, cows, swine, sheep, rats, pets, cats, dogs and guinea pigs. In some embodiments, the subject is a female. In other embodiments, the subject is a male. In some embodiments, the subject is an infant, a child, or an adult. In certain embodiments, the subject has an elevated level of IL-6, IL-1β and TNFα.

In some embodiments, the methods reduce mucus production in the subject.

In some embodiments, the method is a method of reducing the proliferation or activation of eosinophils in the subject. In some embodiments, the method is a method of reducing the proliferation or activation of lymphocytes in the subject. In some embodiments, the method is a method of reducing the proliferation or activation of macrophages in the subject. In some embodiments, the method is a method of reducing the proliferation or activation of T cells in the subject. In some embodiments, the method is a method of reducing the proliferation or activation of B cells in the subject. In some embodiments, the method is a method of reducing the proliferation or activation of neutrophils in the subject. In some embodiments, the method is a method of reducing the proliferation or activation of basophils in the subject. In some embodiments, the method is a method of reducing the proliferation or activation of a combination of Macrophages, T cells, B cells, Neutrophils, Eosinophils, Basophils, or Lymphocytes in the subject.

In another aspect, provided herein are uses of the compound having the structure of Formula (I) in the manufacture of a medicament for the treatment of an autoimmune and/or inflammatory disease, e.g., an IL-6, IL-1β and/or TNFα-mediated disease. In some embodiments of the uses, the compound is compound 1. In some embodiments of the uses, the compound is compound 10.

Elevated levels of IL-6, IL-1β and/or TNFα have been found in patients with various diseases, and studies have shown that IL-6, IL-1β, and/or TNFα contribute to these diseases' pathogeneses.

These IL-6-, IL-1β, and/or TNFα-mediated diseases may include diseases that affect the cardiac system, such as Giant Cell Myocarditis, Amyloidosis, Viral Myocarditis, and/or Rheumatic Fever.

These IL-6-, IL-1β, and/or TNFα-mediated diseases may include diseases that affect the auditory system, such as Autoimmune inner ear disease and/or Meniere's disease.

These IL-6-, IL-1β, and/or TNFα-mediated diseases may include diseases that affect the endocrine system, such as Graves' disease, Hashimoto's thyroiditis, Juvenile/Type 1 Diabetes, and/or Amyloidosis.

These IL-6-, IL-1β, and/or TNFα-mediated diseases may include diseases that affect the gastrointestinal system, such as Crohn's disease, Eosinophilic esophagitis, Inflammatory Bowel Disease, Ulcerative Colitis, and/or Celiac Disease.

These IL-6-, IL-1β, and/or TNFα-mediated diseases may include diseases that affect the hematologic system, such as Cold agglutinin disease, Evan's syndrome, Hemolytic anemia, Hypoproliferative anemia, Pernicious anemia, Antiphospholipid syndrome, Agammaglobulinemia, Hypogammaglobulinemia, Hemophagocytic lymphohistiocytosis, paroxysmal nocturnal hemoglobinuria, sickle cell disease and/or Reperfusion Injury.

These IL-6-, IL-1β, and/or TNFα-mediated diseases may include diseases that affect the hepatic system, such as Primary sclerosing cholangitis, Primary biliary cirrhosis, and/or Autoimmune hepatitis.

These IL-6-, IL-1β, and/or TNFα-mediated diseases may include diseases that affect the immune system, such as Allergic rhinitis, Anaphylaxis, Hypersensitivities, Lupus (SLE), Mastocytosis, Perennial allergy, Seasonal allergy, Sjogren's syndrome, Transplant rejection, Food allergy, Celiac disease, Agammaglobulinemia, Hypogammaglobulinemia, Scleroderma, Selective IgA Deficiency, and/or Microscopic polyangiitis.

These IL-6-, IL-1β, and/or TNFα-mediated diseases may include diseases that affect the infectious systemic response, such as Chagas Disease.

These IL-6-, IL-1β, and/or TNFα-mediated diseases may include diseases that affect the lymph system, such as Castleman Disease and/or Sarcoidosis.

These IL-6-, IL-1β, and/or TNFα-mediated diseases may include diseases that affect the muscular system, such as Dermatomyositis, Inclusion body myositis, some types of Myopathy, Polymyositis, Viral myocarditis, Guillain-Barre syndrome, Fibromyalgia, Myasthenia gravis, Scleroderma, and/or Juvenile myositis.

These IL-6-, IL-1β, and/or TNFα-mediated diseases may include diseases that affect the neurological system, such as Guillain-Barre Syndrome, Devic's disease (neuromyelitis optica), Multiple sclerosis, Transverse myelitis, Optic neuritis, and/or Myasthenia gravis.

These IL-6-, IL-1β, and/or TNFα-mediated diseases may include diseases that affect the optic system, such as Uveitis and/or Optic neuritis.

These IL-6-, IL-1β, and/or TNFα-mediated diseases may include diseases that affect the psychiatric system, such as autism.

These IL-6-, IL-1β, and/or TNFα-mediated diseases may include diseases that affect the renal system, such as Glomerulonephritis, and/or IgA Nephropathy.

These IL-6-, IL-1β, and/or TNFα-mediated diseases may include diseases that affect the respiratory system, such as asthma and/or sarcoidosis.

These IL-6-, IL-1β, and/or TNFα-mediated diseases may include diseases that affect the rheumatic system, such as Ankylosing spondylitis, Anti-GBM/Anti-TBM nephritis, Chronic recurrent multifocal osteomyelitis, Cogan's syndrome, Goodpasture's syndrome (anti-GBM), Juvenile arthritis, Polymyalgia rheumatica, Rheumatoid arthritis, CREST syndrome, Eosinophilic fasciitis, Psoriatic arthritis, Antiphospholipid syndrome, Amyloidosis, and/or rheumatic fever.

These IL-6-, IL-1β, and/or TNFα-mediated diseases may include diseases that affect the dermal and connective tissue system, such as CREST syndrome, Eosinophilic fasciitis, acne vulgaris, Atopic dermatitis, Discoid lupus, Henoch-Schonlein purpura, Lichen planus, Lichen sclerosus, Pemphigus, Psoriasis, Vitiligo, Juvenile myositis, Sarcoidosis, Psoriatic arthritis, Scleroderma, and/or Rheumatic fever.

These IL-6-, IL-1β, and/or TNFα-mediated diseases may include diseases that affect the urological system, such as chronic prostatitis and/or interstitial cystitis.

These IL-6-, IL-1β, and/or TNFα-mediated diseases may include diseases that affect the reproductive system, such as Endometriosis and/or pelvic inflammatory disease.

These IL-6-, IL-1β, and/or TNFα-mediated diseases may include diseases that affect the vascular system, such as Giant cell arteritis, Granulomatosis with polyangiitis (Wegener's), Kawasaki syndrome, Polyarteritis nodosa, Temporal arteritis/Giant cell arteritis, Vasculitis, Scleroderma, Microscopic Polyangiitis, and/or Reperfusion Injury.

In some embodiments, the disease or condition is an eosinophilic disorder selected from Eosinophilic asthma, Eosinophilic cardiomyopathy Eosinophilic colitis, Eosinophilic cystitis, Eosinophilic enteritis, Eosinophilic esophagitis (EoE), Eosinophilic fasciitis, Eosinophilic gastritis, Eosinophilic gastroenteritis, Eosinophilic granulomatosis with polyangiitis, Eosinophilic pneumonia, and Hypereosinophilic syndrome.

In some embodiments, the disease or condition is selected from EoE, asthma, inflammatory bowel diseases, rheumatoid arthritis, or multiple sclerosis. In certain embodiments, the disease or condition is asthma, inflammatory bowel disease, or type 1 diabetes. In certain preferred embodiments, the disease or condition is EoE. EoE is a chronic immune and antigen-mediated disease that is characterized by eosinophilic infiltration into the tissue of the esophagus, resulting in difficulty swallowing, food impaction, regurgitation or vomiting, and decreased appetite. It is defined by the symptoms as well as the finding of a high number of eosinophils found in the esophageal tissue through endoscopic biopsy (eosinophils are not normally found in the esophagus).

Currently, there are no approved drugs in the US for the treatment of EoE. Rather, there is a trial-and-error approach of different classes of treatment, ranging from food elimination, off-label steroid use, and surgical intervention. Between 40-50% of patients do not respond to first line treatments.

In some embodiments, provided herein are methods of reducing IL-6-, IL-1β, and/or TNFα production from a cell, comprising contacting the cell with a composition comprising the compound having the structure of Formula (I) or (II). In some embodiments of the methods, the compound is compound 1. In some embodiments of the methods, the compound is compound 10.

In some embodiments of any of the methods disclosed herein, the compound of Formula (I) is selected from

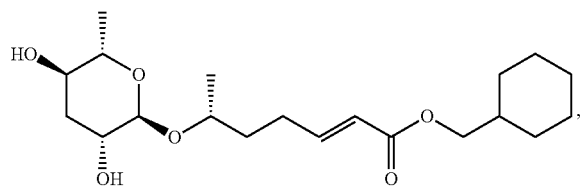

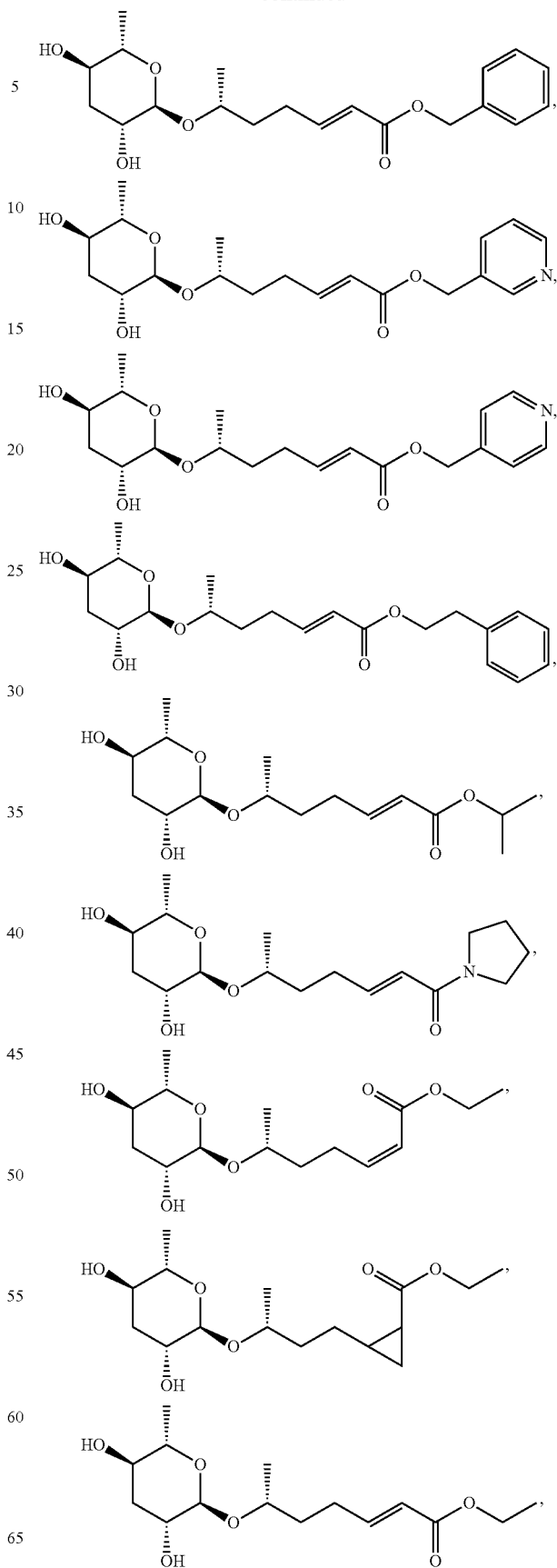

35
-continued
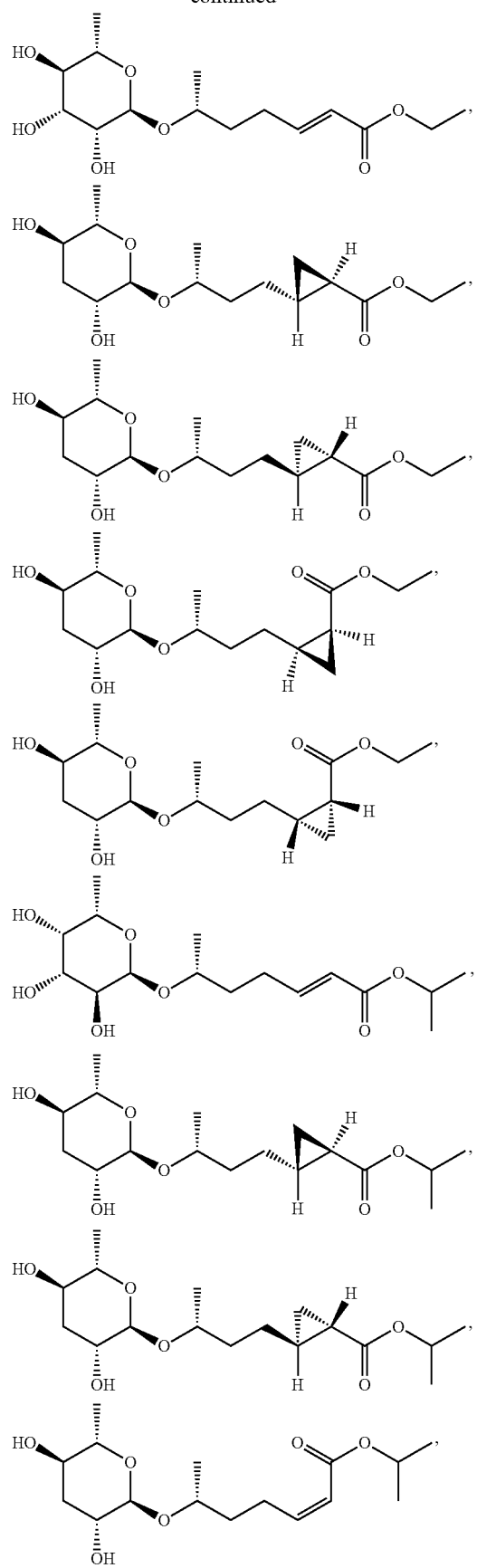
36
-continued
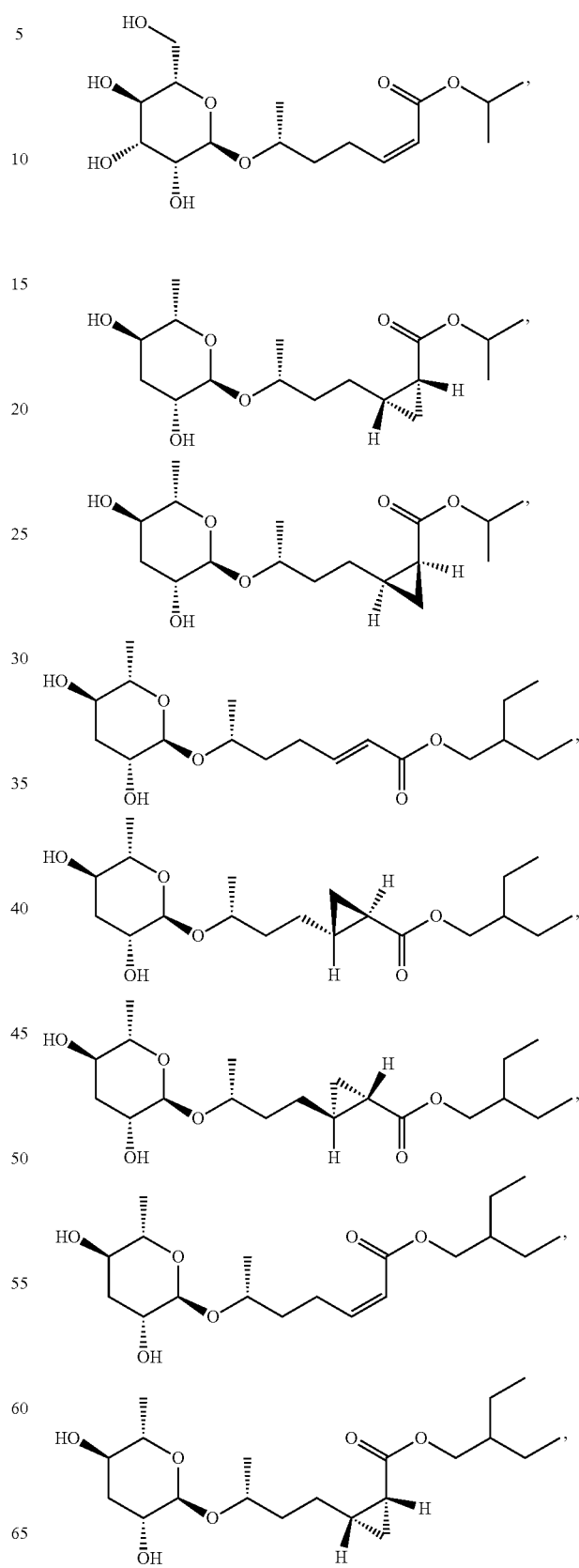

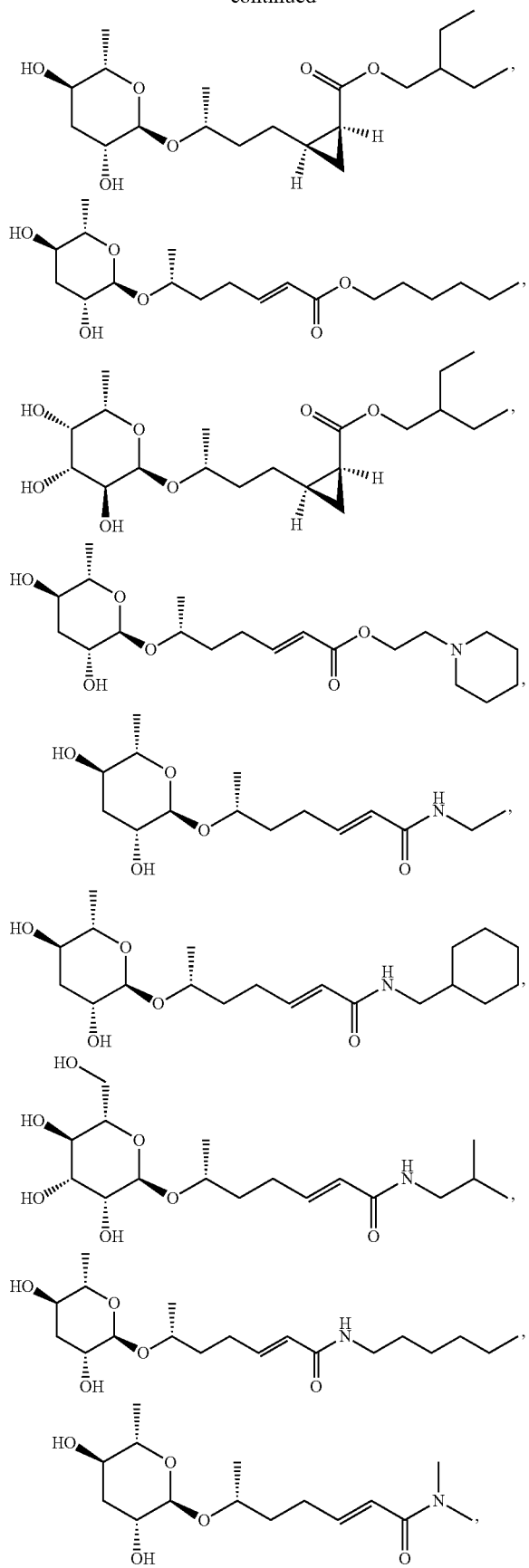
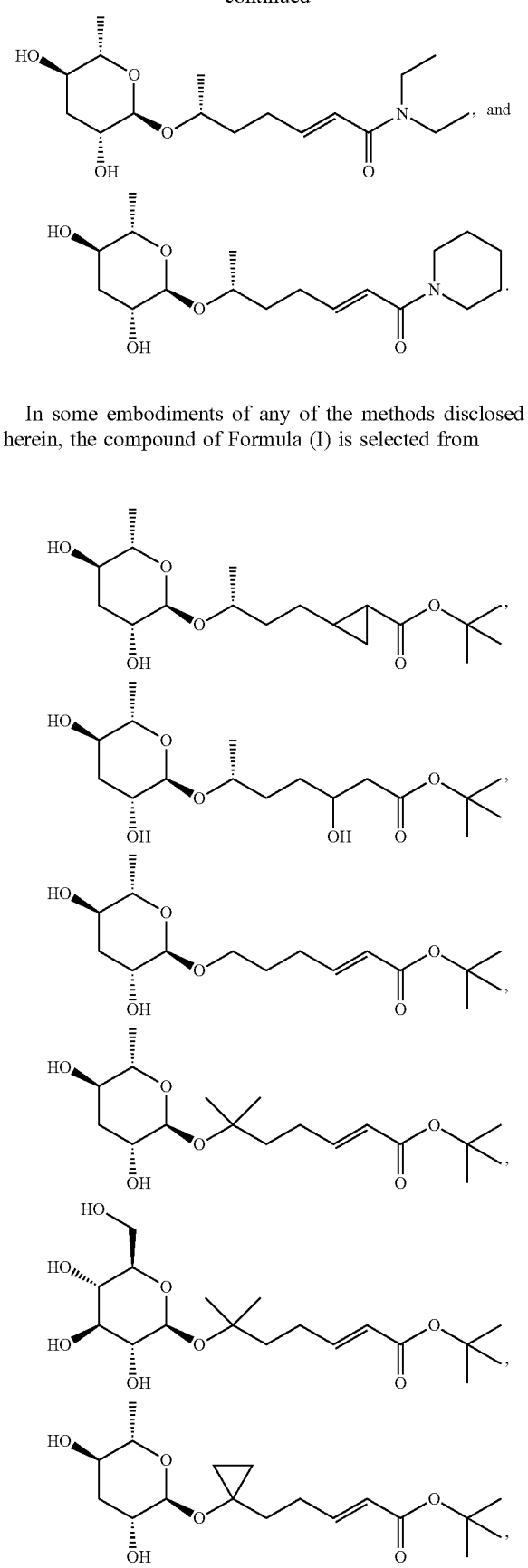
In some embodiments of any of the methods disclosed herein, the compound of Formula (I) is selected from

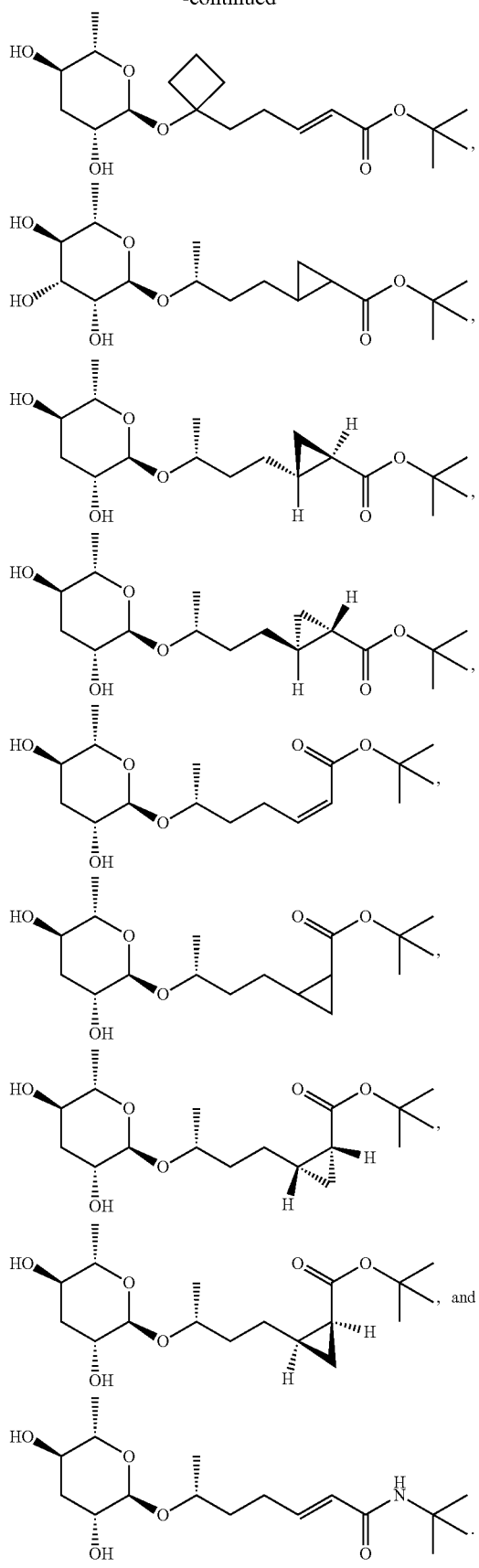
In some embodiments of any of the methods, the compound of Formula (II) is selected from
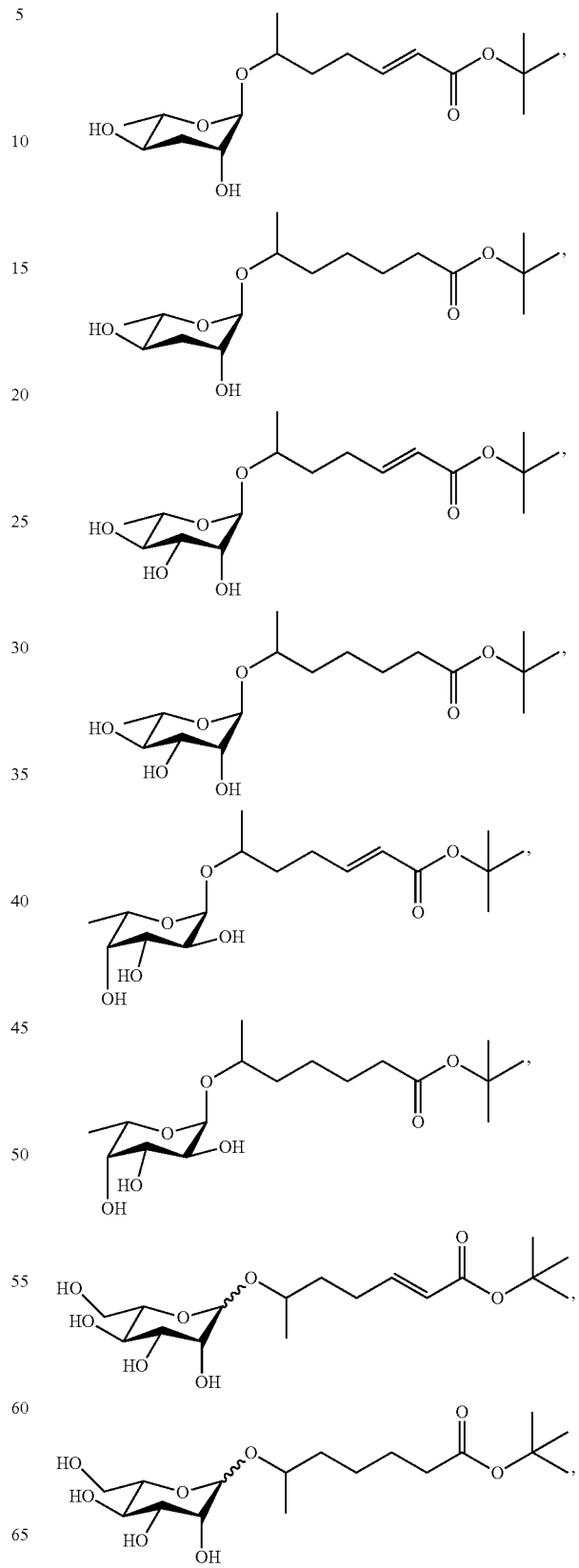

-continued

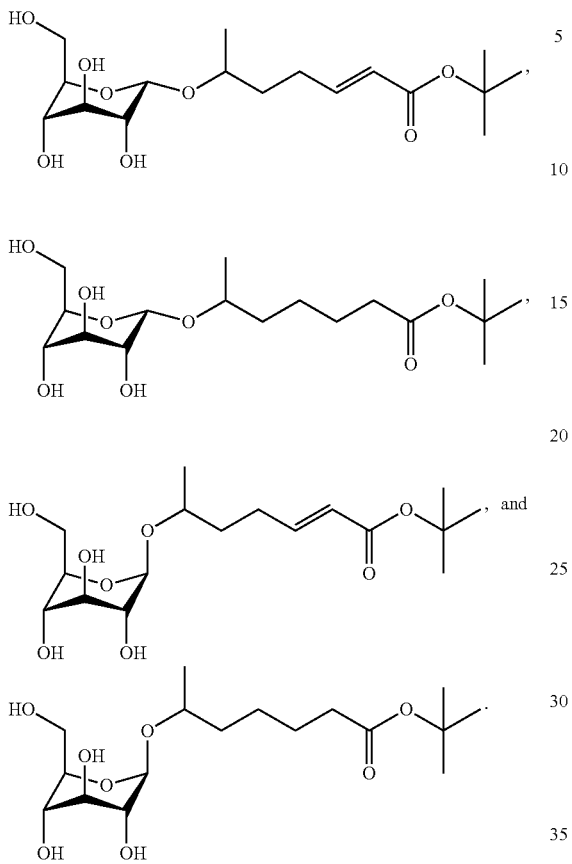

Such methods may be performed in vivo or in vitro.

In some embodiments, administration of the compound having the structure of Formula (I) modulate drug metabolism and pharmacokinetics compared to other ascaroside compounds or derivatives, such as ascr #7. In some embodiments, administration of the compound having the structure of Formula (I) or (II) modulates one or more of the following: IL-6 production from a cell, IL-1β production from a cell, TNFα production from a cell, CCL26 production from a cell, stability in hepatocytes, stability in plasma, bidirectional permeability in various cells or systems (e.g., intestinal barrier), plasma protein binding, CYP inhibition, metabolites (e.g., produced in the liver), and/or compound absorption (e.g., based on lipophilicity).

Pharmaceutical Compositions

In another aspect, provided herein are pharmaceutical formulations comprising a pharmaceutically acceptable carrier; and the compound having the structure of Formula (I):

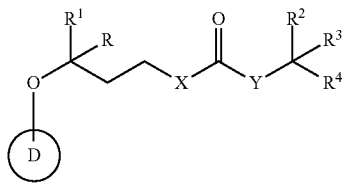

Formula (I)

wherein
Ring D is selected from

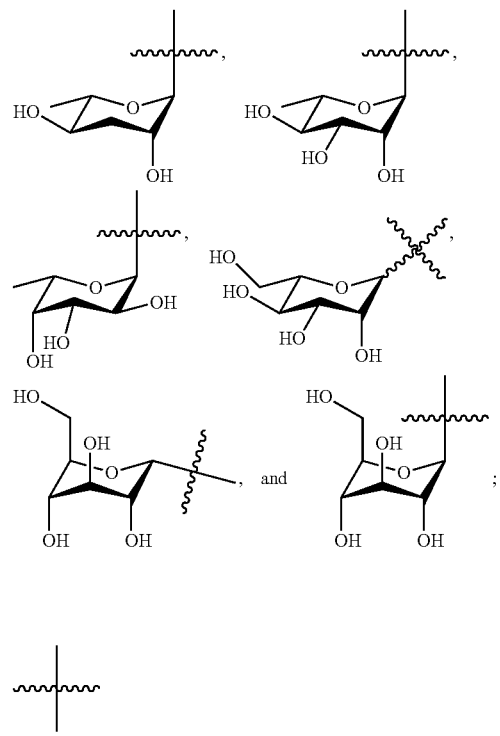

represents the point of attachment of Ring D to the oxygen atom;

X is —C($R^5$)$_2$—C($R^5$)$_2$— or E or Z—CH=CH—;

Y is O or $NR^6$;

R is H or $CH_3$, $R^1$ is H or $CH_3$;
  or, R and $R^1$, taken together with the carbon atom to which they are bonded, form a 3- or 4-membered carbocyclic ring;

$R^2$ is H or $CH_3$;

$R^3$ is H or $CH_3$;

$R^4$ is $CH_3$, $CH_2CH_3$, a straight- or branched-chain $C_3$-$C_6$ alkyl, a $C_5$-$C_7$ cycloalkyl, a 6-membered aryl or heteroaryl, an aryl-substituted $C_1$-$C_6$ alkyl, or a heterocyclyl-substituted $C_1$-$C_6$ alkyl;

$R^5$, independently for each occurrence, is H or OH,
  or two instances of $R^5$, taken together with the carbon atom or carbon atoms to which they are bonded, form a 3-membered carbocyclic ring; and $R^6$ is H or $C_1$-$C_6$ alkyl,
  or, when Y is $NR^6$, $R^4$ and $NR^6$, taken together with the carbon atom to which they are bonded, form a 5- or 6-membered heterocyclic ring.

In some embodiments of the pharmaceutical formulations, X is —C($R^5$)$_2$—C($R^5$)$_2$—.

In some embodiments, X is E or Z—CH=CH—. In some embodiments, X is —C(H)$_2$—C(H)$_2$—.

In some embodiments, X is —C(H)(OH)—C(H)$_2$—.

In some embodiments, X—C($R^5$)$_2$—C($R^5$)$_2$, two instances of $R^5$, taken together with the carbon atom or carbon atoms to which they are bonded, form a 3-membered carbocyclic ring. In some embodiments, X is

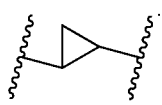 [SMILES: *C1CC1*]

In some embodiments, X is

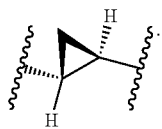 [SMILES: *[C@@H]1C[C@H]1*]

In some embodiments, X is

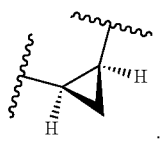 [SMILES: *[C@@H]1C[C@@H]1*]

In some embodiments, X is

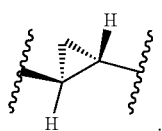

In some embodiments, X is

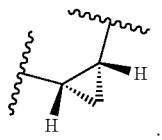 [SMILES: *[C@@H]1C[C@@H]1*]

In some embodiments of the pharmaceutical formulations, Y is $NR^6$. In some embodiments, Y is $NR^6$, wherein $R^6$ is H. In some embodiments, Y is $NR^6$, wherein $R^6$ is $C_1$-$C_6$ alkyl. In some embodiments, Y is $NR^6$, wherein $R^6$ is $CH_3$. In some embodiments, Y is $NR^6$, wherein $R^6$ is $CH_2CH_3$. In some embodiments, Y is $NR^6$, wherein $R^4$ and $NR^6$, taken together with the carbon atom to which they are bonded, form a 5- or 6-membered heterocyclic ring. In some embodiments, Y is O.

In some embodiments of the pharmaceutical formulations, R and $R^1$ are each $CH_3$. In some embodiments, R and $R^1$ are each $CH_3$. In some embodiments, R is $CH_3$; and $R^1$ is H. In some embodiments, R and $R^1$, taken together with the carbon atom to which they are bonded, form a cyclopropyl. In some embodiments, R and $R^1$, taken together with the carbon atom to which they are bonded, form a cyclobutyl.

In some embodiments of the pharmaceutical formulations, $R^2$ is H; $R^3$ is H or $CH_3$; and $R^4$ is $CH_3$, $CH_2CH_3$, a straight- or branched-chain $C_3$-$C_6$ alkyl, a $C_5$-$C_7$ cycloalkyl, a 6-membered aryl or heteroaryl, an aryl-substituted $C_1$-$C_6$ alkyl, or a heterocyclyl-substituted $C_1$-$C_6$ alkyl, or, when Y is $NR^6$, $R^4$ and $NR^6$, taken together with the carbon atom to which they are bonded, form a 5- or 6-membered heterocyclic ring. In some embodiments, $R^2$, $R^3$ and $R^4$ are each $CH_3$. In some embodiments, $R^2$ is H; $R^3$ is $CH_3$; and $R^4$ is $CH_3$. In some embodiments, $R^2$ is H; $R^3$ is H; and $R^4$ is $CH_2CH_3$. In some embodiments, $R^2$ is H; $R^3$ is H; and $R^4$ is $CH(CH_2CH_3)_2$. In some embodiments, $R^2$ is H; $R^3$ is H; and $R^4$ is $CH(CH_2CH_3)_2$. In some embodiments, $R^2$ is H; $R^3$ is H; and $R^4$ is cyclohexyl. In some embodiments, $R^2$ is H; $R^3$ is H; and $R^4$ is phenyl. In some embodiments, $R^2$ is H; $R^3$ is H; and $R^4$ is pyridinyl.

In some embodiments of the pharmaceutical formulations, the compound of Formula (I) is selected from

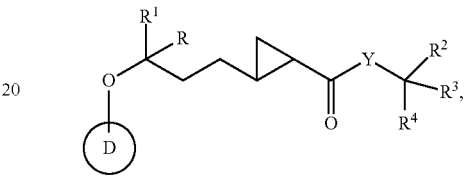

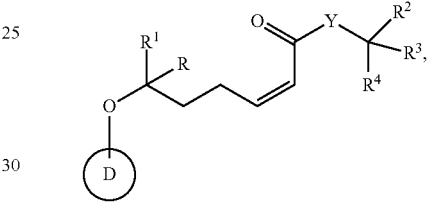

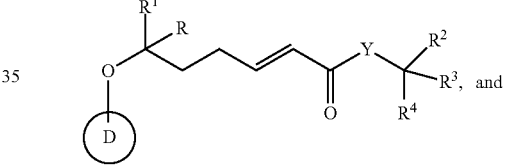

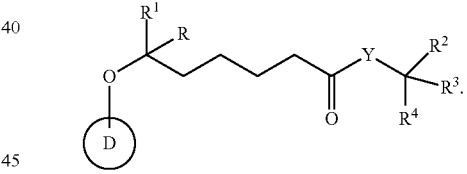

In some embodiments of the pharmaceutical formulations, the compound of Formula (I) is selected from

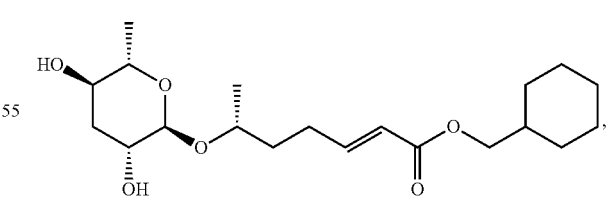

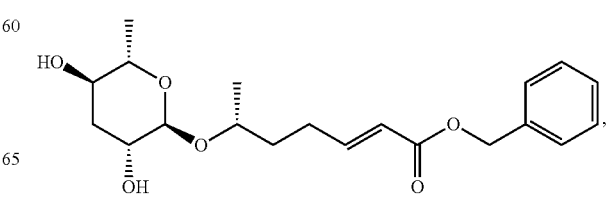

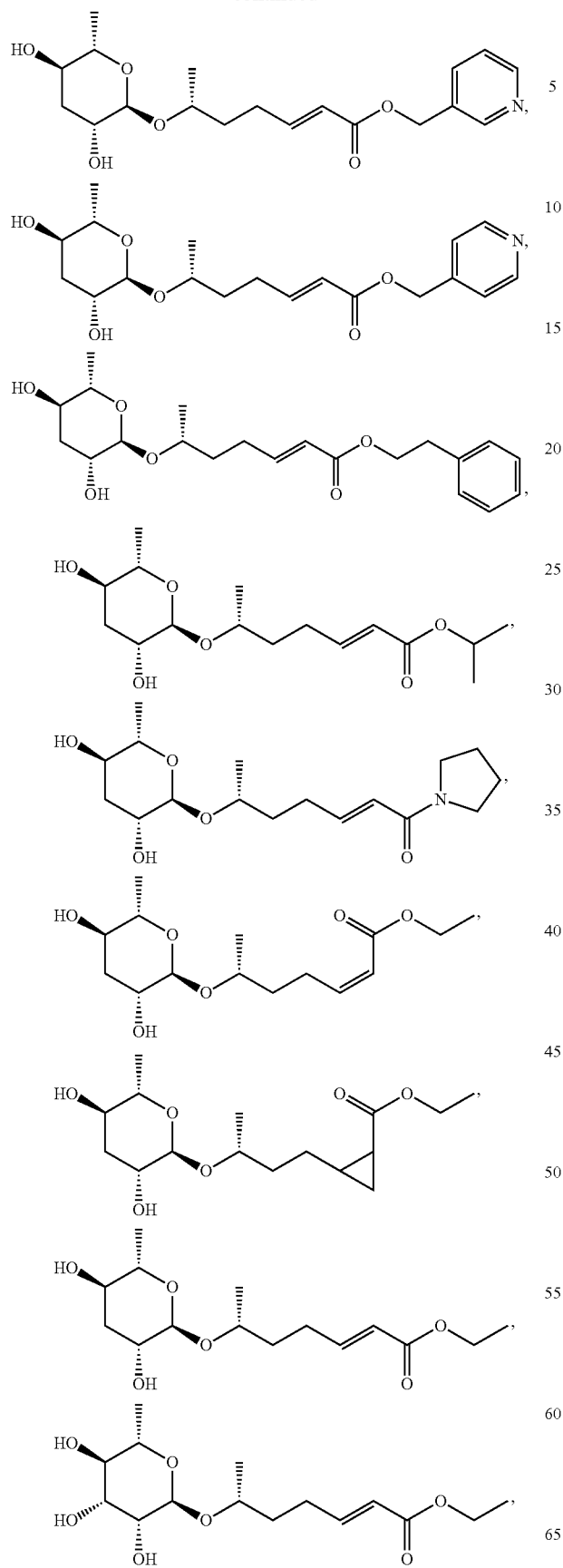
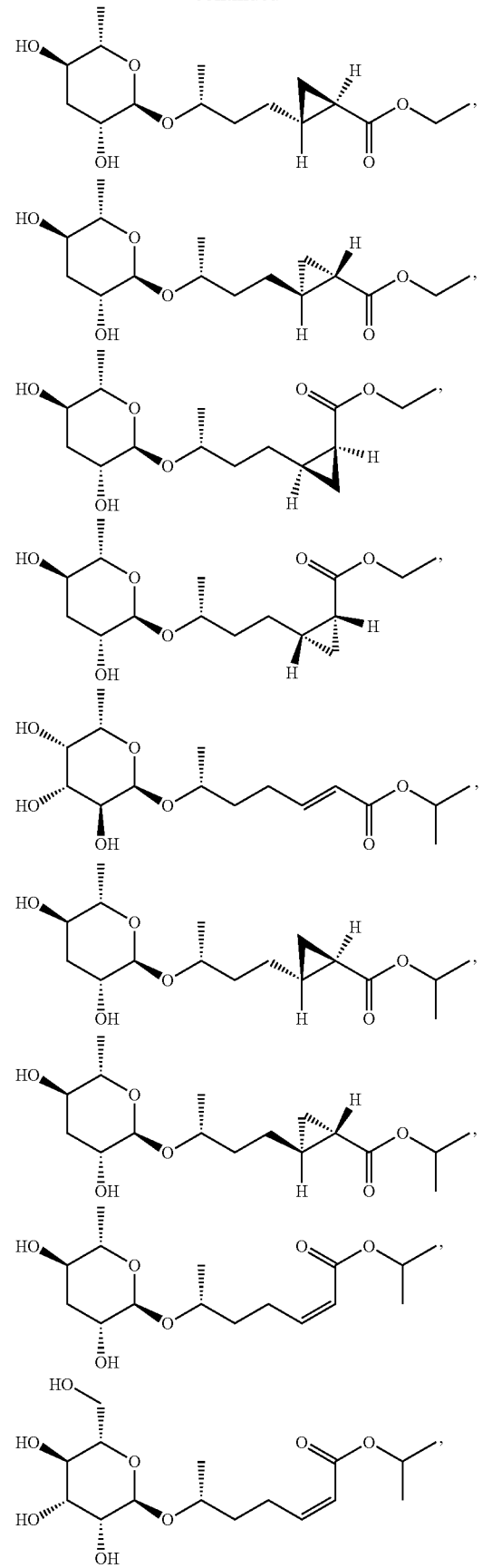

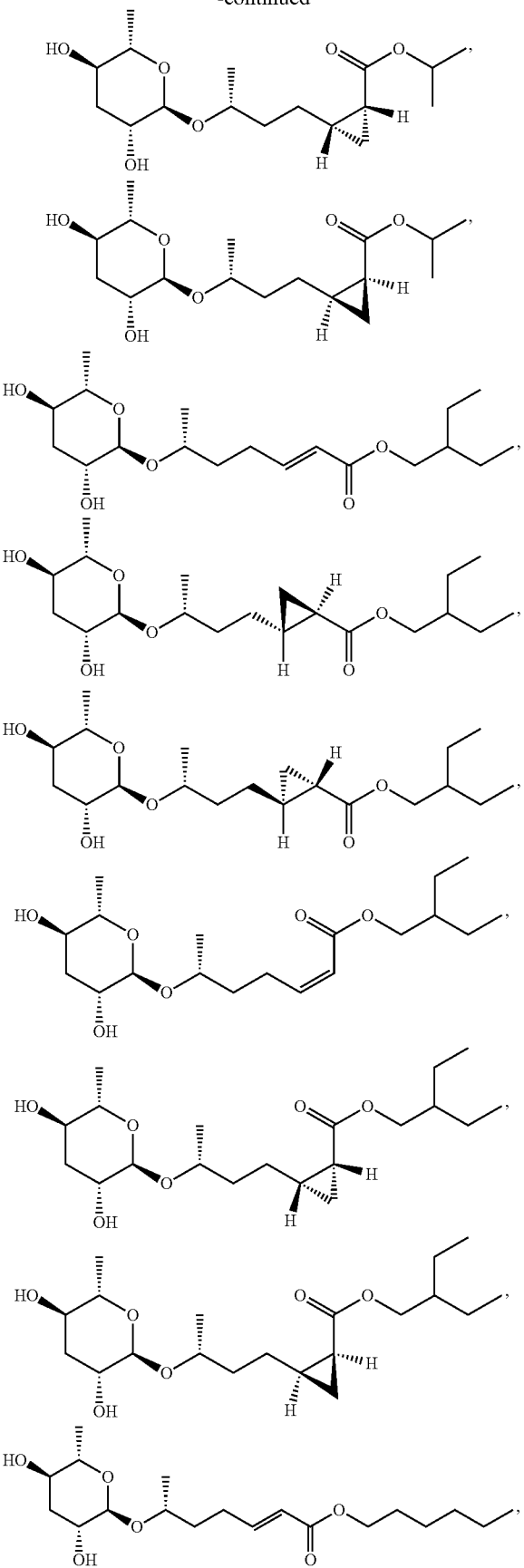
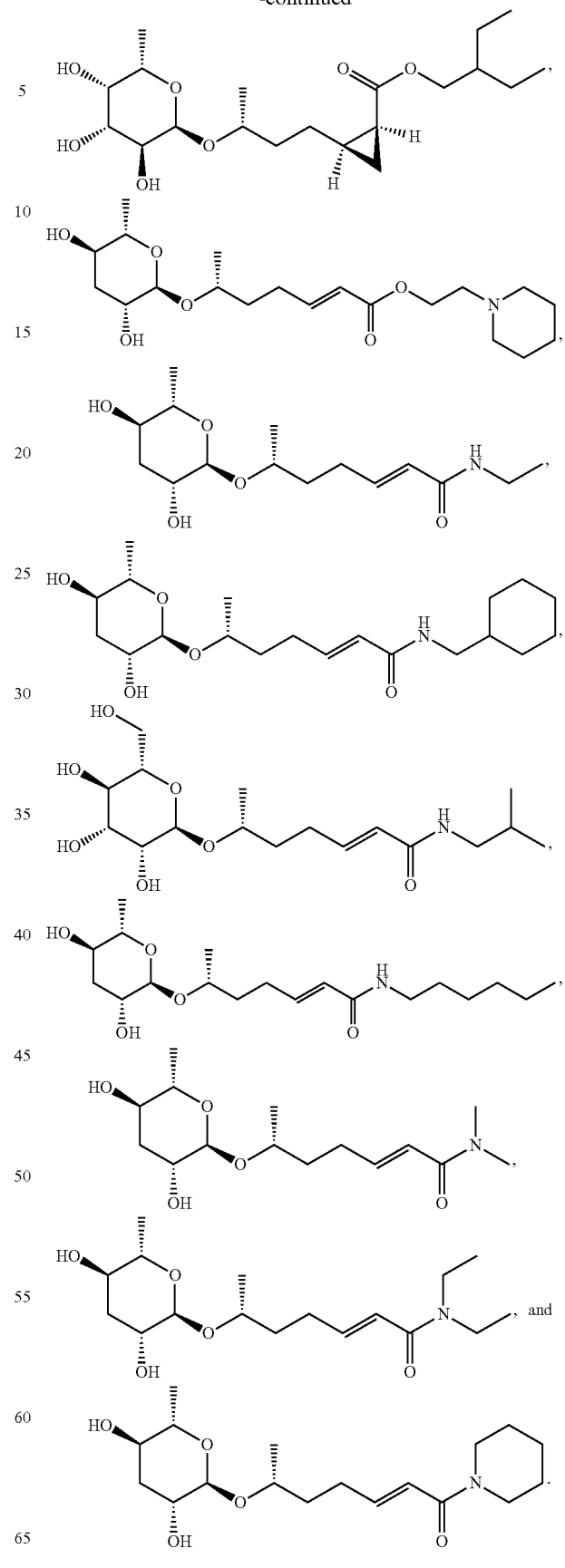

In some embodiments of the pharmaceutical formulations, the compound of Formula (I) is selected from
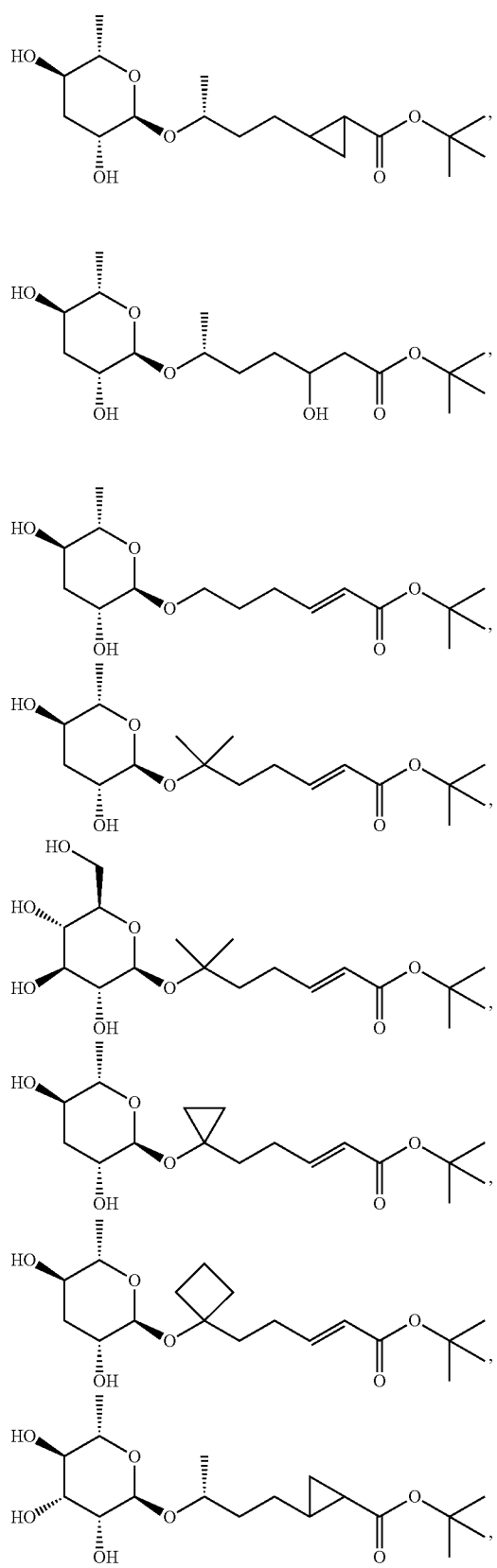
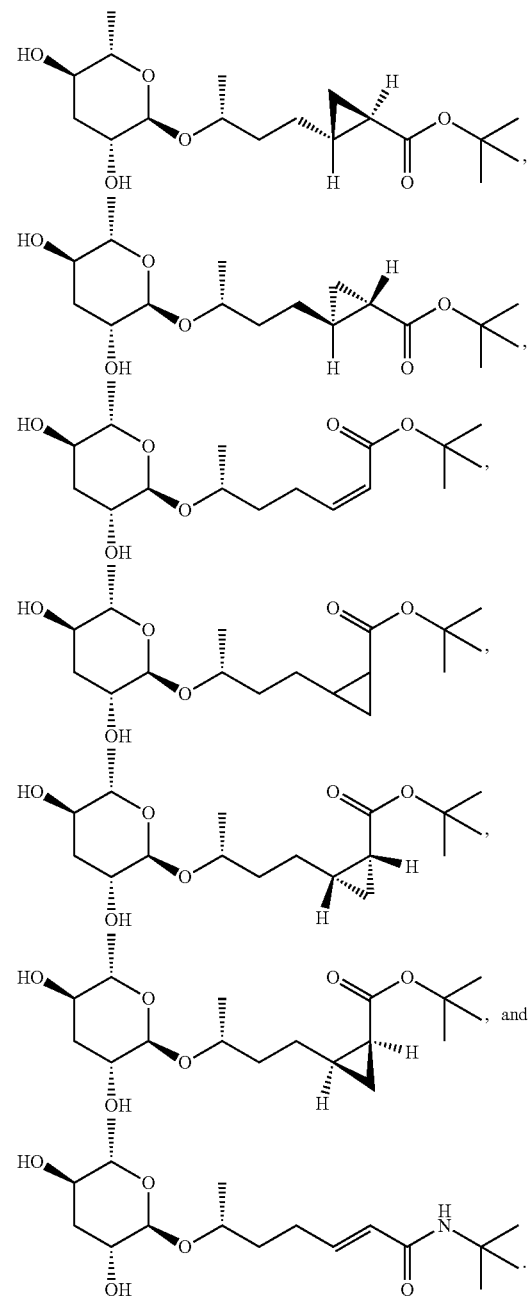
In another aspect, provided herein are pharmaceutical formulations comprising a pharmaceutically acceptable carrier; and the compound having the structure of Formula (II):
Formula (II)
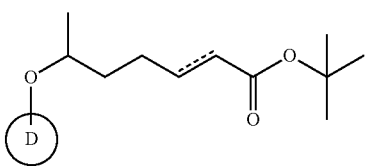

wherein
Ring D is selected from

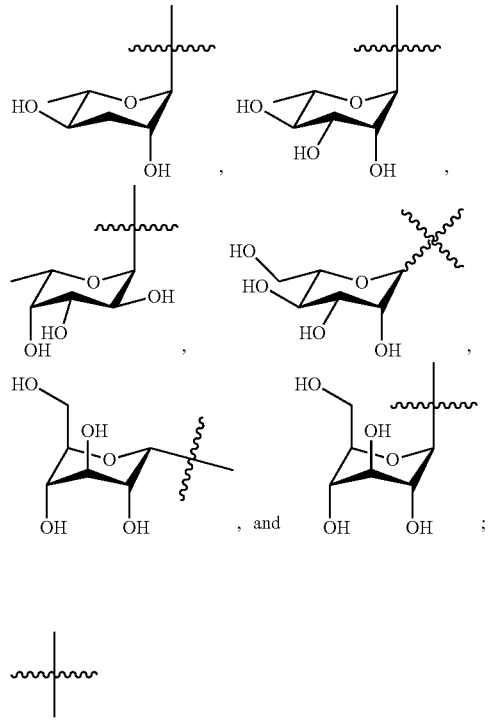

represents the point of attachment of Ring D to the oxygen atom; and

⫽ is a double bond or a single bond.

In some embodiments of the pharmaceutical formulations, the compound of Formula (II) is a compound with the following structural formula:

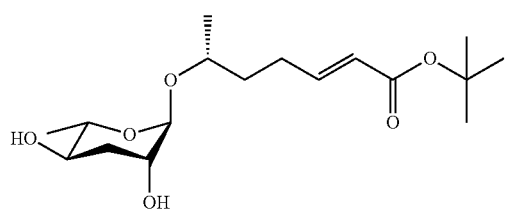

In some embodiments of the pharmaceutical formulations, the compound of Formula (II) is a compound with the following structural formula:

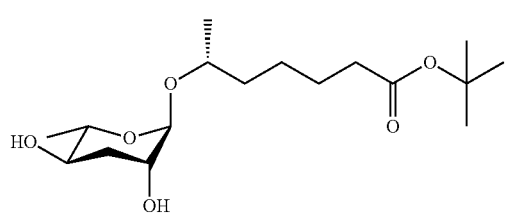

In some embodiments of the pharmaceutical formulations, the compound of Formula (II) is selected from

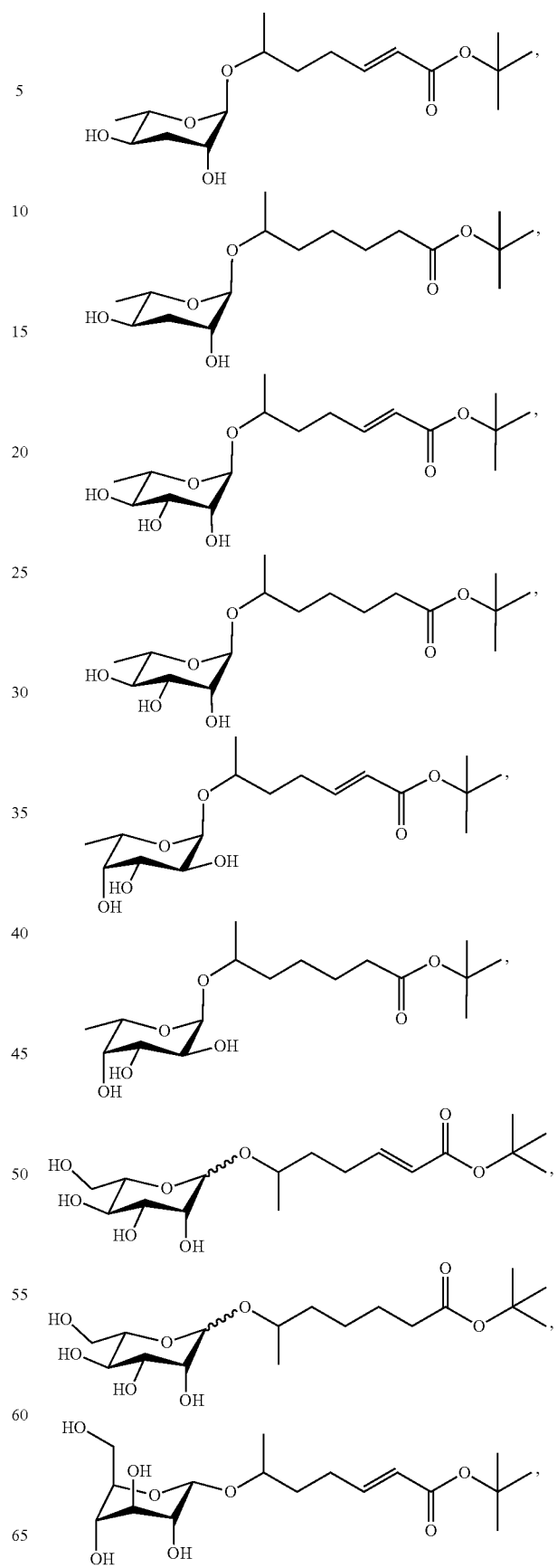

-continued

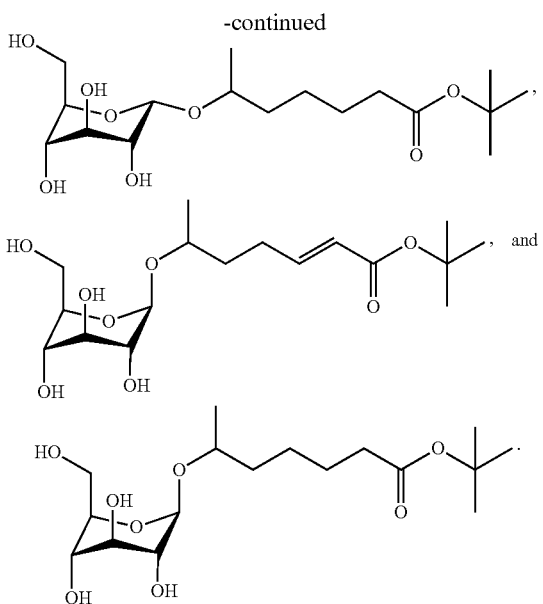

The compounds, compositions and methods described herein may be utilized to treat a subject in need thereof. In certain embodiments, the subject is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutical composition (preparation, formulation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

One of skill in the art would appreciate that a method of administering a formulation or composition of the disclosure would depend on factors such as the age, weight, and physical condition of the subject being treated, and the disease or condition being treated. The skilled worker would, thus, be able to select a method of administration optimal for a subject on a case-by-case basis.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Example ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The subject receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In some embodiments, the different therapeutic compound is a steroid. In some embodiments, the different therapeutic compound is a steroid selected from a hydrocortisone type, an acetonide, a betamethasone type, an ester, a halogenated steroid, and a labile prodrug ester. In some embodiments, the steroid is selected from alclometasone dipropionate, aldosterone, amcinonide, beclometasone, betamethasone, betamethasone dipropionate, betamethasone valerate, budesonide, ciclesonide, clobetasol propionate, clobetasone butyrate, corticosterone, cortisol, cortisone, cortisone acetate, desonide, dexamethasone (DEX), fluocinolone acetonide, fluocinonide, fluocortolone, fluprednidene acetate, halcinonide, halometasone, hydrocortisone, hydrocortisone aceponate, hydrocortisone acetate, hydrocortisone buteprate, hydrocortisone butyrate, hydrocortisone valerate, methylprednisone, mometasone, mometasone furoate, prednicarbate, prednisolone, prednisone, triamcinolone acetonide, and tixocortol pivalate. In some embodiments, the steroid is DEX. In some embodiments, the compound of Formula (I) is conjointly administered with a steroid. In some embodiments, the compound of Formula (I) is conjointly administered with DEX.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The following example is provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Synthesis of Compound 1

The compound was synthesized according to the following scheme.

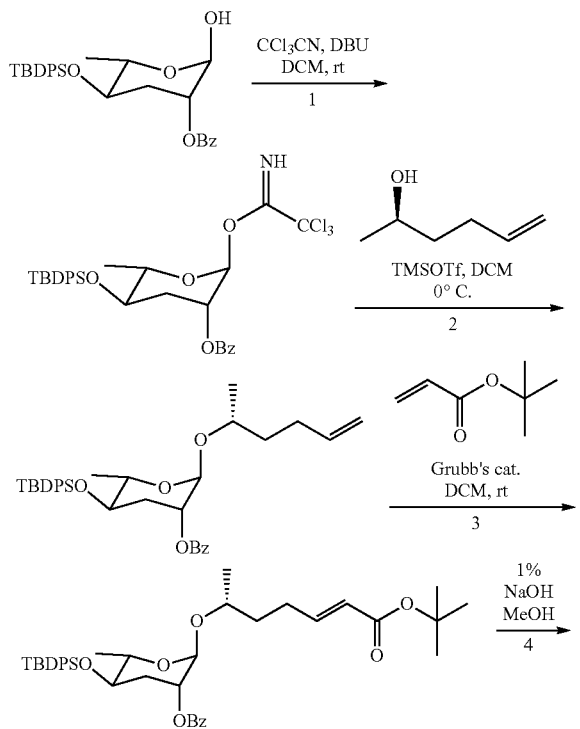

Synthesis of Compound 10

The compound was synthesized according to the following scheme.

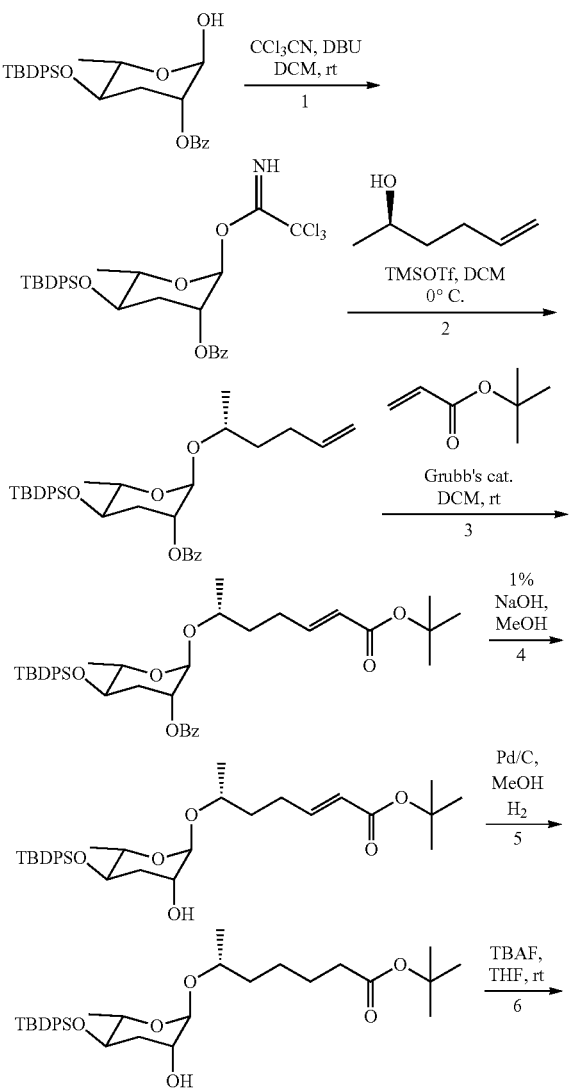

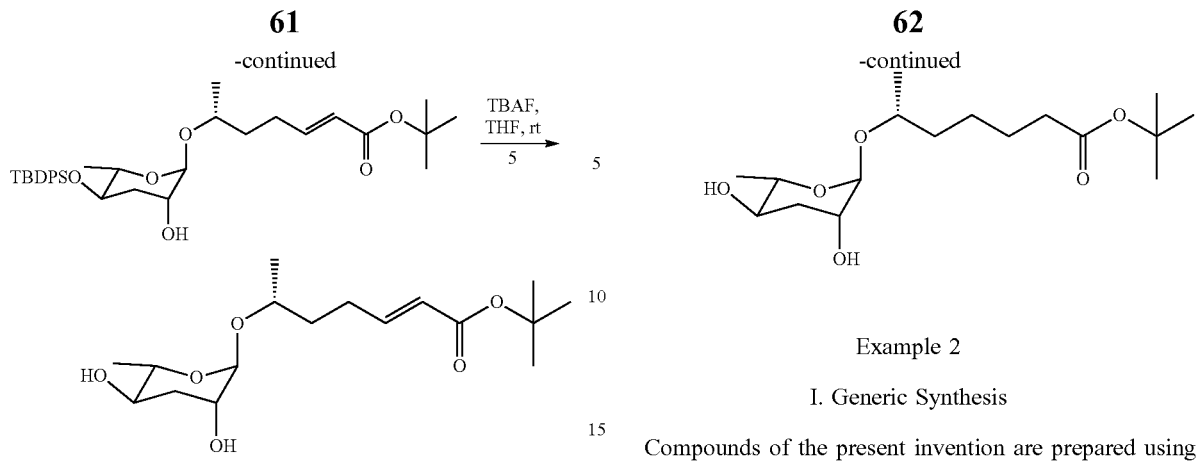

Example 2

I. Generic Synthesis

Compounds of the present invention are prepared using methods illustrated in the general synthetic schemes and experimental procedures detailed below. These general synthetic schemes and experimental procedures are presented for purposes of illustration and are not intended to be limiting. Starting materials used to prepare compounds of the present invention are commercially available or can be prepared using routine methods known in the art. Where present, names of compounds were generated using ChemAxon's Instant JChem v6.1 for Desktop and IUPAC Naming Plugin or ChemDraw Professional 16.0.1.4 (61).

General methods for the synthesis of ascaroside pheromones and related compounds have been previously described in the literature, e.g. Jeong P. Y. et al. Chemical structure and biological activity of the *Caenorhabditis elegans* dauer-inducing pheromone. *Nature* 2005, 433 (7025), 541-545; Martin, R. et al. Improved Synthesis of an Ascaroside Pheromone Controlling Dauer Larva Development in *Caenorhabditis elegans*. *Synthesis* 2009, 20, 3488-3492; and Zhang, Y. K. et al. Improved Synthesis for Modular Ascarosides Uncovers Biological Activity. *Org. Lett.* 2017, 19, 2837-2840, each of which are hereby incorporated by reference.

Protected carbohydrates (I) with a free anomeric hydroxyl group are activated by making O-glycosyl trichloroacetimidates (II), which are prepared using trichloroacetonitrile ($Cl_3CCN$) under basic conditions (e.g. DBU, DIPEA, etc.). Scheme 1 illustrated the reaction of O-glycosyl trichloroacetimidates (II) with a Lewis acid, such as $BF_3 \cdot OEt_2$ or TMSOTf, in the presence of an alcohol to afford O-glycosylated products (III).

Scheme 1.
General Synthesis of O-Glycosylated
Products (III)
from O-Glycosyl Trichloroacetimidates (II).

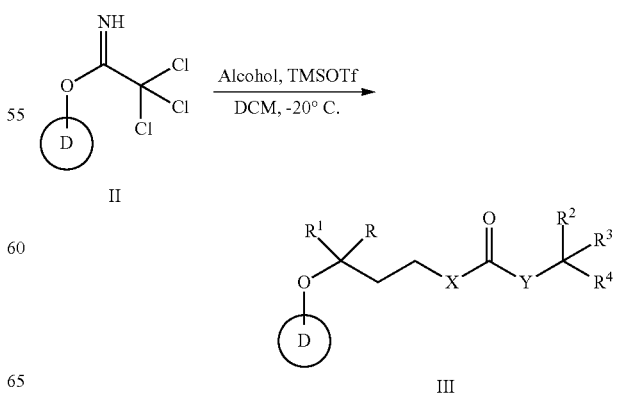

Scheme 2 illustrates the reaction of O-glycosylated terminal olefins (IV) with suitable α,β-unsaturated esters or amides using Grubb's olefin metastasis catalysis (e.g. dichloro[1,3-bis(2,6-isopropylphenyl)-2-imidazolidinylidene](benzylidene) (tricyclohexylphosphine) ruthenium (II), (1,3-bis(2,4,6-trimethylphenyl)-2-imidazolidinylidene) dichloro(phenylmethylene) (tricyclohexylphosphine) ruthenium, benzylidene-bis(tricyclohexylphosphine) dichlororuthenium, bis(tricyclohexylphosphine) benzylidine ruthenium(IV) dichloride, etc.) to afford O-glycosylated (E)-isomer α,β-unsaturated esters or amides (V).

Scheme 2. General Synthesis of O-Glycosylated (E)-Isomer α,β-Unsaturated Esters or Amides (V) from O-Glycosylate Terminal Olefins (IV).

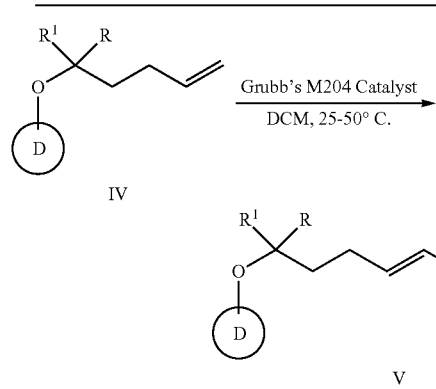

Scheme 3 illustrates the oxidation of O-glycosylated terminal olefins (IV) to afford O-glycosylated aldehydes (VI) using Lemieux oxidation ($OsO_4$ and $NaIO_4$) or ozonolysis ($O_3$) conditions.

Scheme 3.
General Synthesis of O-Glycosylated Aldehydes (VI) from O-Glycosylate Terminal Olefins (IV).

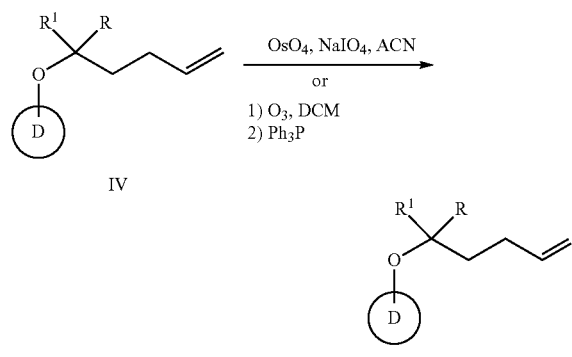

Scheme 4 illustrates the Still-Gennari olefination reaction of O-glycosylated aldehydes (IV) to afford O-glycosylated (Z)-isomer α,β-unsaturated esters or amides (VII). (Z)-Stereospecific Still-Gennari olefination conditions utilize bistrifluoroethylphosphonates (e.g. bis(2,2,2-trifluoroethyl) (methoxycarbonylmethyl)phosphonate), bis(2,2,2-trifluoroethyl) (ethoxycarbonylmethyl) phosphonate), etc.), a strong base such as KHMDS, and a cation savanger, such as 18-crown-6.

Scheme 4.
General Synthesis of O-Glycosylated (Z)-Isomer α,β-Unsaturated Esters or Amides (VII) from O-Glycosylated Aldehydes (VI).

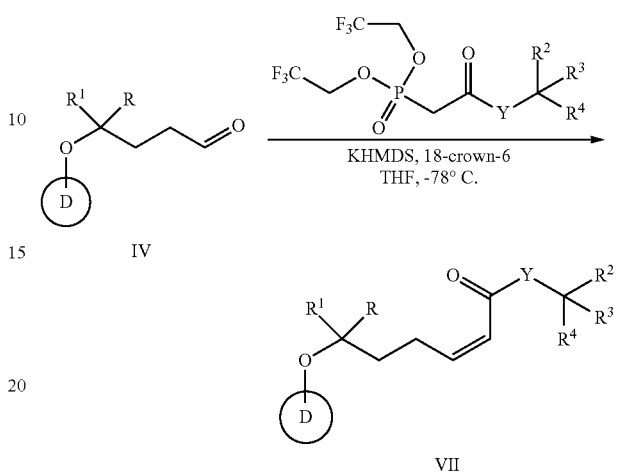

Scheme 5 illustrates the coupling of O-glycosylated carboxylic acids (VIII) with alcohols to form O-glycosylated esters (IX). O-Glycosylated carboxylic acids (VIII) are made by base or acid hydrolysis of simple esters (e.g. methyl, ethyl, tert-butyl) derived from the Grubb's olefin metastasis approach (Scheme 2). Several esterification methods are possible from VIII to IX ketone carbamate esters IV: 1) IIIV is coupled with alcohols (HO—$C(R^2)(R^3)(R^4)$) using a coupling reagent (e.g. N,N'-dicyclohexylcarbodiimide (DCC), EDC, HBTU, HATU, TBTU, PyBOP, etc.) under basic conditions (e.g. triethylamine, diisopropylethylamine, pyridine, N,N-4-dimethylaminopyridine, etc.); 2) IIIV is alkylated with an activated alkane (X—$C(R^2)(R^3)(R^4)$), where X=OTf, OTs, OMs, I, Br, and Cl) under basic conditions (e.g. NaOH, NaH, $NaCO_3$, $K_2CO_3$, $Cs_2CO_3$, $NaHCO_3$, etc.); and 3) IIIV is esterified with alcohols (HO—$C(R^2)(R^3)(R^4)$) using Mitsunobu conditions (e.g. diethyl azodicarboxylate and triphenylphosine, or similar reagents).

Scheme 5.
General Synthesis of O-Glycosylated Esters (IX) from O-Glycosylated Carboxylic Acids (VIII).

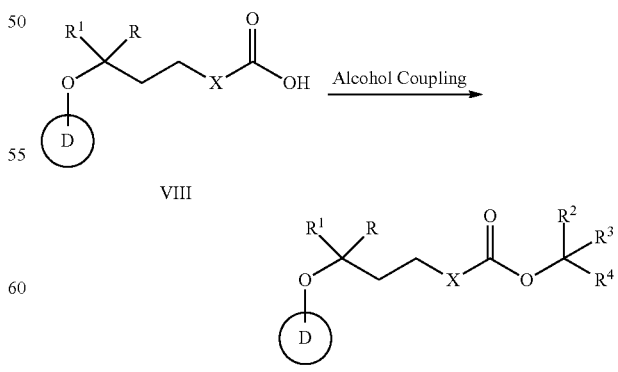

Scheme 6 illustrates the coupling of O-glycosylated carboxylic acids (VIII) with amines to form O-glycosylated amides (X). Standard amide coupling conditions between amines (N(C—(R²)(R³)(R⁴))R⁶) and coupling reagent (e.g. N,N'-dicyclohexylcarbodiimide (DCC), EDC, HBTU, HATU, TBTU, PyBOP, etc.) under basic conditions (e.g. triethylamine, diisopropylethylamine, pyridine, N,N-4-dimethylaminopyridine).

Scheme 6. General Synthesis of O-Glycosylated Amides (X) from O-Glycosylated Carboxylic Acids (VIII).

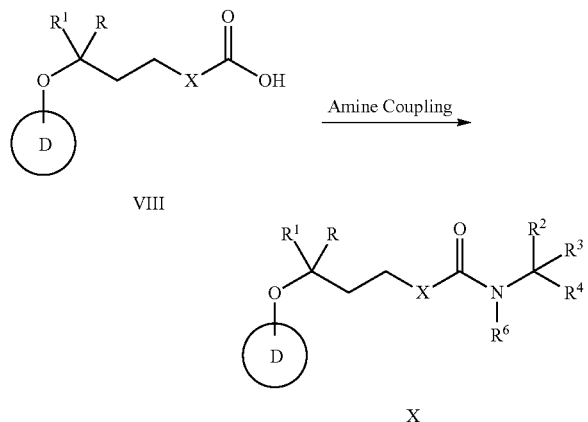

Scheme 7 illustrates the cyclopropanation of O-glycosylated terminal olefins (IV) to form O-glycosylated trans-cyclopropyl esters or amides (XI) under standard diazo cyclopropanation conditions using a rhodium tetracarboxylate catalyst (e.g. rhodium(II) acetate dimer, rhodium(II) trifluoroacetate dimer, tetrakis[N-phthaloyl-(S)-tert-leucinato]dirhodium, dirhodium(II)tetrakis [methyl 2-pyrrolidone-5(S)-carboxylate], etc.).

Scheme 7. General Synthesis of O-Glycosylated trans-Cyclopropyl Esters or Amides (XI) from O-Glycosylate Terminal Olefins (IV).

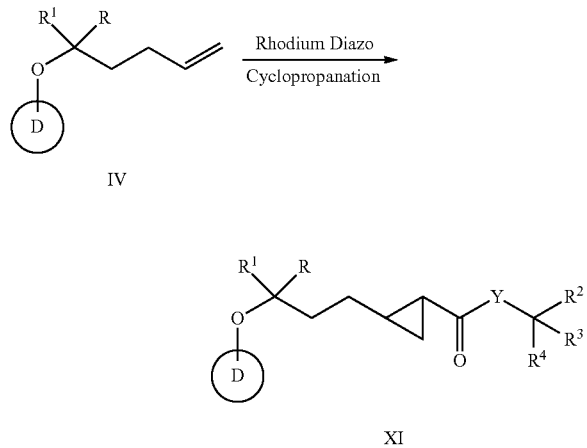

Scheme 8 illustrates the cyclopropanation of O-glycosylated (Z)-isomer α,β-unsaturated esters or amides (VII) to form O-glycosylated cis-cyclopropyl esters or amides (XII). Several methods are possible using Corey-Chaykovsky cyclopropanation conditions (e.g. dimethyloxosulfonium methylide, made using trimethylsulfoxonium iodide in DMSO and sodium hydride) or Simmons-Smith conditions (e.g. iodomethylzinc iodide, made using diiodomethane and zinc-copper couple).

Scheme 8. General Synthesis of O-Glycosylated cis-Cyclopropyl Esters or Amides (XII) from O-Glycosylated (Z)-Isomer α,β-Unsaturated Esters or Amides (VII) from O-Glycosylated Aldehydes (VI).

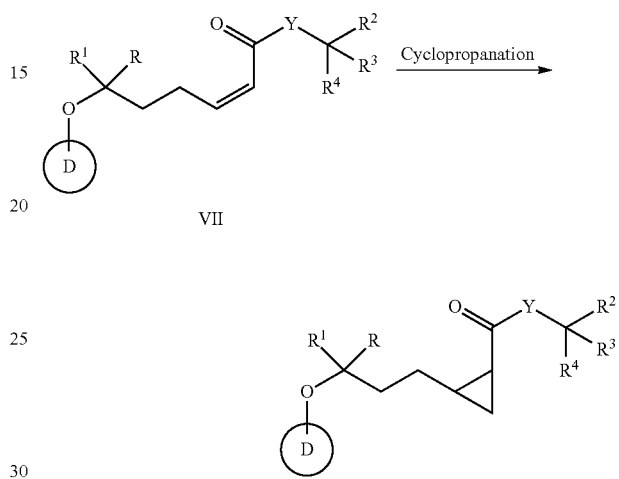

II. Experimental Section

General Information:

All chemical reagents were purchased commercially and were used without further purification unless otherwise noted. Reactions were done under air/nitrogen atmosphere according to the requirements. Column chromatography was performed on silica gel 60 (230-400 mesh) and analytical TLC was performed on plates coated with silica gel. TLC plates were stained with ceric ammonium molybdate (CAM), p-anisaldehyde (Anis), potassium permanganate (KMnO4), or ninhydrin staining solutions. Routine $^1$H NMR spectra were recorded using an Automated Varian Inova 500 MHz (MestReNova Software: version 14.1.2-25024) or a Bruker 400 MHz using common deuterated solvens such as deuterium oxide, chloroform-d, or methanol-$d_4$. LCMS was accomplished using a Shimadzu LC-20AD Pump and LCMS-2020 Single Quadrupole Liquid Chromatograph Mass Spectrometer. Mass spectrometry was done using an Agilent 1290 UHPLC system with G4212 DAD and a G6140 MS detector (ESI: positive or negative ion mode). The samples were analyzed using an Agilent Eclipse-Plus Cis column (2.1 mm×50 mm) with gradient elution (Mobile Phase A: 0.05% TFA in water; Mobile Phase B: acetonitrile with 0.1% AcOH or 0.025% TFA) at a flow rate of 0.5-1.0 mL/min. Gas chromatography analyses were conducted using an Agilent GC equipped with a flame ionization detector using a Agilent J&W CYCLOSIL-B (30 m×250 μm×0.25 μm) column (Conditions: Inlet Temperature: 200° C.; Run Time: 60 min; Flow: 1 mL/min; Carrier Gas: Helium; Detector Temperature: 240° C.).

Preparation of (2S,3R,5R,6S)-5-(benzoyloxy)-2-methyl-6-[(trichloroethanimidoyl) oxy]oxan-3-yl benzoate (C-01)

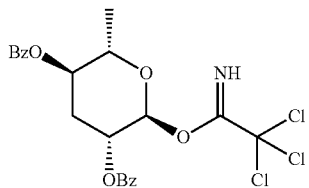

(2S,3R,5R)-5-(Benzoyloxy)-6-hydroxy-2-methyloxan-3-yl benzoate (40.0 g, 112 mmol, 1.00 eq.) was dissolved in DCM (200 mL) and trichloroacetonitrile (81.0 g, 561 mmol, 56.2 mL, 5.00 eq.) was added to the reaction. The mixture was degassed with nitrogen 3 times and cooled to 0° C. DBU (8.54 g, 56.1 mmol, 8.46 mL, 0.50 eq.) was added dropwise to the reaction at 0° C. and stirred at 0° C. for 1.5 h. TLC showed the reaction was complete (3:1 petroleum ether-ethyl acetate, SM $R_f$=0.45, $R_f$(C-01)=0.80). The resulting black liquid C-01 was used directly without further purification.

Preparation of (2S,3R,5R,6S)-5-((tert-butyldiphenylsilyl)oxy)-6-methyl-2-(2,2,2-trichloro-1-iminoethoxy)tetrahydro-2H-pyran-3-yl benzoate (C-02)

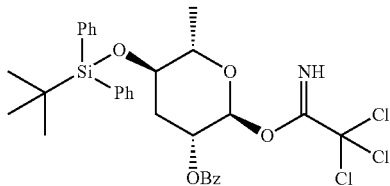

To a stir solution of (2R,3R,5R,6S)-5-((tert-butyldiphenylsilyl)oxy)-2-hydroxy-6-methyltetrahydro-2H-pyran-3-yl benzoate (7.30 g, 14.90 mmol) in DCM (50 mL) was added $CCl_3CN$ (3.10 mL, 29.80 mmol) and DBU (0.210 mL, 1.50 mmol). The resulting mixture was stirred at room temperature under nitrogen for 18 h. The reaction was concentrated in vacuo then purified by the column chromatography (220 g silica gel, 0% to 30% acetone in hexanes) to afford C-02 (4.5 g, 48% yield) as a white foam. $^1$H NMR (500 MHz, $CDCl_3$) δ 8.65 (s, 1H), 7.81-7.76 (m, 2H), 7.71-7.65 (m, 4H), 7.61 (ddt, J=8.8, 7.4, 1.3 Hz, 1H), 7.46-7.41 (m, 2H), 7.40-7.37 (m, 1H), 7.37-7.32 (m, 3H), 7.32-7.29 (m, 2H), 6.14 (s, 1H), 5.16 (dt, J=4.5, 2.1 Hz, 1H), 4.09-4.01 (m, 1H), 3.76 (ddd, J=11.1, 9.3, 4.4 Hz, 1H), 2.12 (ddd, J=14.1, 11.2, 3.0 Hz, 1H), 2.07-2.00 (m, 1H), 1.35 (d, J=6.2 Hz, 3H), 1.08 (s, 9H). Mass Analysis (ESI, +ve)=634.2 [M+H].

Using the above protocols, Table 1 summarizes additional carbohydrate starting materials that are prepared from commercial reagents after installing suitable protecting groups.

TABLE 1

Trichloroethanimidoyl Carbohydrates.

| # | Carbohydrate Core | Structure |
|---|---|---|
| C-01 | L-Rhamnose (6-Deoxy-L-mannose) CAS# 10030-85-0 | 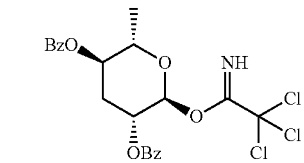 |
| C-02 | L-Rhamnose (6-Deoxy-L-mannose) CAS# 10030-85-0 | 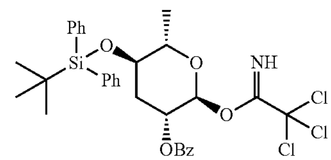 |
| C-03 | L-Rhamnose (6-Deoxy-L-mannose) CAS# 10030-85-0 | 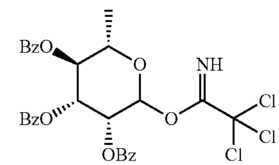 |
| C-04 | L-(−)-Fucose (6-Deoxy-L-galactose) CAS # 2438-80-4 | 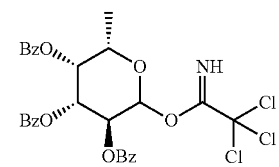 |
| C-05 | L-(−)-Mannose CAS # 10030-8-05 | 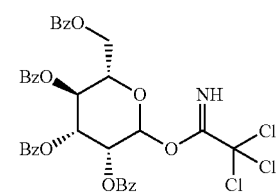 |
| C-06 | D-Glucose CAS# 492-62-6 | 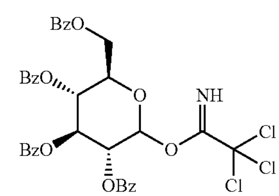 |

Preparation of (2R)-hex-5-en-2-ol (I-01)

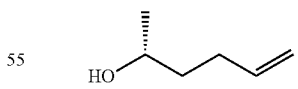

(R)-(+)-Propylene oxide (99.0 g, 1.70 mol, 119 mL, 1.00 eq.) was dissolved in THF (534 mL). Copper (I) bromide (24.4 g, 170 mmol, 5.19 mL, 0.10 eq.) was added to the reaction mixture as a solid. The reaction was cooled to −70° C. under nitrogen atmosphere and allylmagnesium bromide (1 M, 2.22 L, 1.30 eq.) was added to the reaction dropwise over 4 h. The reaction was warmed to 15° C. and stirred at 15° C. for 4 h. TLC showed the reaction was complete (5:1 petroleum ether-ethyl acetate, $R_f$(I-01)=0.39). The reaction was quenched with aqueous ammonium chloride (1.0 L) at 0° C. and then extracted with MTBE (3×5.0 L). The layers were separated and the organic layers were washed with brine (2×2.0 L). The combined organic layers were dried over sodium sulfate, filtered, and concentrate in vacuo at 30° C. The residue was purified by column chromatography (silica gel, 5:1 petroleum ether-ethyl acetate) to afford I-01 (43.3 g, 25% yield) as a yellow oil. $^1$H NMR (400 MHz, CDCl$_3$) δ 5.87-5.80 (m, 1H), 5.06-4.95 (m, 1H), 3.84-3.82 (m, 1H), 3.81-3.79 (m, 1H), 2.18-2.11 (m, 1H), 1.61-1.52 (m, 2H), 1.19 (d, J=6.0 Hz, 3H). Chiral GC: 99.9% ee.

Preparation of (2S,3R,5R,6R)-5-(benzoyloxy)-6-[(2R)-hex-5-en-2-yloxy]-2-methyloxan-3-yl benzoate (T-01)

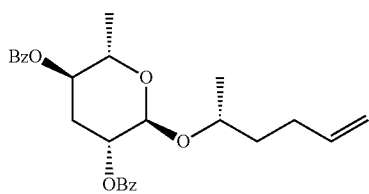

To the crude solution of C-01 was added 4 Å molecular sieves and the reaction was degassed with nitrogen 3 times. Compound I-01 (12.3 g, 123 mmol, 1.10 eq.) was added to the reaction at 25° C. and the mixture was cooled to −20° C. TMSOTf (12.4 g, 55.9 mmol, 10.1 mL, 0.50 eq.) was added dropwise to the reaction at −20° C. The mixture was stirred at −20° C. for 1.5 h. TLC showed the reaction was complete (3:1 petroleum ether-ethyl acetate, SM R$_f$ (C-01)=0.80, R$_f$ (T-01)=0.88). Water (500 mL) was added to quench the reaction and the mixture was extracted with DCM (3×300 mL). The layers were separated and the organic layers were washed with brine (2×50 mL). The combined organic layers were dried over sodium sulfate, filtered, and concentrate in vacuo. The residue was purified by column chromatography (silica gel, 2:1 petroleum ether-ethyl acetate) to afford T-01 (29.0 g, 59% yield) as a yellow oil. $^1$H NMR (400 MHz, CDCl$_3$) δ 8.14-8.05 (m, 4H), 7.59-7.27 (m, 6H), 5.94-5.86 (m, 1H), 5.17-4.98 (m, 5H), 4.17-4.13 (m, 1H), 3.92-3.87 (m, 1H), 2.46-2.42 (m, 1H), 2.27-2.20 (m, 3H), 1.79-1.63 (m, 2H), 1.32 (d, J=4.2 Hz, 3H), 1.23 (d, J=4.2 Hz, 3H).

Preparation of (2R,3R,5R,6S)-2-[(2R)-hex-5-en-2-yloxy]-6-methyloxane-3,5-diol (T-02)

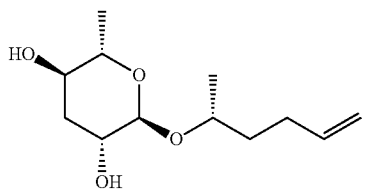 [SMILES: C=CCC[C@@H](C)O[C@@H]1O[C@@H](C)[C@H](O)C[C@H]1O]

Compound T-01 (23.0 g, 52.4 mmol, 1.00 eq.) was dissolved into THF (160 mL) and then water (230 mL) was added at 25° C. LiOH·H$_2$O (22.0 g, 524 mmol, 10.0 eq.) was added as a solid to the reaction mixture and the reaction was heated to 70° C. After stirring for 16 h, TLC showed the reaction was complete (5:1 petroleum ether-ethyl acetate, SM R$_f$(T-01)=0.24, R$_f$(T-02)=0.00). The mixture was concentrated at 40° C. in vacuo to remove THF. Water (400 mL) was added and the mixture was extracted with ethyl acetate (3×400 mL). The layers were separated and the organic layers were washed with brine (2×400 mL). The combined organic layers were dried over sodium sulfate, filtered, and concentrate in vacuo to afford T-02 (12 g, crude) as a colorless oil, which was used directly without further purification.

Preparation of tert-butyl({[(2S,3R,5R,6R)-5-[(tert-butyldimethylsilyl)oxy]-6-[(2R)-hex-5-en-2-yloxy]-2-methyloxan-3-yl]oxy})dimethylsilane (T-03)

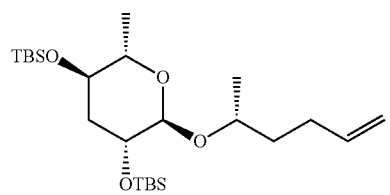 [SMILES: C=CCC[C@@H](C)O[C@@H]1O[C@@H](C)[C@H](O[Si](C)(C)C(C)(C)C)C[C@H]1O[Si](C)(C)C(C)(C)C]

Compound T-02 (11.0 g, 47.7 mmol, 1.00 eq.) was dissolved in THF (70 mL) and silver nitrate (20.2 g, 119 mmol, 2.50 eq.) and imidazole (13.0 g, 191 mmol, 4.00 eq.) were added as solids. The reaction was cooled to 0° C. under nitrogen atmosphere. tert-Butyldimethylsilyl chloride (21.6 g, 143 mmol, 3.00 eq.) was added to the reaction and stir for 16 h at 25° C. TLC showed the reaction was complete. Water (200 mL) was added and the mixture was extracted with ethyl acetate (3×150 mL). The layers were separated and the organic layers were washed with brine (2×100 mL). The combined organic layers were dried over sodium sulfate, filtered, and concentrate in vacuo. The residue was purified by column chromatography (silica gel, 20:1 to 10:1 petroleum ether-ethyl acetate) to afford T-03 (14.0 g, 64% yield) as a yellow oil.

Preparation of (3R,5R,6R)-2-methyl-6-(pent-4-en-1-yloxy)tetrahydro-2H-pyran-3,5-diyl dibenzoate (T-04)

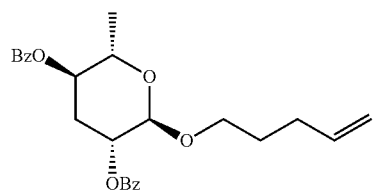

To a solution of (2R,3R,5R)-2-hydroxy-6-methyltetrahydro-2H-pyran-3,5-diyl dibenzoate (0.300 g, 0.842 mmol) in DCM (15 mL) was added 4-penten-1-ol (0.260 mL, 2.52 mmol) and 4 Å molecular sieve (0.100 g). The reaction mixture was cooled to 0° C. followed by adding BF$_3$·Et$_2$O (0.420 mL, 3.37 mmol) dropwise via the syringe. The resulting mixture was warmed up to room temperature and stirred for 4 h then quenched with triethylamine (2 mL). The solvent was concentrated in vacuo and the crude product was purified by the column chromatography (24 g silica gel, 0% to 30% acetone in hexanes) to afford T-04 (0.200 g, 56%) as a colorless oil. $^1$H NMR (500 MHz, CDCl$_3$) δ 8.16-8.11 (m, 2H), 8.08-8.03 (m, 2H), 7.64-7.57 (m, 2H), 7.52-7.45 (m, 4H), 5.88 (ddt, J=16.9, 10.2, 6.6 Hz, 1H), 5.26-5.17 (m, 2H), 5.14-5.00 (m, 2H), 4.85 (s, 1H), 4.10 (dd, J=9.7, 6.2 Hz, 1H), 3.81 (dt, J=9.7, 6.6 Hz, 1H), 3.55 (dt, J=9.6, 6.4 Hz, 1H), 2.44 (dt, J=13.4, 3.9 Hz, 1H), 2.28-2.20 (m, 3H), 1.84-1.75 (m, 2H), 1.32 (d, J=6.2 Hz, 3H). Mass Analysis (ESI, +ve)=425.2 [M+H].

Preparation of (2R,3R,5R,6S)-5-((tert-butyldiphenylsilyl)oxy)-2-(((R)-hex-5-en-2-yl)oxy)-6-methyl-tetrahydro-2H-pyran-3-yl benzoate (T-05)

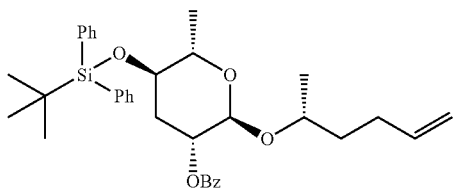

To a stirred solution of C-02 (0.570 g, 0.900 mmol) in DCM (5 mL) was added (2R)-(−)-hex-5-en-2-ol (0.165 mL, 1.35 mmol). The resulting mixture was cooled to 0° C. followed by treatment with TMSOTf (0.080 mL, 0.450 mmol). The reaction mixture was warmed to room temperature and stirred under nitrogen for 2 h. The resulting mixture was partitioned between water (5 mL) and DCM (10 mL). The organic layer was washed with saturated aqueous NaHCO$_3$ (5 mL), brine (5 mL), dried over magnesium sulfate, filtered, and concentrated. The crude product was purified by the column chromatography (40 g silica gel, 0% to 30% acetone in hexanes) to afford T-05 (0.420 g, 82% yield) as a light brown oil. $^1$H NMR (500 MHz, CDCl$_3$) δ 7.77-7.73 (m, 2H), 7.72-7.66 (m, 4H), 7.58 (ddt, J=8.8, 7.2, 1.3 Hz, 1H), 7.43-7.38 (m, 3H), 7.37-7.29 (m, 5H), 5.91 (ddt, J=16.9, 10.2, 6.5 Hz, 1H), 5.12 (dq, J=17.1, 1.7 Hz, 1H), 5.07-5.02 (m, 1H), 4.90 (td, J=3.1, 1.4 Hz, 1H), 4.78 (s, 1H), 3.96-3.89 (m, 1H), 3.87-3.79 (m, 1H), 3.68 (ddd, J=11.2, 9.2, 4.3 Hz, 1H), 2.31-2.16 (m, 2H), 2.06 (ddd, J=14.0, 11.3, 3.0 Hz, 1H), 1.93-1.86 (m, 1H), 1.76 (dddd, J=13.4, 9.3, 7.4, 5.9 Hz, 1H), 1.65-1.58 (m, 1H), 1.29 (d, J=6.2 Hz, 3H), 1.17 (d, J=6.1 Hz, 3H), 1.08 (s, 9H). Mass Analysis (ESI, +ve)=573.2 [M+H].

Using the above protocols, the following carbohydrate alkane starting materials are made from the compounds in Table 2 and terminal alkene alcohols. Disubstituted alkene alcohols are made from ketones (e.g. acetone, cyclopropanone, cyclobutanone) by reaction with 3-butenylmagnesium bromide.

TABLE 2

Carbohydrates Terminal Alkenes.

| # | Structure |
|---|---|
| T-01 | |
| T-02 | 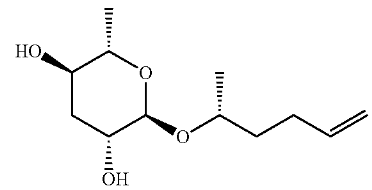 [SMILES: C=CCC[C@@H](C)O[C@@H]1O[C@@H](C)[C@H](O)C[C@H]1O] |
| T-03 | 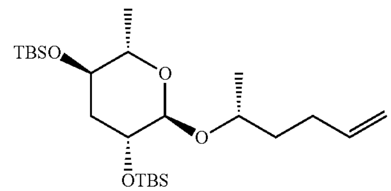 [SMILES: C=CCC[C@@H](C)O[C@@H]1O[C@@H](C)[C@H](O[Si](C)(C)C(C)(C)C)C[C@H]1O[Si](C)(C)C(C)(C)C] |
| T-04 | 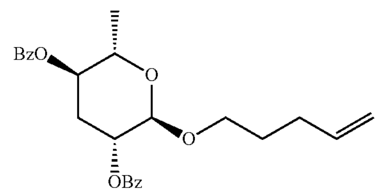 |
| T-05 | 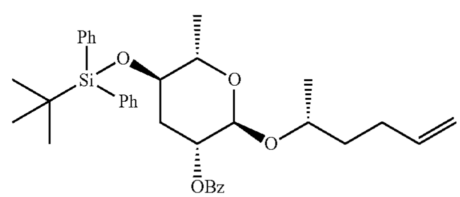 |
| T-06 | 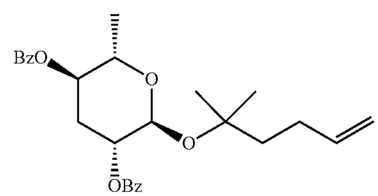 |
| T-07 | 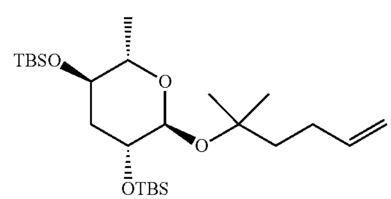 [SMILES: C=CCCC(C)(C)O[C@@H]1O[C@@H](C)[C@H](O[Si](C)(C)C(C)(C)C)C[C@H]1O[Si](C)(C)C(C)(C)C] |
| T-08 | 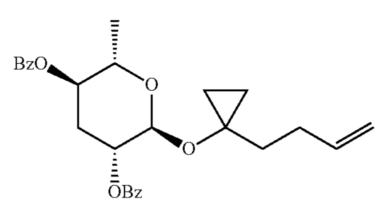 |

TABLE 2-continued

Carbohydrates Terminal Alkenes.

| # | Structure |
|---|---|
| T-09 | 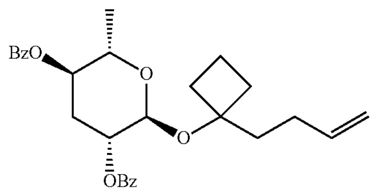 |
| T-10 | 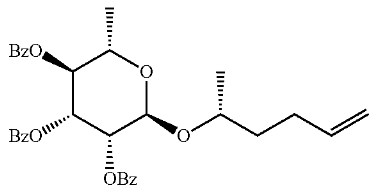 |
| T-11 | 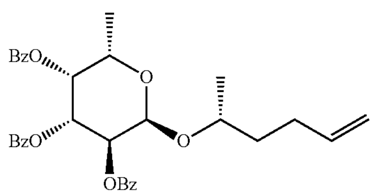 |
| T-12 | 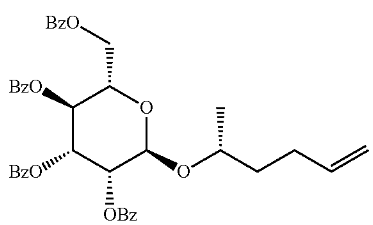 |
| T-13 | 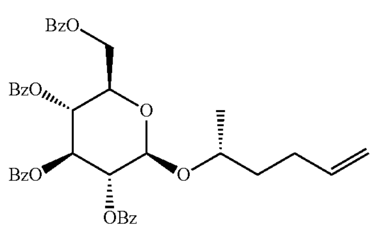 |
| T-14 | 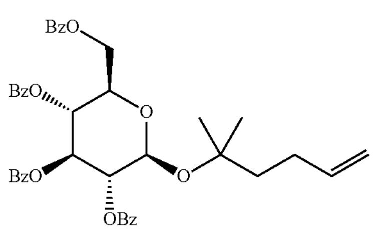 |

Preparation of tert-butyl({[(2S,3R,5R,6R)-5-[(tert-butyldimethylsilyl)oxy]-2-methyl-6-{[(2R)-4-(oxiran-2-yl)butan-2-yl]oxy}oxan-3-yl]oxy})dimethylsilane (I-02)

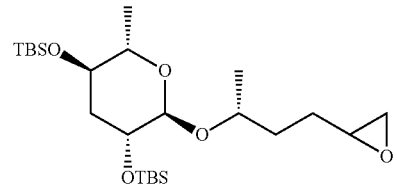 [SMILES: C[C@H](CCC1CO1)O[C@@H]1O[C@@H](C)[C@H](O[Si](C)(C)C(C)(C)C)C[C@H]1O[Si](C)(C)C(C)(C)C]

Compound T-03 (6.00 g, 13.0 mmol, 1.00 eq.) was dissolved into DCM (42 mL). m-CPBA (3.95 g, 18.3 mmol, 80% purity, 1.40 eq.) was added as a solid to the reaction mixture at 0° C. The reaction mixture was stirred at 25° C. for 16 h. TLC showed the reaction was complete (5:1 petroleum ether-ethyl acetate, SM $R_f$ (T-03)=0.61, $R_f$ (I-02)=0.43). The mixture was filtered, the solid was washed with DCM, and the filtrate was collected. The organic filtrate was washed with aqueous $NaHSO_3$ (3×70 mL) and aqueous $NaHCO_3$ (3×70 mL). The combined organic layers were dried over sodium sulfate, filtered, and concentrate in vacuo. The residue was purified by column chromatography (silica gel, 10:1 petroleum ether-ethyl acetate) to afford I-02 (5.78 g, 81% yield) as a colorless oil. $^1$H NMR (400 MHz, $CDCl_3$) δ 4.53 (s, 1H), 3.89-3.49 (m, 4H), 2.93 (brs, 1H), 2.79-2.75 (m, 1H), 2.50-2.43 (m, 1H), 1.80-1.41 (m, 6H), 1.19-1.11 (m, 6H), 0.90-0.87 (m, 18H), 0.00 (s, 12H).

Preparation of (4R)-4-{[(2R,3R,5R,6S)-3,5-bis[(tert-butyldimethylsilyl)oxy]-6-methyloxan-2-yl]oxy}pentanal (I-03)

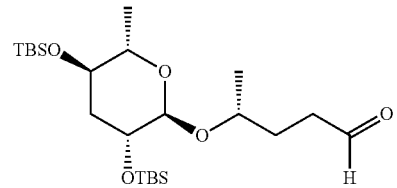 [SMILES: C[C@H](CCC=O)O[C@@H]1O[C@@H](C)[C@H](O[Si](C)(C)C(C)(C)C)C[C@H]1O[Si](C)(C)C(C)(C)C]

Compound T-03 (3.00 g, 6.54 mmol, 1.00 eq.) was dissolved in DCM (100 mL). Ozone was bubbled into the mixture at −70° C. for 10 min until the solution turns blue. Oxygen was bubbled into the reaction mixture at −70° C. for 20 min until the blue solution turns colorless. Triphenylphosphine (5.14 g, 19.6 mmol, 3.00 eq.) was added to the reaction mixture as a solid. The reaction was stirred at 25° C. for 16 h. TLC showed the reaction was complete (5:1 petroleum ether-ethyl acetate). The solvent was concentrate in vacuo and the residue was purified by column chromatography (silica gel, 5:1 petroleum ether-ethyl acetate) to afford I-03 (2.02 g, 67% yield) as a colorless oil. $^1$H NMR (400 MHz, $CDCl_3$) δ 9.81 (s, 1H), 4.54 (s, 1H), 3.88-3.50 (m, 4H), 2.60-2.50 (m, 2H), 1.86-1.76 (m, 4H), 1.18-1.13 (m, 6H), 0.90-0.74 (m, 18H), 0.06 (s, 12H).

Preparation of (2R,3R,5R,6S)-5-((tert-butyldiphenylsilyl)oxy)-2-(((2R)-5,6-dihydroxyhexan-2-yl)oxy)-6-methyltetrahydro-2H-pyran-3-yl benzoate (I-04)

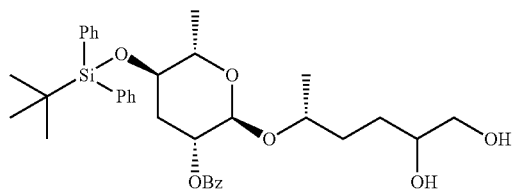

To a solution of T-05 (0.300 g, 0.524 mmol) in THF (3 mL) and water (1 mL) was added 4-methylmorpholine N-oxide (0.25 mL, 1.05 mmol) and osmium tetroxide (0.34 mL, 0.0524 mmol, 4% weight in water). The reaction mixture was stirred at room temperature under nitrogen for 18 h. The resulting mixture was quenched with saturated aqueous NaHCO$_3$(2 mL) then partitioned between ethyl acetate (10 mL) and water (5 mL). The aqueous layer was extracted with ethyl acetate (2×10 mL). The combined organic layers were dried over magnesium sulfate, filtered, and concentrated. The crude product was purified by the column chromatography (24 g silica gel, 0% to 40% acetone in hexanes) to afford I-04 (0.280 g, 88% yield) as a colorless paste. $^1$H NMR (500 MHz, CDCl$_3$) δ 7.76-7.73 (m, 2H), 7.72-7.65 (m, 4H), 7.58 (ddt, J=8.7, 7.4, 1.3 Hz, 1H), 7.43-7.38 (m, 3H), 7.38-7.29 (m, 6H), 4.90 (s, 1H), 4.79 (s, 1H), 3.93-3.85 (m, 2H), 3.84-3.78 (m, 1H), 3.75 (ddt, J=10.1, 6.8, 3.6 Hz, 1H), 3.71-3.64 (m, 1H), 3.58-3.51 (m, 1H), 2.35 (dd, J=13.0, 4.3 Hz, 1H), 2.10-2.00 (m, 2H), 1.95-1.87 (m, 2H), 1.83-1.69 (m, 2H), 1.69-1.61 (m, 2H), 1.31-1.27 (m, 3H), 1.19 (d, J=6.1 Hz, 3H), 1.08 (s, 9H). Mass Analysis (ESI, +ve)=607.2 [M+H].

Preparation of (2R,3R,5R,6S)-5-((tert-butyldiphenylsilyl)oxy)-6-methyl-2-(((R)-5-oxopentan-2-yl)oxy)tetrahydro-2H-pyran-3-yl benzoate (I-05)

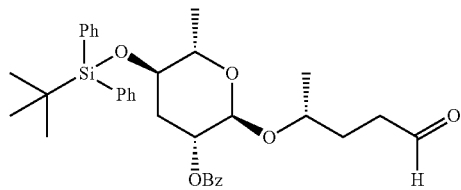

To a solution of I-04 (0.280 g, 0.462 mmol) in THF (2 mL) and water (2 mL) was added NaIO$_4$ (0.224 g, 1.05 mmol). The reaction mixture was stirred at room temperature under nitrogen for 18 h. The resulting mixture was quenched with saturated aqueous NaHCO$_3$ (2 mL) then partitioned between ethyl acetate (10 mL) and water (5 mL). The aqueous layer was extracted with ethyl acetate (2×10 mL). The combined organic layers were dried over magnesium sulfate, filtered, and concentrated. The crude product was purified by the column chromatography (24 g silica gel, 0% to 30% acetone in hexanes) to afford I-05 (0.150 g, 57% yield) as a colorless paste. $^1$H NMR (500 MHz, CDCl$_3$) δ 9.89 (t, J=1.6 Hz, 1H), 7.76-7.72 (m, 2H), 7.72-7.66 (m, 4H), 7.60-7.56 (m, 1H), 7.43-7.38 (m, 3H), 7.38-7.29 (m, 5H), 4.88 (td, J=3.2, 2.0 Hz, 1H), 4.77 (s, 1H), 3.91-3.80 (m, 2H), 3.67 (ddd, J=11.2, 9.1, 4.3 Hz, 1H), 2.64 (dddd, J=10.9, 8.3, 6.8, 1.6 Hz, 2H), 2.01 (ddd, J=14.0, 11.2, 3.0 Hz, 1H), 1.96-1.86 (m, 3H), 1.29 (d, J=6.2 Hz, 3H), 1.19 (d, J=6.1 Hz, 3H), 1.08 (s, 8H). Mass Analysis (ESI, +ve)=575.1 [M+H].

Preparation of tert-butyl (2E,6R)-6-{[(2R,3R,5R,6S)-3,5-dihydroxy-6-methyloxan-2-yl]oxy}hept-2-enoate (1)

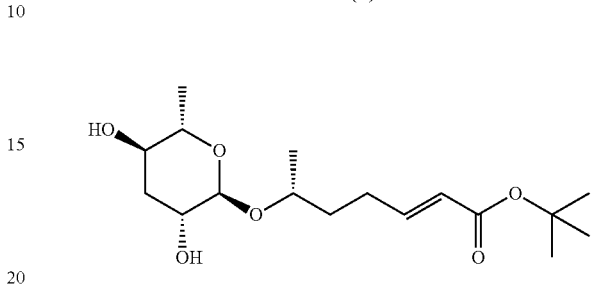

Compound T-02 (5.00 g, 21.7 mmol, 1.00 eq.) was dissolved into DCM (330 mL) and tert-butyl acrylate (13.9 g, 108 mmol, 15.7 mL, 5.00 eq.) was added to the reaction mixture at 15° C. Grubb's M204 catalyst (1.84 g, 2.17 mmol, 0.10 eq.) was added to the reaction at 15° C. and the mixture was degasses with nitrogen 3 times. The reaction was heated to 50° C. and stirred at 50° C. for 16 h. TLC showed the reaction was complete (5:1 petroleum ether-ethyl acetate, SM R$_f$(T-02)=0.50, R$_f$(1)=0.00). The solvent was concentrate in vacuo and the residue was purified by column chromatography (silica gel, 100% ethyl acetate) and then purified again by prep-HPLC (Column: Agela DuraShell C$_{18}$ 250×25 mm, 10 μm; Mobile Phase A: Water 0.05% ammonia hydroxide (v/v), Mobile Phase B: ACN; Gradient B %: 12%-46%, Runtime: 22 min) to afford 1 (2.00 g, 6.05 mmol, 28% yield) as a reddish brown oil. $^1$H NMR (400 MHz, CDCl$_3$) δ 6.94-6.87 (m, 1H), 5.79-5.75 (m, 1H), 4.79 (s, 1H), 3.85-3.81 (m, 2H), 3.67-3.62 (m, 2H), 2.32-2.29 (m, 2H), 1.48 (s, 9H), 1.28 (d, J=6.0 Hz, 3H), 1.15 (d, J=6.0 Hz, 3H). LCMS Analysis (positive mode)=353.2 [M+Na].

Preparation of tert-butyl 2-[(3R)-3-{[(2R,3R,5R,6S)-3,5-bis[(tert-butyldimethylsilyl)oxy]-6-methyloxan-2-yl]oxy}butyl]cyclopropane-1-carboxylate (I-06)

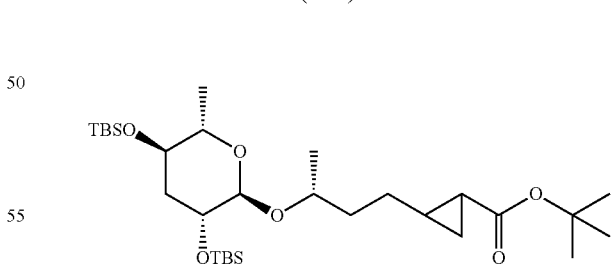

tert-Butyl 2-diethoxyphosphorylacetate (398 mg, 1.58 mmol, 1.50 eq.) was dissolved into 1,4-dioxane (3.5 mL) and cooled to 15° C. Sodium tert-butoxide (121 mg, 1.26 mmol, 1.20 eq.) was added to the reaction mixture under nitrogen atmosphere. The reaction mixture was stirred at 15° C. for 1 h. Compound I-03 (500 mg, 1.05 mmol, 1.00 eq.) was added and the mixture was heated at 130° C. for 16 h. TLC showed the reaction was complete (5:1 petroleum ether-ethyl acetate). Acetic acid was added to the mixture to quench the reaction and to bring the pH to 7. Brine (2.0 mL) and water (5.0 mL) were added to the mixture and the reaction was extracted with ethyl acetate (3×3.0 mL). The layers were separated and the organic layers were washed with aqueous NaHCO₃ (2×10 mL). The combined organic layers were dried over sodium sulfate, filtered, and concentrate in vacuo. The residue was purified by preparative TLC (silica gel, 5:1 petroleum ether-ethyl acetate) to afford I-06 (100 mg, 17% yield) as a colorless oil. ¹H NMR (400 MHz, CDCl₃) δ 4.54 (s, 1H), 3.86-3.74 (m, 2H), 3.66-3.56 (m, 2H), 1.80-1.78 (5H), 1.28 (s, 9H), 1.30-1.26 (m, 2H), 1.19-1.09 (m, 6H), 0.90-0.89 (m, 18H), 0.68-0.05 (m, 12H).

Preparation of tert-butyl 2-[(3R)-3-{[(2R,3R,5R, 6S)-3,5-dihydroxy-6-methyloxan-2-yl]oxy}butyl] cyclopropane-1-carboxylate (2)

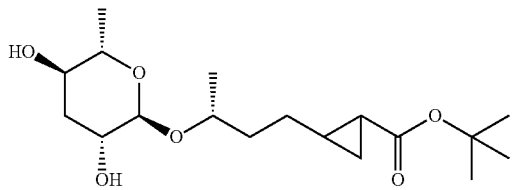 [SMILES: C[C@H](CCC1CC1C(=O)OC(C)(C)C)O[C@@H]1O[C@@H](C)[C@H](O)C[C@H]1O]

Compound I-06 (500 mg, 872 µmol, 1.00 eq.) was dissolved in THF (3.5 mL) and Et₃N·3HF (1.41 g, 8.73 mmol, 1.42 mL, 10.0 eq.) was added to the reaction mixture at 15° C. The reaction was stirred at 50° C. for 16 h. LCMS showed the reaction was complete. Aqueous NaHCO₃ was added to bring the pH to 8 and the mixture was concentrated in vacuo. The residue was purified by column chromatography (silica gel, 5:1 petroleum ether-ethyl acetate) to afford 2 (130 mg, 43% yield) as a colorless oil. ¹H NMR (400 MHz, CDCl₃) δ 4.70 (s, 1H), 3.84-3.80 (m, 2H), 3.66-3.58 (m, 2H), 2.10-2.01 (m, 1H), 1.87-1.76 (m, 2H), 1.71-1.51 (m, 4H), 1.44 (s, 9H), 1.35-1.19 (m, 6H), 1.15-1.03 (m, 4H), 0.66-0.56 (m, 1H). LCMS Analysis (positive mode)=367.2 [M+Na].

Preparation of methyl (2E,6R)-6-{[(2R,3R,5R,6S)-3,5-bis[(tert-butyldimethylsilyl)oxy]-6-methyloxan-2-yl]oxy}hept-2-enoate (I-07)

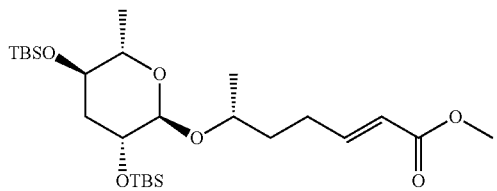 [SMILES: COC(=O)/C=C/CC[C@@H](C)O[C@@H]1O[C@@H](C)[C@H](O[Si](C)(C)C(C)(C)C)C[C@H]1O[Si](C)(C)C(C)(C)C]

Compound T-03 (10.0 g, 21.8 mmol, 1.00 eq.) was dissolved into DCM (300 mL) and methyl acrylate (9.38 g, 108 mmol, 9.81 mL, 5.00 eq.) was added to the reaction mixture at 25° C. Grubb's M204 catalyst (1.85 g, 2.18 mmol, 0.10 eq.) was added to the reaction mixture at 25° C. and then the mixture was heated to 50° C. The reaction mixture was stirred at 50° C. for 16 h. TLC showed the reaction was complete (5:1 petroleum ether-ethyl acetate, SM R_f(T-03)=0.61, R_f (I-07)=0.44). The solvent was concentrate in vacuo and the residue was purified by column chromatography (silica gel, 5:1 petroleum ether-ethyl acetate) to afford I-07 (8.3 g, 74% yield) as a colorless oil. ¹H NMR (400 MHz, CDCl₃) δ 6.97-6.80 (m, 1H), 5.79 (d, J=15.6 Hz, 1H), 4.48 (s, 1H), 4.07-4.03 (m, 2H), 3.71 (s, 3H), 3.59-3.45 (m, 2H), 2.31-2.22 (m, 2H), 1.74-1.69 (m, 4H), 1.19 (d, J=7.2 Hz, 3H), 1.12 (d, J=6.0 Hz, 3H), 0.84-0.83 (m, 18H), 0.01-0.00 (m, 12H). LCMS Analysis (positive mode)=539.3 [M+Na].

Preparation of (2E,6R)-6-{[(2R,3R,5R,6S)-3,5-bis [(tert-butyldimethylsilyl)oxy]-6-methyloxan-2-yl] oxy}hept-2-enoic acid (I-08)

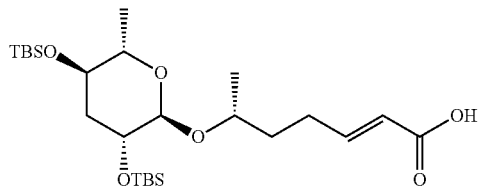 [SMILES: C[C@H](CC/C=C/C(=O)O)O[C@@H]1O[C@@H](C)[C@H](O[Si](C)(C)C(C)(C)C)C[C@H]1O[Si](C)(C)C(C)(C)C]

Compound I-07 (8.30 g, 16.0 mmol, 1.00 eq.) was dissolved in a mixture of methanol (83 mL), water (41.5 mL), and THF (58 mL). A solution of LiOH·H₂O (1.35 g, 32.1 mmol, 2.00 eq.) in water (41.5 mL) was added to the mixture at 25° C. The reaction was stirred at 50° C. for 3 h. TLC showed the reaction was complete (5:1 petroleum ether-ethyl acetate, SM R_f (I-07)=0.8, R_f (I-08)=0.17). 1N HCl was added to the reaction mixture to make the pH=2. The mixture was extracted with ethyl acetate (3×30 mL). The layers were separated and the organic layers were washed with brine (40 mL). The combined organic layers were dried over sodium sulfate, filtered, and concentrate in vacuo to afford I-08 (7.3 g, crude) as a brown oil, which was used directly without further purification.

Compound cyclohexylmethyl (2E,6R)-6-{[(2R,3R, 5R,6S)-3,5-bis[(tert-butyldimethylsilyl)oxy]-6-methyloxan-2-yl]oxy}hept-2-enoate (I-09)

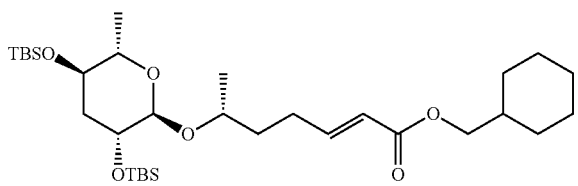 [SMILES: C[C@H](CC/C=C/C(=O)OCC1CCCCC1)O[C@@H]1O[C@@H](C)[C@H](O[Si](C)(C)C(C)(C)C)C[C@H]1O[Si](C)(C)C(C)(C)C]

Compound I-08 (1.00 eq.) and alcohol (3.00 eq.) were dissolved in DCM (3.5 mL). DCC (1.10 eq.) and DMAP (0.80 eq.) were added to the solution as solids and the reaction mixture was stirred at 25° C. for 16 h. TLC showed the reaction was complete (5:1 petroleum ether-ethyl acetate). The solvent was concentrate in vacuo and the residue was purified by column chromatography (silica gel, petroleum ether-ethyl acetate) to afford I-09 as a yellow oil which was used directly in the final deprotection step. ¹H NMR (400 MHz, CDCl₃) δ 6.97-6.91 (m, 1H), 5.82 (d, J=15.6 Hz, 1H), 4.48 (s, 1H), 3.88-3.47 (m, 6H), 2.29-2.11 (m, 2H), 1.74-1.65 (m, 9H), 1.25-0.80 (m, 14H), 0.84-0.83 (m, 18H), 0.00 (s, 12H).

The following compounds were prepared using the above procedure:

Compound benzyl (2E,6R)-6-{[(2R,3R,5R,6S)-3,5-bis[(tert-butyldimethylsilyl)oxy]-6-methyloxan-2-yl]oxy}hept-2-enoate (I-10)

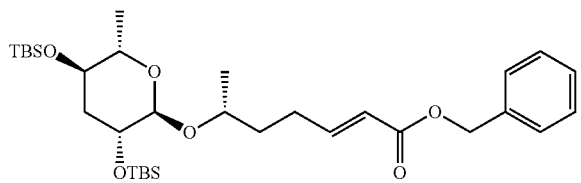 [SMILES: C[C@H](CC/C=C/C(=O)OCc1ccccc1)O[C@@H]1O[C@@H](C)[C@H](O[Si](C)(C)C(C)(C)C)C[C@H]1O[Si](C)(C)C(C)(C)C]

Yellow oil. ¹H NMR (400 MHz, CDCl₃) δ 7.31-7.28 (m, 5H), 7.02-6.96 (m, 1H), 5.84 (d, J=15.6 Hz, 1H), 5.11 (s, 2H), 4.48-4.47 (m, 1H), 3.75-3.70 (m, 2H), 3.59-3.46 (m, 2H), 2.30-2.22 (m, 2H), 1.74-1.65 (m, 4H), 1.20-1.02 (m, 8H), 0.84-0.82 (m, 18H), 0.00 (s, 12H).

Compound pyridin-3-ylmethyl (2E,6R)-6-{[(2R,3R,5R,6S)-3,5-bis[(tert-butyldimethylsilyl)oxy]-6-methyloxan-2-yl]oxy}hept-2-enoate (I-11)

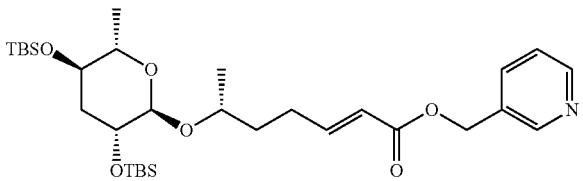 [SMILES: C[C@H](CC/C=C/C(=O)OCc1cccnc1)O[C@@H]1O[C@@H](C)[C@H](O[Si](C)(C)C(C)(C)C)C[C@H]1O[Si](C)(C)C(C)(C)C]

Yellow oil. ¹H NMR (400 MHz, CDCl₃) δ 8.58-8.51 (m, 2H), 7.66-7.64 (m, 1H), 7.26-7.22 (m, 1H), 7.01-6.95 (m, 1H), 5.83 (d, J=16.0 Hz, 1H), 5.11 (s, 2H), 4.48-4.47 (m, 1H), 3.75-3.70 (m, 2H), 3.59-3.48 (m, 2H), 2.31-2.23 (m, 1H), 1.74-1.68 (m, 4H), 1.20-1.02 (m, 9H), 0.84-0.68 (m, 18H), 0.00 (s, 12H).

Compound pyridin-4-ylmethyl (2E,6R)-6-{[(2R,3R,5R,6S)-3,5-bis[(tert-butyldimethylsilyl)oxy]-6-methyloxan-2-yl]oxy}hept-2-enoate (I-12)

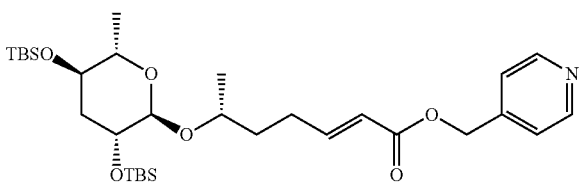 [SMILES: C[C@H](CC/C=C/C(=O)OCc1ccncc1)O[C@@H]1O[C@@H](C)[C@H](O[Si](C)(C)C(C)(C)C)C[C@H]1O[Si](C)(C)C(C)(C)C]

Yellow oil. ¹H NMR (400 MHz, CDCl₃) δ 8.55-8.53 (m, 2H), 7.15-7.10 (m, 2H), 7.03-7.69 (m, 1H), 5.88 (d, 15.6 Hz, 1H), 5.11 (s, 2H), 4.48-4.47 (m, 1H), 3.76-3.70 (m, 2H), 3.60-3.49 (m, 2H), 2.35-2.26 (m, 2H), 1.74-1.69 (m, 4H), 1.19-1.03 (m, 8H), 0.84-0.68 (m, 18H), 0.00 (s, 12H).

Compound 2-phenylethyl (2E,6R)-6-{[(2R,3R,5R,6S)-3,5-bis[(tert-butyldimethylsilyl)oxy]-6-methyloxan-2-yl]oxy}hept-2-enoate (I-13)

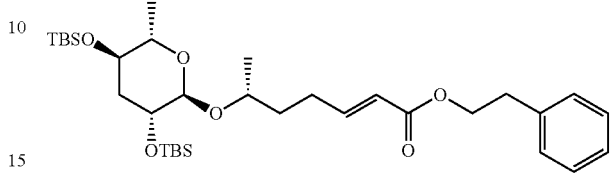

Yellow oil. ¹H NMR (400 MHz, CDCl₃) δ 7.26-7.20 (m, 2H), 7.18-7.14 (m, 3H), 6.93-6.89 (m, 1H), 5.77 (d, J=15.6 Hz, 1H), 4.48-4.47 (m, 1H), 4.29-4.22 (m, 2H), 3.73-3.70 (m, 2H), 3.58-3.49 (m, 2H), 2.92-2.86 (m, 3H), 2.31-2.11 (m, 2H), 1.75-1.51 (m, 4H), 1.15-1.01 (m, 8H), 0.84-0.68 (m, 18H), 0.00 (s, 12H).

Compound cyclohexylmethyl (2E,6R)-6-{[(2R,3R,5R,6S)-3,5-dihydroxy-6-methyloxan-2-yl]oxy}hept-2-enoate (3)

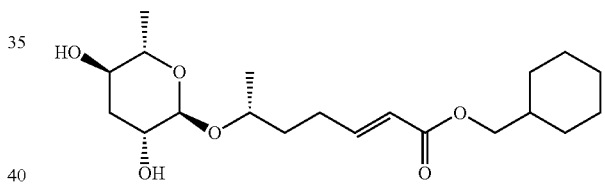

Compound I-09 (1.00 eq.) was dissolved in THF (7 V) and Et₃N·3HF (10 eq.) was added. The reaction was stirred at 50° C. for 4 h. LCMS showed the reaction was complete. The solvent was concentrate in vacuo and the residue was purified by prep-HPLC (Column: Phenomena Luna C₁₈ 200 mm×40 mm, 10 μm; Mobile Phase A: Water w/0.2% formic acid and Mobile Phase B: ACN; Gradient B %: 30% to 70%; Runtime: 8 min) to obtain crude product. Purify the crude product by SFC Purify the crude product by SFC (Instrument: Thar SFC80 preparative SFC; Column: REGIS (S,S) WHELK-01 (250 mm×30 mm, 10 μm); Mobile Phase A: Supercritical CO₂ and Mobile Phase B: Ethanol; Isocratic: B %=30%; Flow rate: 55 mL/min; Wavelength: 220 nm; Column Temperature: 40° C. System Back Pressure: 100 bar; Runtime: 10 min) to afford 26.0 mg of 3 a colorless oil. ¹H NMR (400 MHz, CDCl₃) δ 7.00 (dt, J=15.6, 7.0 Hz, 1H), 5.85 (d, J=15.6 Hz, 1H), 4.70 (s, 1H), 3.94 (d, J=6.4 Hz, 2H), 3.87-3.77 (m, 4H), 3.67-3.52 (m, 2H), 2.42-2.27 (m, 2H), 2.17-2.02 (m, 1H), 1.82-1.57 (m, 10H), 1.28 (d, J=6.4 Hz, 3H), 1.26-1.17 (m, 2H), 1.16 (d, J=6.4 Hz, 3H), 1.07-0.92 (m, 2H). LCMS Analysis (positive mode)=393.2 [M+Na]; 98.9% LCMS purity.

The following compounds were prepared using the above procedure:

Compound benzyl (2E,6R)-6-{[(2R,3R,5R,6S)-3,5-dihydroxy-6-methyloxan-2-yl]oxy}hept-2-enoate (4)

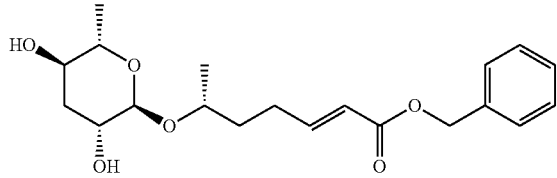 [SMILES: C[C@H](CC/C=C/C(=O)OCc1ccccc1)O[C@@H]1O[C@@H](C)[C@H](O)C[C@H]1O]

Compound 4: 6.5 mg of a colorless oil. $^1$H NMR (400 MHz, CDCl$_3$) δ 7.38-7.32 (m, 5H), 7.05 (dt, J=15.6, 7.5 Hz, 1H), 5.90 (d, J=15.6 Hz, 1H), 5.18 (s, 2H), 4.69 (s, 1H), 3.86-3.80 (m, 2H), 3.63-3.54 (m, 2H), 2.35-2.31 (m, 2H), 2.06 (d, J=13.2 Hz, 1H), 1.81-1.56 (m, 5H), 1.26 (d, J=6.0 Hz, 3H), 1.15 (d, J=6.0 Hz, 3H). LCMS Analysis (positive mode)=387.2 [M+Na]; 92.7% LCMS purity.

Compound pyridin-3-ylmethyl (2E,6R)-6-{[(2R,3R,5R,6S)-3,5-dihydroxy-6-methyloxan-2-yl]oxy}hept-2-enoate (5)

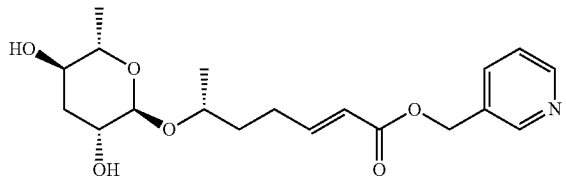 [SMILES: C[C@H](CC/C=C/C(=O)OCc1cccnc1)O[C@@H]1O[C@@H](C)[C@H](O)C[C@H]1O]

Compound 5: 26.1 mg of a colorless oil. $^1$H NMR (400 MHz, CDCl$_3$) δ 8.64 (d, J=1.6 Hz, 1H), 8.59-8.57 (m, 1H), 7.71 (dd, J=6.0, 2.0 Hz, 1H), 7.30 (dd, J=7.6, 4.3 Hz, 1H), 7.07 (dm, J=15.6 Hz, 1H), 5.88 (dd, J=15.6, 1.6 Hz, 1H), 5.19 (s, 2H), 4.70 (s, 1H), 3.85-3.80 (m, 2H), 3.63-3.59 (m, 2H), 2.36-2.32 (m, 2H), 2.00-2.10 (m, 1H), 1.82-1.59 (m, 5H), 1.26 (d, J=6.0 Hz, 3H), 1.15 (d, J=6.0 Hz, 3H). LCMS Analysis (positive mode)=366.2 [M+H]; 98.3% LCMS purity.

Compound pyridin-4-ylmethyl (2E,6R)-6-{[(2R,3R,5R,6S)-3,5-dihydroxy-6-methyloxan-2-yl]oxy}hept-2-enoate (6)

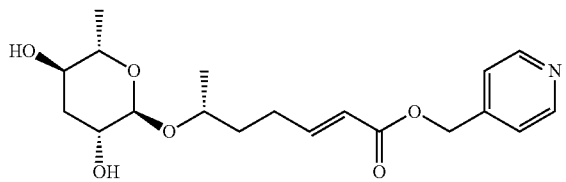 [SMILES: C[C@H](CC/C=C/C(=O)OCc1ccncc1)O[C@@H]1O[C@@H](C)[C@H](O)C[C@H]1O]

Compound 6: 26.4 mg of a colorless oil. $^1$H NMR (400 MHz, CDCl$_3$) δ 8.604 (d, J=4.8 Hz, 2H), 7.268 (d, J=4.0 Hz, 2H), 7.11 (dt, J=15.6, 7.0 Hz, 1H), 5.943 (d, J=14.4 Hz, 1H), 5.192 (s, 2H), 4.709 (s, 1H), 3.89-3.81 (m, 2H), 3.66-3.59 (m, 2H), 2.47-2.32 (m, 2H), 2.12-2.04 (m, 1H), 1.87-1.64 (m, 5H), 1.27 (d, J=6.0 Hz, 3H), 1.16 (d, J=6.0 Hz, 3H). LCMS Analysis (positive mode)=366.2 [M+H]; 99.7% LCMS purity.

Compound 2-phenylethyl (2E,6R)-6-{[(2R,3R,5R,6S)-3,5-dihydroxy-6-methyloxan-2-yl]oxy}hept-2-enoate (7)

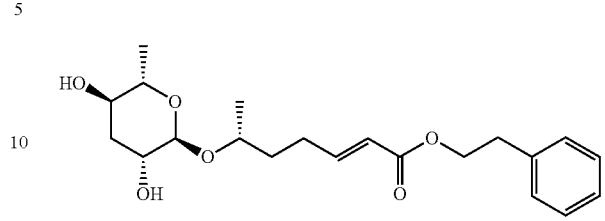

Compound 7: 26.1 mg of a colorless oil. $^1$H NMR (400 MHz, CDCl$_3$) δ 7.33-7.22 (m, 5H), 7.00 (dd, J=15.6, 7.8 Hz, 1H), 5.84 (d, J=15.6 Hz, 1H), 4.70 (s, 1H), 4.35 (t, J=7.2 Hz, 2H), 3.84-3.84 (m, 2H), 3.63-3.57 (m, 2H), 2.97 (t, J=7.2 Hz, 2H), 2.30-2.20 (m, 2H), 2.08 (d, J=12.8 Hz, 1H), 1.83-1.45 (m, 5H), 1.27 (d, J=6.0 Hz, 3H), 1.16 (d, J=6.0 Hz, 3H). LCMS Analysis (positive mode)=401.2 [M+Na]; 87.1% LCMS purity.

Preparation of (2R,3R,5R,6S)-5-((tert-butyldiphenylsilyl)oxy)-2-(((R,E)-7-isopropoxy-7-oxohept-5-en-2-yl)oxy)-6-methyltetrahydro-2H-pyran-3-yl benzoate (I-14)

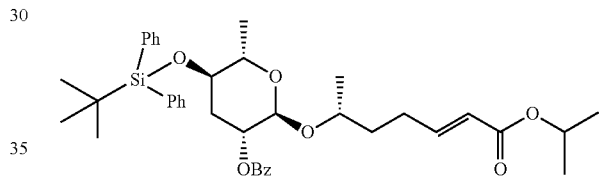

Using the same procedure to make I-07, to a solution of T-05 (0.200 g, 0.349 mmol) in DCM (5 mL) was added isopropyl acrylate (0.090 mL, 0.699 mmol) and Grubb's M204 catalyst (0.015 g, 0.0174 mmol) and after isolation and purification afforded I-14 (0.130 g, 57% yield) as a colorless paste. $^1$H NMR (500 MHz, CDCl$_3$) δ 7.76-7.73 (m, 2H), 7.72-7.66 (m, 4H), 7.58 (ddt, J=8.7, 7.1, 1.3 Hz, 1H), 7.44-7.38 (m, 3H), 7.38-7.29 (m, 5H), 7.04 (dt, J=15.7, 6.8 Hz, 1H), 5.90 (dt, J=15.7, 1.6 Hz, 1H), 5.10 (p, J=6.3 Hz, 2H), 4.89 (dt, J=4.5, 2.1 Hz, 1H), 4.77 (s, 1H), 3.91-3.80 (m, 2H), 3.68 (ddd, J=11.2, 9.2, 4.3 Hz, 1H), 2.51-2.25 (m, 3H), 2.04 (ddd, J=14.0, 11.2, 3.0 Hz, 2H), 1.90 (dt, J=14.0, 3.8 Hz, 1H), 1.79 (dddd, J=13.4, 9.4, 5.7, 3.8 Hz, 1H), 1.72-1.63 (m, 1H), 1.29 (dd, J=6.3, 5.1 Hz, 9H), 1.17 (d, J=6.1 Hz, 3H), 1.08 (s, 9H). Mass Analysis (ESI, +ve)=660.2 [M+H].

Preparation of isopropyl (R,E)-6-(((2R,3R,5R,6S)-5-((tert-butyldiphenylsilyl)oxy)-3-hydroxy-6-methyltetrahydro-2H-pyran-2-yl)oxy)hept-2-enoate (I-15)

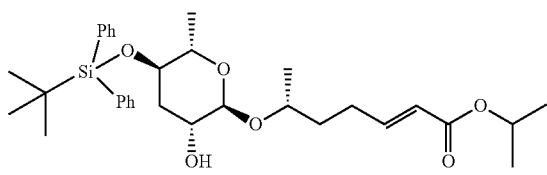 [SMILES: CC(C)OC(=O)/C=C/CC[C@@H](C)O[C@@H]1O[C@@H](C)[C@H](O[Si](c2ccccc2)(c2ccccc2)C(C)(C)C)C[C@H]1O]

To a solution of I-14 (0.130 g, 0.197 mmol) in isopropanol (5 mL) was added 1% aq. NaOH (2.3 mL, 0.591 mmol). The reaction mixture was stirred at room temperature under nitrogen for 18 h. The resulting mixture was partitioned between ethyl acetate (10 mL) and water (5 mL). The aqueous layer was extracted with ethyl acetate (2×10 mL). The combined organic layers were dried over magnesium sulfate, filtered, and concentrated. The crude product was purified by the column chromatography (24 g silica gel, 0% to 30% acetone in hexanes) to afford I-15 (0.060 g, 55% yield) as a colorless oil. $^1$H NMR (500 MHz, CDCl$_3$) δ 7.75-7.66 (m, 4H), 7.48-7.43 (m, 2H), 7.43-7.37 (m, 4H), 7.02 (dt, J=15.6, 6.8 Hz, 1H), 5.89 (dt, J=15.6, 1.6 Hz, 1H), 5.10 (p, J=6.3 Hz, 1H), 4.63-4.58 (m, 1H), 3.82 (ddd, J=7.8, 6.3, 5.1 Hz, 1H), 3.77 (dd, J=8.9, 6.2 Hz, 1H), 2.45-2.27 (m, 3H), 1.90-1.71 (m, 4H), 1.69-1.61 (m, 2H), 1.29 (d, J=6.3 Hz, 6H), 1.19 (d, J=6.2 Hz, 3H), 1.14 (d, J=6.1 Hz, 3H), 1.08 (s, 9H). Mass Analysis (ESI, +ve)=555.1 [M+H].

Preparation of isopropyl (R,E)-6-(((2R,3R,5R,6S)-3,5-dihydroxy-6-methyltetrahydro-2H-pyran-2-yl)oxy)hept-2-enoate (8)

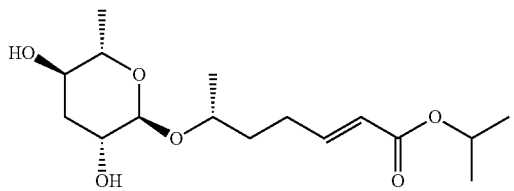

To a solution of I-15 (0.055 g, 0.099 mmol) in THF (3 mL) was added 1.0 M TBAF (0.500 mmol, 0.500 mL) in THF. The reaction mixture was stirred at room temperature under nitrogen for 18 h. The resulting mixture was concentrated and the crude product was purified by the column chromatography (24 g silica gel, 0% to 15% MeOH in DCM) to afford 8 (0.013 g, 42% yield) as a colorless oil. $^1$H NMR (500 MHz, CDCl$_3$) δ 7.01 (dt, J=15.7, 6.8 Hz, 1H), 5.84 (dt, J=15.6, 1.6 Hz, 1H), 5.08 (p, J=6.2 Hz, 1H), 4.77-4.69 (m, 1H), 3.90-3.85 (m, 1H), 3.83 (q, J=2.9 Hz, 1H), 3.70-3.65 (m, 1H), 3.60 (ddd, J=11.0, 9.1, 4.4 Hz, 1H), 2.34 (ttd, J=8.5, 6.8, 1.7 Hz, 2H), 2.10 (dddd, J=13.0, 4.5, 3.5, 1.0 Hz, 1H), 1.85 (ddd, J=13.2, 10.9, 3.0 Hz, 2H), 1.78-1.69 (m, 3H), 1.30 (d, J=6.1 Hz, 3H), 1.28 (d, J=6.3 Hz, 6H), 1.18 (d, J=6.1 Hz, 3H). Mass Analysis (ESI, +ve)=317.2.1 [M+H].

Preparation of (2R,3R,5R,6S)-2-(((2R)-7-(tert-butoxy)-5-hydroxy-7-oxoheptan-2-yl)oxy)-5-((tert-butyldiphenylsilyl)oxy)-6-methyltetrahydro-2H-pyran-3-yl benzoate (I-16)

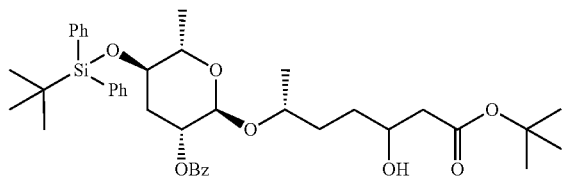

To an oven-dry 25-mL 3-neck round-bottom flask, equipped with a low-temperature thermometer and nitrogen inlet, was added tert-butyl acetate (0.140 mL, 1.044 mmol) and THF (5 mL). The resulting mixture was cooled to −75° C. followed by addition of 1.96 M LDA (0.400 mL, 0.783 mmol) dropwise via syringe. The reaction mixture was stirred at −75° C. for 2 h then (2R,3R,5R,6S)-5-((tert-butyldiphenylsilyl)oxy)-6-methyl-2-(((R)-5-oxopentan-2-yl)oxy)tetrahydro-2H-pyran-3-yl benzoate (0.150 g, 0.261 mmol) was added in THF (3 mL) dropwise via syringe. The reaction mixture was stirred for another hour then quenched with saturated aqueous ammonium chloride (1 mL), warmed to room temperature, and partitioned between ethyl acetate (10 mL) and water (5 mL). The aqueous layer was extracted with ethyl acetate (2×10 mL). The combined organic layers were dried over magnesium sulfate, filtered, and concentrated. The crude product was purified by the column chromatography (24 g silica gel, 0% to 30% acetone in hexanes) to afford I-16 (0.090 g, 50% yield). $^1$H NMR (500 MHz, CDCl$_3$) δ 7.76-7.72 (m, 2H), 7.72-7.66 (m, 4H), 7.60-7.55 (m, 1H), 7.43-7.38 (m, 3H), 7.37-7.29 (m, 5H), 4.89 (d, J=3.6 Hz, 1H), 4.77 (s, 1H), 4.10-3.99 (m, 2H), 3.93-3.79 (m, 3H), 3.67 (tdd, J=9.1, 4.2, 2.3 Hz, 1H), 3.27 (s, 1H), 2.52 (ddd, J=16.4, 4.7, 3.0 Hz, 1H), 2.42 (ddd, J=16.4, 9.1, 0.8 Hz, 1H), 2.03 (dt, J=11.3, 3.0 Hz, 1H), 1.89 (dt, J=13.7, 3.7 Hz, 1H), 1.80-1.63 (m, 4H), 1.51 (d, J=1.5 Hz, 9H), 1.28 (dd, J=6.3, 3.2 Hz, 3H), 1.17 (d, J=6.1 Hz, 3H), 1.08 (s, 9H). Mass Analysis (ESI, +ve)=691.2 [M+H].

Preparation of tert-butyl (6R)-6-(((2R,3R,5R,6S)-5-((tert-butyldiphenylsilyl)oxy)-3-hydroxy-6-methyl-tetrahydro-2H-pyran-2-yl)oxy)-3-hydroxyheptanoate (I-17)

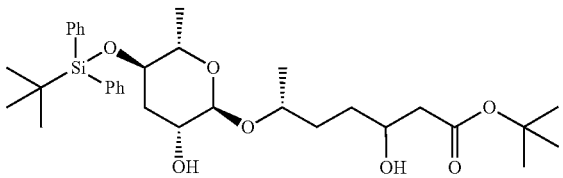

Using the same procedure to make I-15, to a solution of I-16 (0.090 g, 0.130 mmol) in methanol (3 mL) was added 1% aq. NaOH (0.520 mL, 0.520 mmol) and after isolation and purification afforded I-17 (0.035 g, 46% yield) as a colorless paste. $^1$H NMR (300 MHz, CDCl$_3$) δ 8.13-8.07 (m, 1H), 7.71-7.59 (m, 5H), 7.48 (dd, J=8.4, 6.9 Hz, 2H), 7.39 (dp, J=9.3, 6.1, 4.9 Hz, 5H), 4.59 (s, 1H), 4.01 (s, 1H), 3.76 (dd, J=14.1, 7.1 Hz, 2H), 3.64 (d, J=13.4 Hz, 2H), 2.49-2.32 (m, 2H), 2.17 (d, J=0.6 Hz, 2H), 1.88-1.73 (m, 2H), 1.62 (ddd, J=21.8, 11.3, 5.7 Hz, 5H), 1.47 (t, J=0.9 Hz, 9H), 1.15 (d, J=6.2 Hz, 3H), 1.11 (d, J=6.1 Hz, 3H), 1.05 (s, 9H). Mass Analysis (ESI, +ve)=587.1 [M+H].

Preparation of tert-butyl (6R)-6-(((2R,3R,5R,6S)-3,5-dihydroxy-6-methyltetrahydro-2H-pyran-2-yl)oxy)-3-hydroxyheptanoate (9)

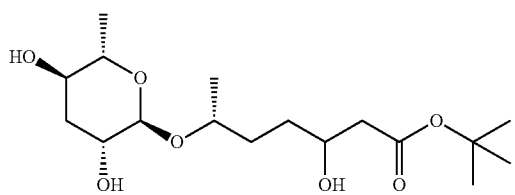 [SMILES: C[C@H](CCC(O)CC(=O)OC(C)(C)C)O[C@@H]1O[C@@H](C)[C@H](O)C[C@H]1O]

To a solution of I-17 (0.035 g, 0.060 mmol) in THF (2 mL) was added 1.0 M TBAF (0.30 mmol, 0.300 mL) in THF. The reaction mixture was stirred at room temperature under nitrogen for 18 h. The resulting mixture was concentrated and the crude product was purified by the column chromatography (24 g silica gel, 0% to 15% MeOH in DCM) to afford 9 (0.015 g, 75%) as a colorless oil. $^1$H NMR (500 MHz, CDCl$_3$) δ 4.76-4.70 (m, 1H), 4.07-3.99 (m, 1H), 3.91-3.80 (m, 2H), 3.72-3.65 (m, 1H), 3.60 (dddd, J=11.4, 9.1, 4.6, 2.4 Hz, 1H), 3.36-3.30 (m, 1H), 2.44 (t, J=3.3 Hz, 1H), 2.39 (dd, J=8.9, 3.6 Hz, 1H), 2.13-2.07 (m, 1H), 1.85 (dddd, J=13.2, 11.1, 3.0, 2.1 Hz, 2H), 1.73-1.64 (m, 3H), 1.63-1.55 (m, 2H), 1.49 (s, 9H), 1.30 (dd, J=6.2, 3.6 Hz, 3H), 1.17 (dd, J=6.1, 1.8 Hz, 3H). Mass Analysis (ESI, +ve)=349.1 [M+H].

Preparation of (2R,3R,5R,6S)-2-(((R,E)-7-(tert-butoxy)-7-oxohept-5-en-2-yl)oxy)-5-((tert-butyldiphenylsilyl)oxy)-6-methyltetrahydro-2H-pyran-3-yl benzoate (I-18)

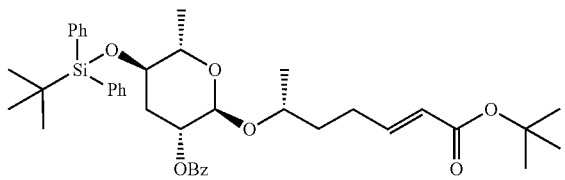

Using the same procedure to make I-09, to a solution of T-05 (0.300 g, 0.524 mmol) in DCM (5 mL) was added tert-butyl acrylate (0.230 mL, 1.572 mmol) and Grubb's M204 catalyst (0.025 g, 0.0262 mmol) and after isolation and purification afforded I-18 (0.300 g, 85% yield) as a colorless paste. $^1$H NMR (500 MHz, CDCl$_3$) δ 7.79-7.76 (m, 2H), 7.75-7.69 (m, 4H), 7.61 (ddt, J=8.7, 7.1, 1.3 Hz, 1H), 7.46-7.41 (m, 3H), 7.40-7.33 (m, 5H), 6.98 (dt, J=15.6, 6.8 Hz, 1H), 5.88 (dt, J=15.6, 1.6 Hz, 1H), 4.92 (s, 1H), 4.80 (s, 1H), 3.94-3.84 (m, 2H), 3.71 (ddd, J=11.1, 9.1, 4.3 Hz, 1H), 2.49-2.31 (m, 3H), 2.08 (ddd, J=14.0, 11.2, 2.9 Hz, 1H), 1.94 (dt, J=13.4, 3.8 Hz, 1H), 1.87-1.78 (m, 1H), 1.71 (ddd, J=13.3, 9.2, 5.0 Hz, 1H), 1.56 (s, 9H), 1.33 (d, J=6.2 Hz, 3H), 1.21 (d, J=6.1 Hz, 3H), 1.12 (s, 9H). Mass Analysis (ESI, +ve)=673.1 [M+H].

Preparation of tert-butyl (R,E)-6-(((2R,3R,5R,6S)-5-((tert-butyldiphenylsilyl)oxy)-3-hydroxy-6-methyl-tetrahydro-2H-pyran-2-yl)oxy)hept-2-enoate (I-19)

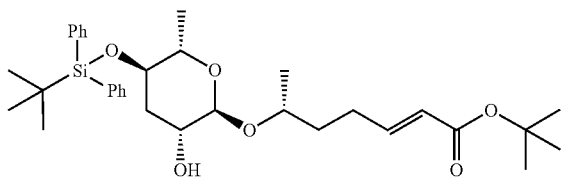 [SMILES: C[C@H](CC/C=C/C(=O)OC(C)(C)C)O[C@@H]1O[C@@H](C)[C@H](O[Si](c2ccccc2)(c2ccccc2)C(C)(C)C)C[C@H]1O]

Using the same procedure to make I-15, to a solution of I-18 (0.300 g, 0.446 mmol) in MeOH (5 mL) was added 1% aq. NaOH (3.5 mL, 0.892 mmol) and after isolation and purification I-19 (0.170 g, 67% yield) as a colorless oil. $^1$H NMR (500 MHz, CDCl$_3$) δ 7.74-7.67 (m, 4H), 7.48-7.37 (m, 6H), 6.93 (dt, J=15.6, 6.8 Hz, 1H), 5.83 (dt, J=15.6, 1.6 Hz, 1H), 4.61 (d, J=1.6 Hz, 1H), 3.84-3.75 (m, 2H), 3.69-3.62 (m, 2H), 2.43-2.26 (m, 3H), 1.89-1.80 (m, 2H), 1.78-1.71 (m, 1H), 1.68-1.62 (m, 1H), 1.51 (s, 9H), 1.19 (d, J=6.2 Hz, 3H), 1.14 (d, J=6.1 Hz, 3H), 1.08 (s, 9H). Mass Analysis (ESI, +ve)=569.2 [M+H].

Preparation of tert-butyl (R)-6-(((2R,3R,5R,6S)-5-((tert-butyldiphenylsilyl)oxy)-3-hydroxy-6-methyl-tetrahydro-2H-pyran-2-yl)oxy)heptanoate (I-20)

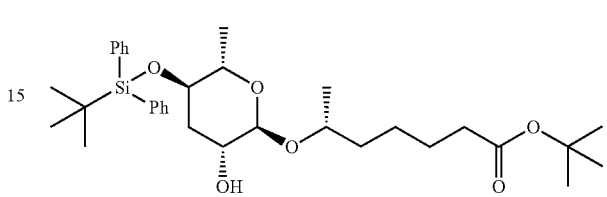

To a solution of I-19 (0.060 mL), which was attached with 3-way valve, in methanol (3 mL) was added Pd/C (0.015 g, 0.0105 mmol, 10% wt in wet version). The reaction mixture was first vacuumed then purged with nitrogen—this vacuumed-then-nitrogen purge procedure was repeated 3 times to ensure only nitrogen was in the flask. After the last vacuum, a hydrogen balloon was attached to the 3-way valve. The reaction mixture was stirred at room temperature under hydrogen for 18 h. The resulting mixture was filtered through a pad of Celite®. The filtrate was concentrated in vacuo to afford I-20 (0.045 g, 74% yield). $^1$H NMR (500 MHz, CDCl$_3$) δ 7.73-7.66 (m, 4H), 7.46-7.42 (m, 2H), 7.42-7.37 (m, 4H), 4.60 (s, 1H), 3.83-3.76 (m, 2H), 3.65 (dq, J=9.0, 4.8 Hz, 2H), 3.52 (s, 2H), 2.32-2.25 (m, 2H), 1.87 (ddd, J=13.6, 10.7, 3.0 Hz, 1H), 1.83-1.77 (m, 1H), 1.71-1.61 (m, 3H), 1.50 (d, J=0.5 Hz, 2H), 1.48 (s, 9H), 1.19 (d, J=6.2 Hz, 3H), 1.12 (d, J=6.1 Hz, 3H), 1.08 (d, J=1.9 Hz, 9H). Mass Analysis (ESI, +ve)=571.2 [M+H].

Preparation of tert-butyl (R)-6-(((2R,3R,5R,6S)-3,5-dihydroxy-6-methyltetrahydro-2H-pyran-2-yl)oxy)heptanoate (10)

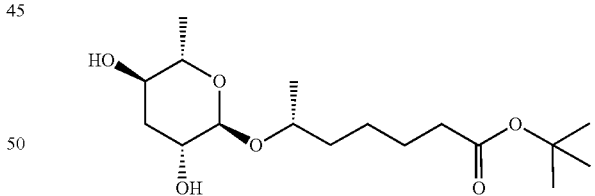

To a solution of I-20 (0.045 g, 0.079 mmol) in THF (2 mL) was added 1.0 M TBAF (0.35 mmol, 0.350 mL) in THF. The reaction mixture was stirred at room temperature under nitrogen for 18 h. The resulting mixture was concentrated and the crude product was purified by the column chromatography (24 g silica gel, 0% to 15% MeOH in DCM) to afford 10 (0.012 g, 46% yield) as a light brown paste. $^1$H NMR (500 MHz, CDCl$_3$) δ 4.75-4.71 (m, 1H), 3.89-3.79 (m, 3H), 3.72 (dd, J=9.2, 6.2 Hz, 1H), 3.59 (ddd, J=11.4, 9.2, 4.7 Hz, 1H), 3.38 (d, J=3.5 Hz, 1H), 2.25 (t, J=7.3 Hz, 2H), 2.15-2.07 (m, 1H), 1.86 (ddd, J=13.1, 11.3, 3.0 Hz, 2H), 1.67-1.61 (m, 3H), 1.60-1.54 (m, 2H), 1.46 (s, 9H), 1.32-1.29 (m, 3H), 1.15 (d, J=6.1 Hz, 3H). Mass Analysis (ESI, +ve)=333.2 [M+H].

Preparation of (2R,3R,5R)-2-(((E)-6-(tert-butoxy)-6-oxohex-4-en-1-yl)oxy)-6-methyltetrahydro-2H-pyran-3,5-diyl dibenzoate (I-21)

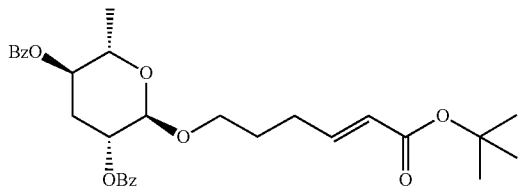

Using the same procedure to make I-07, to a solution of T-04 (0.200 g, 0.471 mmol) in DCM (5 mL) was added tert-butyl acrylate (0.205 mL, 1.41 mmol) and Grubb's M204 catalyst (0.020 g, 0.0235 mmol) and after isolation and purification afforded I-21 (0.180 g, 73% yield). $^1$H NMR (300 MHz, CDCl$_3$) δ 8.17-8.10 (m, 2H), 8.09-8.02 (m, 2H), 7.61 (td, J=7.3, 1.7 Hz, 2H), 7.54-7.41 (m, 4H), 6.92 (dt, J=14.6, 6.9 Hz, 1H), 5.83 (d, J=16.0 Hz, 1H), 5.27-5.13 (m, 2H), 4.84 (s, 1H), 4.07 (dd, J=9.9, 6.1 Hz, 1H), 3.81 (dt, J=9.9, 6.5 Hz, 1H), 3.55 (dt, J=9.9, 6.1 Hz, 1H), 2.44 (d, J=13.9 Hz, 1H), 2.35 (q, J=7.2 Hz, 2H), 2.28-2.14 (m, 1H), 1.91-1.78 (m, 2H), 1.50 (s, 8H), 1.32 (d, J=6.2 Hz, 3H). Mass Analysis (ESI, +ve)=525.1 [M+H].

Preparation of tert-butyl (E)-6-(((2R,3R,5R)-3,5-dihydroxy-6-methyltetrahydro-2H-pyran-2-yl)oxy) hex-2-enoate (11)

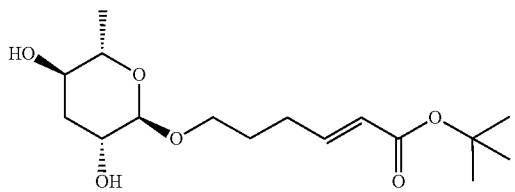 [SMILES: C[C@@H]1O[C@@H](OCCC/C=C/C(=O)OC(C)(C)C)[C@H](O)C[C@H]1O]

To a solution of I-21 (0.180 g, 0.344 mmol) in methanol (2 mL) was added K$_2$CO$_3$ (0.014 g, 0.103 mmol). The reaction mixture was stirred at room temperature under nitrogen for 18 h. The resulting mixture was concentrated and the crude product was purified by the column chromatography (24 g silica gel, 0% to 15% MeOH in DCM) to afford 11 (0.070 g, 70% yield). $^1$H NMR (500 MHz, CDCl3) δ 6.90 (dt, J=15.6, 7.0 Hz, 1H), 5.79 (dt, J=15.6, 1.6 Hz, 1H), 4.59 (d, J=1.7 Hz, 1H), 3.88 (s, 1H), 3.79-3.71 (m, 1H), 3.68-3.57 (m, 2H), 3.48 (dt, J=9.8, 5.9 Hz, 1H), 2.31 (qd, J=7.2, 1.6 Hz, 2H), 2.14-2.07 (m, 1H), 1.92-1.75 (m, 4H), 1.51 (s, 8H), 1.32 (d, J=5.9 Hz, 3H). Mass Analysis (ESI, +ve)=317.2 [M+H].

Preparation of tert-butyl (2E)-6-{[(2S,3R,5R,6S)-3,5-bis[(tert-butyldimethylsilyl)oxy]-6-methyloxan-2-yl]oxy}-6-methylhept-2-enoate (I-22)

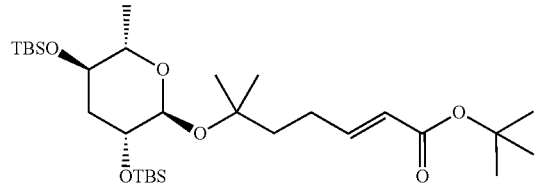 [SMILES: C[C@@H]1O[C@@H](OC(C)(C)CC/C=C/C(=O)OC(C)(C)C)[C@H](O[Si](C)(C)C(C)(C)C)C[C@H]1O[Si](C)(C)C(C)(C)C]

To a stirred solution of T-07 (0.75 mmol) in DCM (5 mL) is added tert-butyl acrylate (1.50 mmol) and Grubb's M204 catalyst (0.035 mmol). The mixture is stirred at room temperature under nitrogen for 18 h. The reaction is quenched with water (1 mL) and then partitioned between water (5 mL) and DCM (10 mL). The organic layer is washed with water (5 mL), brine (5 mL), dried over magnesium sulfate, filtered, and concentrated. The crude product is purified by the column chromatography (ethyl acetate-hexanes) to afford I-22.

Preparation of tert-butyl (2E)-6-{[(2S,3R,5R,6S)-3,5-dihydroxy-6-methyloxan-2-yl]oxy}-6-methylhept-2-enoate (12)

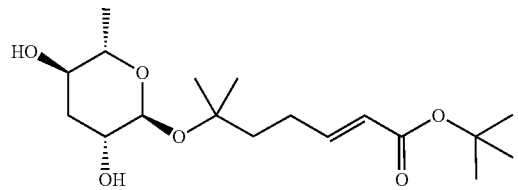 [SMILES: C[C@@H]1O[C@@H](OC(C)(C)CC/C=C/C(=O)OC(C)(C)C)[C@H](O)C[C@H]1O]

To a solution of I-22 (0.2 mmol) in THF (5 mL) is added 1.0 M TBAF (0.500 mmol, 0.500 mL) in THF. The reaction mixture is stirred at room temperature under nitrogen for 18 h. The resulting mixture is concentrated and the crude product is purified by the column chromatography (0% to 15% MeOH in DCM) to afford 12.

Preparation of (2R,3R,5R,6S)-5-((tert-butyldiphenylsilyl)oxy)-2-(((R,E)-7-ethoxy-7-oxohept-5-en-2-yl)oxy)-6-methyltetrahydro-2H-pyran-3-yl benzoate (I-23)

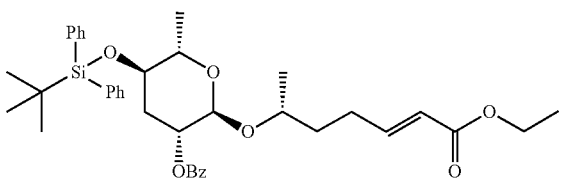

To a stirred solution of T-05 (0.420 g, 0.734 mmol) in DCM (5 mL) was added ethyl acrylate (0.160 mL, 1.470 mmol) and Grubb's M204 catalyst (0.031 g, 0.0367 mmol). The reaction mixture was stirred at room temperature under nitrogen for 18 h. The reaction mixture was quenched with water (1 mL) and then partitioned between water (5 mL) and DCM (10 mL). The organic layer was washed with water (5 mL), brine (5 mL), dried over magnesium sulfate, filtered, and concentrated. The crude product was purified by the column chromatography (40 g silica gel, 0% to 25% ethyl acetate in hexanes) to afford I-23 (0.340 g, 72% yield) as a clear oil. $^1$H NMR (500 MHz, CDCl$_3$) δ 7.76-7.72 (m, 2H), 7.71-7.66 (m, 4H), 7.60-7.55 (m, 1H), 7.43-7.38 (m, 4H), 7.37-7.30 (m, 6H), 7.05 (dt, J=15.7, 6.8 Hz, 1H), 5.92 (dt, J=15.6, 1.6 Hz, 1H), 4.93-4.86 (m, 1H), 4.77 (s, 1H), 4.23 (q, J=7.1 Hz, 2H), 3.92-3.80 (m, 2H), 3.68 (ddd, J=11.1, 9.1, 4.3 Hz, 1H), 2.48-2.30 (m, 3H), 2.04 (ddd, J=14.0, 11.2, 3.0 Hz, 1H), 1.93-1.87 (m, 2H), 1.84-1.76 (m, 1H), 1.72-1.64 (m, 1H), 1.33 (t, J=7.1 Hz, 3H), 1.29 (d, J=6.2 Hz, 3H), 1.18 (d, J=6.1 Hz, 3H), 1.09 (s, 9H). Mass Analysis (ESI, +ve)=645.1 [M+H].

Preparation of (R,E)-6-(((2R,3R,5R,6S)-5-((tert-butyldiphenylsilyl)oxy)-3-hydroxy-6-methyltetrahydro-2H-pyran-2-yl)oxy)hept-2-enoic acid (I-24)

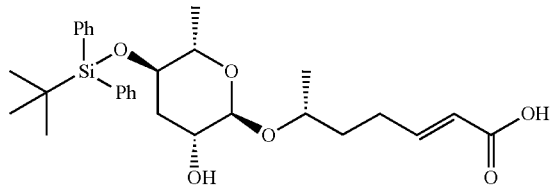 [SMILES: C[C@H](CC/C=C/C(=O)O)O[C@@H]1O[C@@H](C)[C@H](O[Si](c2ccccc2)(c2ccccc2)C(C)(C)C)C[C@H]1O]

To a stirred solution of I-23 (0.340 g, 0.527 mmol) in 1,4-dioxane (8 mL) was added lithium hydroxide (0.050 g, 2.11 mmol) and water (2 mL). The reaction mixture was heated at 60° C. under nitrogen for 18 h. The reaction mixture was cooled to room temperature and acidified with 1 M HCl to pH=5-6. The resulting mixture was extracted with 20% isopropanol in chloroform (3×10 mL). The combined organic layers were washed with brine (5 mL), dried over magnesium sulfate, filtered, and concentrated. The crude product was purified by the column chromatography (24 g silica gel, 5% to 40% ethyl acetate in hexanes with AcOH) to afford I-24 (0.220 g, 81% yield) as a white foam. $^1$H NMR (500 MHz, CDCl$_3$) δ 7.74-7.67 (m, 4H), 7.49-7.43 (m, 2H), 7.40 (tdd, J=8.1, 6.6, 1.1 Hz, 4H), 7.16 (dt, J=15.7, 6.8 Hz, 1H), 5.93 (dt, J=15.7, 1.6 Hz, 1H), 4.62 (d, J=1.8 Hz, 1H), 3.87-3.80 (m, 1H), 3.79-3.73 (m, 1H), 3.71-3.62 (m, 2H), 2.41 (ddq, J=31.7, 15.7, 8.4 Hz, 3H), 1.90-1.81 (m, 2H), 1.80-1.73 (m, 2H), 1.72-1.63 (m, 2H), 1.19 (d, J=6.3 Hz, 3H), 1.15 (d, J=6.1 Hz, 3H), 1.08 (s, 9H). Mass Analysis (ESI, +ve)=513.2 [M+H].

Preparation of (R,E)-6-(((2R,3R,5R,6S)-5-((tert-butyldiphenylsilyl)oxy)-3-hydroxy-6-methyltetrahydro-2H-pyran-2-yl)oxy)-1-(pyrrolidin-1-yl)hept-2-en-1-one (I-25)

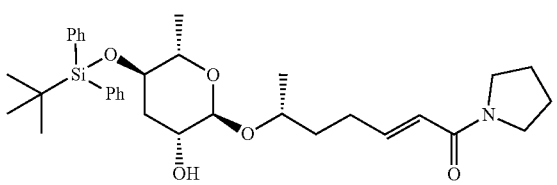 [SMILES: C[C@H](CC/C=C/C(=O)N1CCCC1)O[C@@H]1O[C@@H](C)[C@H](O[Si](c2ccccc2)(c2ccccc2)C(C)(C)C)C[C@H]1O]

To a stirred solution of I-24 (0.075 g, 0.146 mmol) in DCM (3 mL) was added DIPEA (0.130 mL, 0.732 mmol), pyrrolidine (0.040 mL, 0.439 mmol), EDCI (0.065 mL, 0.293 mmol), and HOBT (0.056 g, 0.366 mmol). The reaction mixture was stirred at room temperature under nitrogen for 18 h. The reaction mixture was quenched with saturated aqueous ammonium chloride (1 mL) then partitioned between water (5 mL) and DCM (10 mL). The aqueous layer was extracted with 20% isopropanol in chloroform (2×5 mL). The combined organic layers were dried over magnesium sulfate, filtered, and concentrated. The crude product was purified by the column chromatography (24 g silica gel, 10% to 40% acetone in hexanes) to afford I-25 (0.035 g, 40% yield) as a clear oil. $^1$H NMR (500 MHz, CDCl$_3$) δ 7.73-7.67 (m, 4H), 7.47-7.42 (m, 2H), 7.42-7.37 (m, 4H), 7.00 (dt, J=15.1, 6.9 Hz, 1H), 6.18 (dt, J=15.1, 1.6 Hz, 1H), 4.60 (d, J=1.8 Hz, 1H), 3.85-3.76 (m, 2H), 3.69-3.62 (m, 2H), 3.55 (t, J=6.6 Hz, 3H), 2.47-2.37 (m, 1H), 2.36-2.27 (m, 1H), 1.93 (s, 3H), 1.87 (ddd, J=13.5, 10.6, 3.1 Hz, 2H), 1.83-1.74 (m, 3H), 1.65 (dq, J=8.8, 4.7, 3.7 Hz, 1H), 1.32-1.26 (m, 1H), 1.19 (d, J=6.3 Hz, 3H), 1.14 (d, J=6.1 Hz, 3H), 1.07 (s, 9H). Mass Analysis (ESI, +ve)=588.2 [M+Na].

Preparation of (R,E)-6-(((2R,3R,5R,6S)-3,5-dihydroxy-6-methyltetrahydro-2H-pyran-2-yl)oxy)-1-(pyrrolidin-1-yl)hept-2-en-1-one (13)

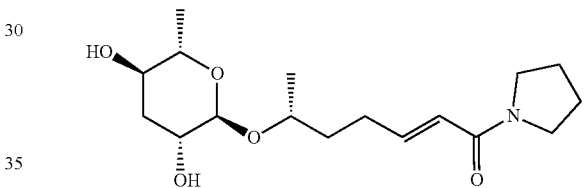

To a stirred solution of I-25 (0.030 g, 0.053 mmol) in THF (2 mL) was added 1.0 M TBAF (0.27 mmol, 0.270 mL) in THF. The reaction mixture was stirred at room temperature under nitrogen for 18 h. The resulting mixture was concentrated. The crude product was purified by the column chromatography (24 g silica gel, 0% to 15% MeOH in DCM) to afford 13 (0.010 g, 60% yield) as a colorless paste. $^1$H NMR (500 MHz, CDCl$_3$) δ 7.06 (dt, J=15.2, 7.0 Hz, 1H), 6.14 (dt, J=15.2, 1.6 Hz, 1H), 4.74-4.69 (m, 1H), 3.93-3.86 (m, 1H), 3.82 (td, J=3.2, 1.7 Hz, 1H), 3.73-3.65 (m, 1H), 3.53 (t, J=6.8 Hz, 5H), 2.37 (qt, J=7.1, 1.6 Hz, 2H), 2.12 (dddd, J=13.0, 4.5, 3.3, 1.0 Hz, 1H), 2.01-1.95 (m, 4H), 1.94-1.90 (m, 1H), 1.90-1.85 (m, 2H), 1.78-1.68 (m, 2H), 1.28 (d, J=6.2 Hz, 3H), 1.18 (d, J=6.1 Hz, 3H). Mass Analysis (ESI, +ve)=328.1 [M+H].

Preparation of ethyl (2Z,6R)-6-{[(2R,3R,5R,6S)-3,5-bis[(tert-butyldimethylsilyl)oxy]-6-methyloxan-2-yl]oxy}hept-2-enoate (I-26)

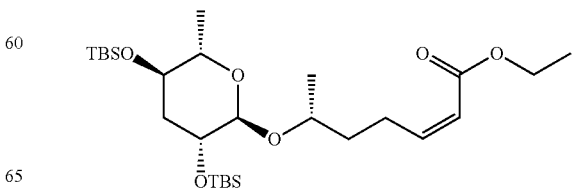

Ethyl bis(2,2,2-trifluoroethyl)phosphonoacetate (0.25 mmol) and 18-crown-6 (0.25 mmol) are dissolved in THF (1.0 mL) and cooled to −78° C. 1.0 M KHMDS (0.25 mmol) in THF is added and the reaction is stirred at −78° C. for 30 min. Aldehyde I-03 (0.15 mmol) is added as a solution in THF (1.0 mL) and the reaction is stirred at −78° C. for 2 h and then warmed to room temperature. The mixture is quenched with aq. ammonium chloride solution (50 mL) and extracted with ethyl acetate (2×50 mL). The layers are separated and the organic layers are washed with water (2×40 mL), brine (30 mL), and the combined organic layers are dried over magnesium sulfate, filtered, and concentrate in vacuo. The crude product is purified by the column chromatography (petroleum ether-ethyl acetate) to afford I-26.

Preparation of ethyl (2Z,6R)-6-{[(2R,3R,5R,6S)-3,5-dihydroxy-6-methyloxan-2-yl]oxy}hept-2-enoate (14)

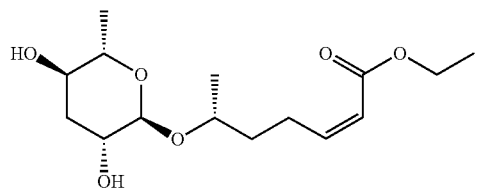

To a solution of I-26 (0.2 mmol) in THF (3 mL) is added 1.0 M TBAF (0.250 mmol, 0.250 mL) in THF. The reaction mixture is stirred at room temperature under nitrogen for 18 h. The resulting mixture is concentrated and the crude product is purified by the column chromatography (0% to 15% MeOH in DCM) to afford 14.

Preparation of ethyl 2-[(3R)-3-{[(2R,3R,5R,6S)-3,5-bis[(tert-butyldimethylsilyl)oxy]-6-methyloxan-2-yl]oxy}butyl]cyclopropane-1-carboxylate (I-27)

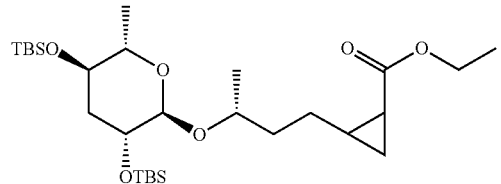 [SMILES: CCOC(=O)C1CC1CC[C@@H](C)O[C@@H]1O[C@@H](C)[C@H](O[Si](C)(C)C(C)(C)C)C[C@H]1O[Si](C)(C)C(C)(C)C]

A solution of methylene iodide (1.0 mmol) and zinc-copper couple dust (15 mg) in diethyl ether (15 mL) is stirred for 30 min and then I-26 (0.5 mmol) is added to the solution. After the reaction is refluxed for 60 hr, the mixture is poured into aq. ammonium chloride solution (50 mL). The mixture is extracted with ethyl acetate (2×50 mL). The layers are separated and the organic layers are washed with water (2×40 mL), aqueous thiosulfate (30 mL), and the combined organic layers are dried over magnesium sulfate, filtered, and concentrate in vacuo. The crude product is purified by the column chromatography (ethyl acetate-hexane) to afford I-27.

Preparation of ethyl 2-[(3R)-3-{[(2R,3R,5R,6S)-3,5-dihydroxy-6-methyloxan-2-yl]oxy}butyl]cyclopropane-1-carboxylate (15)

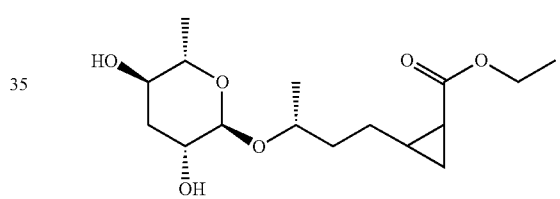

To a solution of I-27 (0.1 mmol) in THF (3 mL) is added 1.0 M TBAF (0.150 mmol, 0.150 mL) in THF. The reaction mixture is stirred at room temperature under nitrogen for 18 h. The resulting mixture is concentrated and the crude product is purified by the column chromatography (0% to 15% MeOH in DCM) to afford 15.

Using the protocols described above, compounds 16-56, which are exemplified in Table 3, are prepared.

TABLE 3

| Ascaroside Derivatives | |
|---|---|
| No. | Structure |
| 1 | 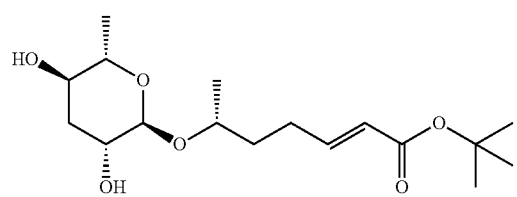 [SMILES: C[C@H](CC/C=C/C(=O)OC(C)(C)C)O[C@@H]1O[C@@H](C)[C@H](O)C[C@H]1O] |

TABLE 3-continued
Ascaroside Derivatives
| No. | Structure |
|---|---|
| 2 | 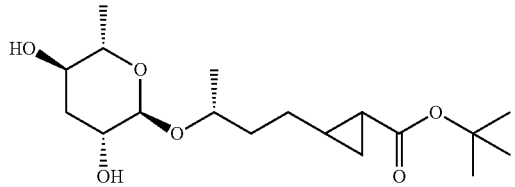 [SMILES: C[C@H](CCC1CC1C(=O)OC(C)(C)C)O[C@@H]1O[C@@H](C)[C@H](O)C[C@H]1O] |
| 3 | 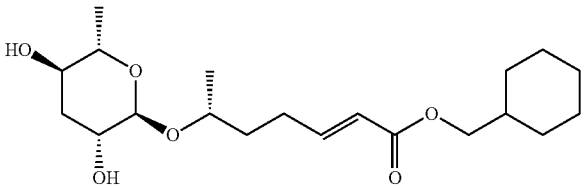 [SMILES: C[C@H](CC/C=C/C(=O)OCC1CCCCC1)O[C@@H]1O[C@@H](C)[C@H](O)C[C@H]1O] |
| 4 | 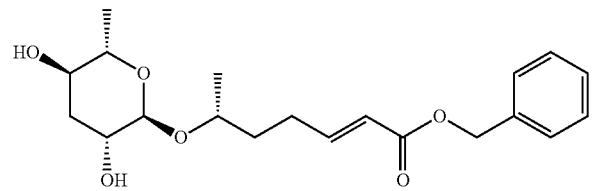 [SMILES: C[C@H](CC/C=C/C(=O)OCc1ccccc1)O[C@@H]1O[C@@H](C)[C@H](O)C[C@H]1O] |
| 5 | 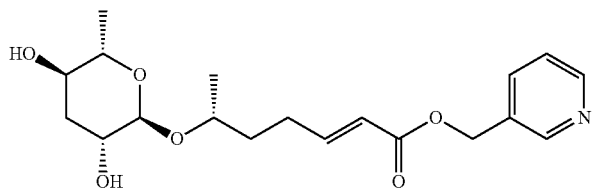 [SMILES: C[C@H](CC/C=C/C(=O)OCc1cccnc1)O[C@@H]1O[C@@H](C)[C@H](O)C[C@H]1O] |
| 6 | 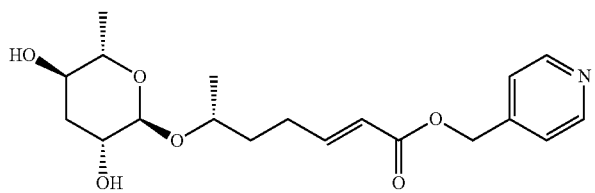 [SMILES: C[C@H](CC/C=C/C(=O)OCc1ccncc1)O[C@@H]1O[C@@H](C)[C@H](O)C[C@H]1O] |
| 7 | 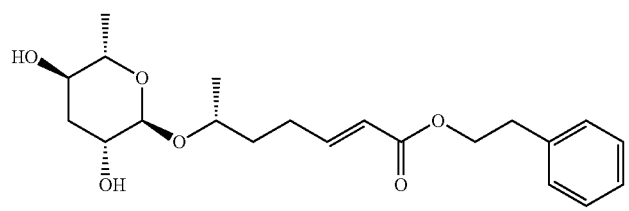 [SMILES: C[C@H](CC/C=C/C(=O)OCCc1ccccc1)O[C@@H]1O[C@@H](C)[C@H](O)C[C@H]1O] |
| 8 | 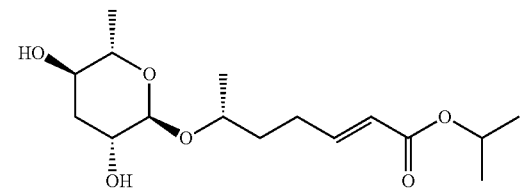 [SMILES: CC(C)OC(=O)/C=C/CC[C@@H](C)O[C@@H]1O[C@@H](C)[C@H](O)C[C@H]1O] |

TABLE 3-continued
Ascaroside Derivatives
| No. | Structure |
|---|---|
| 9 | 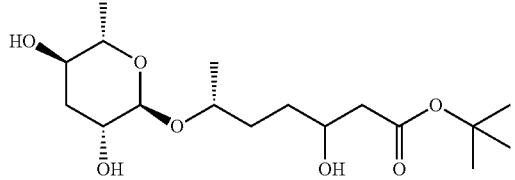 |
| 10 | 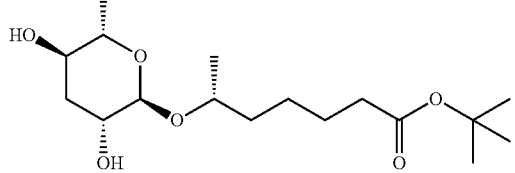 |
| 11 | 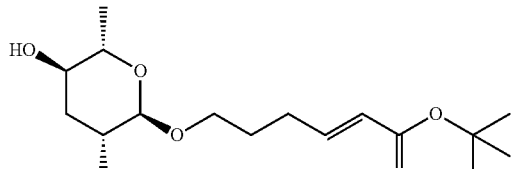 |
| 12 | 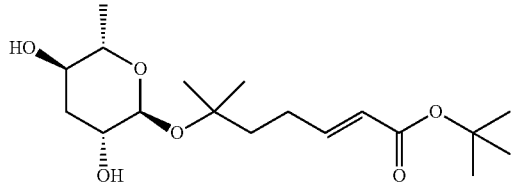 [SMILES: C[C@@H]1O[C@@H](OC(C)(C)CC/C=C/C(=O)OC(C)(C)C)[C@H](O)C[C@H]1O] |
| 13 | 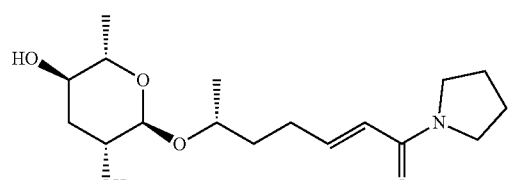 |
| 14 | 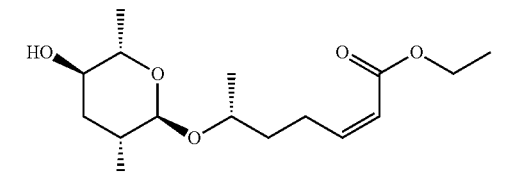 |
| 15 | 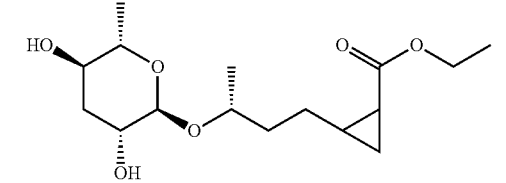 [SMILES: CCOC(=O)C1CC1CC[C@@H](C)O[C@@H]1O[C@@H](C)[C@H](O)C[C@H]1O] |
| 16 | 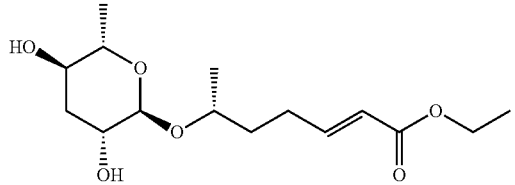 [SMILES: CCOC(=O)/C=C/CC[C@@H](C)O[C@@H]1O[C@@H](C)[C@H](O)C[C@H]1O] |

TABLE 3-continued

| Ascaroside Derivatives | |
|---|---|
| No. | Structure |

17

18

19

20

21

22

23

TABLE 3-continued

| | Ascaroside Derivatives |
|---|---|
| No. | Structure |

24

25

26

27

28

29

30

TABLE 3-continued

Ascaroside Derivatives

| No. | Structure |
|---|---|
| 31 | 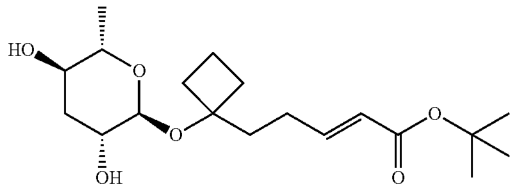 [SMILES: C[C@@H]1O[C@@H](OC2(CC/C=C/C(=O)OC(C)(C)C)CCC2)[C@H](O)C[C@H]1O] |
| 32 | 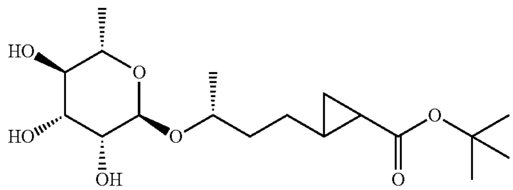 [SMILES: C[C@H](CCC1CC1C(=O)OC(C)(C)C)O[C@@H]1O[C@@H](C)[C@H](O)[C@@H](O)[C@H]1O] |
| 33 | 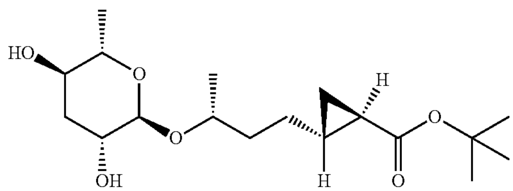 [SMILES: C[C@H](CC[C@@H]1C[C@H]1C(=O)OC(C)(C)C)O[C@@H]1O[C@@H](C)[C@H](O)C[C@H]1O] |
| 34 | 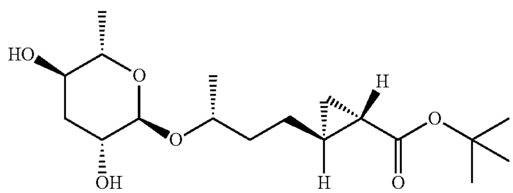 [SMILES: C[C@H](CC[C@H]1C[C@@H]1C(=O)OC(C)(C)C)O[C@@H]1O[C@@H](C)[C@H](O)C[C@H]1O] |
| 35 | 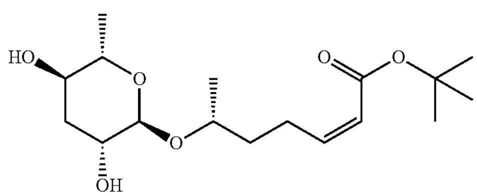 [SMILES: C[C@H](CC/C=C\C(=O)OC(C)(C)C)O[C@@H]1O[C@@H](C)[C@H](O)C[C@H]1O] |
| 36 | 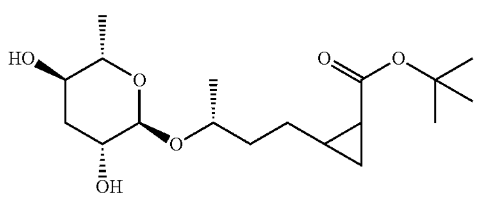 [SMILES: C[C@H](CCC1CC1C(=O)OC(C)(C)C)O[C@@H]1O[C@@H](C)[C@H](O)C[C@H]1O] |
| 37 | 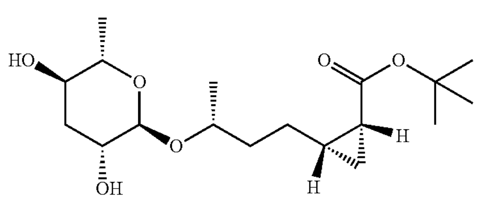 [SMILES: C[C@H](CC[C@H]1C[C@H]1C(=O)OC(C)(C)C)O[C@@H]1O[C@@H](C)[C@H](O)C[C@H]1O] |
| 38 | 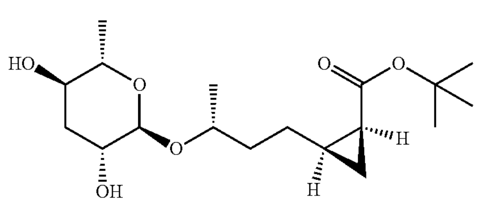 [SMILES: C[C@H](CC[C@@H]1C[C@@H]1C(=O)OC(C)(C)C)O[C@@H]1O[C@@H](C)[C@H](O)C[C@H]1O] |

TABLE 3-continued

| | Ascaroside Derivatives |
|---|---|
| No. | Structure |

39

40

41

42

43

44

45

TABLE 3-continued
Ascaroside Derivatives
| No. | Structure |
|---|---|
| 46 | 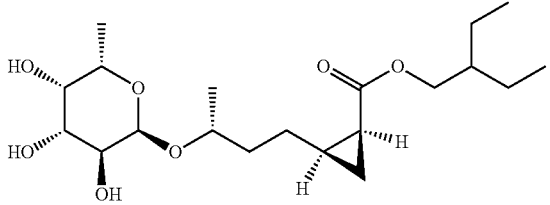 [SMILES: CCC(CC)COC(=O)[C@H]1C[C@H]1CC[C@@H](C)O[C@@H]1O[C@@H](C)[C@@H](O)[C@@H](O)[C@@H]1O] |
| 47 | 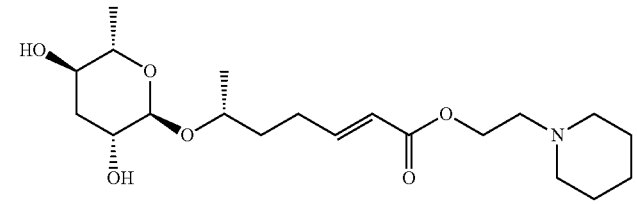 [SMILES: C[C@H](CC/C=C/C(=O)OCCN1CCCCC1)O[C@@H]1O[C@@H](C)[C@H](O)C[C@H]1O] |
| 48 | 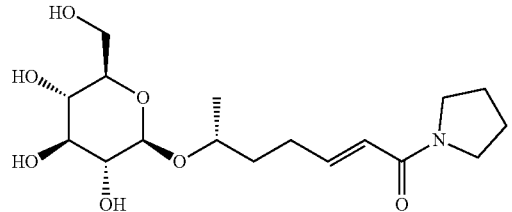 [SMILES: C[C@H](CC/C=C/C(=O)N1CCCC1)O[C@@H]1O[C@H](CO)[C@@H](O)[C@H](O)[C@H]1O] |
| 49 | 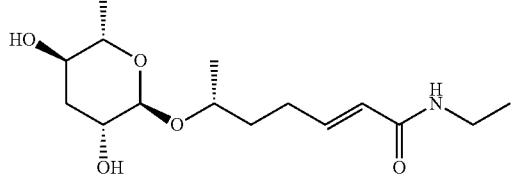 |
| 50 | 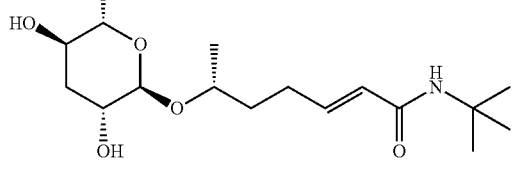 |
| 51 | 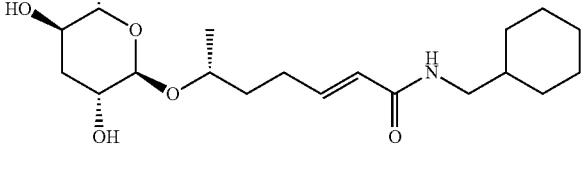 |
| 52 | 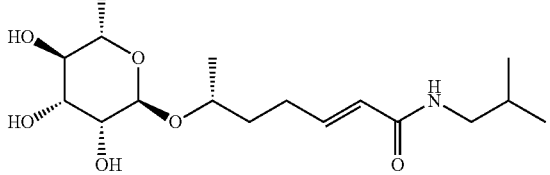 |

TABLE 3-continued

Ascaroside Derivatives

| No. | Structure |
|---|---|
| 53 | (structure) |
| 54 | (structure) |
| 55 | (structure) |
| 56 | (structure) |

Example 3

Stimulation of THP-1 Cells: Testing the Effect of Compounds 1 and 10

Compound 1 and compound 10 significantly reduce IL-6 and TNFα secretion in vitro in human cells. Specifically, compound 1 and compound 10 both reduce IL-6 and TNFα in a stimulated culture of immortalized monocytic THP-1 cells.

Human immortalized monocytic THP-1 cells were maintained in phenol red free RPMI 1640 medium containing 10% (v/v) fetal bovine serum (FBS), 2 mM L-glutamine, penicillin (100 units/mL), streptomycin (100 μg/mL), amphotericin B (2.5 μg/mL), and 50 μM beta-mercaptoethanol (BME) at 37° C. with 5% (v/v) $CO_2$. THP-1 cells were seeded in 1 mL of THP-1 medium (cell culture medium containing 10% (v/v) FBS, 2 mM L-glutamine, penicillin (100 units/mL), streptomycin (100 μg/mL), amphotericin B (2.5 μg/mL), and 50 μM BME)/well at a density of 1 million cells/mL in six-well plates. Cells were differentiated by adding 100 nM phorbol 12-myristate 13-acetate (PMA) to each well before incubating cells for 5.5 h at 37° C. with 5% (v/v) $CO_2$. Without removing the media, different concentrations (either 0, 0.1, 1, 10, 100, or 200 μM) of 1 and 10 were added to each well. Cells were stimulated, within 30 min by adding 20 ng/mL interferon gamma (IFN-γ) and 100 ng/mL lipopolysaccharide (LPS) to each well. Following stimulation, the THP-1 cells were incubated for 72 h at 37° C. with 5% (v/v) $CO_2$. Supernatant was collected and stored at −80° C. until use.

Figure 1B:
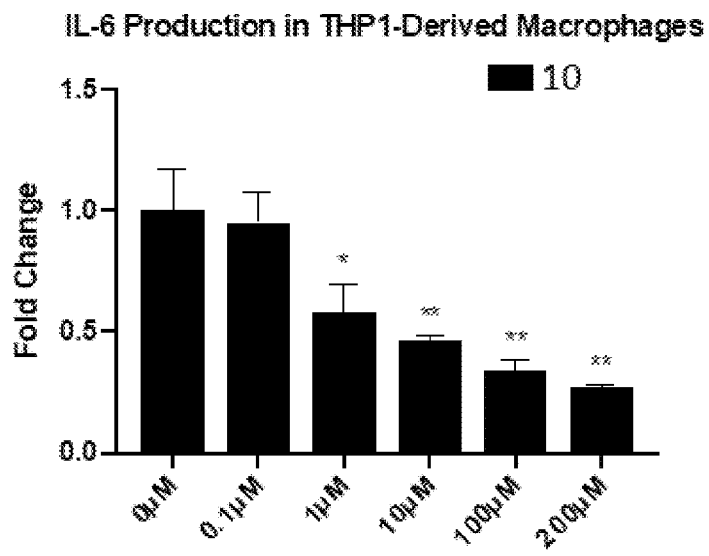
FIG. 1B shows that compound 10 diminishes the amount of IL-6 released by THP-1 derived macrophages 72 h post stimulation in an in vitro assay.

IL-6 release from supernatant collected at 72 hours post stimulation was measured using the AlphaLISA Human IL-6 detection kit. Results after 72 h are shown in FIGS. 1A, 1B, 2A, and 2B. FIG. 1A shows the fold change of IL-6 levels secreted by the THP1-derived macrophages when applying different concentrations of 1 (which is indicated by the bars labeled "0.1, 1, 10, 100 or 200 μM") in comparison to the highest levels of IL-6 secreted by the THP1-derived macrophages containing no compound 1, (which is indicated by the bar labeled "0 μM"). Administration of several concentrations of 1 reduced these levels significantly. FIG. 1B shows the fold change of IL-6 levels secreted by the THP1-derived macrophages when applying different concentrations of 10 (which is indicated by the bars labeled "0.1, 1, 10, 100 or 200 μM") in comparison to the highest levels of IL-6 secreted by the THP1-derived macrophages containing no compound 10, (which is indicated by the bar labeled "0 μM"). Administration of several concentrations of 10 reduced these levels significantly.

Figure 2A:
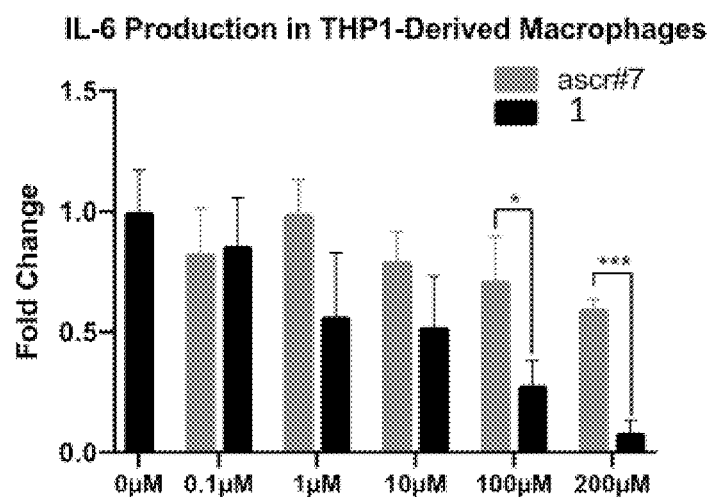
FIG. 2A shows that compound 1 diminishes the amount of IL-6 released by in THP-1 derived macrophages, more than ascr #7, 72 h post stimulation in an in vitro assay.
Figure 2B:
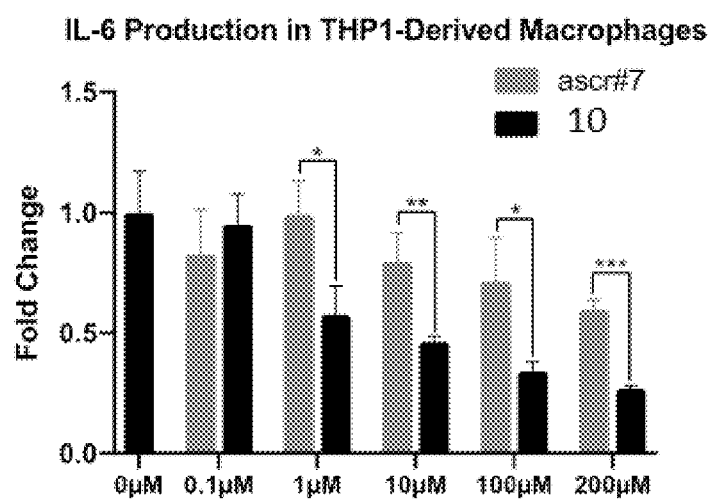
FIG. 2B shows that compound 10 diminishes the amount of IL-6 released by in THP-1 derived macrophages, more than ascr #7, 72 h post stimulation in an in vitro assay.

FIG. 2A shows the fold change of IL-6 levels secreted by the THP1-derived macrophages when applying different concentrations of ascr #7 (which is indicated by the grey bars labeled "0.1, 1, 10, 100, or 200 μM") or 1 (which is indicated by the black bars labeled "0.1, 1, 10, 100, or 200 μM") in comparison to the highest levels of IL-6 secreted by the THP1-derived macrophages containing no compound 1 or ascr #7, (which is indicated by the bars labeled "0 μM"). Levels of IL-6 are significantly reduced with administration of different concentrations of ascr #7 and even more significantly reduced with 1 at several concentrations. FIG. 2B shows the fold change of IL-6 levels secreted by the THP1-derived macrophages when applying different concentrations of ascr #7 (which is indicated by the grey bars labeled "0.1, 1, 10, 100, or 200 µM") or 10 (which is indicated by the black bars labeled "0.1, 1, 10, 100, or 200 µM") in comparison to the highest levels of IL-6 secreted by the THP1-derived macrophages containing no compound 10 or ascr #7, (which is indicated by the bars labeled "0 µM"). Levels of IL-6 are significantly reduced with administration of different concentrations of ascr #7 and even more significantly reduced with 10 at several concentrations.

Figure 3A:
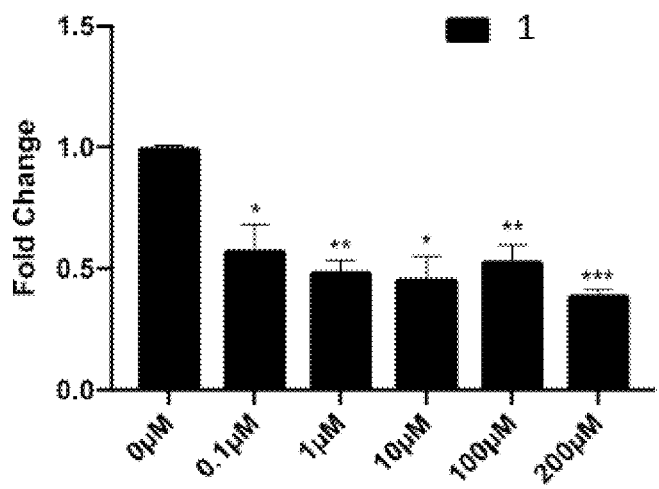
FIG. 3A shows that compound 1 diminishes the amount of TNFα released by in THP-1 derived macrophages 72 h post stimulation in an in vitro assay.
Figure 3B:
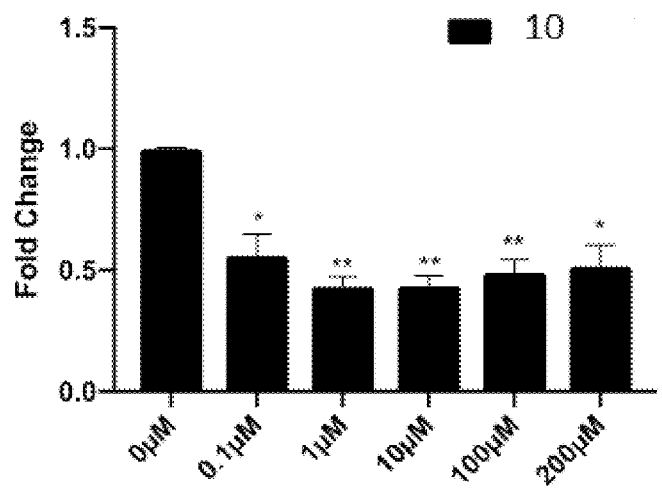
FIG. 3B shows that compound 10 diminishes the amount of TNFα released by in THP-1 derived macrophages 72 h post stimulation in an in vitro assay.

TNFα release from supernatant collected at 72 hours post stimulation was measured using the AlphaLISA Human TNFα detection kit. Results after 72 h are shown in FIGS. 3A and 3B. FIG. 3A shows the fold change of TNFα levels secreted by the THP1-derived macrophages when applying different concentrations of 1 (which is indicated by the bars labeled "0.1, 1, 10, 100 or 200 µM") in comparison to the highest levels of TNFα secreted by the THP1-derived macrophages containing no compound 1, (which is indicated by the bar labeled "0 µM"). Administration of several concentrations of 1 reduced these levels significantly. FIG. 3B shows the fold change of TNFα levels secreted by the THP1-derived macrophages when applying different concentrations of 10 (which is indicated by the bars labeled "0.1, 1, 10, 100 or 200 µM") in comparison to the highest levels of TNFα secreted by the THP1-derived macrophages containing no compound 10, (which is indicated by the bar labeled "0 µM"). Administration of several concentrations of 10 reduced these levels significantly.

Example 4

Stability of the Compound 1 in Hepatocytes 10 mM of 1 was provided as a 1000× stock solution in dimethylsulfoxide (DMSO), and the stock solution was diluted to 1 mM with DMSO in 96-well plates. 30 mM of positive compounds (7-ethoxycoumarin and 7-hydroxycoumarin) were provided as a 1000× stock solution in DMSO, and the stock solution was diluted to 3 mM with DMSO in 96-well plates. 20 µL of 1000× stock solution of each compound were pipetted and was mixed with 380 µL of 45% MeOH/H2O to obtain 50 µM of 1 and 150 µM of the positive control compound solutions to form 50× intermediate solutions. 20 µL of 50× intermediate solution of each compound were pipetted and was mixed with 450 µL of pre-warmed incubation medium to obtain 5 µM of 1 and 15 µM of the positive control compound solutions to form 5× working solutions. The incubation medium was Williams' Medium E (no phenol red) containing 2 mM L-glutamine and 25 mM HEPES. 10 µL of 5× working solutions of each compound were pipetted into appropriate wells in a 96-well plate for time points of 0 minutes, 15 minutes, 30 minutes, 60 minutes, and 90 minutes in duplicates. The plates with compounds were kept warm in an incubator at 37° C.

A cell suspension was prepared by thawing cryopreserved cells, isolating the cells, and suspending the cells in thawing medium. The thawing medium was Williams' Medium E containing 5% fetal bovine serum and 30% Percoll solution and other supplements. The cells suspension was diluted using pre-warmed incubation medium at a density of 0.625× 10⁶ cells/mL. Cell viability was tested using trypan blue exclusion after thawing.

The reaction was started by aliquoting 40 µL of the 0.625×10⁶ cells/mL suspension into each well in the 96-well plate containing 10 µL of compound solutions. Sample plates containing 15 minutes, 30 minutes, 60 minutes, and 90 minutes were incubated immediately in an incubator at 37° C. with 5% Co₂.

TABLE 4

The final concentrations of each component in the incubation medium.

| Component | Final Concentration |
| --- | --- |
| Hepatocyte | 0.5 × 10⁶ cells/mL |
| Compound 1 | 1 µM |
| Positive Compound | 3 µM |
| MeOH | 0.86% |
| DMSO | 0.10% |

0 minute samples were added stop solution before adding the cells. The stop solution was acetonitrile containing 200 ng/mL tolbutamide and labetalol as internal standards. Medium control (MC) sample plates for 0 minutes and 90 minutes (T0-MC and T90-MC) were incubated using the same condition as above as the time points with compounds in incubation medium only without cells.

At each corresponding time point, the reaction was stopped by quenching. Sample plates were vortexed immediately and were placed on a plate shaker at 500 rpm for 10 min, then the plates were centrifuged at 3220×g for 20 min. 50 µL/well of supernatant of positive controls in the sample plates were transferred to another set of 96-deep-well plates which contain 150 µL/well of ultra-water according to the plate map, and 100 µL/well of supernatant of the well containing 1 was transferred for LC/MS/MS analysis.

The remaining percentage of 1 after incubation was calculated according to the following equation.

$$\% \text{ Remaining (at Appointed Time)} = \frac{\text{Peak Area Ratios of Test Article versus Internal Standard at Appointed Time}}{\text{Peak Area Ratios of Test Article versus Internal Standard at 0 min}} \times 100\%$$

The following equation of first order kinetics is used to calculate $t_{1/2}$ and $CL_{int}$.

$$C_t = C_0 \cdot e^{-k \cdot t},$$

$$\text{when } C_t = \frac{1}{2}C_0,$$

$$t_{1/2} = \frac{\ln 2}{k} = \frac{0.693}{k}.$$

$$CL_{int(hep)} = k / \text{million cells per mL}$$

$$CL_{int(liver)} = CL_{int(hep)} * \text{liver weight (g/kg body weight)} * \text{hepatocellularity}.$$

Results are shown in FIG. 4. Ascr #7 had a half-life of greater than 216.8 minutes in mouse, rat, and human hepatocytes. Compound 1 had a half-life of 23.1 minutes in rat hepatocytes and a half-life of 106 minutes in human hepatocytes.

Example 5

Stability of Compound 1 in Plasma

The pH of plasma was adjusted to 7.4±0.1 if required. 1 mM intermediate solution was prepared by diluting 10 μL of the 10 mM stock solution of 1 with 90 μL DMSO; 1 mM intermediate of positive control propantheline bromide was prepared by diluting 10 μL of the stock solution with 90 μL ultra-pure water. 100 μM dosing solution was prepared by diluting 10 μL of the 1 mM intermediate solution with 90 μL of 45% MeOH/H$_2$O. 98 μL of blank plasma was spiked with 2 μL of the 100 μM dosing solution to achieve a final concentration of 2 μM of the compound in duplicate. Samples were incubated at 37° C. in a water bath. At each time point (0, 10, 30, 60 and 120 min), 400 μL of stop solution (200 ng/mL tolbutamide plus 200 ng/mL labetalol in 50% ACN/MeOH) was added and was mixed thoroughly to precipitate protein. Sample plates were centrifuged at 4,000 rpm for 10 min. An aliquot of supernatant (100 μL) was transferred from each well and was mixed with 200 μL ultra-pure water. The samples were shaken at 800 rpm for about 10 min before LC/MS/MS analysis.

The remaining percentage of compound 1 (test article) after incubation was calculated according to the following equation.

% Remaining (at Appointed Time) =

$$\frac{\text{Peak Area Ratios of Test Article versus Internal Standard at Appointed Time}}{\text{Peak Area Ratios of Test Article versus Internal Standard at 0 min}} \times 100\%$$

Results are shown in FIGS. 5A and 5B. 103.4%, 99.8%, and 89.8% of ascr #7 remained in mouse, rat, and human plasma, respectively, after 120 minutes. 19.2% and 86.5% of the compound of 1 remained in rat and human plasma, respectively, after 120 minutes.

Example 6

Bidirectional Permeability of Compound 1 in Caco-2 Cells

Caco-2 cells purchased from ATCC were seeded onto polyethylene membranes (PET) in 96-well BD Insert plates at 1×10$^5$ cells/cm$^2$, and the medium was refreshed every 4~5 days until to the 21st to 28th day for formation of a confluent cell monolayer.

The transport buffer in the study was Hank's balanced salt solution (HBSS) with 10 mM HEPES at pH 7.40±0.05. Compound 1 was tested at 2 μM bi-directionally in duplicate. Digoxin was tested at 10 μM bi-directionally in duplicate, while nadolol and metoprolol were tested at 2 μM in A to B direction in duplicate. Final DMSO concentration was adjusted to less than 1%. The plate was incubated for 2 hours in an incubator at 37±1° C., with 5% CO$_2$ at saturated humidity without shaking. All samples after mixing with acetonitrile containing internal standard were centrifuged at 4000 rpm for 10 min. Subsequently, 100 μL of supernatant solution was diluted with 100 μL distilled water for LC/MS/MS analysis. Concentrations of compound 1 and warfarin in starting solution, donor solution, and receiver solution were quantified by LC/MS/MS methodologies, using peak area ratio of analyte/internal standard.

After transport assay, a lucifer yellow rejection assay was performed to determine the integrity of the Caco-2 cell monolayer.

The apparent permeability coefficient P$_{app}$ (cm/s) was calculated using the equation:

$$P_{app}=(dC_r/dt)\times V_r/(A\times C_0)$$

where dC$_r$/dt is the cumulative concentration of compound in the receiver chamber as a function of time (μM/s); V$_r$ is the solution volume in the receiver chamber (0.075 mL on the apical side, 0.25 mL on the basolateral side); A is the surface area for the transport, i.e. 0.0804 cm$^2$ for the area of the monolayer; Co is the initial concentration in the donor chamber (μM).

The efflux ratio was calculated using the equation:

$$\text{Efflux Ratio}=P_{app}(BA)/P_{app}(AB)$$

Percent recovery was calculated using the equation:

$$\% \text{ Recovery}=100\times[(V_r\times C_r)+(V_d\times C_d)]/(V_d\times C_0)$$

where V$_d$ is the volume in the donor chambers (0.075 mL on the apical side, 0.25 mL on the basolateral side); C$_d$ and C$_r$ are the final concentrations of transport compound in donor and receiver chambers, respectively.

Results are shown in FIG. 6. Ascr #7 exhibited low bidirectional permeability in CaCo-2 cells. Compound 1 exhibited high bidirectional permeability in CaCo-2 cells.

Example 7

Plasma Protein Binding of Compound 1—HTD

HT-Dialysis plate (Model HTD 96 b, Cat #1006) and the dialysis membrane (molecular weight cut off 12-14 KDa, Cat #1101) can be purchased from HT Dialysis LLC (Gales Ferry, CT).

The plasma was thawed under running cold tap water and centrifuged at 3220×g for 5 min to remove any clots. The pH value was checked and recorded. Only plasma within range of pH 7.0 to pH 8.0 was used. The dialysis membrane was pretreated according to the manufacturer's instructions. Briefly, the dialysis membrane strips were soaked in ultra-pure water at room temperature for approximately 1 hr. After that, each membrane strip that contained 2 membranes was separated and soaked in ethanol:water (20:80 v:v) for approximately 20 min. The membrane was rinsed and soaked for 20 min in ultra-pure water.

Aliquots of 50 μL loading plasma (matrix) containing compound 1 or warfarin in triplicate were transferred to the appropriate wells of a sample collection plate. The samples were matched with dialysis buffer to obtain a final volume of 100 μL with a volume ratio of plasma (matrix):dialysis buffer (1:1, v:v) in each well. The dialysis buffer was 100 mM sodium phosphate and 150 mN NaCl at pH 7.4. The stop solution was added to the time 0 (T$_0$) samples of 1 and warfarin. The plate was sealed and was shaken at 800 rpm for 10 min. Then the T$_0$ samples were stored at 2-8° C.

An aliquot of 150 μL of the loading plasma (matrix) containing compound 1 or warfarin was transferred to the donor side of each dialysis well in triplicate, and 150 μL of the dialysis buffer was loaded to the receiver side of the well. Then the plate was rotated at approximately 100 rpm in a humidified incubator with 5% CO$_2$ at 37±1° C. for 4 hours.

At the end of the dialysis, aliquots of 50 μL samples from the buffer side and plasma (matrix) side of the dialysis device were transferred to new 96-well plates (sample collection plates). An equal volume of buffer or plasma was added to each sample well for a final volume of 100 μL with volume ratio of plasma (matrix): dialysis buffer at 1:1 (v:v) in each well. All samples were further processed by protein precipitation for LC/MS/MS analysis.

The % Unbound, % Bound, % Recovery and % Remaining were calculated using the following equations:

%Unbound=100×F/T

%Bound=100−%Unbound

%Recovery=100×(F+T)/T₀

F=the compound 1 concentration on the receiver side of the membrane/Correction Factor.
T=the compound 1 concentration on the donor side of the membrane/Correction Factor.
$T_0$=the compound 1 concentration at time zero/Correction Factor.
Correction Factor=volume of aliquot/total volume.

Results are shown in FIG. 7. Ascr #7 had percent unbound values of 86.8% and 94.6% in human and rat plasma, respectively. Compound 1 had a percent unbound value of 32.9% in human plasma.

Example 8

5 in 1 CYP Inhibition Assay of Compound 1 (1 Concentration, n=2)

CYP450 dependent activities were determined using a marker substrate cocktail. For each reaction, enzyme activities in the presence and absence of test compound (10 μM) were measured in duplicate. A known inhibitor for each isoform, tested at a single concentration (3 μM, n=2), was included as positive control.

Incubation mixtures containing microsomes, substrate, and standard inhibitor or test compound were warmed at 37° C. for 10 minutes. Reactions were initiated by addition of the NADPH and incubated for 10 min.

Generation of metabolites from the substrate reactions was determined by LC-MS/MS.

Results are shown in FIG. 8. Ascr #7 inhibited cytochrome P450 isoforms 1A2, 2C9, 2C19, 2D6, and 3A4 at 2.3%, 0.0%, 4.0%, 4.6%, and 0.0% respectively. Compound 1 inhibited cytochrome P450 isoforms 1A2, 2C9, 2C19, 2D6, and 3A4 at 10.9%, 4.3%, 16.2%, 10.1%, and 1.0% respectively.

Example 9

Metabolite Identification of Compound 1 in Liver Hepatocytes

Compound 1 is at a concentration of 10 μM, and 7-ethoxycoumarin at 30 μM is used as a positive control. The incubation medium is Williams' Medium E (no phenol red) containing 2 mM L-glutamine and 25 mM HEPES, and cryopreserved mouse hepatocytes at a density of $1.0 \times 10^6$ cells/mL are used to seed a 96-well plate. The total incubation volume in the 96-well plate is 200 μL with incubation at 37° C. in 5% $CO_2$/95% humidity for time points of 0 minutes and 120 minutes in at least duplicates. Protein is precipitated with 800 μL of acetonitrile with 0.1% formic acid and is further centrifuged. The supernatant is dried with $N_2$. The residue is reconstituted with 200 μL of 10% acetonitrile with 0.1% formic acid and 15 μL is injected into LCMS for analysis using the following parameters.

TABLE 5

| Substrate | Reaction (isoform) | Standard Inhibitor | Analyte |
|---|---|---|---|
| Phenacetin | O-deethylation (CYP1A2) | α-Naphthoflavone | Acetaminophen |
| Diclofenac | 4'-hydroxylation (CYP2C9) | sulfaphenazole | 4'-Hydroxy diclofenac |
| S-Mephenytoin | 4'-hydroxylation (CYP2C19) | (+)-N-3-benzylnirvanol | 4'-Hydroxy mephenytoin |
| Dextromethorphan | O-demethylation (CYP2D6) | quinidine | Dextrophan |
| Midazolam | 1'-hydroxylation (CYP3A4) | ketoconazole | 1'-Hydroxy midazolam |

After incubation, ice cold acetonitrile was added to terminate the reaction.

TABLE 6

LC-MS Parameters for Metabolite Identification in Samples

| | | | | |
|---|---|---|---|---|
| LC System: | ACQUITY UPLC | | | |
| Column: | ACQUITY UPLC ® HSS T3 1.8 μm 2.1 × 100 mm | | | |
| Column temperature: | 40° C. | | | |
| Autosampler temperature: | 8° C. | | | |
| Mobile phase A: | 0.1% formic acid in $H_2O$ | | | |
| Mobile phase B: | 0.1% formic acid in $CH_3CN$ | | | |

| Gradient time program: | Step | Total Time(min) | Flow Rate (μL/min) | A (%) | B (%) |
|---|---|---|---|---|---|
| | 0 | 0.00 | 500 | 100.0 | 0.0 |
| | 1 | 1.00 | 500 | 100.0 | 0.0 |
| | 2 | 7.00 | 500 | 90.0 | 10.0 |
| | 3 | 13.00 | 500 | 80.0 | 20.0 |
| | 4 | 18.00 | 500 | 0.0 | 100.0 |

TABLE 6-continued

LC-MS Parameters for Metabolite Identification in Samples

| | | | | |
|---|---|---|---|---|
| 5 | 18.10 | 500 | 100.0 | 0.0 |
| 6 | 20.00 | 500 | 100.0 | 0.0 |

| | |
|---|---|
| Mass system: | Xevo G2 QTOF |
| Ionization Mode: | ES+ |
| Capillary: | 3.0 kV |
| Sampling Cone: | 35.0 V |
| Extraction Cone: | 4.0 V |
| Source Temperature: | 100 °C. |
| Desolvation Temperature: | 400 °C. |
| Cone Gas Flow: | 50 L/h |
| Desolvation Gas Flow: | 800 L/h |
| CE: | 28-34 eV |
| Scan Mode: | $MS^E$, MSMS |

TABLE 7

LC-MS Parameters for Positive Control 7-Ethoxycoumarin

| | |
|---|---|
| LC System: | ACQUITY UPLC |
| Column: | ACQUITY UPLC ® HSS T3 1.8 μm 2.1 × 100 mm |
| Column temperature: | 40° C. |
| Autosampler temperature: | 4° C. |
| Mobile phase A: | 0.1% formic acid in $H_2O$ |
| Mobile phase B: | 0.1% formic acid in $CH_3CN$ |

| Gradient time program: | Step | Total Time(min) | Flow Rate (μL/min) | A (%) | B (%) |
|---|---|---|---|---|---|
| | 0 | 0.00 | 500 | 98.0 | 2.0 |
| | 1 | 1.00 | 500 | 98.0 | 2.0 |
| | 2 | 8.00 | 500 | 85.0 | 15.0 |
| | 3 | 14.00 | 500 | 60.0 | 40.0 |
| | 4 | 16.00 | 500 | 20.0 | 80.0 |
| | 5 | 17.90 | 500 | 10.0 | 90.0 |
| | 6 | 18.00 | 500 | 98.0 | 2.0 |
| | 7 | 20.00 | 500 | 98.0 | 2.0 |

| | |
|---|---|
| Mass system: | Xevo G2 QTOF |
| Ionization Mode: | ES+ |
| Capillary: | 3.0 kV |
| Sampling Cone: | 30.0 V |
| Extraction Cone: | 4.0 V |
| Source Temperature: | 100 °C. |
| Desolvation Temperature: | 400 °C. |
| Cone Gas Flow: | 50 L/h |
| Desolvation Gas Flow: | 800 L/h |
| CE: | 16-18 eV |
| Scan Mode: | $MS^E$ |

$MS^E$: Alternate switching of Collision Energy (CE) from low to high in QTOF MS, providing data independent (data rich) files. (1: TOF MS) for low CE, (2: TOF MS) for elevated CE.

Example 10

Efficacy of Compound 1 in Animal Model of Dust Mite Asthma

A model of airway inflammation in C57bl/6 wild type mice using repetitive intranasal challenges of aeoroallergenic House Dust Mite (HDM) (*D. pteronyssinus*) (acute model with 9 exposures) is used to study efficacy of compound 1. Mice are exposed to 60 μg of HDM (or PBS alone as a control) in 35 μL 1× DPBS on 3 consecutive days per week, for 3 weeks. The level of eosinophilic airway inflammation is evaluated 24 hours following the last HDM (or PBS) challenge by determining the percentage of eosinophils in bronchoalveolar lavage fluid (BAL) via flow cytometry.

The HDM intranasal procedure involves placing a mouse in the isoflurane/$O_2$ chamber until breathing deeply with the oxygen tank set to 1 L/min and the isoflurane tank set to 3 L/min. 35 μL of HDM (or PBS) is administered into the mouse's nostril while gently closing the mouse's mouth to encourage breathing through the nose to aid in HDM delivery to the lungs. The mouse is held upright for 10 seconds and returned mouse to ISO/$O_2$ chamber for approximately 2 minutes or until deep breathing returns. The mouse is held upright for 10 seconds and is placed in a recovery cage.

Bronchoalveolar lavage fluid (BAL) is collected from the mouse after sacrifice. Briefly, FACS buffer is injected into the lungs through a catheter in the trachea lumen to extract bronchoalveolar cells. Lung tissue is also harvested as tissue cassettes using paraffin embedding and fixing with 10% formalin. Lung tissue is stained using hematoxylin and eosin, and histology will be analyzed.

BAL cells are counted using a 1:10 dilution of BAL sample in Turks. BAL samples are stained for flow cytometry using antibodies mixtures including PE-Cy7 CD45, PE Siglec-F, PE IgG2a, APC Cd11c, and APC IgG. All samples are centrifuged at 300×g 4° C. for 5 minutes, and the supernatant is discarded. The cell pellet is resuspended in 40

µL of FACS buffer, and 10 µL of each stain is added to an aliquot of $0.4 \times 10^6$ cells. The samples are placed in the dark for 25 minutes. 400 µL of FACS buffer is added to each sample, and the samples are centrifuged at 300×g 4° C. for 5 minutes. The supernatant is discarded, and 100 µL of 2% paraformaldehyde diluted in FACS buffer is added to the cell pellet in each tube. The cells are fixed by incubating the tubes in the dark at room temperature for 5 minutes. 400 µL of FACS buffer is added to each sample to dilute the fixative, and the samples are centrifuged at 300×g 4° C. for 5 minutes. The supernatant is discarded, and the cell pellet is resuspended in 400 µL of FACS buffer.

The BAL samples are analyzed via flow cytometry. Data can be acquired using a Beckman Gallios Flow Cytometer using Kaluza Software, and FlowJo can be used to quantify the percentage of eosinophils in each sample. The percentage of eosinophils in HDM-challenged mice is compared to the percentage of eosinophils in PBS-treated mice. Eosinophils in lung histology is quantified via hematoxylin and eosin staining.

Example 11

Stimulation of THP-1 Cells: Testing the Effect at 6 or 36 Hours Post Stimulation.

Human immortalized monocytic THP-1 cells were maintained in phenol red free RPMI 1640 medium containing 10% (v/v) fetal bovine serum (FBS), 2 mM L-glutamine, penicillin (100 units/mL), streptomycin (100 µg/mL), amphotericin B (2.5 µg/mL), and 50 µM beta-mercaptoethanol (BME) at 37° C. with 5% (v/v) $CO_2$. THP-1 cells were seeded in 1 mL of THP-1 medium (cell culture medium containing 10% (v/v) FBS, 2 mM L-glutamine, penicillin (100 units/mL), streptomycin (100 µg/mL), amphotericin B (2.5 g/mL), and 50 µM BME)/well at a density of $1 \times 10^6$ cells/mL in six-well plates. Cells were differentiated by adding 10, 50, or 100 nM phorbol 12-myristate 13-acetate (PMA) to each well before incubating cells for 5.5 h at 37° C. with 5% (v/v) $CO_2$. Without removing the media, different concentrations (either 0, 0.1, 1.0, 10, 100, 200, or 500 µM) of the compound were added to each well. Cells were stimulated, within 30 min by adding 20 ng/mL interferon gamma (IFNγ) and 100 ng/mL lipopolysaccharide (LPS) to each well. Following stimulation, the THP-1 cells were incubated for 6 or 36 hours at 37° C. with 5% (v/v) CO2. Supernatant was collected and stored at −80° C. until use.

Figure 9:
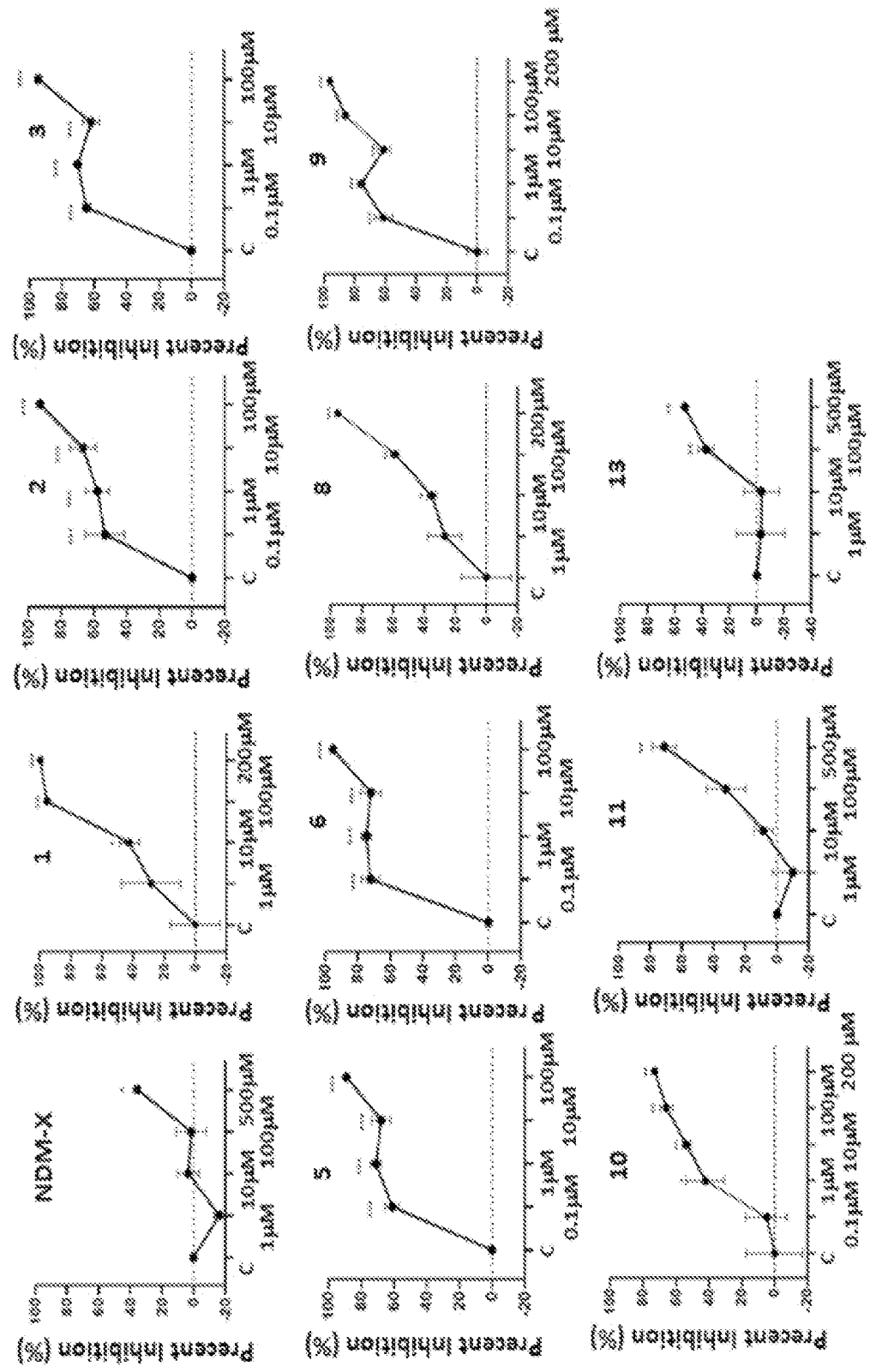
FIG. 9 Compounds 1, 2, 3, 5, 6, 8, 9, 10, 11, and 13 inhibit IL-6 in statistically significant dose dependent manner in human macrophage cells (THP-1).
Figure 9:
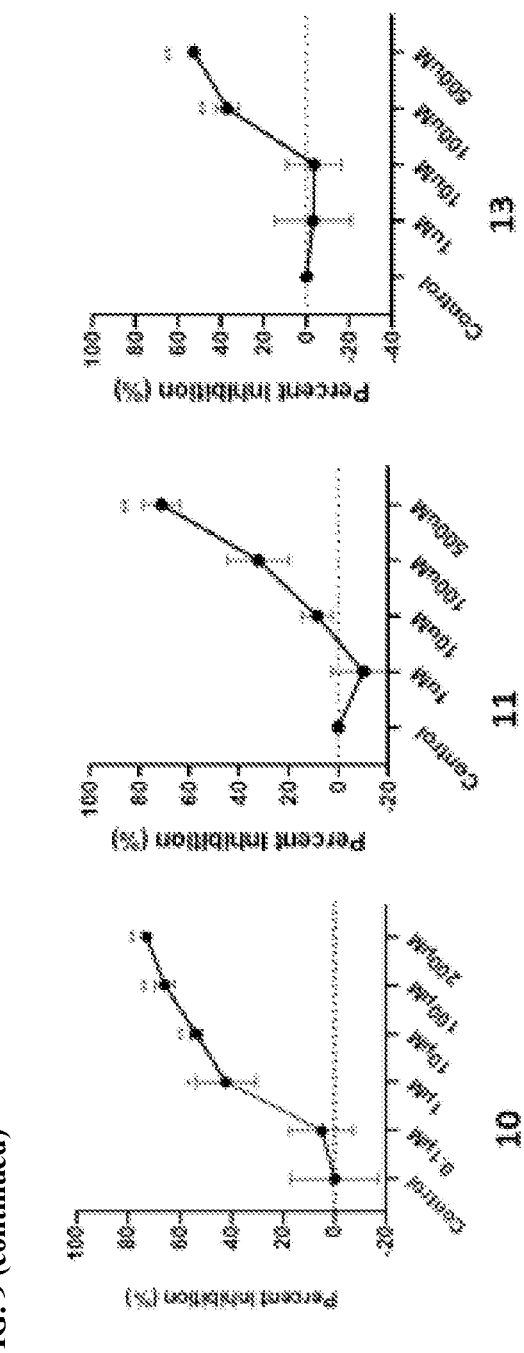

IL-6 released from supernatants collected at 6 or 36 hours post stimulation with IFNγ and LPS were measured using the AlphaLISA Human IL-6 detection kit. FIG. 9 showed with Control (stimulated with IFNγ and LPS but no administration of compound) representing zero percent inhibition, the percent inhibition relative to Control of IL-6 levels secreted by the THP1-derived macrophages when applying different concentrations of the compounds from 0.1 to 500 µM. Pre-treatment with increasing concentrations of the representative compounds 1, 2, 3, 5, 6, 8, 9, 10, 11, and 13 inhibited IL-6 expression in statistically significant, dose-dependent manner in THP1 human macrophage cells. The analogs shown in FIG. 9 demonstrated far superior inhibition of IL-6 expression in THP1 cells than the blocking observed with NDM-X.

Example 12

Stimulation of BEAS-2B Human Lung Epithelial Virus Transformed Cells: Testing the Effect of the Compounds BEAS-2B cells were maintained in Bronchial Epithelial Cell Growth Basal Medium (BEBM) containing all the recommended supplements for the Bronchial Epithelial Cell Growth Medium (BEGM; Lonza #CC-4175) and allowed to attain approximately 70% confluency with media changed every 2-3 days at 37° C. with 5% (v/v) $CO_2$. Tissue culture flasks/vessels were pre-coated with a mixture of 0.01 mg/mL fibronectin (Sigma), 0.03 mg/ml bovine collagen type I (Sigma) and 0.01 mg/mL bovine serum albumin dissolved in the BEBM. BEAS-2B cells were seeded with 0.5 ml of $1 \times 10^6$ cells/mL in BEGM per well on 24-well plates and incubated overnight at 37° C. with 5% (v/v) $CO_2$. The cells are pre-treated with different concentrations of compounds (0, 1.0, 10, 100, 1000 µM) for 1 hour prior to stimulation. To stimulate the cells, 10 ng/mL of Interleukin-1 beta (IL-1β), 10 ng/mL of Lipopolysaccharides (LPS), or 20 ng/mL of IL-1$ is added to the wells without removing the media and incubated for 48 hours at 37° C. with 5% (v/v) $CO_2$. Supernatants were collected and stored at −80° C. until quantitative detection assays are performed.

Human Eotaxin, Monocyte Chemoattractant Protein-1 (MCP-1), Interleukin-6 (IL-6), Interleukin-25 (IL-25), Interleukin-33 (IL-33), Thymic stromal lymphopoietin (TSLP), and Granulocyte-Macrophage Colony-Stimulating Factor (GM-CSF) released from supernatants collected post stimulation were measured using Human Magnetic Luminex® Assay Kit. Human CCL5/RANTES was measured using an Enzyme-Linked Immunosorbent Assay (ELISA)-based analysis.

Figure 10A:
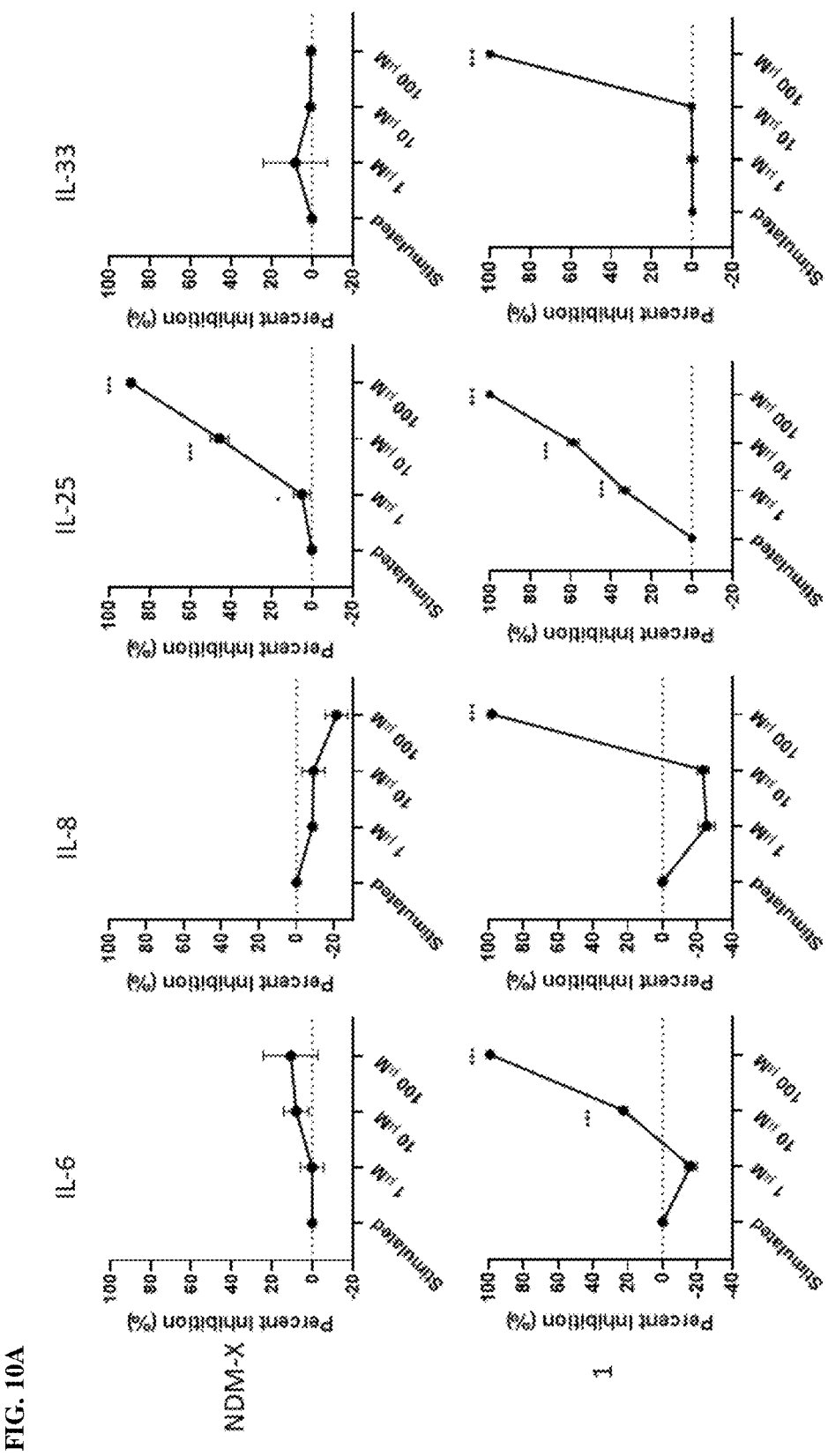
FIG. 10A Compound 1 inhibits IL1β-induced multiple inflammatory cytokines (IL-6, IL-8, IL-25, IL-33) in human lung epithelial cells (BEAS-2B).
Figure 10B:
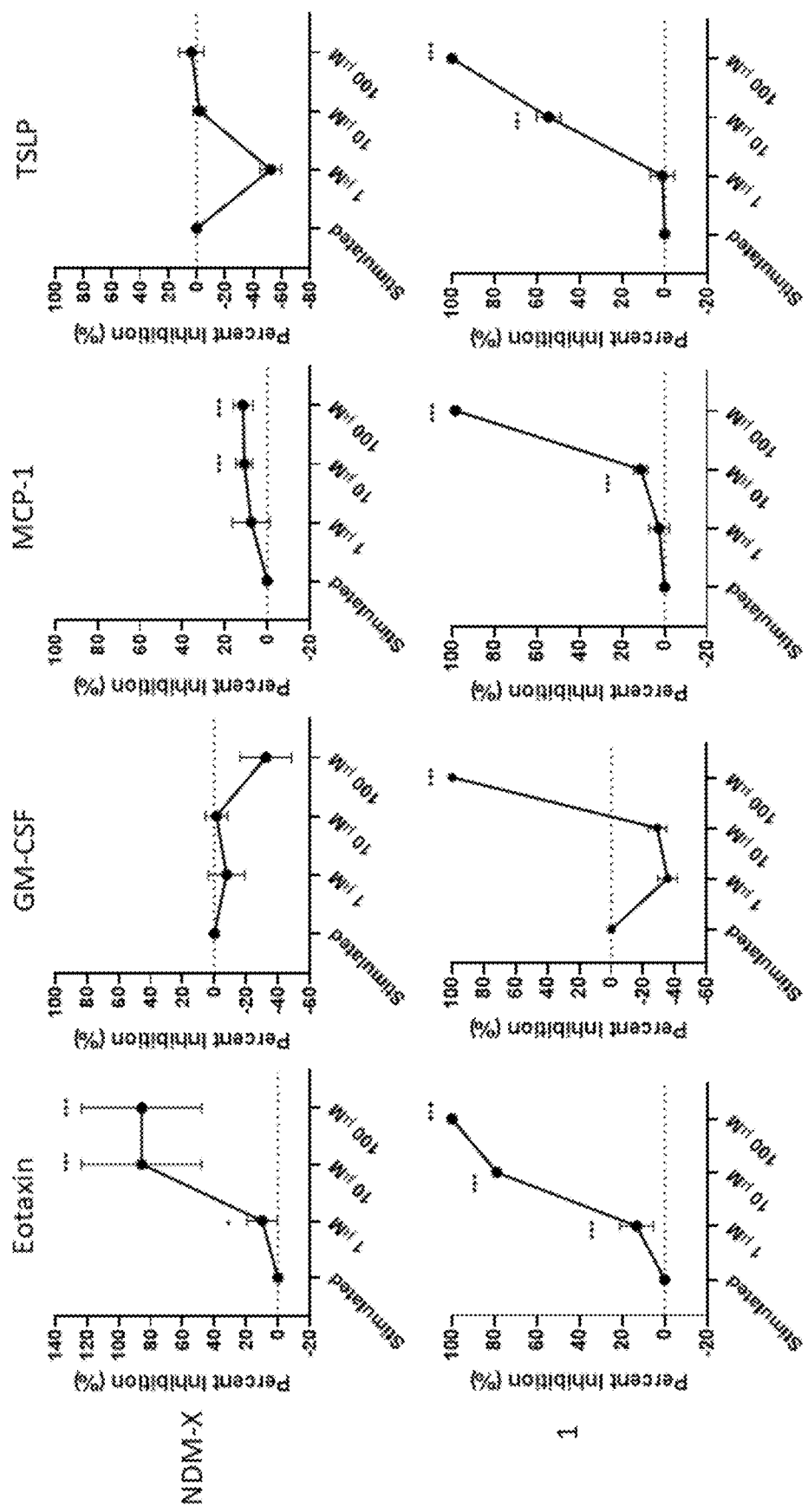
FIG. 10B Compound 1 inhibits IL1β-induced multiple inflammatory cytokines (Eotaxin, GMCSF, MCP-1, TSLP) in human lung epithelial cells (BEAS-2B).

FIGS. 10A and 10B, with Stimulated (induced with 10 ng/mL of IL-1β but no treatment with compound) representing zero percent inhibition, showed the percent inhibition relative to Stimulated of IL-6, IL-8, IL-25, IL-33, Eotaxin, GMCSF, MCP-1, and TSLP expression in EPC2 human primary esophageal keratinocytes when induced with 10 ng/mL of IL-1β.

In FIG. 10A, NDM-X did not show convincing inhibition of IL-6, IL-8, and IL-33 expression induced by 10 ng/mL of IL-1β in BEAS-2B human lung epithelial cells with exception to IL-25 expression. However, in the same FIG. 10A, 100 µM of 1 demonstrated statistically significant, complete inhibition of IL-6, IL-8, IL-25, and IL-33 expression induced by 10 ng/mL of IL-1β in BEAS-2B human lung epithelial cells. Regarding IL-1β-induced IL-25 expression, NDM-X and 1 showed very similar profiles with statistically significant, dose-dependent inhibition.

In FIG. 10B, NDM-X did not demonstrate convincing inhibition of GM-CSF, MCP-1, and TSLP expression stimulated by 10 ng/mL of IL-1β in BEAS-2B human lung epithelial cells with exception to Eotaxin expression. Whereas, in the same FIG. 10B, 100 µM of 1 showed statistically significant, complete inhibition of GM-CSF, MCP-1, and TSLP expression. NDM-X and 1 showed very similar profiles with statistically significant, dose-dependent inhibition of Eotaxin expression in BEAS-2B human lung epithelial cells when simulated with 10 ng/mL of IL-1β.

Figure 11A:
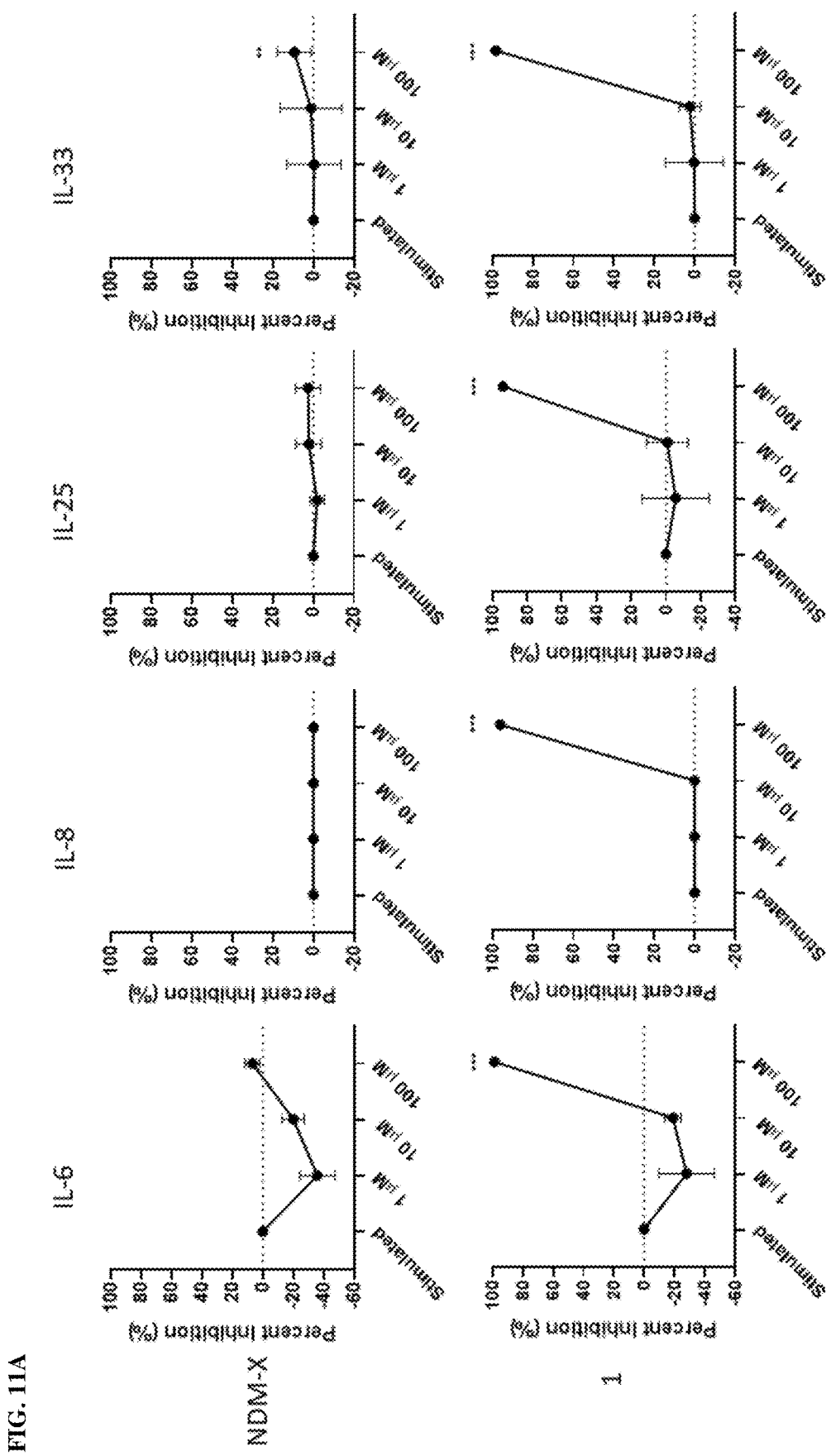
FIG. 11A Compound 1 inhibits IL1β-induced multiple inflammatory cytokines (IL-6, IL-8, IL-25, IL-33) in human lung epithelial cells (BEAS-2B).
Figure 11B:
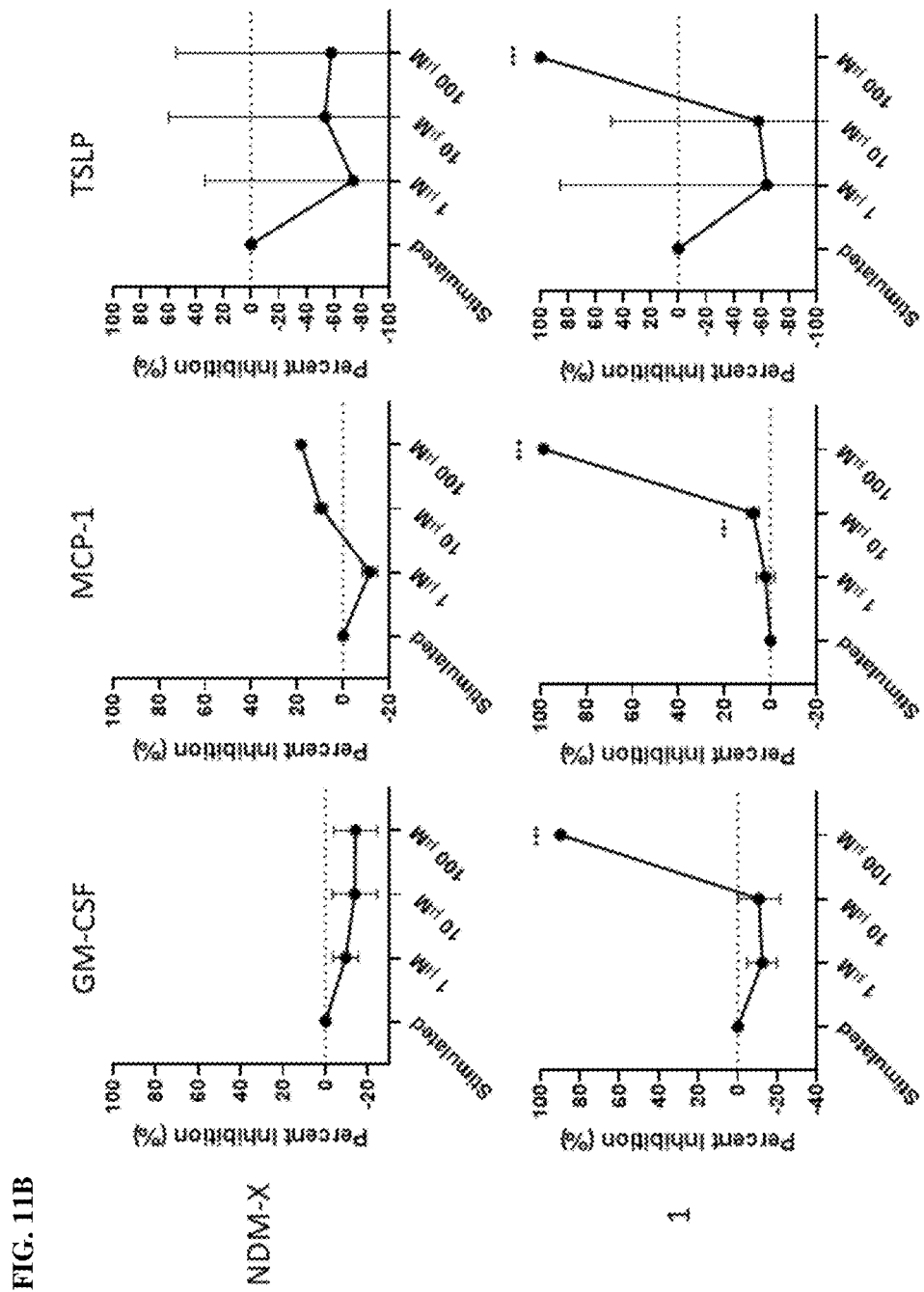
FIG. 11B Compound 1 inhibits LPS-induced multiple inflammatory cytokines (GMCSF, MCP-1, TSLP) in human lung epithelial cells (BEAS-2B).

With Stimulated (induced with 10 ng/mL of LPS but no treatment with compound) representing zero percent inhibition, FIGS. 11A and 11B demonstrated the percent inhibition relative to Stimulated of IL-6, IL-8, IL-25, IL-33, Eotaxin, GMCSF, MCP-1, and TSLP expression in BEAS-2B human lung epithelial cells when stimulated by 10 ng/mL of LPS. NDM-X, in FIG. 11A, did not show convincing inhibition of IL-6, IL-8, IL25, and IL-33 expression induced by 10 ng/mL of LPS in BEAS-2B human lung epithelial cells. However, 100 µM of 1 demonstrated complete, statistically significant inhibition of expression of multiple inflammatory cytokines. In FIG. 11B, while NDM-X did not show convincing inhibition of GM-CSF, MCP-1, and TSLP expression induced by 10 ng/mL of LPS in BEAS-2B human lung epithelial cells, statistically significant, complete inhibition of expression of multiple inflammatory cytokines was observed with at 100 µM of 1.

Figure 12:
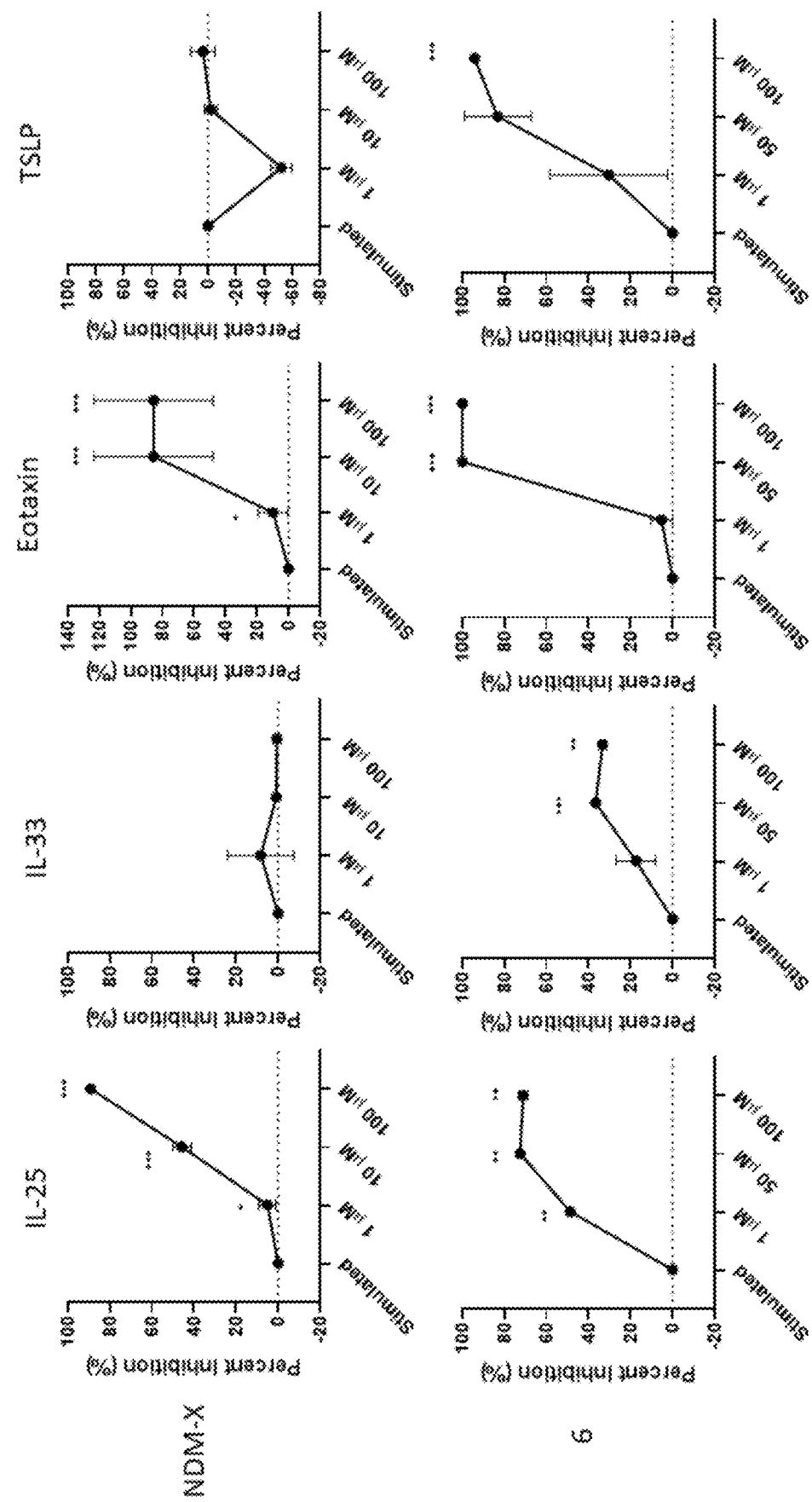
FIG. 12 Compound 6 inhibits IL1β-induced multiple inflammatory cytokines (IL-25, IL-33, Eotaxin, TSLP) in human lung epithelial cells (BEAS-2B).

In the same BEAS-2B assay with Stimulated (induced with 20 ng/mL of IL-1β but treatment with of compound) representing zero percent inhibition, FIG. 12 showed the percent inhibition relative to Stimulated of IL-25, IL-33, Eotaxin, and TSLP expression in BEAS-2B human lung epithelial cells when stimulated by 20 ng/mL of IL-1β. Compound 6, in FIG. 12, showed statistically significant inhibition of IL-33, Eotaxin, and TSLP expression induced by 20 ng/mL of IL-1β in BEAS-2B human lung epithelial cells and this blocking is superior to the attenuation observed with NDM-X. However, in the same FIG. 12, Compound 6 demonstrated robust inhibition of IL-25 expression at 1 mM concentration that topped out at 60% even at 100 µM but NDM-X showed statistically significant, dose-dependent blocking in BEAS-2B human lung epithelial cells induced with 20 ng/mL of IL-1β.

Figure 13:
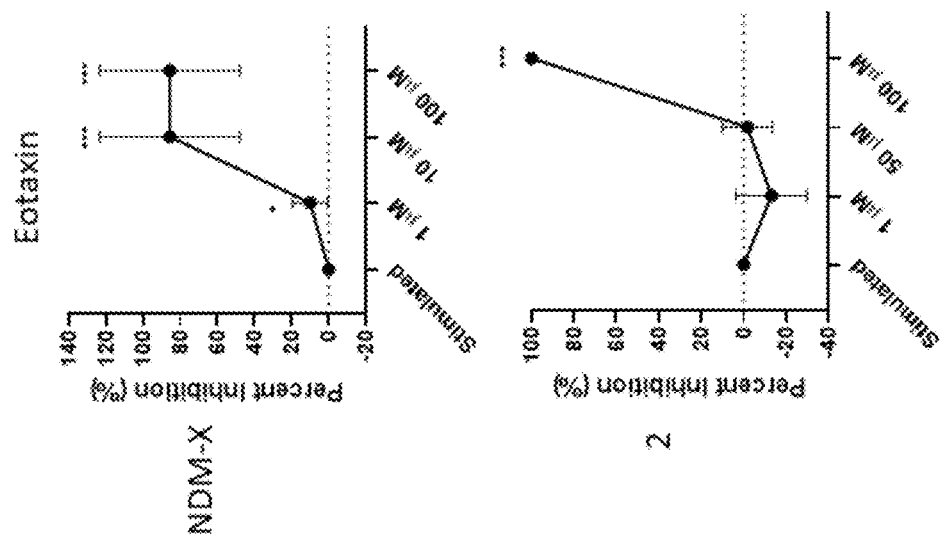
FIG. 13 Compound 2 inhibits IL1β-induced Eotaxin inflammatory cytokine in human lung epithelial cells (BEAS-2B).

FIG. 13, with Stimulated (induced with 20 ng/mL of IL-1β but no treatment with compound) representing zero percent inhibition, the percent inhibition relative to Stimulated of Eotaxin expression in BEAS-2B human lung epithelial cells when stimulated by 20 ng/mL of IL-1β. Compound 2, a representative compound, showed statistically significant, complete inhibition of Eotaxin expression induced by 20 ng/mL of IL-1β in BEAS-2B human lung epithelial cells, whereas NDM-X achieved statistically significant, almost complete blocking at 10 and 100 µM concentrations.

Example 13

Stimulation of Blood Derived Naïve T Cells with *Dermatophagoides Pteronyssinus* (House Dust Mite) Antigen: Testing the Effect of the Compounds Naïve T cells from peripheral blood samples were collected and processed using MACSxpress® Whole Blood Pan T Cell Isolation Kit (Miltenyi Biotec), according to the manufacturer's protocol. Isolated naïve T cells were cultured in RPMI medium supplemented with 5% Fetal Bovine Serum (FBS) at 37° C. with 5% (v/v) $CO_2$. T cells were seeded in 24 well plates at a density of $0.5 \times 10^6$ cells per well. The cells were pre-treated with the compounds (0, 0.1, 1.0, 10, 100 µM) for 1 hour prior to stimulation. Cells were stimulated with 10 mg/mL of *Dermatophagoides pteronyssinus* (Der p1) antigen. After 48 hours, fresh 10 mg/mL of Der p1 was added and continued incubating for a further 72 hours at 37° C. with 5% (v/v) $CO_2$. Overall T cells were stimulated with 10 mg/mL of Der p1 antigen for 5 days before supernatants were collected and stored at −80° C. until quantitative detection assays are performed.

Human Interleukin-4 (IL-4), Interleukin-5 (IL-5), Interleukin-6 (IL-6), Interleukin-8 (IL-8), Interleukin-13 (IL-1β), Interleukin-23 (IL-23), and Interferon gamma (IFNγ) released from supernatants collected post stimulation were measured using Human Magnetic Luminex® Assay Kit. Human Transforming Growth Factor beta (TGFβ) was measured using an Enzyme-Linked Immunosorbent Assay (ELISA)-based analysis.

Figure 14:
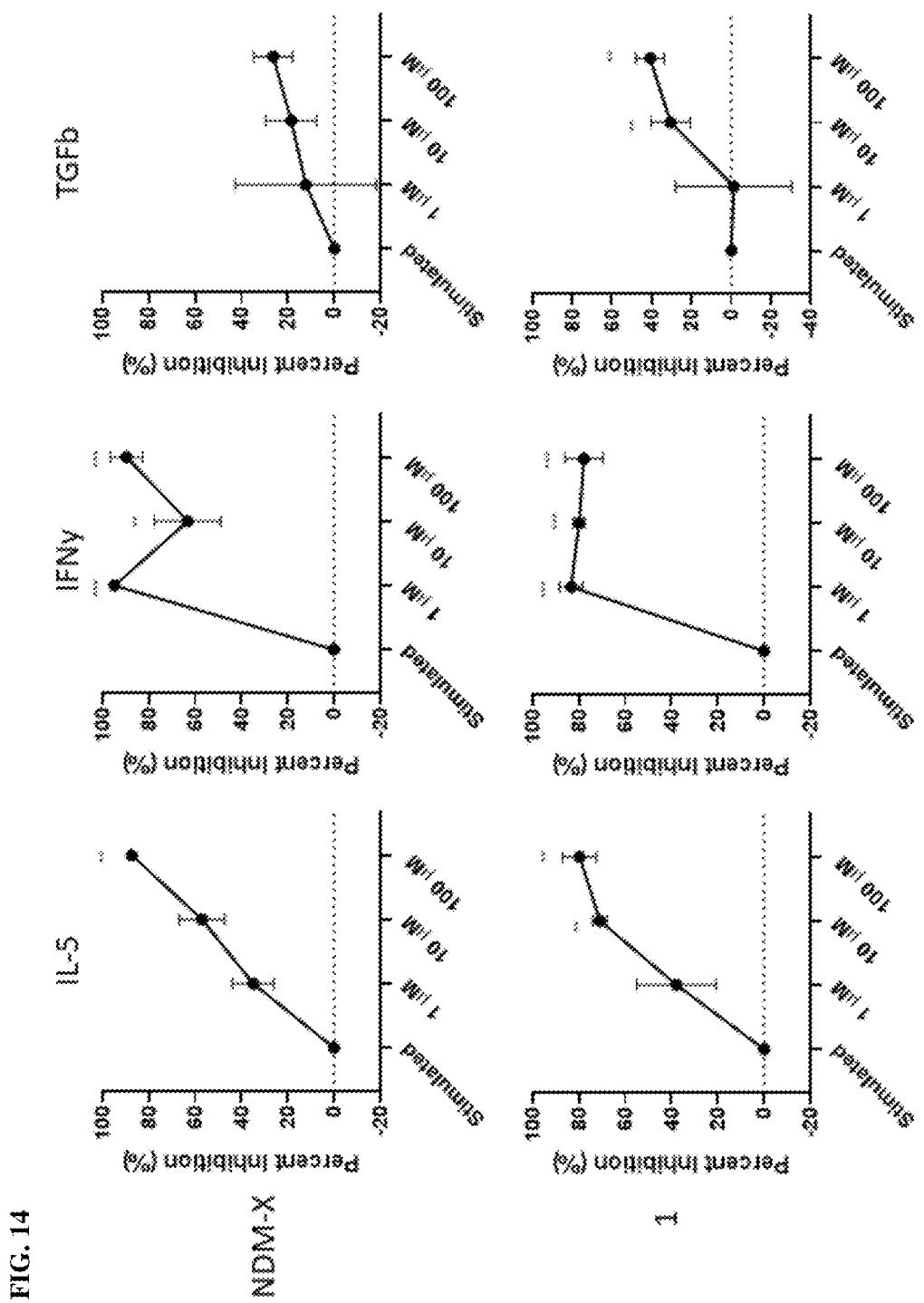
FIG. 14 Compound 1 inhibits multiple inflammatory cytokines (IL-5, IFNγ, TGFβ) in statistically significant dose dependent manner in human T cells.

FIG. 14 with Stimulated (induced with Der p1 antigen but no treatment with compound) representing zero percent inhibition, showed the percent inhibition relative to Stimulated of IL-5, IFNγ, and TGFβ expression in isolated human naïve T cells that have been challenged with Der p1 antigen for 5 days. In FIG. 14, Compound 1, a representative compound, demonstrated inhibition of multiple inflammatory cytokines, such as IL-5, IFNγ, and TGFβ, in a statistically significant, dose-dependent manner. In the same FIG. 14, NDM-X showed dose-dependent inhibition of IL-5 expression, statistically significant, robust blocking of IFNγ expression, and slight attenuation of TGFβ expression. Overall, FIG. 14 showed 1 inhibited the expression of multiple inflammatory cytokines in statistically significant, dose-dependent manner that is superior to blocking observed with NDM-X in human T cells that are challenged with Der p1 antigen.

Figure 15:
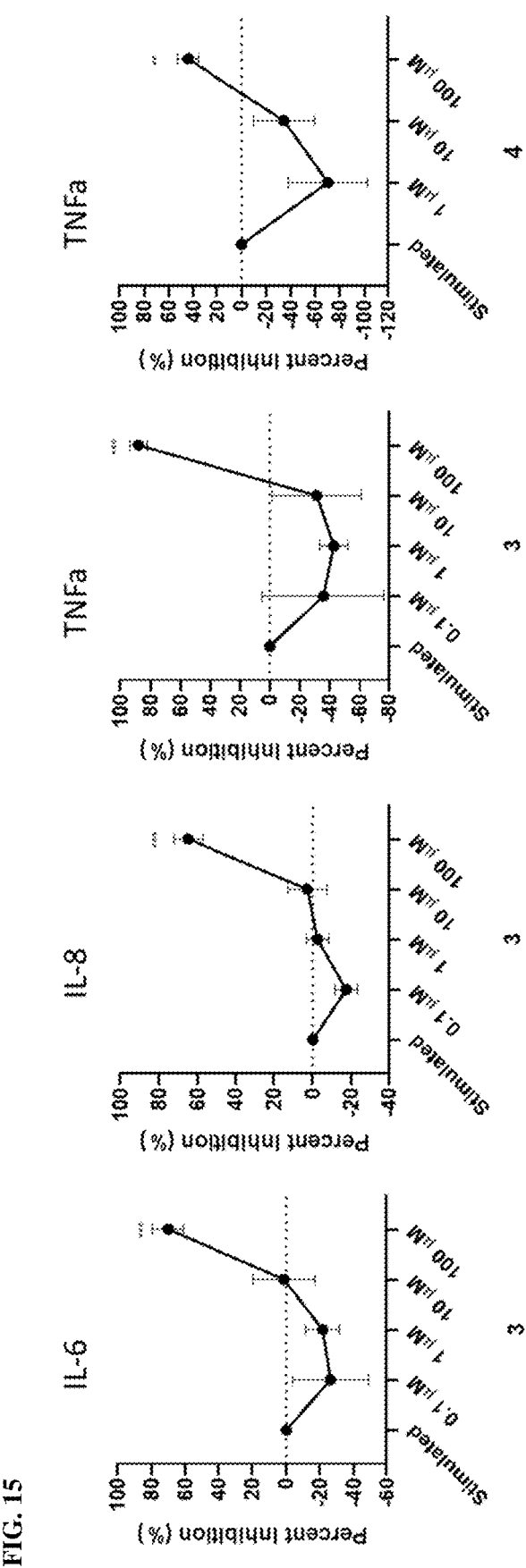
FIG. 15 Compound 3 and 4 inhibit inflammatory cytokines (IL-6, IL-8, TNFα) in human T cells.

In the same T cell assay, FIG. 15 with Stimulated (induced with Der p1 antigen but no treatment with compound) representing zero percent inhibition, showed the percent inhibition relative to Stimulated of IL-6, IL-8, and TNFα expression. Representative compounds, 3 and 4, showed statistically significant inhibition of IL-6, IL-8, and TNFα expression at 100 µM concentration in human T cells that are challenged with Der p1 antigen.

Example 14

Stimulation of A549 Human Lung Carcinoma Cell Line: Testing the Effect of the Compounds A549 cells are cultured in DMEM supplemented with 2 mM glutamine and 10% Fetal Bovine Serum (FBS) at 37° C. with 5% (v/v) $CO_2$. Cells are grown to approximately 80% confluency before being passage and media is changed every 2-3 days. A549 cells are seeded in 24-well plates at a density of $0.5 \times 10^6$ cells per well at 37° C. with 5% (v/v) $CO_2$. The cells are pre-treated with the compounds (0, 1.0, 10, 100 µM) for 1 hour prior to addition of 10 ng/mL of TNFα and 10 ng/mL of IL-1β for 48 hours at 37° C. with 5% (v/v) $CO_2$. Supernatants were collected and stored at −80° C. until quantitative detection assays are performed.

Human Eotaxin, Monocyte Chemoattractant Protein-1 (MCP-1), Interleukin-6 (IL-6), Interleukin-25 (IL-25), Interleukin-33 (IL-33), Thymic stromal lymphopoietin (TSLP), and Granulocyte-Macrophage Colony-Stimulating Factor (GM-CSF) released from supernatants collected post stimulation were measured using Human Magnetic Luminex® Assay Kit. Human CCL5/RANTES was measured using an Enzyme-Linked Immunosorbent Assay (ELISA)-based analysis.

Figure 16:
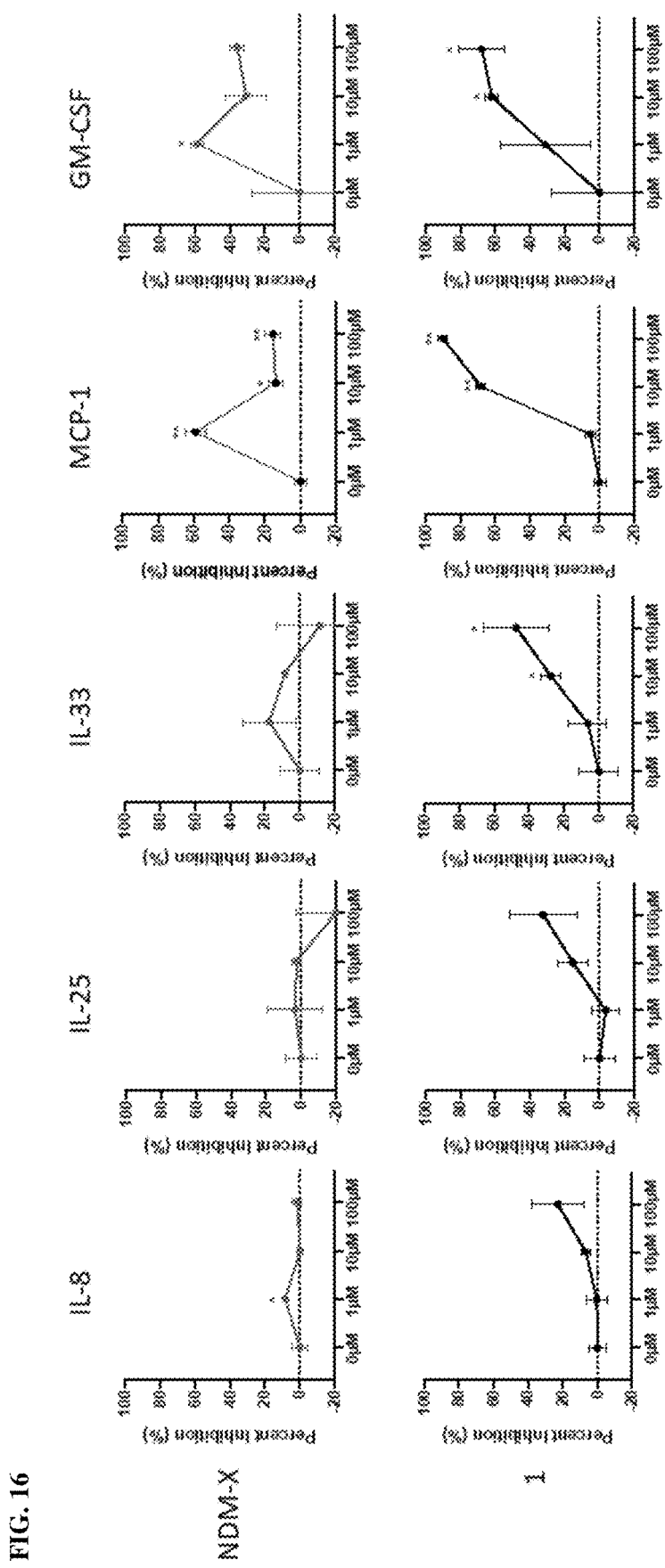
FIG. 16 Compound 1 inhibits multiple inflammatory cytokines (IL-8, IL-25, IL-33, MCP-1, GM-CSF) in human alveolar epithelial cells (A549).

FIG. 16 with Stimulated (induced with TNFα and IL-1β but no treatment with compound) representing zero percent inhibition, showed the percent inhibition relative to Stimulated of IL-8, IL-25, IL-33, MCP-1, and GM-CSF expression in A549 human lung carcinoma cell line when induced with 10 ng/mL of TNFα and 10 ng/mL of IL-1β for 48 hours. In FIG. 16, compound 1, a representative compound, demonstrated statistically significant, dose-dependent inhibition of IL-33, MCP-1, and GM-CSF expression induced by TNFα and IL-1β in A549 human alveolar epithelial cells. In the same FIG. 16, the percent inhibition profiles exhibited by 1 are far superior than compared to profiles exhibited by NDM-X. While NDM-X did not influence IL-8 and IL25 expression induced by TNFα and IL-1β in A549 human alveolar epithelial cells, 1 showed dose-dependent inhibition in FIG. 16.

Figure 17:
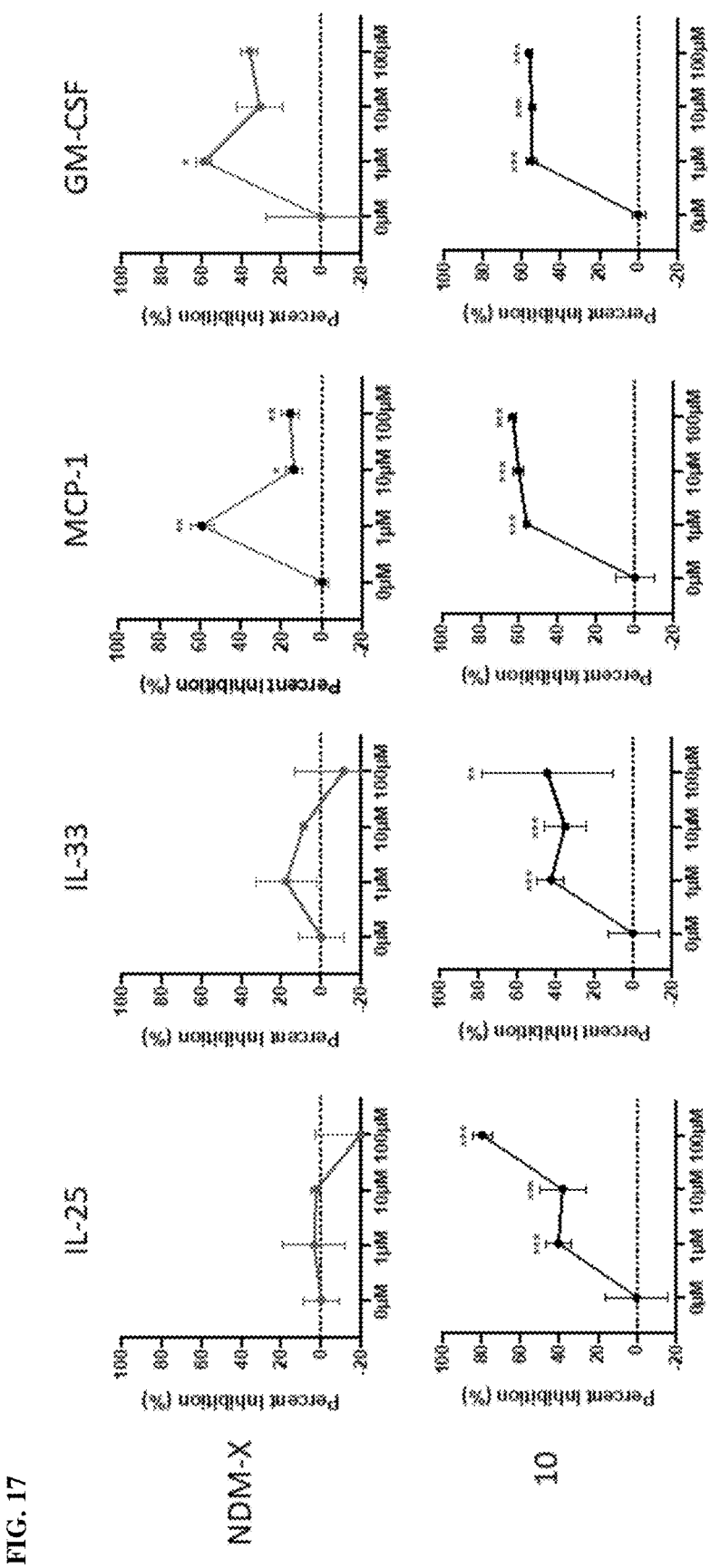
FIG. 17 Compound 10 inhibits multiple inflammatory cytokines (IL-25, IL-33, MCP-1, GM-CSF) in human alveolar epithelial cells (A549).

With Stimulated (induced with TNFα and IL-1 but no treatment with compound) representing zero percent inhibition, FIG. 17 showed the percent inhibition relative to Stimulated of IL-25, IL-33, MCP-1, and GM-CSF expression in A549 human lung carcinoma cell line when induced with 10 ng/mL of TNFα and 10 ng/mL of IL-1β for 48 hours. In FIG. 17, another representative compound, compound 10, demonstrated overall statistically significant, dose-dependent inhibition that is superior to NDM-X blocking of multiple inflammatory cytokines, including IL-25, IL-33, MCP-1, and GM-CSF expression in A549 human lung carcinoma cell line when induced with TNFα and IL-1β. However, NDM-X demonstrated statistically significant but not dose-dependent inhibition of MCP-1 and GM-CSF expression induced by TNFα and IL-1β.

Figure 18:
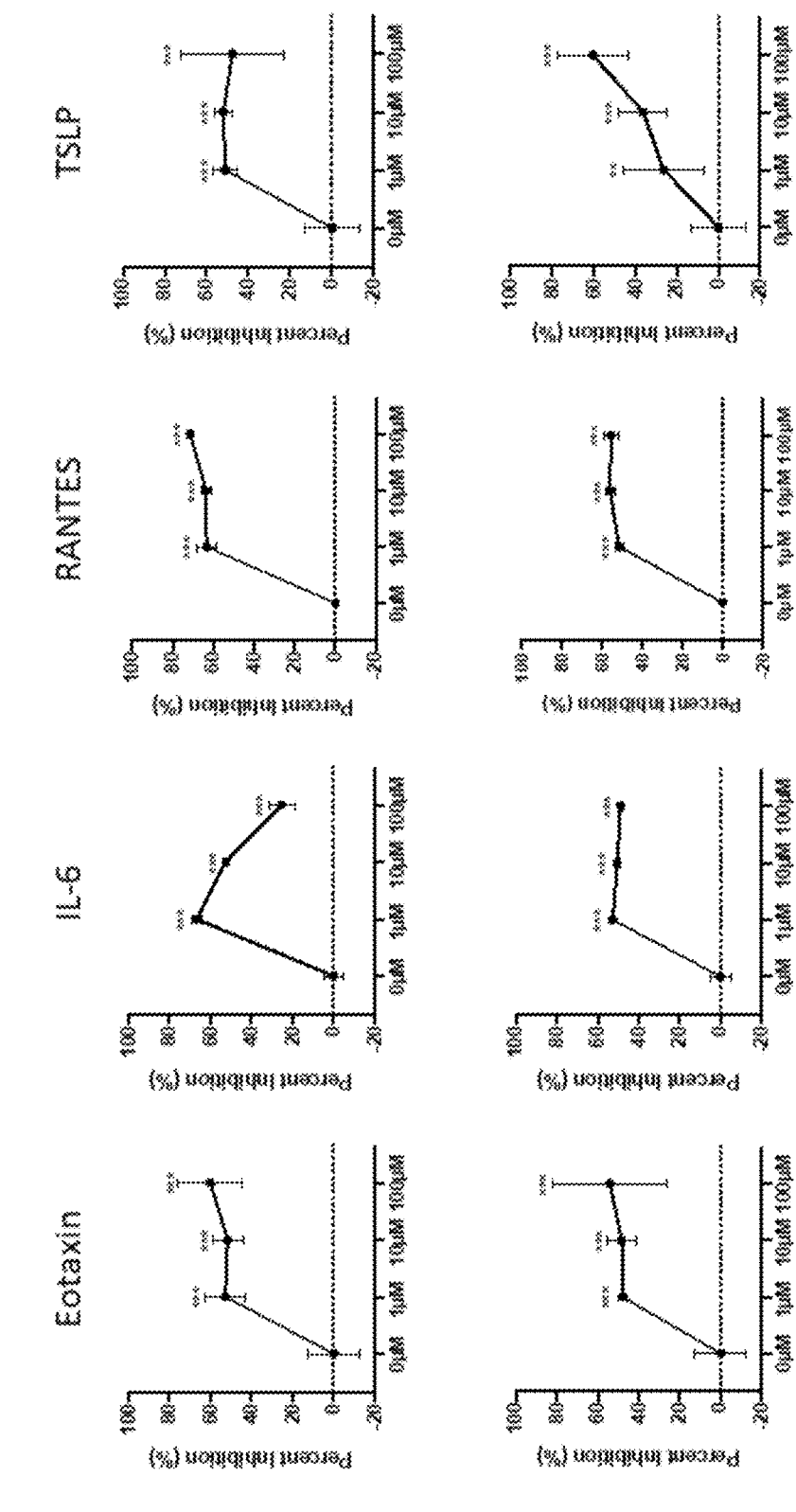
FIG. 18 Compound 1 and 10 inhibit multiple inflammatory cytokines (Eotaxin, IL-6, RANTES, TSLP) in human alveolar epithelial cells (A549).

FIG. 18, with Stimulated (induced with TNFα and IL-1β but no treatment with compound) representing zero percent inhibition, showed the percent inhibition relative to Stimulated of Eotaxin, IL-6, RANTES, and TSLP expression in A549 human lung carcinoma cell line when induced with 10 ng/mL of TNFα and 10 ng/mL of IL-1β for 48 hours. In FIG. 18, representative compounds, 1 and 10 both demonstrated robust, statistically significant inhibition of Eotaxin, IL-6, RANTES, and TSLP expression induced by TNFα and IL-1β in A549 human alveolar epithelial cells.

Example 15

Stimulation of EPC2-hTERT, Immortalized Human Esophageal Keratinocytes: Testing the Effect of the Compounds EPC2-hTERT (EPC2) cells were maintained in supplemented keratinocyte serum-free medium (KSFM) with 0.09 mM calcium chloride containing epidermal growth factor (5 ng/mL), bovine pituitary extract (50 mg/mL), penicillin (100 units/mL), and streptomycin (100 mg/mL) (ThermoFisher #17005042) at 37° C. with 5% (v/v) $CO_2$. EPC2 cells were seeded in 12-well plates at $0.55 \times 10^6$ cells per well in supplemented KSFM at 37° C. with 5% (v/v) $CO_2$ and after 6 hours the old media is removed and changed with fresh media. After overnight incubation, the old media is changed to supplemented KSFM containing 1.8 mM calcium chloride and incubated for 72 hours at 37° C. with 5% (v/v) $CO_2$. After the old media is removed and fresh supplemented KSFM containing 1.8 mM calcium chloride is added, the cells are pre-treated with different concentrations of compounds (0, 1, 10, 100, 500, 1000 µM) for 1 hour prior to stimulation. To stimulate the cells, Poly (I:C) (Tocris #4287) is added to the wells at 10 mg/mL concentration without removing the media and incubated for 24 hours at 37° C. with 5% (v/v) $CO_2$. Supernatants are collected in Eppendorf tubes, centrifuged in a microfuge at maximum speed for 10 minutes at 4° C., and the centrifuged supernatants stored at −80° C. until quantitative detection assays are performed.

Human Interleukin-6 (IL-6), Monocyte Chemoattractant Protein-1 (MCP-1), and Thymic stromal lymphopoietin (TSLP) released from supernatants collected post stimulation were measured using the AlphaLISA detection kit for human IL-6, MCP-1, and TSLP, respectively.

Figure 19A:
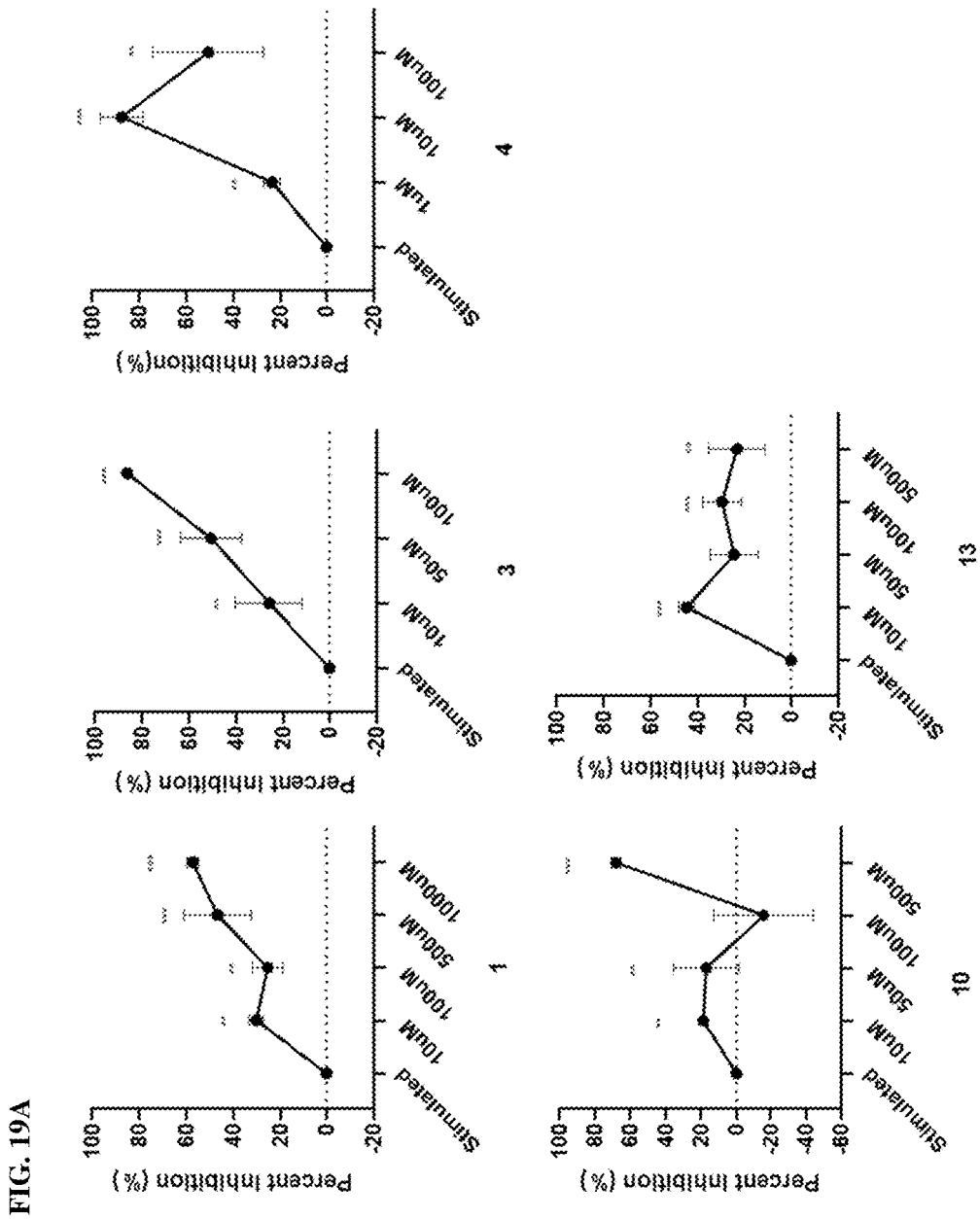
FIG. 19A Compounds 1, 3, 4, 10, and 13 inhibited TSLP expression in statistically significant manner in human primary esophageal keratinocytes (EPC2).

Human TSLP released from supernatants collected at 24 hours post stimulation with Poly(I:C) was measured using the AlphaLISA Human TSLP detection kit. With Stimulated (induced with Poly(I:C) but no treatment with compound) representing zero percent inhibition, FIG. 19A showed the percent inhibition relative to Stimulated of TSLP expression in EPC2 human primary esophageal keratinocytes. Pre-treatment with increasing concentrations of representative compounds 1, 3, 4, and 10 showed statistically significant inhibition of TSLP expression inhibition in EPC2 human primary esophageal keratinocytes that has been induced by Poly (I:C). While compounds 1, 10, and 13 showed robust blocking, compounds 3 and 4 completely inhibited TSLP expression induced by Poly (I:C) in EPC2 human primary esophageal keratinocyte in FIG. 19A.

Figure 19B:
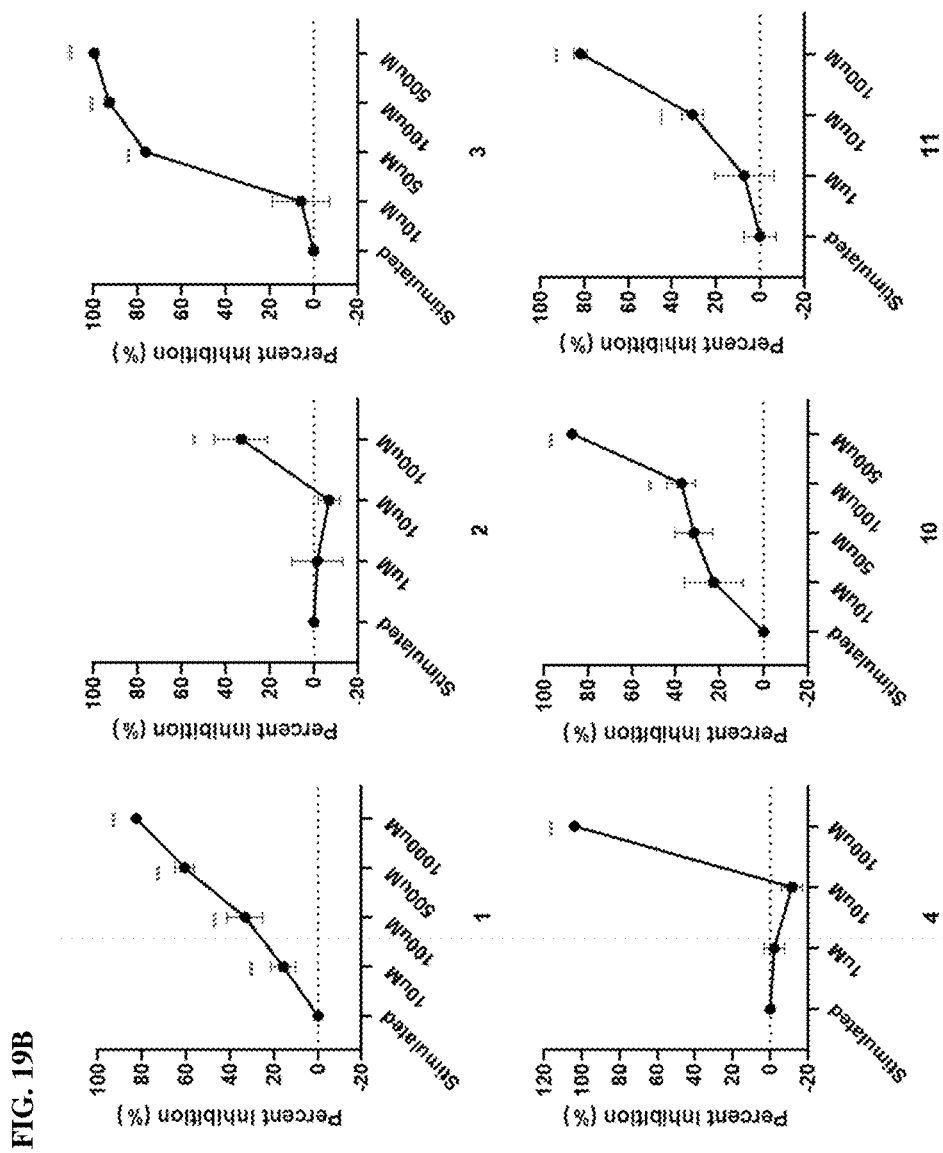
FIG. 19B Compounds 1, 2, 3, 4, and 10 inhibited IL6 expression in statistically significant manner in human primary esophageal keratinocytes (EPC2).

Human IL-6 released from supernatants collected at 24 hours post stimulation with Poly(I:C) was measured using the AlphaLISA Human IL6 detection kit. FIG. 19B, with Stimulated (induced with Poly(I:C) but no treatment with compound) representing zero percent inhibition, showed the percent inhibition relative to Stimulated of IL-6 expression in EPC2 human primary esophageal keratinocytes. Pre-treatment with increasing concentrations of representative compounds Compound 1, 3, 4, and 10 inhibited IL-6 expression in statistically significant, dose-dependent manner in human primary esophageal keratinocytes (EPC2) when stimulated with Poly (I:C). Compound 2 showed robust inhibition of IL-6 expression at 100 µM concentration in FIG. 19B.

Figure 19C:
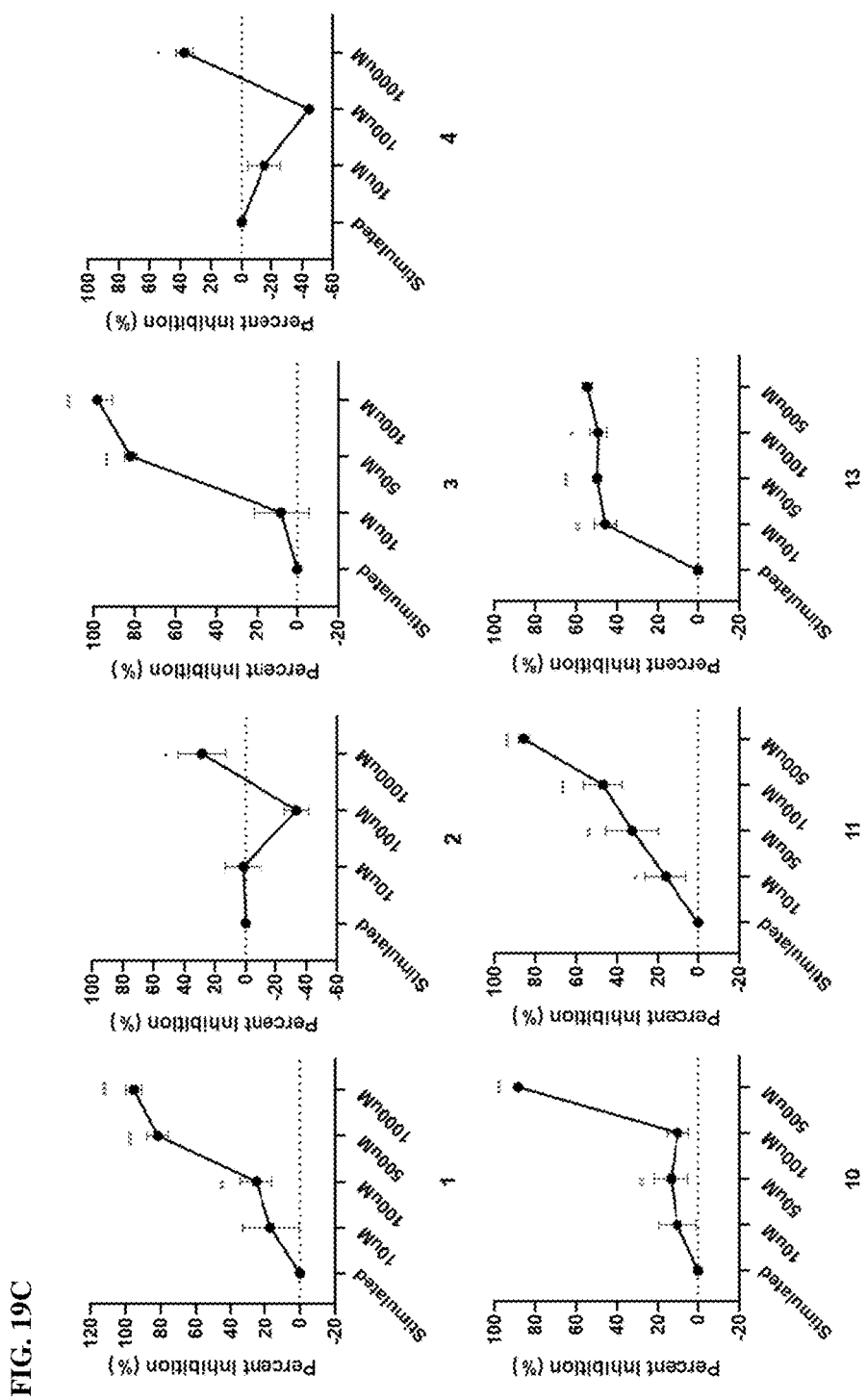
FIG. 19C Compounds 1, 2, 3, 4, 10, 11, and 13 inhibited MCP-1 expression in statistically significant manner in human primary esophageal keratinocytes (EPC2).

Human MCP-1 released from supernatants collected at 24 hours post stimulation with Poly(I:C) was measured using the AlphaLISA Human MCP-1 detection kit. With Stimulated (induced with Poly(I:C) but no treatment with compound) representing zero percent inhibition, FIG. 19C showed the percent inhibition relative to Stimulated of MCP-1 expression in EPC2 human primary esophageal keratinocytes. Pre-treatment with increasing concentrations of representative compounds Compound 1, 3, 10, and 11 inhibited MCP-1 expression in statistically significant, dose-dependent manner in human primary esophageal keratinocytes (EPC2) when stimulated with Poly(I:C). While compound 13 showed robust blocking of MCP-1 expression starting at 1 mM, compounds 2 and 4, only showed inhibition at the highest 100 µM concentration in FIG. 19C.

Example 16

Induction of Eosinophilic Esophagitis (EoE) in a mouse model: Testing the Effect of the Compounds Eosinophilic esophagitis (EoE) is a chronic allergic gastrointestinal disease as a result of a hypersensitivity response in the esophageal mucosa and manifest by dysphagia and food impaction in adults as well as symptoms previously associated with gastro-esophageal reflux disease in children.

From the observation of increased local expression of Interleukin-5 (IL-5) in EoE, transgenic mouse with targeted IL-5 expression to the esophageal squamous epithelia using the Epstein-Barr virus ED-L2 (EBV-ED-L2) gene promoter was generated. The transgenic mouse showed constitutive squamous esophageal epithelial-specific overexpression of IL-5 (L2-IL5 transgenic mice) and resulted in a baseline esophageal eosinophilia. Even though squamous epithelial-specific IL-5 expression alone induced a significant esophageal eosinophilia encompassing the length of the esophagus, this eosinophilia was not accompanied by the density of histopathological changes such as eosinophilic micro abscesses characteristic of EoE. However, L2-IL5 transgenic mice upon sensitization and subsequent localized topical esophageal challenge with 4-ethoxymethylene-2-phenyl-2-oxazolin-5-one (OXA), a molecule known to induce T-helper cell (Th) type 2 responses, developed key histopathological features, including epithelial hyperplasia and eosinophilic micro abscesses that erupt through the epithelium into the esophageal lumen. Immunohistochemical staining of the eosinophil secondary granule major basic protein (MBP-1) was used to assess the induced esophageal eosinophilia and eosinophil degranulation. The immunohistochemical assessments in wild-type mice revealed that while treatment with OXA showed mild tissue eosinophilia, the vehicle did not. In L2-IL5 transgenic mice, vehicle-treated mice showed statistically higher eosinophilia than observed in wild-type animals. However, this response was small compared to the induced eosinophilia and associated degranulation that occurred in OXA-treated L2-IL5 transgenic mice (Masterson et al. Gut. 2014, 63, 1-25, which is hereby incorporated by reference in its entirety).

Figure 20:
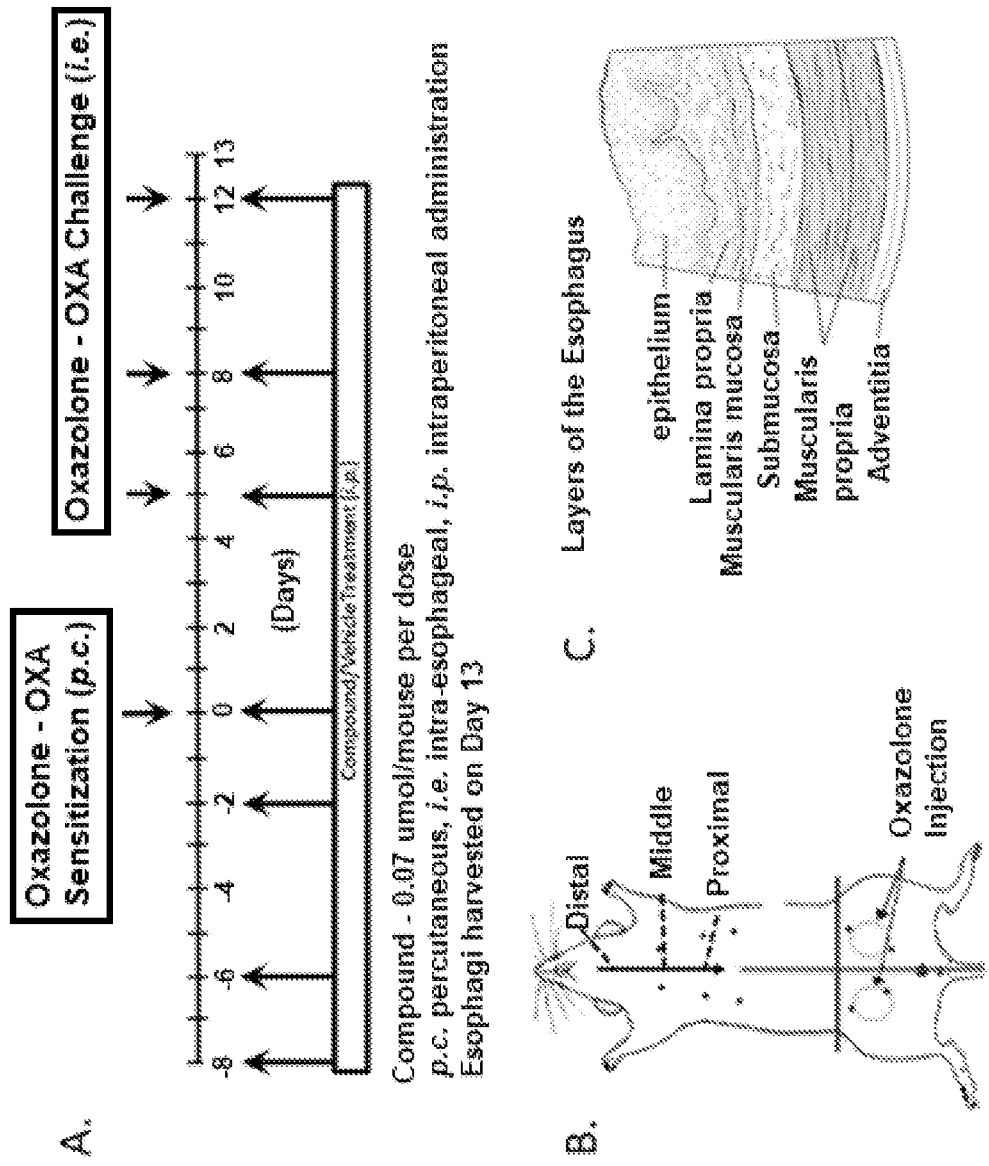
FIG. 20 Schematic Timeline of L2-IL5 Transgenic Mouse Sensitized/Locally Challenged with Oxazolone Antigen—In Vivo Model of Eosinophilic Esophagitis.

Prior to the OXA sensitization and topical local challenge model of delayed contact hypersensitivity, L2-IL5 transgenic mice were intraperitoneally (IP) injected with compounds or vehicle at 8, 4, and 2 days before sensitization at Day zero (schematic timeline in FIG. 20A). Compounds are prepared by dissolving in dimethyl sulfoxide (DMSO) as master stocks. Fresh working stock compounds in water are prepared for each day of injection and 100 µL of working stock or vehicle is IP injected per mouse. On day zero of the OXA sensitization/local challenge, a 2 cm×2 cm area of abdominal skin of anaesthetized experimental animals was shaved and OXA was applied to the skin surface (150 µl of a 3% (w/v) solution of OXA in 4:1 acetone-olive oil vehicle) to initiate the sensitization phase of the protocol. Sensitized mice then received topical OXA challenges of the esophagus by gavage on protocol Day 5, 8 and 12 after OXA sensitization with 100 µL of a 1% (w/v) solution of OXA in 30% ethanol/olive oil vehicle into the proximal esophagus. In addition, compounds or vehicle were IP injected on Day 5, 8, and 12 after OXA sensitization. All mice were sacrificed, and esophagus collected for histology 24 hours following the last OXA challenge on Day 12 (FIG. 20A). Immunohistochemical staining using a rat monoclonal anti-mouse MBP-1 antibody was conducted to highlight esophageal eosinophil infiltration and localized degranulation. A quantitative assessment of the esophageal eosinophil infiltrate in each group of mice was determined across nine high powered field (hpf) of view, three distal (located closer to the mouth (Dis)), three middle (Mid), and three proximal (located closer to the stomach (Prox)) regions and expressed as group mean data of the eosinophil density (ie, eosinophils/400× hpf) (FIG. 20B). In addition, the eosinophilia is recorded according to the different (epithelial, lamina propria, and muscle) cell layers of the esophagus (FIG. 20C). These data are representative of separate experiments with three to nine individual mice per group (*p≤0.05, p≤0.001. *p≤0.0001) (Masterson et al. Gut. 2014, 63, 1-25).

Prior to the OXA sensitization and topical local challenge model of delayed contact hypersensitivity, L2-IL5 transgenic mice were intraperitoneally (IP) injected with 19.2 µg/mouse (assuming 25.0 gram mouse=0.77 mg/kg) High Dose of NDM-X, 23.1 µg/mouse (assuming 25.0 gram mouse=0.92 mg/kg) High Dose of Compound 1, or vehicle on 8, 4, and 2 days before sensitization at Day zero (schematic timeline in FIG. 20A). Compounds are prepared by dissolving in dimethyl sulfoxide (DMSO) at 9.6 µg/L for NMD-X and 11.54 µg/L for 1 to make High Dose master stocks. Prepare fresh High Dose working stocks of 0.192 µg/L of NDM-X in water (20 µL of master stock in 980 L of water) and 0.231 µg/L of 1 in water (22 µL of master stock in 1078 µL of water) for each injection cohort that are used to IP injected 100 µL of working stock per mouse the NDM-X High Dose and 1 High Dose, respectively. On Day zero of the OXA sensitization/local challenge, a 2 cm×2 cm area of abdominal skin of anaesthetized experimental animals was shaved and OXA was applied to the skin surface to initiate the sensitization phase of the protocol. Sensitized mice then received topical OXA challenges of the esophagus by gavage on protocol Day 5, 8 and 12 after OXA sensitization in the proximal esophagus. In addition, compounds or vehicle were IP injected on Day 5, 8, and 12 after OXA sensitization.

Figure 21:
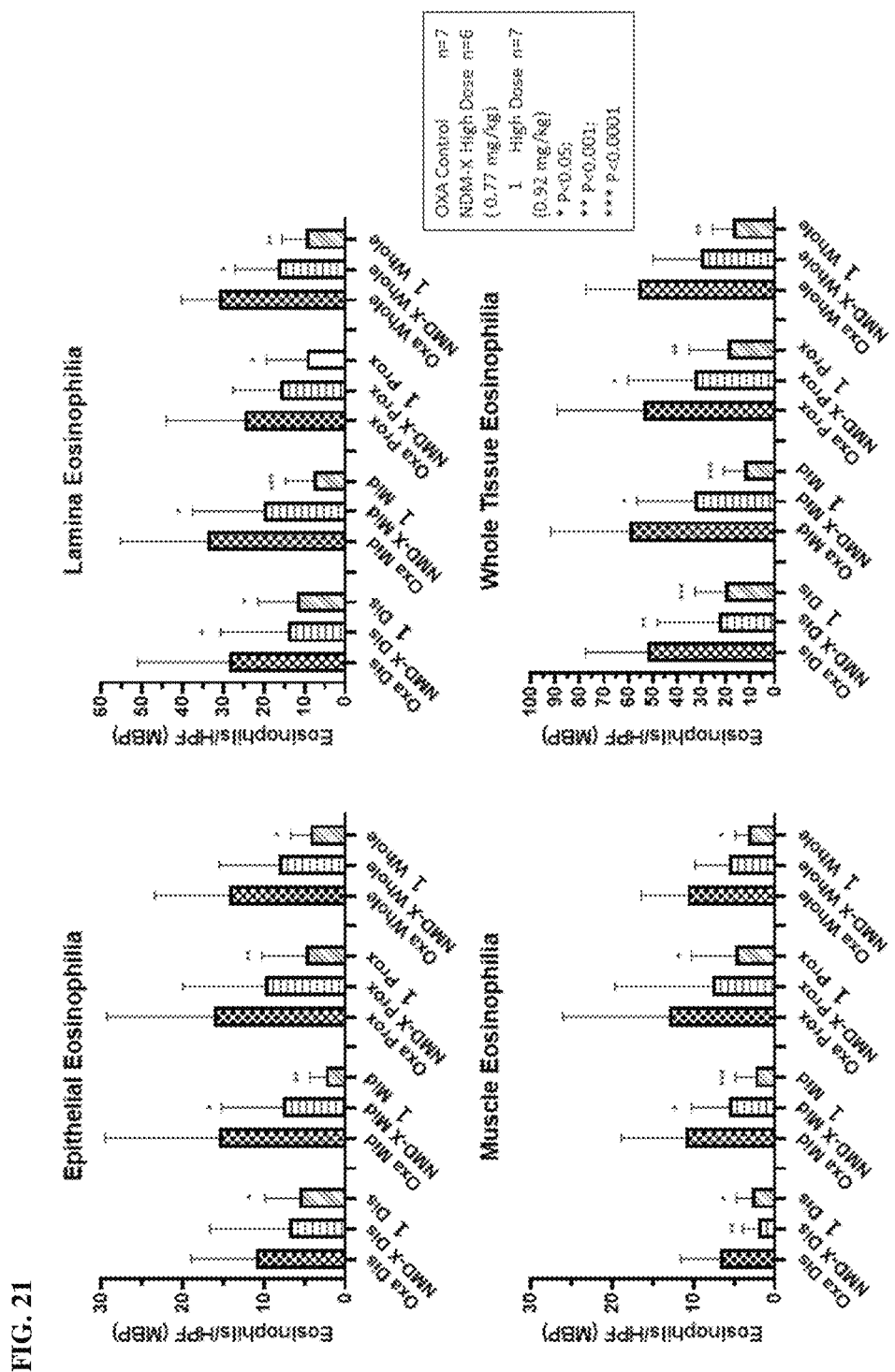
FIG. 21 NDM-X and Compound 1 inhibit in vivo model eosinophilic esophagitis in L2-IL5 Transgenic Mouse Sensitized/Locally Challenged with Oxazolone Antigen.

Shown in FIG. 21 is the quantitative assessment of the eosinophilic esophagitis at Day 13 after sensitization and topical local challenge with OXA in IL2-IL5 transgenic mouse model using high powered magnification microscopy images of the MBP-1 immunohistochemical staining of the mouse esophagus. FIG. 21 showed 0.92 mg/kg 1 High Dose displaying statistically significant inhibition of eosinophilic esophagitis in the epithelial, lamina propria, and muscle layers of the distal, middle, and proximal cell layers of the esophagus resulting in a statistically significant attenuation of the eosinophilia in all the cell layers from distal, middle, and proximal regions of the esophagus. In the same FIG. 21, 0.77 mg/kg NDM-X High Dose demonstrated statistically significant reduction in the eosinophilia in the lamina propria and muscle cell layers of the distal, middle, and proximal regions of the esophagus resulting in a statistically significant attenuation of the eosinophilia in all the cell layers from distal and middle regions of the esophagus. Overall, 0.92 mg/kg 1 High Dose displayed a more robust blocking of eosinophil esophagitis in the mouse model than compared to 0.77 mg/kg NDM-X High Dose. This comparison trend holds true with exception to the eosinophilia in the muscle cell layer of the distal region of the esophagus where 0.77 mg/kg NDM-X High Dose performed slightly better blocking of the eosinophilia than 0.92 mg/kg 1 High Dose but both were statistically significant. These data are representative of an experiment with six to seven individual mice per group (*p≤0.05, p≤0.001. *p≤0.0001).

Prior to the OXA sensitization and topical local challenge model of delayed contact hypersensitivity, L2-IL5 transgenic mice were intraperitoneally (IP) injected with 0.30 µg/mouse (assuming 25.0 gram mouse=0.012 mg/kg) Low Dose of NDM-X, 0.36 g/mouse (assuming 25.0 gram mouse=0.014 mg/kg) Low Dose of 1, or vehicle on 8, 4, and 2 days before sensitization at Day zero (schematic timeline in FIG. 20A). Low Dose master stocks are prepared by dissolving NDM-X and 1 in dimethyl sulfoxide (DMSO) to make a 0.50 µg/L NDM-X and 0.58 µg/L 1. To prepare fresh working stocks, master stocks are diluted with water to make a 0.003 µg/L NDM-X working stock and 0.0036 g/L 1 working stock that are used to IP inject 100 µL per mouse the NDM-X Low Dose and compound 1 Low Dose, respectively.

Figure 22:
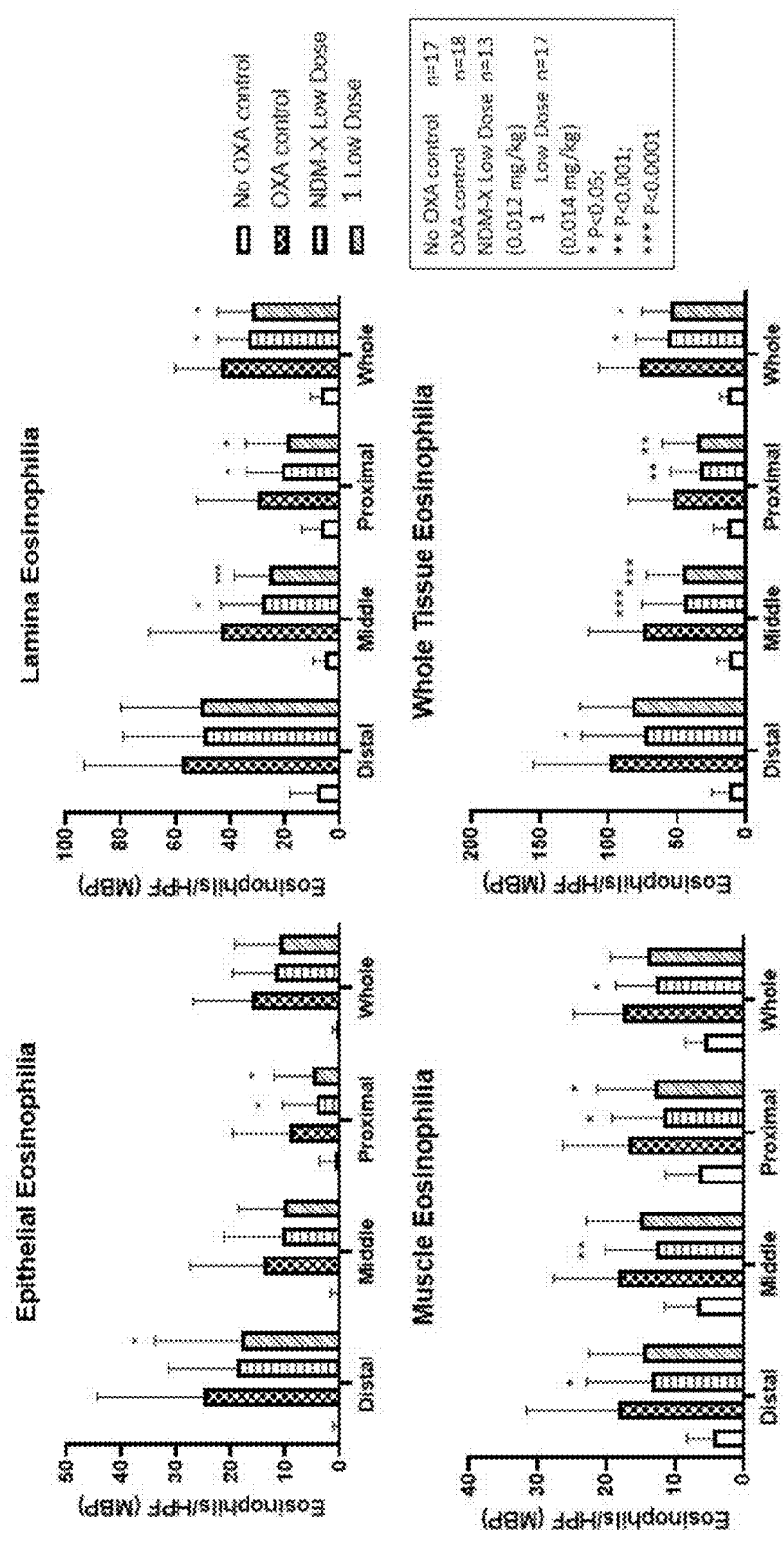
FIG. 22 NDM-X and Compound 1 inhibit in vivo model eosinophilic esophagitis in L2-IL5 Transgenic Mouse Sensitized/Locally Challenged with Oxazolone Antigen.

Shown in FIG. 22 is the quantitative assessment of the eosinophilic esophagitis at Day 13 after sensitization and topical local challenge with OXA in IL2-IL5 transgenic mouse model using high powered magnification microscopy images of the MBP-1 immunohistochemical staining of the mouse esophagus. In contrast to the better inhibition of the eosinophilia observed with 0.92 mg/kg 1 High Dose than compare to 0.77 mg/kg NDM-X High Dose, comparable blocking of the eosinophilia was demonstrated with the 0.014 mg/kg 1 Low Dose and 0.012 mg/kg NDM-X Low Dose in the OXA sensitization and topical local challenge model of delayed contact hypersensitivity in L2-IL5 transgenic mice. In FIG. 22, the 0.014 mg/kg Low Dose 1 showed statistically significant inhibition of the eosinophilia in all cell layers of the proximal region, epithelial cell layer of the distal region, and lamina propria cell layer of the middle section of the esophagus, which results in statistically significant blocking of the eosinophilia in all cell layers of the middle, proximal, and whole tissue of the esophagus. The Low Dose 0.012 mg/kg NDM-X, on the other hand, demonstrated statistically significant inhibition of the eosinophilia in all cell layers of the proximal region, the muscle cell layers in all regions, and the epithelial cell layer of the distal and proximal regions, which results in the statistically significant attenuation of the eosinophilia in all cell layers of all regions in the esophagus OXA sensitization and topical local challenge model of delayed contact hypersensitivity, L2-IL5 transgenic mice.

Prior to the OXA sensitization and topical local challenge model of delayed contact hypersensitivity, L2-IL5 transgenic mice were intraperitoneally (IP) injected with 2.31 μg/mouse (assuming 25.0 gram mouse=0.092 mg/kg) Mid Dose, 23.1 μg/mouse (assuming 25.0 gram mouse=0.92 mg/kg) High Dose or vehicle on 8, 4, and 2 days before sensitization at Day zero (schematic timeline in FIG. 20A). Master stocks are prepared by dissolving 24.8 mg of 1 in 214.6 μL dimethyl sulfoxide (DMSO) to make a 115.6 μg/L Master Stock of 1. 30 μL of the Master Stock of 1 is further diluted with 270 L of DMSO to make the 11.56 μg/L Master Stock 1 High Dose, and 20 μL of the Master Stock 1 High Dose is further diluted with 180 μL of DMSO to make the 1.16 μg/L of the Master Stock 1 Mid Dose. To prepare fresh working stocks, 25 μL of Master Stock 1 Low Dose and Master Stock 1 High Dose are mixed with 1225 μL of water to make the Working Stock 1 Mid Dose (0.0231 μg/L) and Working Stock 1 High Dose (0.231 μg/L), respectively, that are used to IP inject 100 μL per mouse the Mid Dose and High Dose of 1, respectively.

Figure 23:
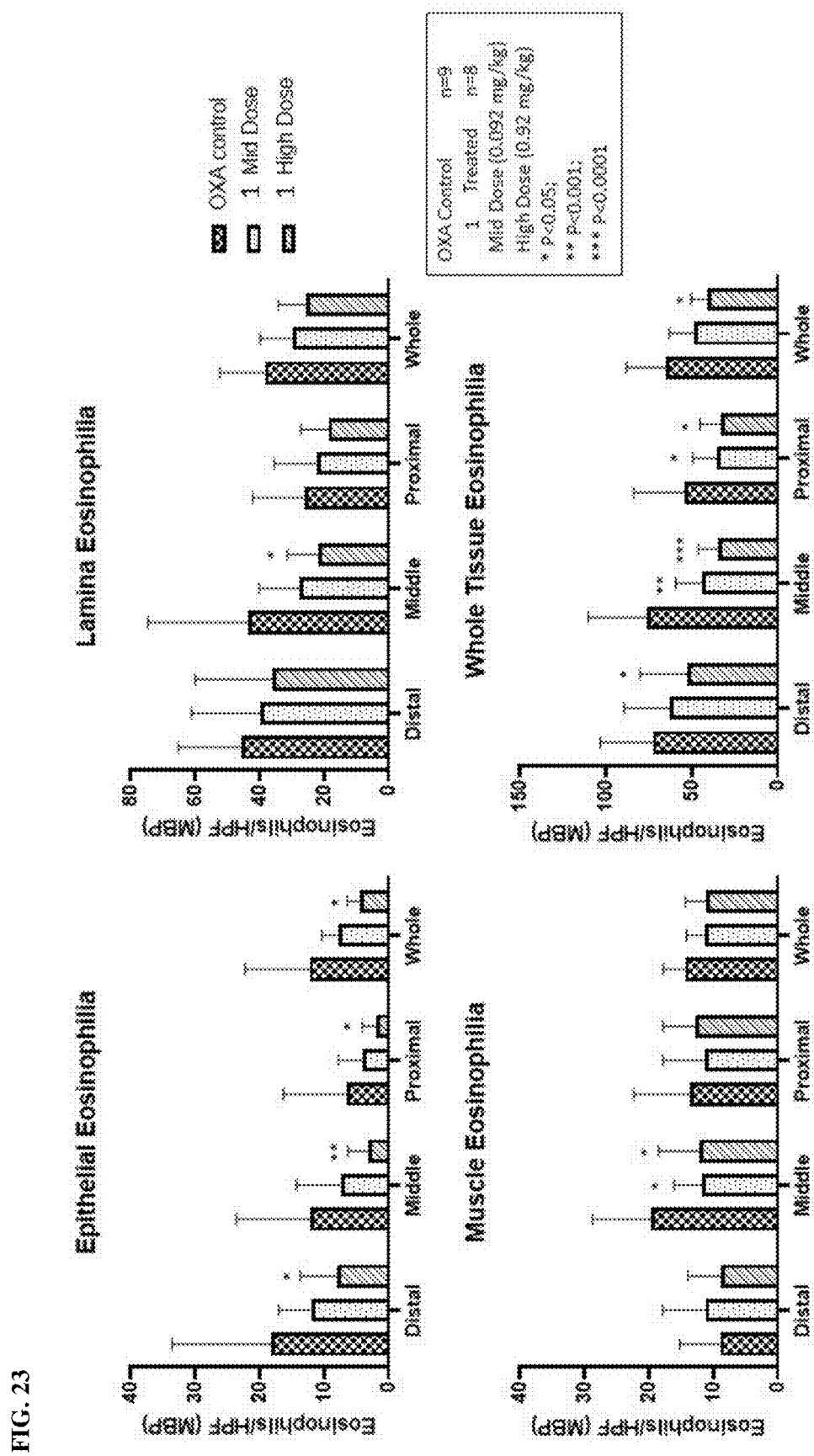
FIG. 23 Compound 1 inhibits in vivo model eosinophilic esophagitis in L2-IL5 Transgenic Mouse Sensitized/Locally Challenged with Oxazolone Antigen.

Shown in FIG. 23 is the quantitative assessment of the eosinophilic esophagitis at Day 13 after sensitization and topical local challenge with OXA in IL2-IL5 transgenic mouse model using high powered magnification microscopy images of the MBP-1 immunohistochemical staining of the mouse esophagus.

In FIG. 23 pre-treatment with IP injection of 0.92 mg/kg High Dose of 1 resulted in statistically significant inhibition of the eosinophilic esophagitis observed in epithelial cell layer of distal, middle, and proximal regions of the esophagus. In addition, the 0.92 mg/kg High Dose of 1 showed statistically significant inhibition of the eosinophilia observed in the lamina propria and muscle cell layers of the middle section of the esophagus. The same High Dose of 1 demonstrated statistically significant reduction in eosinophilia observed in all cell layers of the middle and proximal sections as well as the whole esophagus.

Overall, FIG. 23 showed that pre-treatment with IP injection of 0.092 mg/kg Mid Dose and 0.92 mg/kg High Dose of 1 dose-dependently inhibited eosinophilia in the epithelial, lamina propria, and muscle cell layers of the distal, middle, and proximal regions of the esophagus. These data are representative of an experiment with eight to nine individual mice per group (*$p \leq 0.05$, $p \leq 0.001$. *$p \leq 0.0001$).

Prior to the OXA sensitization and topical local challenge model of delayed contact hypersensitivity, L2-IL5 transgenic mice were intraperitoneally (IP) injected with 0.3 μg/mouse (assuming 25.0 gram mouse=0.012 mg/kg) Low Dose, 19.2 μg/mouse (assuming 25.0 gram mouse=0.77 mg/kg) High Dose of NDM-X, or vehicle 8, 4, and 2 days before sensitization at Day zero (schematic timeline in FIG. 20A). Master stocks are prepared by dissolving NDM-X in dimethyl sulfoxide (DMSO) to make a 0.5 μg/L Master Stock NDM-X Low Dose and 9.9 μg/L Master Stock NDM-X High Dose. To prepare fresh working stocks, Master Stock NDM-X Low Dose is diluted with water to make a 0.003 μg/L Working Stock NDM-X Low Dose and Master Stock NDM-X High Dose is diluted with water to make a 0.192 μg/L Working Stock NDM-X High Dose that are used to IP inject 100 μL per mouse the Low Dose and High Dose of NDM-X, respectively.

Figure 24:
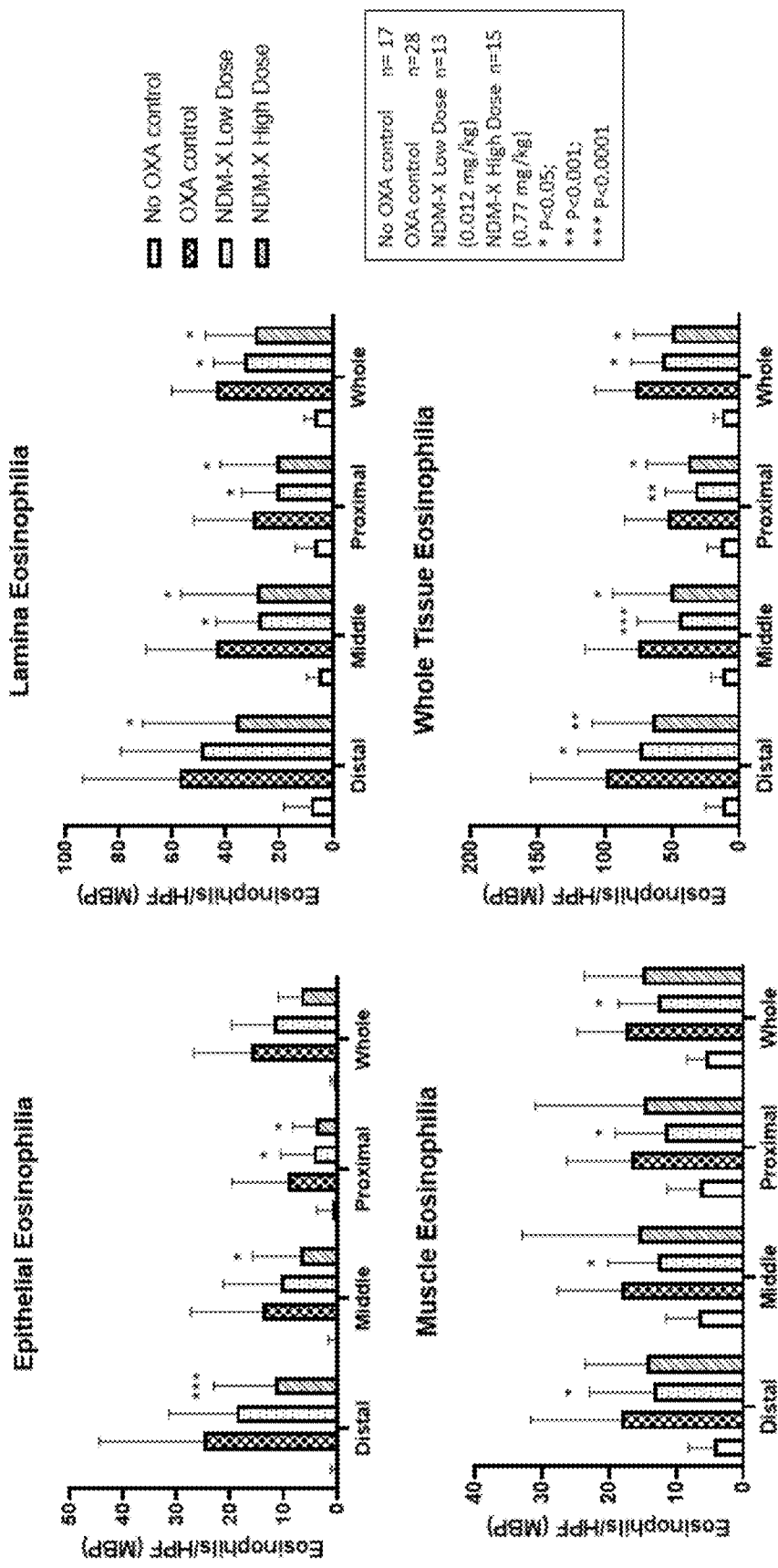
FIG. 24 NDM-X inhibits in vivo model eosinophilic esophagitis in L2-IL5 Transgenic Mouse Sensitized/Locally Challenged with Oxazolone Antigen.

Shown in FIG. 24 is the quantitative assessment of the eosinophilic esophagitis at Day 13 after sensitization and topical local challenge with OXA in IL2-IL5 transgenic mouse model using high powered magnification microscopy images of the MBP immunohistochemical staining of the mouse esophagus. In all cell layers in all regions of the esophagus, FIG. 24 demonstrated that there is a huge increase in the eosinophilia observed with IL2-IL5 transgenic mice that were sensitized and topically, locally challenged with OXA (OXA control) as compared to IL2-IL5 transgenic mice that were not (No OXA control). The overall trend showed that 0.012 mg/kg Low Dose of NDM-X is slightly better than 0.77 mg/kg High Dose of NDM-X in inhibiting the eosinophilia observed in the epithelial, lamina propria, and muscle cell layers of the distal, middle, and proximal regions of the esophagus. However, in the epithelial, lamina propria, and whole cell layers of the distal region of the esophagus with exception to the muscle layer, the 0.77 mg/kg High Dose demonstrated statistically significant reduction of the eosinophilia in a manner that is slightly better than the 0.012 mg/kg Low Dose of NDM-X.

The 0.012 mg/kg Low Dose of NDM-X in FIG. 24 showed statistically significant inhibition of the eosinophilia observed in the epithelial, lamina propria, and muscle cell layers of the distal, middle, and proximal regions of the esophagus resulting in statistically significant attenuation of the eosinophilia in all the cell layers from the distal to proximal regions of the esophagus. The 0.77 mg/kg High Dose of NDM-X demonstrated statistically significant reduction of the eosinophilia in the epithelial and lamina propria cell layers of distal, middle, and proximal regions of the esophagus resulting in statistically significant attenuation of the eosinophilia in all the cell layers from the distal to proximal regions of the esophagus. These data are representative of two to three experiment with three to nine individual mice per group (*$p \leq 0.05$, $p \leq 0.001$. *$p \leq 0.0001$).

Using the protocols described in Examples 3-16, any additional compounds of Table 3 are tested and have similar activity to the compounds tested above.

Example 17

Efficacy in Animal Model of IBD

A T-cell transfer model of colitis where 500,000 CD4+ CD45RBhi cells are transferred to adult Rag1 −/− mice is used. Either the vehicle or 300 ng of any one of compounds 1-56 are administered via intraperitoneal injection at multiple timepoints throughout each week for 30 days. On day 30, the mice are euthanized and colon analysis is performed. T-cell activation and phenotype is also analyzed. The normal mouse colon is long, skinny, and has discrete fecal pellets. The diseased mouse colon, with IBD, has a shortened, dilated colon, with diarrhea instead of discrete fecal pellets.

Example 18

Efficacy in Animal Model of EoE

A mouse model of EoE induces eosinophilia in oxazolone sensitized and challenged L2-IL5 mice.

Intraperitoneal injection with either vehicle or different concentrations of any one of compounds 1-56 is administered to PL2+ mice on at several timepoints prior to skin sensitization with oxazolone and intraperitoneal injection with either vehicle or different concentrations of compound). A 2 cm×2 cm area of the abdominal skin of anaesthetized mice is shaved, and oxazolone is applied to skin surface (150 µL of a 3% (w/v) solution of oxazolone in 4:1 acetone-olive oil vehicle to initiate the sensitization phase). The esophagus is challenged by gavage (i.e.) with a 2% (w/v) solution of oxazolone in 30% ethanol/olive oil vehicle into the proximal esophagus and intraperitoneal injection with either vehicle (100 µL) or different concentrations of compound on subsequent days. Upon experiment completion, the mice are euthanized and the esophagus is analyzed. The esophagus is embedded in paraffin wax and is mounted onto slides. The esophagus samples are stained following MBP IHC protocol, and the distal, middle, and proximal esophagus are analyzed. Eosinophils on esophagus sections stained for MBP are counted.

Example 19

Efficacy in In Vitro Human Esophageal Cells

The effect of any one of compounds 1-56 on CCL26 secretion from Epithelial human telomerase reverse transcriptase (EPC-hTERT) cells can be investigated.

Epithelial human telomerase reverse transcriptase EPC2-hTERT cells are cultured in keratinocyte SFM (KSFM) media with penicillin (100 units/mL) and streptomycin (100 µg/mL) at 37° C. with 5% (v/v) $CO_2$. EPC2-hTERT cells in 350 µL of media/well are seeded at a density of $0.09 \times 10^6$ cells/well in three 24-well plates. The media is changed about 4 hours after seeding. 24 hours after seeding, the media is changed to include DI vehicle and several concentrations of compound) with and without IL-1β. The supernatant is collected, and cells are harvested by adding 350 µL RLT+BME (10 µL BME per 1 mL RLT) per well at several timepoints post treatment. RNA is extracted using Qiagen's Qiashredder and RNeasy kits according to manufacturer's protocol. cDNA is made using the High Capacity cDNA Reverse Transcription Kit. qPCR is run with TaqMan primers and TaqMan Fast Advanced Master Mix.

EQUIVALENTS

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or Example language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

INCORPORATION BY REFERENCE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The invention claimed is:

1. A compound having the structure of Formula (II):

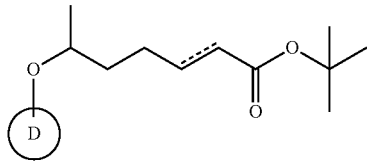

Formula (II)

wherein
Ring D is

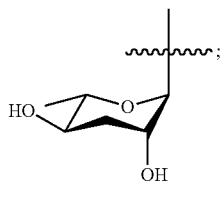

represents the point of attachment of Ring D to the oxygen atom; and ⫽ is a double bond or a single bond.

2. The compound of claim 1, wherein the compound has the structure:

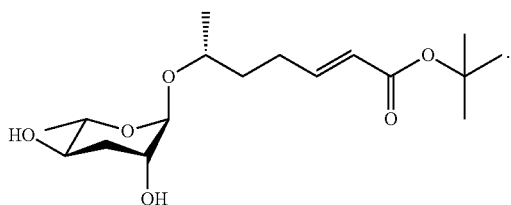

3. The compound of claim 1, wherein the compound has the structure:

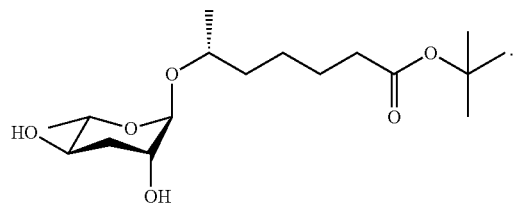

4. The compound of claim 1, wherein the compound is

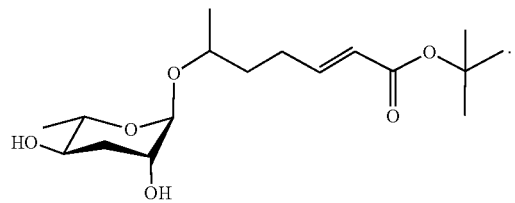

5. A pharmaceutical formulation comprising a pharmaceutically acceptable carrier; and a compound of claim 1.
6. A pharmaceutical formulation comprising a pharmaceutically acceptable carrier; and a compound of claim 2.
7. A pharmaceutical formulation comprising a pharmaceutically acceptable carrier; and a compound of claim 3.
8. A pharmaceutical formulation comprising a pharmaceutically acceptable carrier; and a compound of claim 4.
9. A method of treating a disease or condition in a subject in need thereof, comprising administering to the subject an effective amount of a compound of claim wherein the disease or condition is selected from Acne vulgaris,
Agammaglobulinemia,
Allergic rhinitis,
Amyloidosis,
Anaphylaxis,
Ankylosing spondylitis,
Anti-GBM/Anti-TBM nephritis (anti-glomerular basement membrane antibody disease),
Antiphospholipid syndrome,
Autism,
Autoimmune hepatitis,
Autoimmune inner ear disease,
Atopic dermatitis,
Asthma,
Castleman disease,
Celiac disease,
Chagas disease,
Chronic nonbacterial osteomyelitis,
Chronic prostatitis,
Chronic recurrent multifocal osteomyelitis,
Cogan's syndrome,
Cold agglutinin disease,
CREST syndrome,
Crohn's disease,
Dermatomyositis,
Devic's disease (neuromyelitis optica),
Discoid lupus,
Endometriosis,
Eosinophilic asthma,
Eosinophilic cardiomyopathy,
Eosinophilic colitis,
Eosinophilic cystitis,
Eosinophilic disorder, Eosinophilic enteritis,
Eosinophilic esophagitis (EoE),
Eosinophilic fasciitis,
Eosinophilic gastritis,
Eosinophilic gastroenteritis,
Eosinophilic granulomatosis with polyangiitis,
Eosinophilic pneumonia,
Evan's syndrome,
Fibromyalgia,
Food allergy,
Giant cell arteritis,
Giant cell myocarditis,
Glomerulonephritis,
Goodpasture's syndrome (anti-GBM),
Granulomatosis with polyangiitis (Wegener's),
Graves' disease,
Guillain-Barre syndrome,
Hashimoto's thyroiditis,
Hemolytic anemia (some types),
Hemophagocytic lymphohistiocytosis,
Henoch-Schonlein purpura,
Hypereosinophilic syndrome,
Hypersensitivities,
Hypogammaglobulinemia,
Hypoproliferative anemia,
IgA Nephropathy,
Inclusion body myositis,
Interstitial cystitis,
Inflammatory Bowel Disease,
Juvenile arthritis,
Juvenile/Type I Diabetes,
Juvenile myositis,
Kawasaki syndrome,
Lichen planus,
Lichen sclerosus,
Mastocytosis,
Meniere's disease,
Multiple sclerosis,
Myasthenia gravis,
Myopathy (some types),
Microscopic polyangiitis,
Optic neuritis,
paroxysmal nocturnal hemoglobinuria,
Pemphigus,
Perennial allergy,
Pernicious anemia,
pelvic inflammatory disease,
Polyarteritis nodosa,
Polymyalgia rheumatica,
Polymyositis,
Primary biliary cirrhosis,
Primary sclerosing cholangitis,
Psoriasis,
Psoriatic arthritis,
Reactive arthritis,
Reperfusion Injury,
Rheumatic fever,
Rheumatoid arthritis,
Sarcoidosis,
Scleroderma,
Seasonal allergy,
Selective IgA Deficiency,
sickle cell disease,
Sjogren's syndrome,
Still disease,
systemic Lupus erythematosus (SLE),
Systemic juvenile idiopathic arthritis,
Systemic sclerosis,
Takayasu arthritis,
Temporal arteritis/Giant cell arteritis,
Transplant rejection,
Transverse myelitis,
Ulcerative colitis,
Uveitis,
Vasculitis,
Vitiligo,
Viral myocarditis, and
Wegener's granulomatosis (Granulomatosis with Polyangiitis (GPA)).

10. The method of claim 9, wherein the disease or condition is eosinophilic esophagitis (EoE), asthma, inflammatory bowel diseases, rheumatoid arthritis, or multiple sclerosis.

11. The method of claim 9, wherein the disease or condition is an eosinophilic disorder selected from Eosinophilic asthma, Eosinophilic cardiomyopathy Eosinophilic colitis, Eosinophilic cystitis, Eosinophilic enteritis, Eosinophilic esophagitis (EoE), Eosinophilic fasciitis, Eosinophilic gastritis, Eosinophilic gastroenteritis, Eosinophilic granulomatosis with polyangiitis, Eosinophilic pneumonia, and Hypereosinophilic syndrome.

12. The method of claim 9, wherein the subject is selected from primates, humans, equines, horses, cattle, cows, swine, sheep, rodents, rats, pets, dogs, and guinea pigs.

13. The method of claim 9, wherein the subject is human.

14. The method of claim 9, wherein the method further comprises conjointly administering to the subject an effective amount of a different therapeutic compound.

15. The method of claim 14, wherein the different therapeutic compound is a steroid.

16. The method of claim 14, wherein the different therapeutic compound is dexamethasone.

17. A compound having the structure of Formula (II):

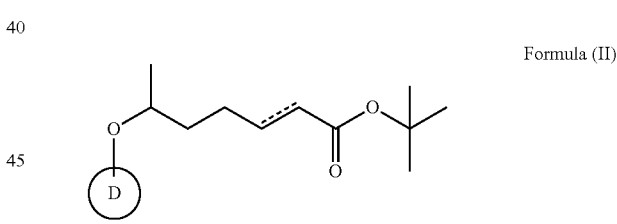

Formula (II)

wherein
Ring D is selected from

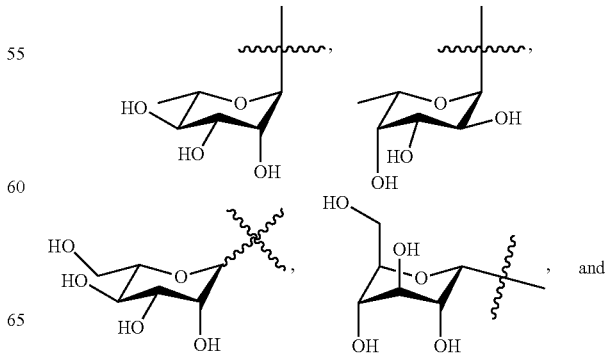

-continued

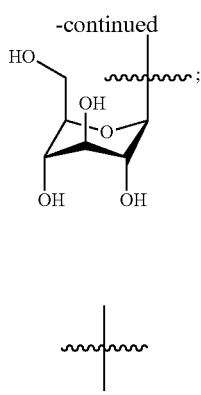

represents the point of attachment of Ring D to the oxygen atom; and ⫽ is a double bond or a single bond.

18. The compound of claim 17, wherein the compound is selected from

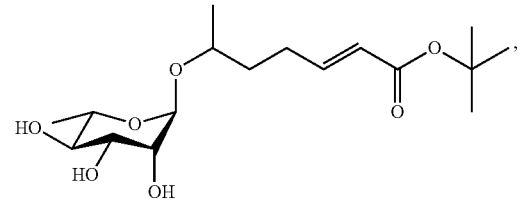

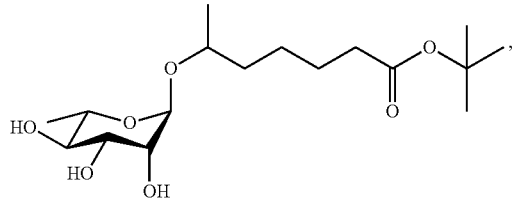

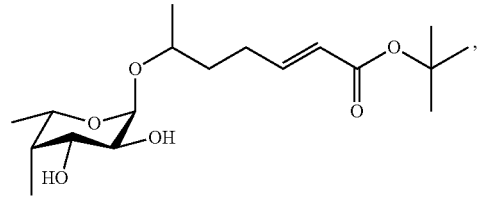

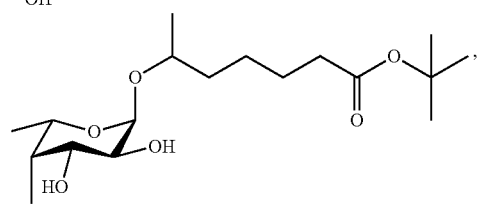

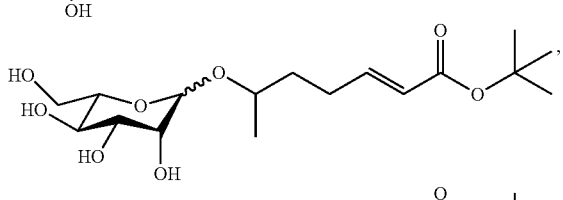

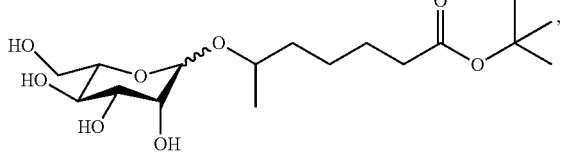

-continued

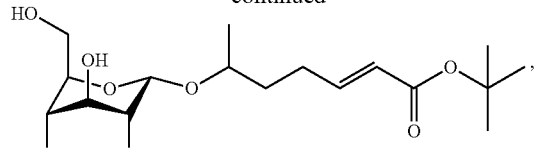

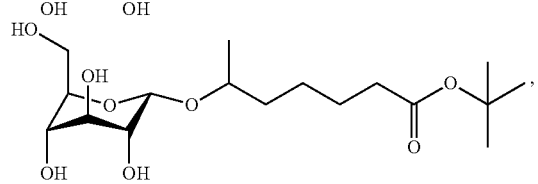

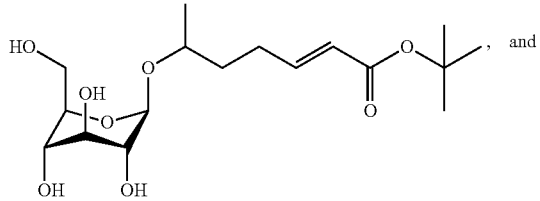

and

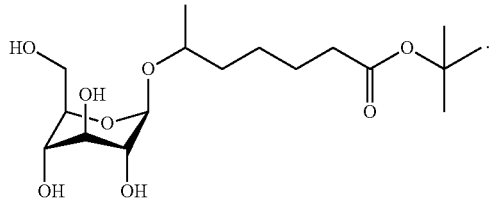

19. A pharmaceutical formulation comprising a pharmaceutically acceptable carrier; and a compound of claim 17.

20. A method of treating a disease or condition in a subject in need thereof, comprising administering to the subject an effective amount of a compound of claim 17 wherein the disease or condition is selected from Acne vulgaris,
Agammaglobulinemia,
Allergic rhinitis,
Amyloidosis,
Anaphylaxis,
Ankylosing spondylitis,
Anti-GBM/Anti-TBM nephritis (anti-glomerular basement membrane antibody disease),
Antiphospholipid syndrome,
Autism,
Autoimmune hepatitis,
Autoimmune inner car disease,
Atopic dermatitis,
Asthma,
Castleman disease,
Celiac disease,
Chagas disease,
Chronic nonbacterial osteomyelitis,
Chronic prostatitis,
Chronic recurrent multifocal osteomyelitis,
Cogan's syndrome,
Cold agglutinin disease,
CREST syndrome,
Crohn's disease,
Dermatomyositis,
Devic's disease (neuromyelitis optica),
Discoid lupus,
Endometriosis,
Eosinophilic asthma,
Eosinophilic cardiomyopathy,
Eosinophilic colitis, Eosinophilic cystitis,
Eosinophilic disorder,
Eosinophilic enteritis,
Eosinophilic esophagitis (EoE),
Eosinophilic fasciitis,
Eosinophilic gastritis,
Eosinophilic gastroenteritis,
Eosinophilic granulomatosis with polyangiitis,
Eosinophilic pneumonia,
Evan's syndrome,
Fibromyalgia,
Food allergy,
Giant cell arteritis,
Giant cell myocarditis,
Glomerulonephritis,
Goodpasture's syndrome (anti-GBM),
Granulomatosis with polyangiitis (Wegener's),
Graves' disease,
Guillain-Barre syndrome,
Hashimoto's thyroiditis,
Hemolytic anemia (some types),
Hemophagocytic lymphohistiocytosis,
Henoch-Schonlein purpura,
Hypereosinophilic syndrome,
Hypersensitivities,
Hypogammaglobulinemia,
Hypoproliferative anemia,
IgA Nephropathy,
Inclusion body myositis,
Interstitial cystitis,
Inflammatory Bowel Disease,
Juvenile arthritis,
Juvenile/Type I Diabetes,
Juvenile myositis,
Kawasaki syndrome,
Lichen planus,
Lichen sclerosus,
Mastocytosis,
Meniere's disease,
Multiple sclerosis,
Myasthenia gravis,
Myopathy (some types),
Microscopic polyangiitis,
Optic neuritis,
paroxysmal nocturnal hemoglobinuria,
Pemphigus,
Perennial allergy,
Pernicious anemia,
pelvic inflammatory disease,
Polyarteritis nodosa,
Polymyalgia rheumatica,
Polymyositis,
Primary biliary cirrhosis,
Primary sclerosing cholangitis,
Psoriasis,
Psoriatic arthritis,
Reactive arthritis,
Reperfusion Injury,
Rheumatic fever,
Rheumatoid arthritis,
Sarcoidosis,
Scleroderma,
Seasonal allergy,
Selective IgA Deficiency,
sickle cell disease,
Sjogren's syndrome,
Still disease,
systemic Lupus erythematosus (SLE),
Systemic juvenile idiopathic arthritis,
Systemic sclerosis,
Takayasu arthritis,
Temporal arteritis/Giant cell arteritis,
Transplant rejection,
Transverse myelitis,
Ulcerative colitis,
Uveitis,
Vasculitis,
Vitiligo,
Viral myocarditis, and
Wegener's granulomatosis (Granulomatosis with Polyangiitis (GPA)).

21. The method of claim 20, wherein the disease or condition is eosinophilic esophagitis (EoE), asthma, inflammatory bowel diseases, rheumatoid arthritis, or multiple sclerosis; or the disease or conditions is an eosinophilic disorder selected from Eosinophilic asthma, Eosinophilic cardiomyopathy Eosinophilic colitis, Eosinophilic cystitis, Eosinophilic enteritis, Eosinophilic esophagitis (EoE), Eosinophilic fasciitis, Eosinophilic gastritis, Eosinophilic gastroenteritis, Eosinophilic granulomatosis with polyangiitis, Eosinophilic pneumonia, and Hypereosinophilic syndrome.

* * * * *